US006063340A

United States Patent [19]
Lewis et al.

[11] Patent Number: 6,063,340
[45] Date of Patent: May 16, 2000

[54] REAGENT CONTAINER FOR AUTOMATED ANALYZER

[75] Inventors: Scott C. Lewis, Amherst; Mary Beth Whitesel, Grafton, both of Ohio

[73] Assignee: Chiron Diagnostics Corporation, E. Walpole, Mass.

[21] Appl. No.: 08/457,702

[22] Filed: Jun. 1, 1995

Related U.S. Application Data

[62] Division of application No. 08/222,559, Apr. 1, 1994, abandoned, which is a continuation of application No. 07/665,196, Mar. 4, 1991, abandoned.

[51] Int. Cl.[7] ................................................ B01L 3/00
[52] U.S. Cl. ...................... 422/102; 366/307; 220/306
[58] Field of Search .................................. 422/102, 104; 436/43, 47; 366/306, 307; 220/306

[56] References Cited

U.S. PATENT DOCUMENTS

| | | | |
|---|---|---|---|
| D. 330,429 | 10/1992 | Lewis et al. . | |
| 3,432,149 | 3/1969 | Stalberg et al. | 422/102 |
| 3,578,291 | 5/1971 | Oberli | 422/102 |
| 3,713,771 | 1/1973 | Taylor et al. | 422/104 |
| 3,791,537 | 2/1974 | Conklin | 214/65 |
| 3,951,608 | 4/1976 | Trod | 422/102 |
| 4,244,459 | 1/1981 | Garrett | 198/389 |
| 4,271,123 | 6/1981 | Curry et al. . | |
| 4,280,815 | 7/1981 | Oberhardt et al. . | |
| 4,349,510 | 9/1982 | Kolehmainen et al. . | |
| 4,366,118 | 12/1982 | Bunce et al. | 422/57 |
| 4,380,580 | 4/1983 | Boguslaski et al. . | |
| 4,383,041 | 5/1983 | Kutsusawa et al. . | |
| 4,396,579 | 8/1983 | Schroeder et al. . | |
| 4,472,352 | 9/1984 | Quesneau et al. | 422/52 |
| 4,477,578 | 10/1984 | Miles et al. . | |
| 4,479,702 | 10/1984 | Mochida et al. | 366/214 |
| 4,539,854 | 9/1985 | Bradshaw et al. . | |
| 4,554,088 | 11/1985 | Whitehead et al. . | |
| 4,652,533 | 3/1987 | Jolley . | |
| 4,672,040 | 6/1987 | Josephson . | |
| 4,731,225 | 3/1988 | Wakatake . | |
| 4,735,778 | 4/1988 | Maruyama et al. | 422/102 |
| 4,737,342 | 4/1988 | Herrmann et al. . | |

(List continued on next page.)

FOREIGN PATENT DOCUMENTS

| | | |
|---|---|---|
| 2032696 | 6/1991 | Canada . |
| 0037079 | 10/1981 | European Pat. Off. . |
| 0216026 | 1/1987 | European Pat. Off. . |
| 0226374 | 6/1987 | European Pat. Off. . |
| 0355823 | 2/1990 | European Pat. Off. . |
| 0358948 | 3/1990 | European Pat. Off. . |
| 0371265 | 6/1990 | European Pat. Off. . |
| 0409606 | 1/1991 | European Pat. Off. . |
| 0410645 | 1/1991 | European Pat. Off. . |
| 2532763 | 8/1976 | Germany . |
| 3402404 | 7/1984 | Germany . |
| 1248041 | 10/1989 | Japan . |
| 8000100 | 1/1980 | WIPO . |

OTHER PUBLICATIONS

International Laboratory, 12(5), pp. 48–56 (1982), Rawlins et al, "Design Principles For A Modern Luminometer".

*Primary Examiner*—Long V. Le
*Attorney, Agent, or Firm*—Arthur S. Morgenstern; Charles L. Gagnebin, III; Robert P. Blackburn

[57] ABSTRACT

An analyzer for performing automated assay testing. The analyzer includes a storage and conveyor system for conveying cuvettes to an incubation or processing conveyor, a storage and selection system for test sample containers, a storage and selection system for reagent containers, sample and reagent aspirating and dispensing probes, a separation system for separating bound from unbound tracer or labeled reagent, a detection system and date collection/processing system All of the sub-units of the machine are controlled by a central processing unit to coordinate the activity of all of the subunits of the analyze. The analyzer is specifically suited for performing heterogeneous binding assay protocols, particularly immunoassays.

4 Claims, 82 Drawing Sheets

U.S. PATENT DOCUMENTS

| | | |
|---|---|---|
| 4,745,181 | 5/1988 | Law et al. . |
| 4,755,055 | 7/1988 | Johnson et al. .......................... 356/440 |
| 4,772,453 | 9/1988 | Lisenbee . |
| 4,778,763 | 10/1988 | Makiguchi et al. . |
| 4,797,258 | 1/1989 | Mochida . |
| 4,803,050 | 2/1989 | Mack . |
| 4,808,380 | 2/1989 | Minekane .................................. 422/64 |
| 4,816,418 | 3/1989 | Mack et al. . |
| 4,818,883 | 4/1989 | Anderson et al. . |
| 4,826,319 | 5/1989 | Namba et al. . |
| 4,849,177 | 7/1989 | Jordan ...................................... 422/64 |
| 4,859,583 | 8/1989 | Heller et al. . |
| 4,863,690 | 9/1989 | Berthold et al. . |
| 4,906,433 | 3/1990 | Minekane . |
| 4,918,192 | 4/1990 | Law . |
| 4,925,629 | 5/1990 | Schramm . |
| 4,927,769 | 5/1990 | Chang et al. . |
| 4,931,256 | 6/1990 | Mack et al. . |
| 4,931,402 | 6/1990 | Abplanalp . |
| 4,933,147 | 6/1990 | Hollar et al. . |
| 4,937,048 | 6/1990 | Sakai et al. . |
| 4,946,958 | 8/1990 | Campbell et al. . |
| 4,952,518 | 8/1990 | Johnson et al. . |
| 4,956,148 | 9/1990 | Gradone . |
| 4,965,049 | 10/1990 | Lillig et al. . |
| 5,008,082 | 4/1991 | Shaw . |
| 5,089,424 | 2/1992 | Khalil et al. . |
| 5,128,103 | 7/1992 | Wang . |
| 5,128,105 | 7/1992 | Berthold et al. . |
| 5,158,895 | 10/1992 | Ashihara et al. . |
| 5,175,086 | 12/1992 | Takekawa . |
| 5,183,638 | 2/1993 | Wakatake .................................. 422/64 |
| 5,202,091 | 4/1993 | Lisenbee . |
| 5,215,714 | 6/1993 | Okada et al. . |
| 5,279,943 | 1/1994 | Mathis et al. . |

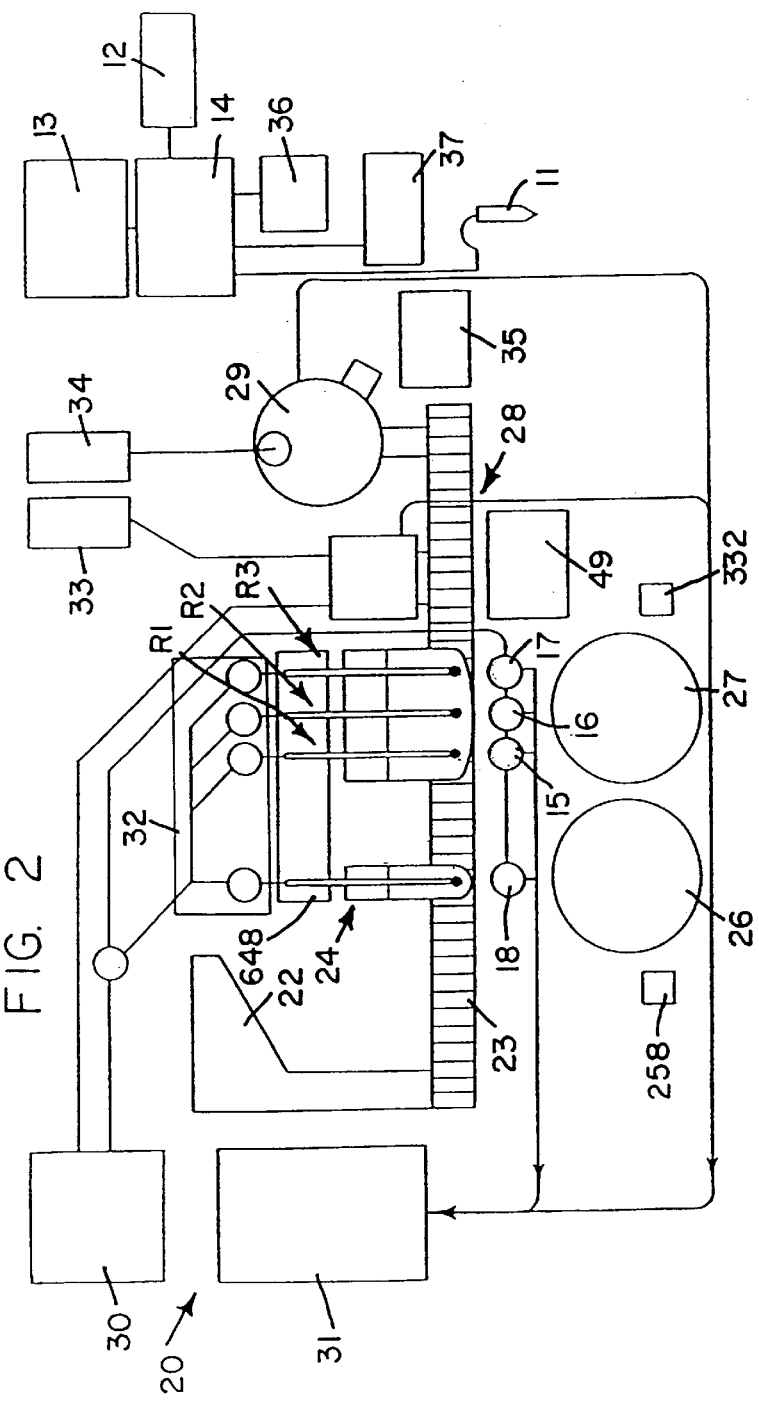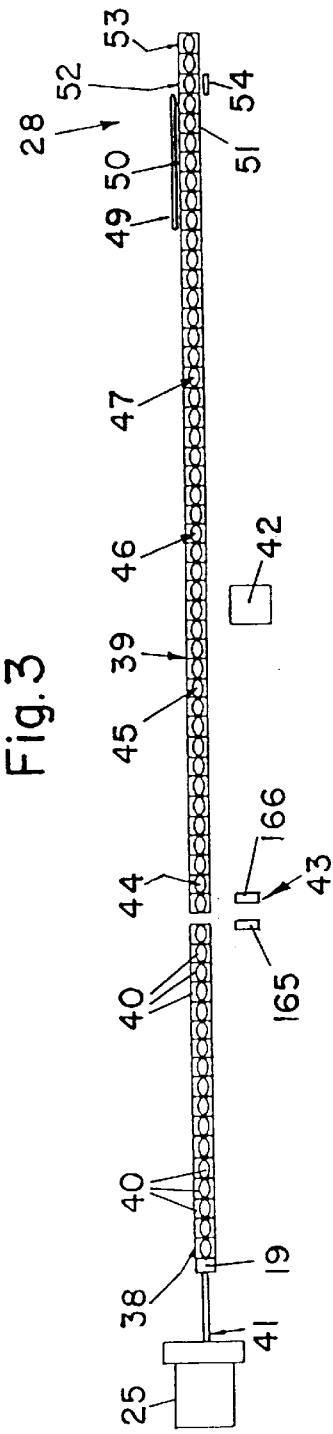

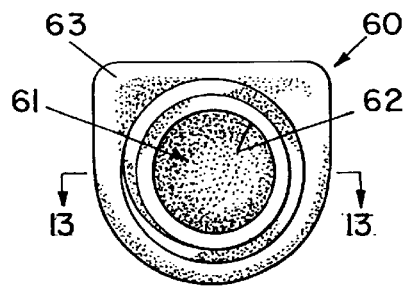
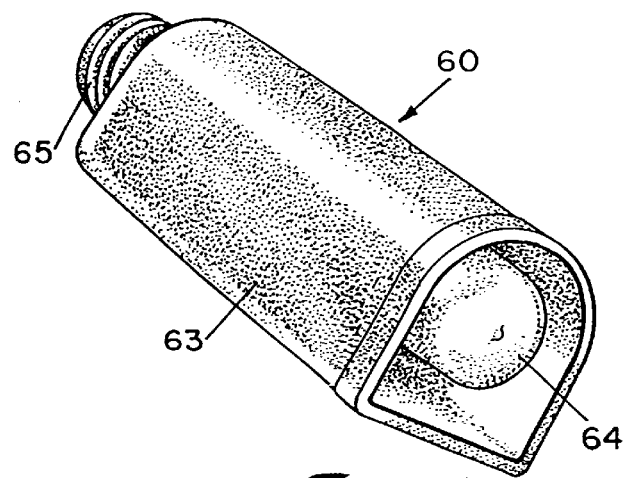
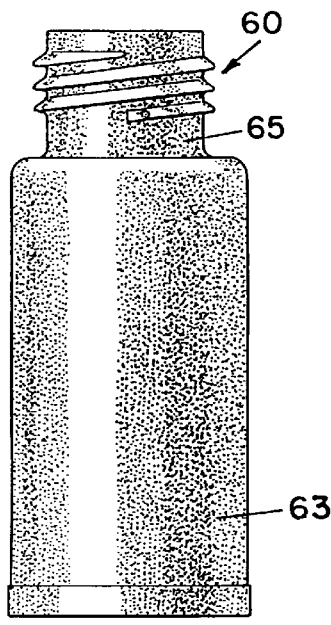
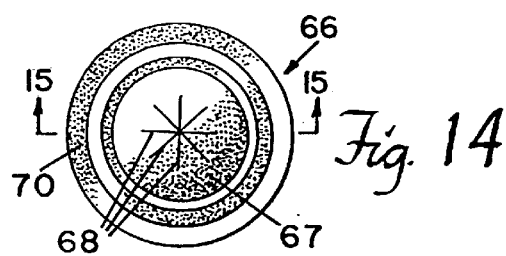
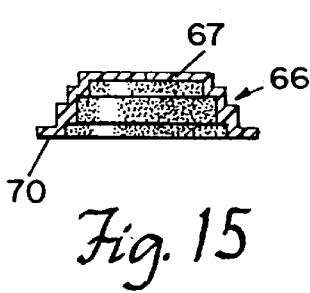
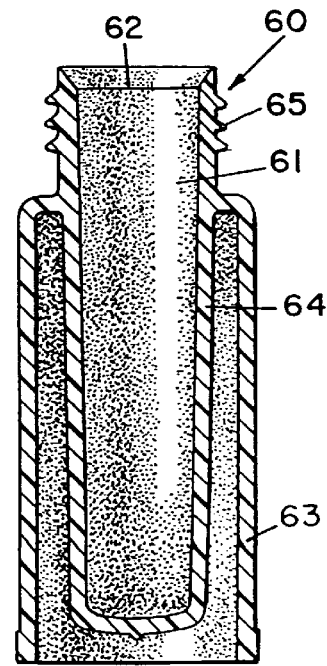
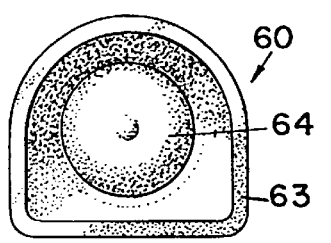

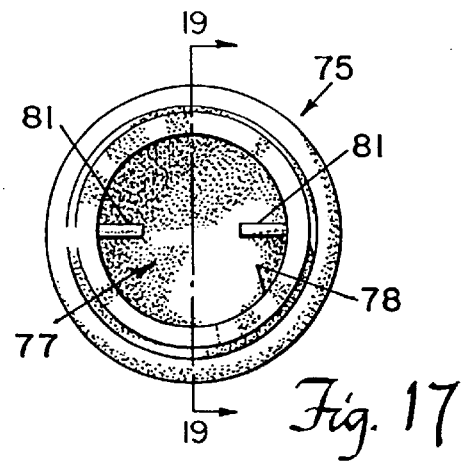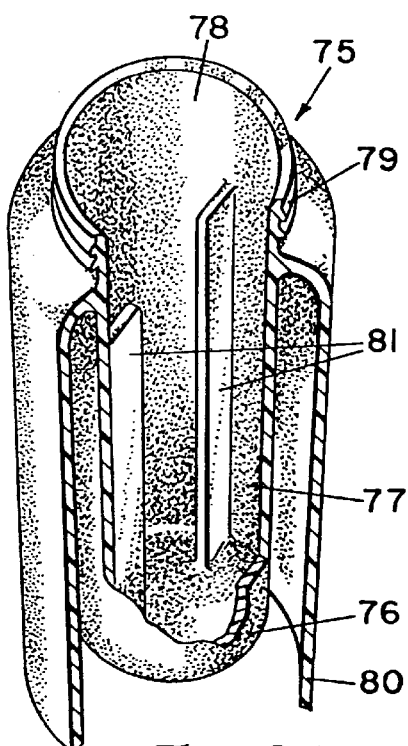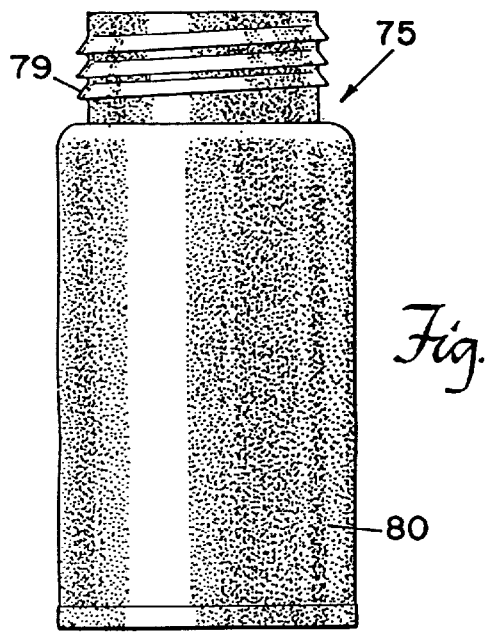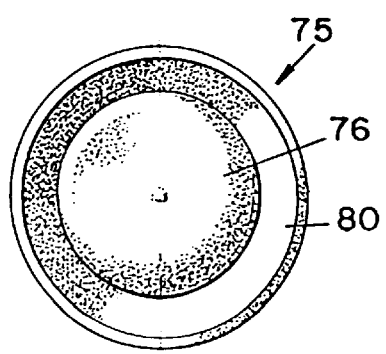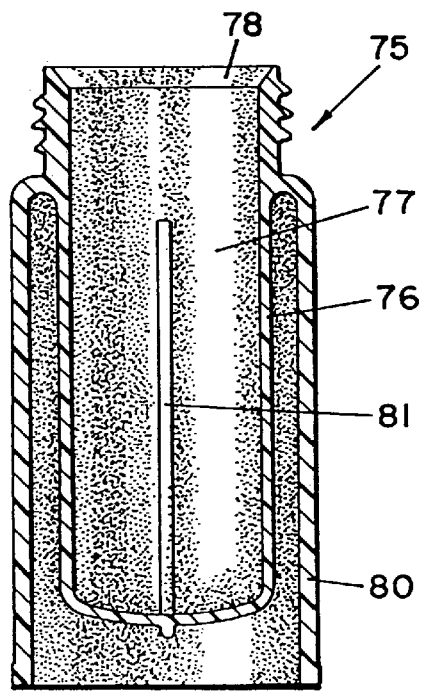
Fig. 17
Fig. 20
Fig. 16
Fig. 18
Fig. 19

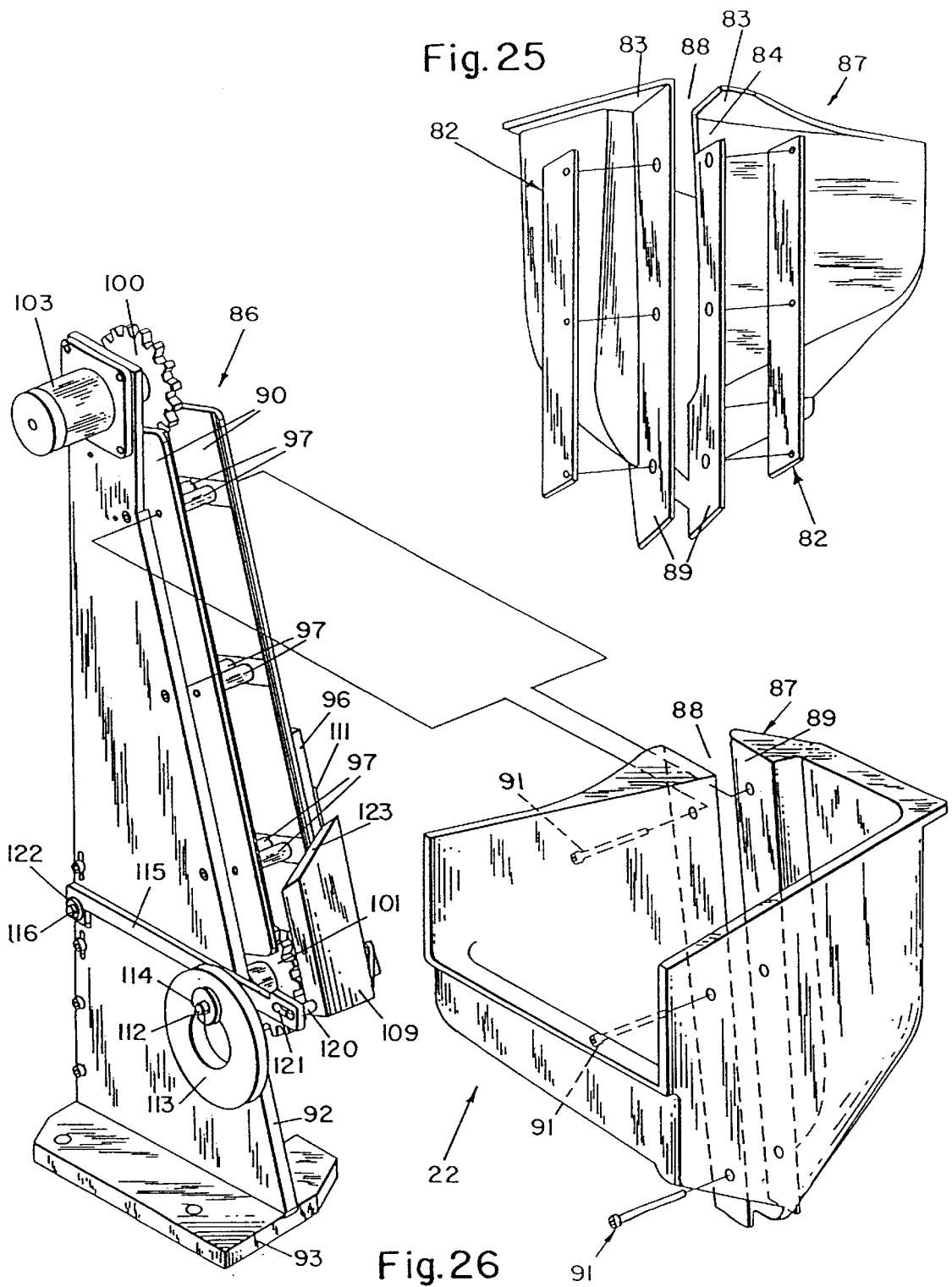

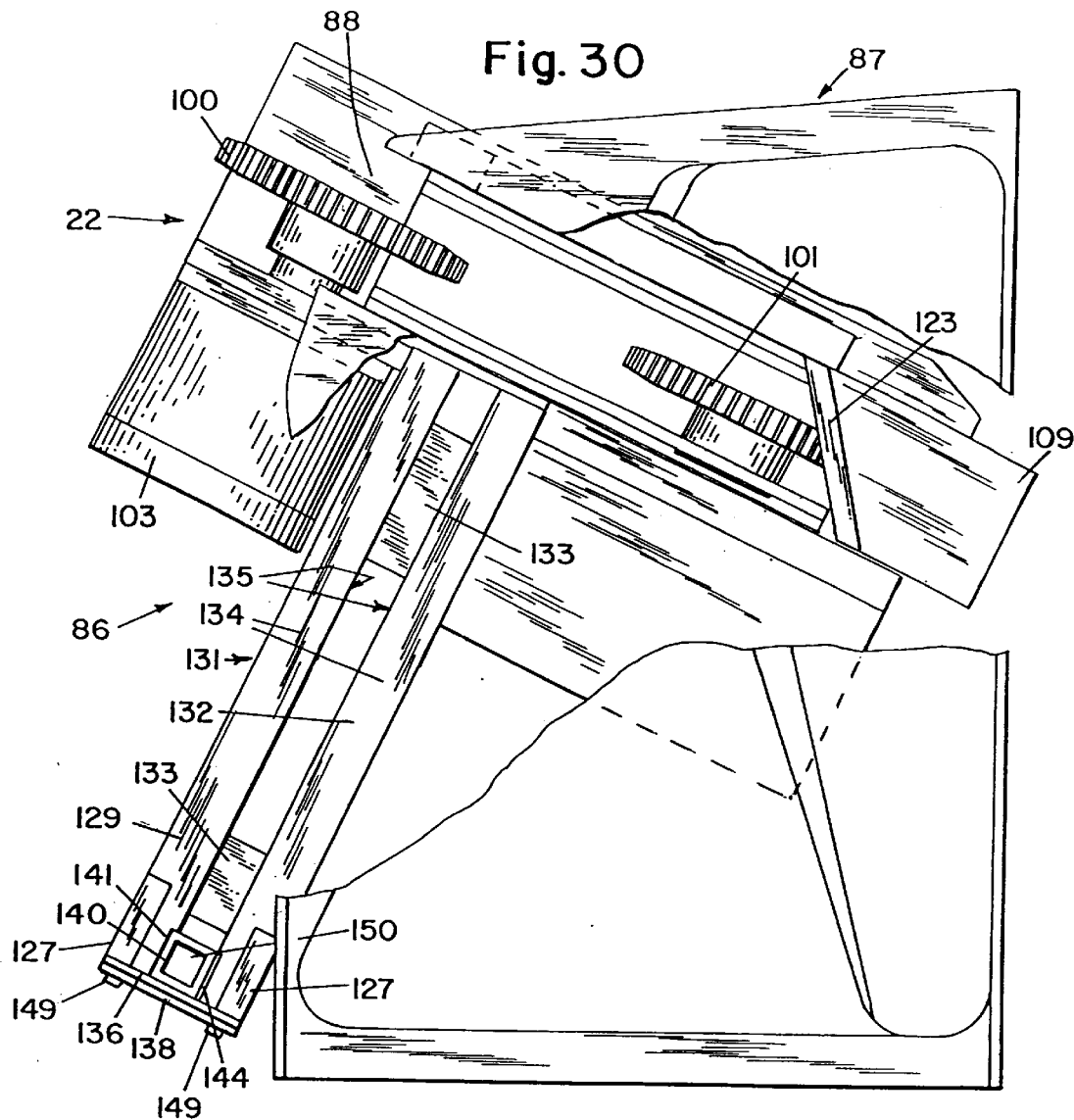
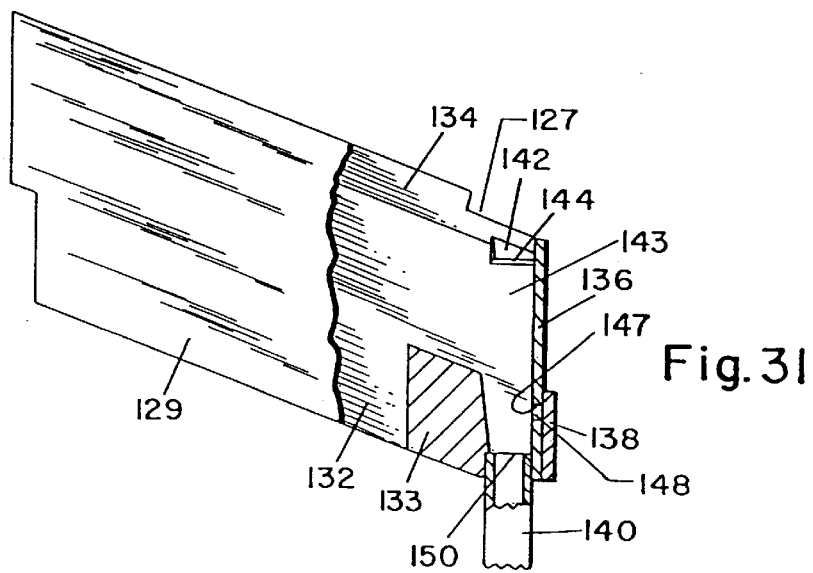

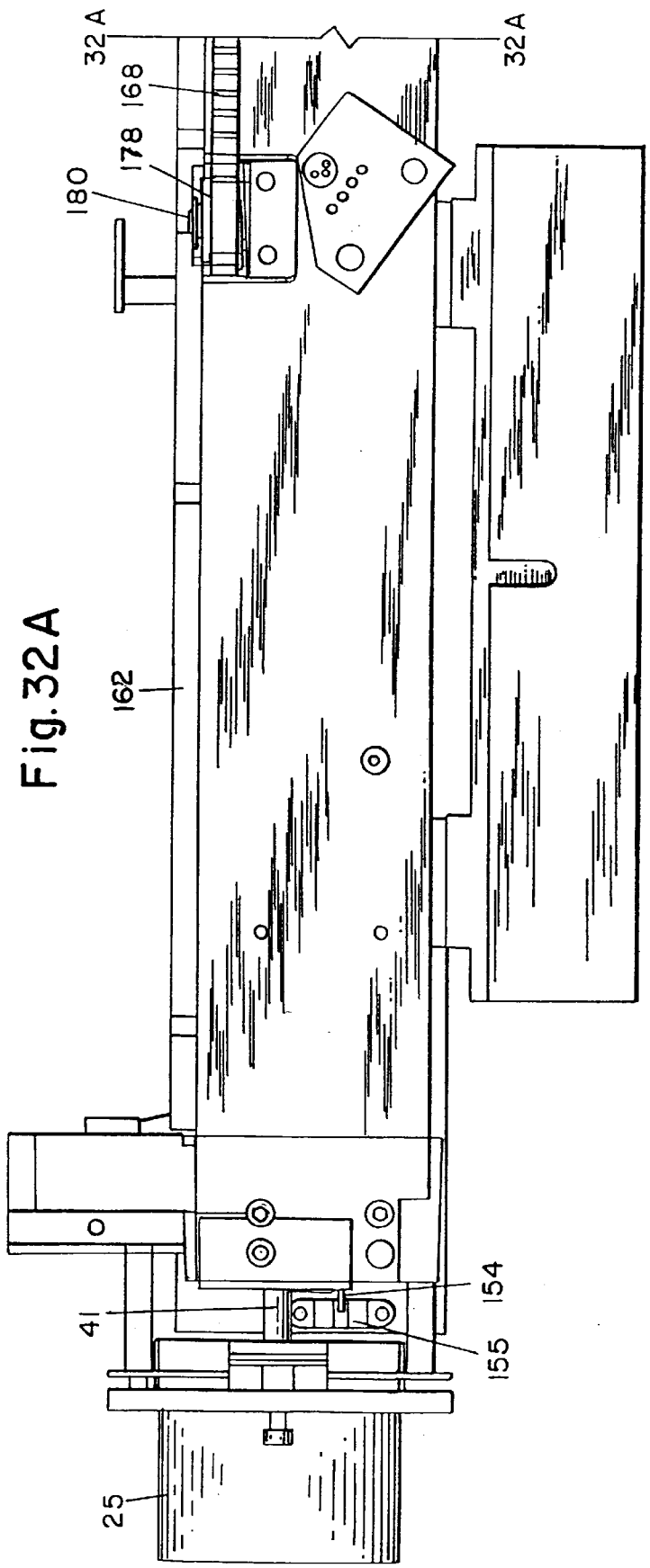

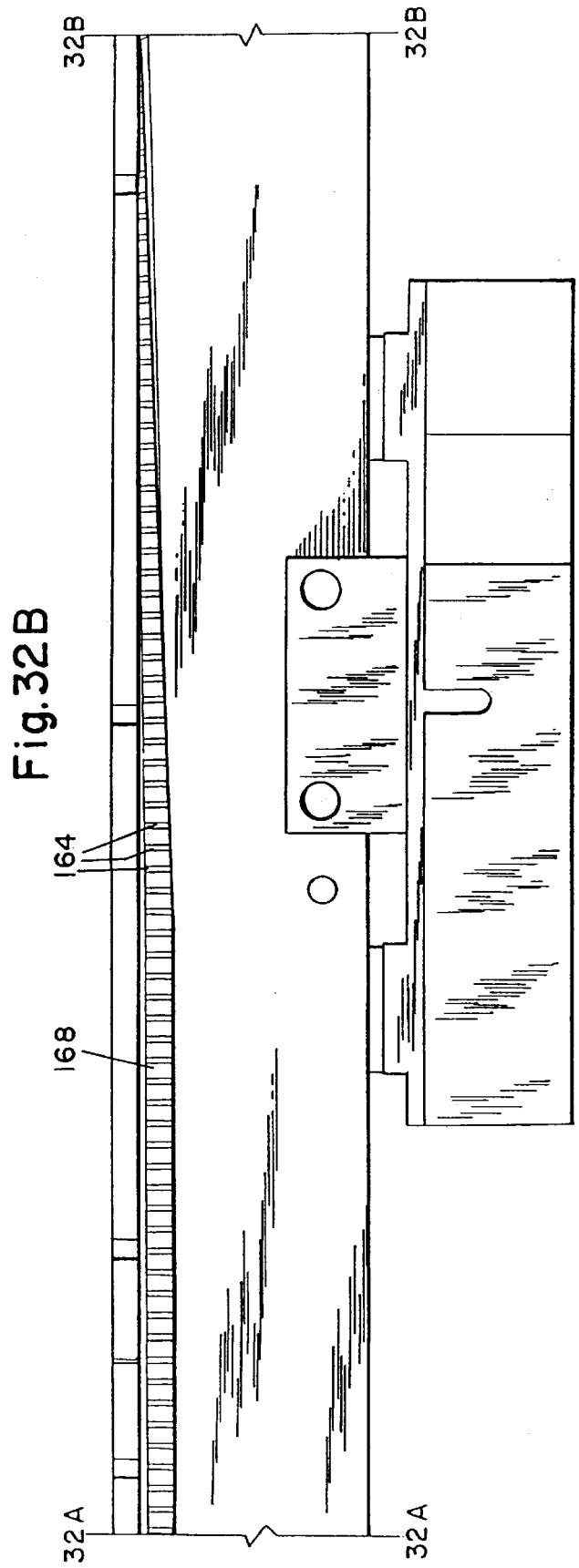

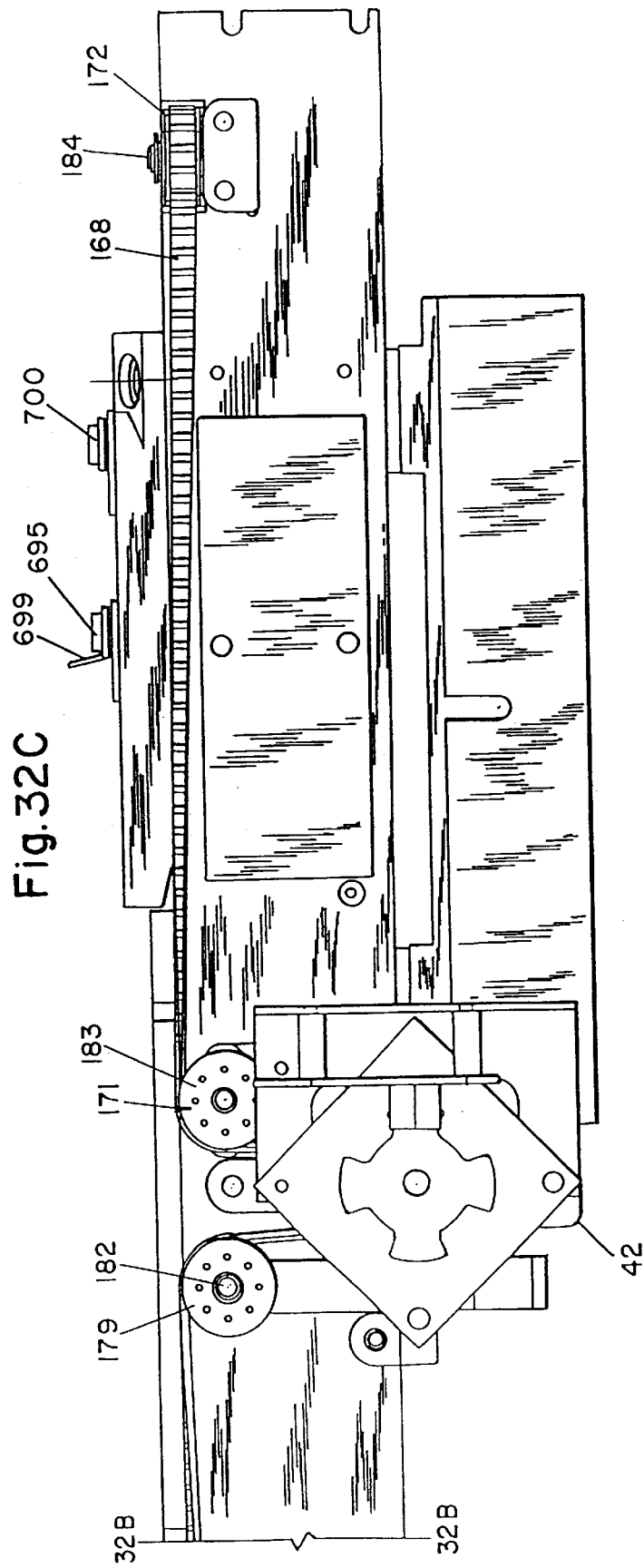

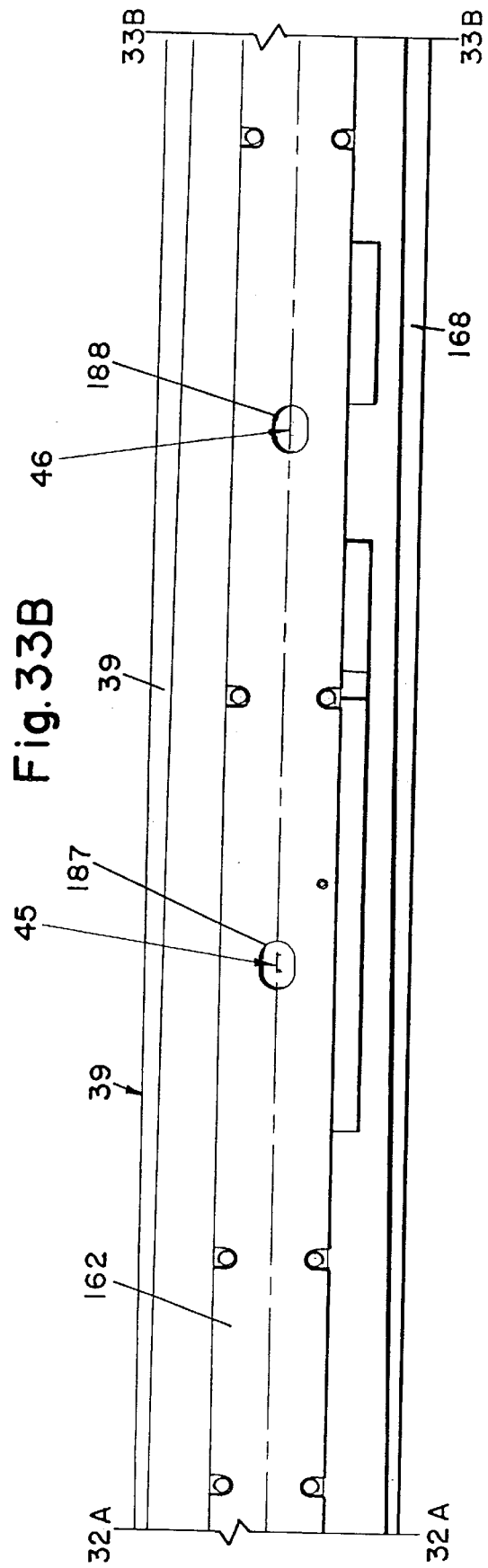

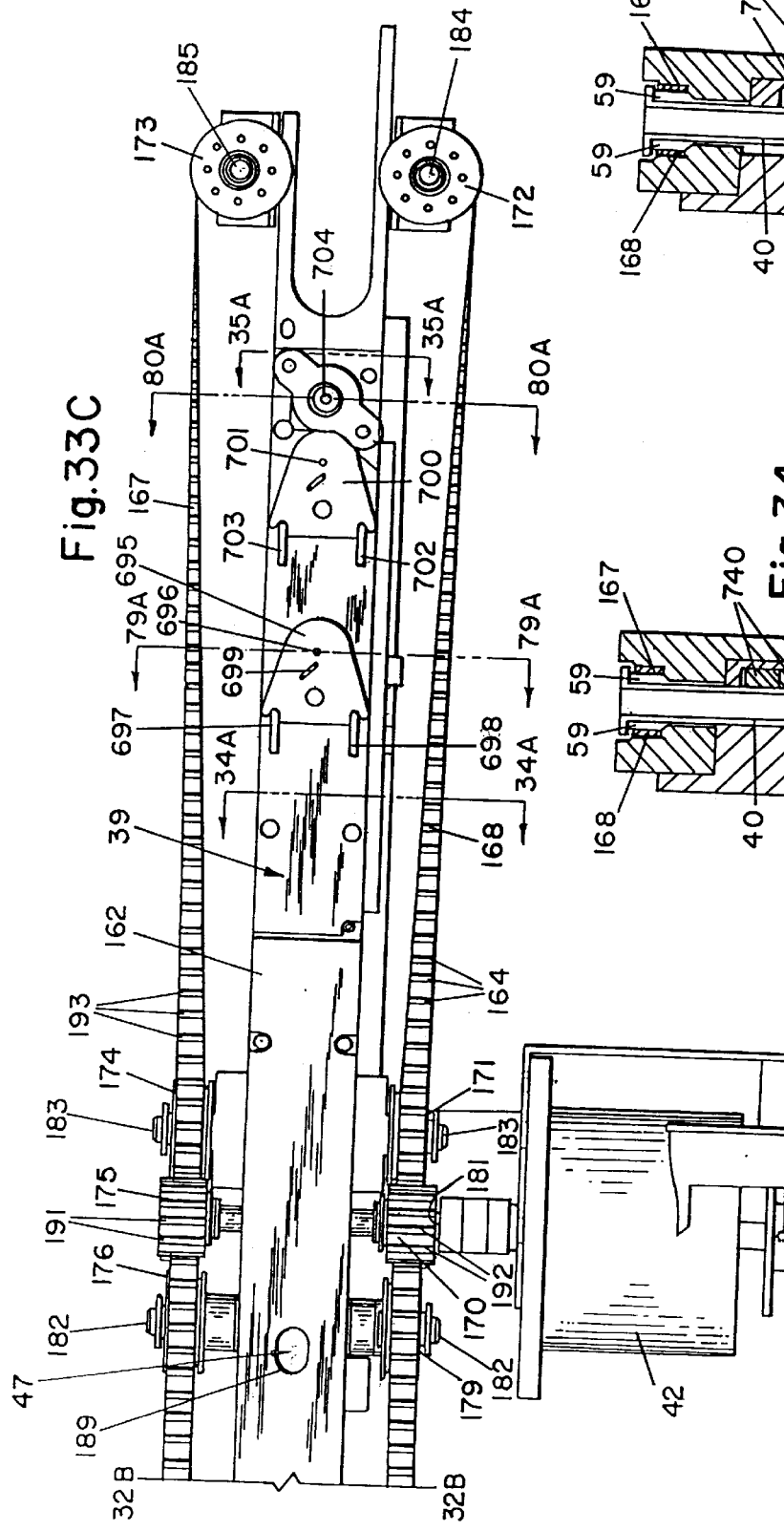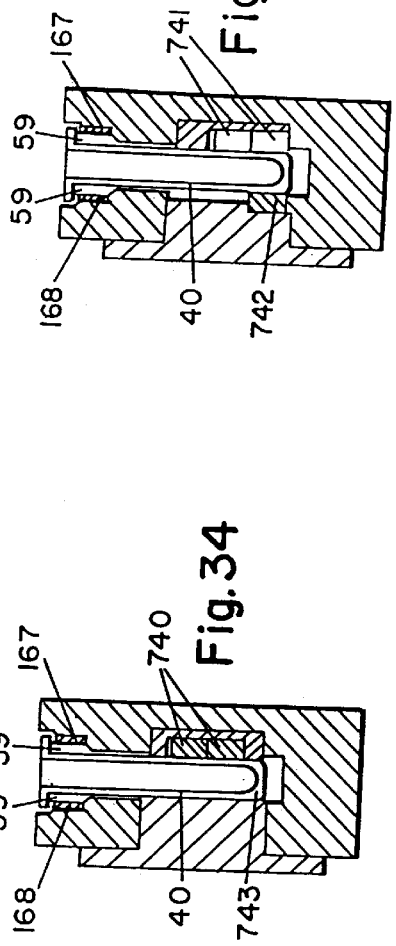

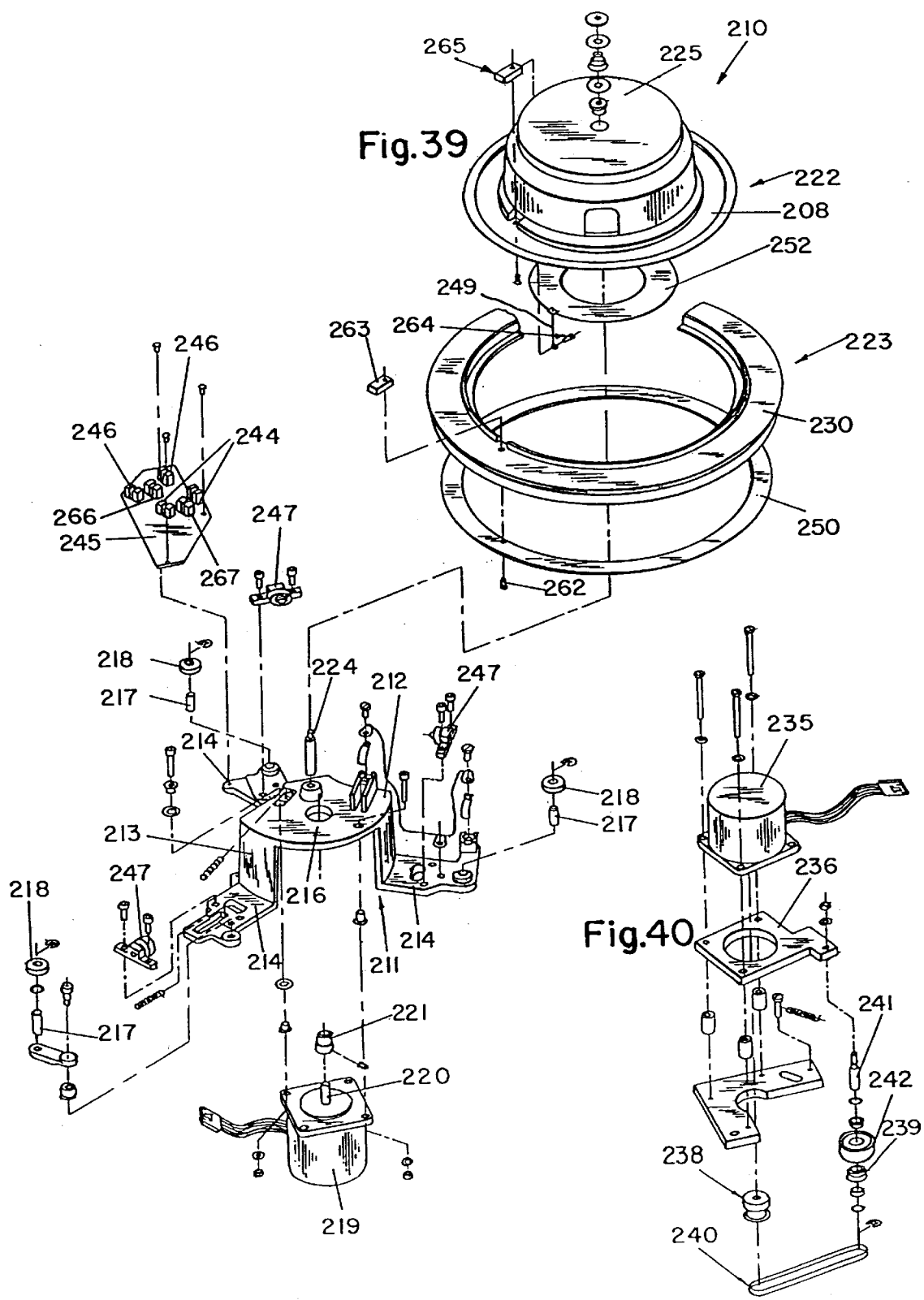

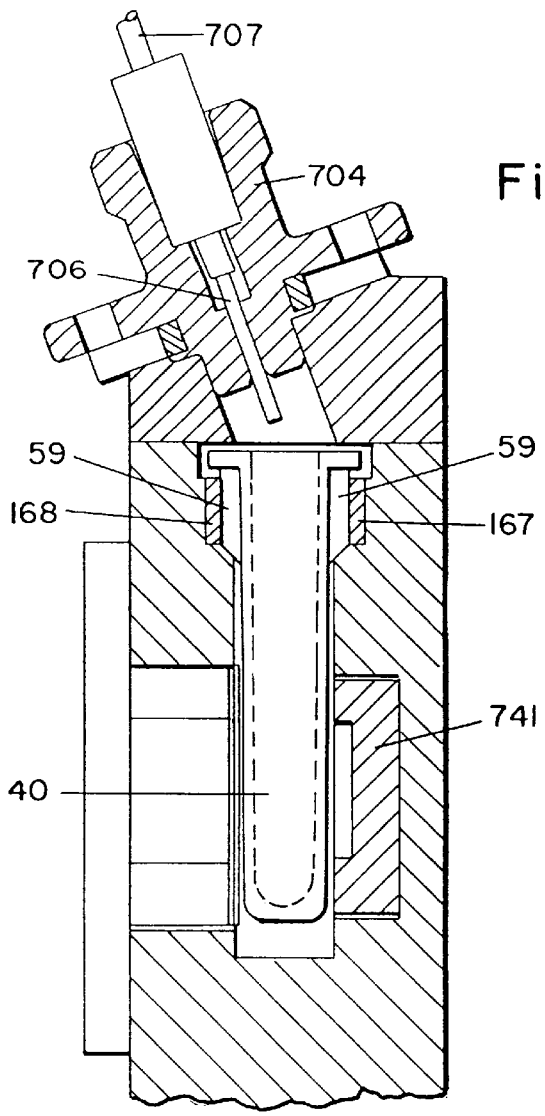
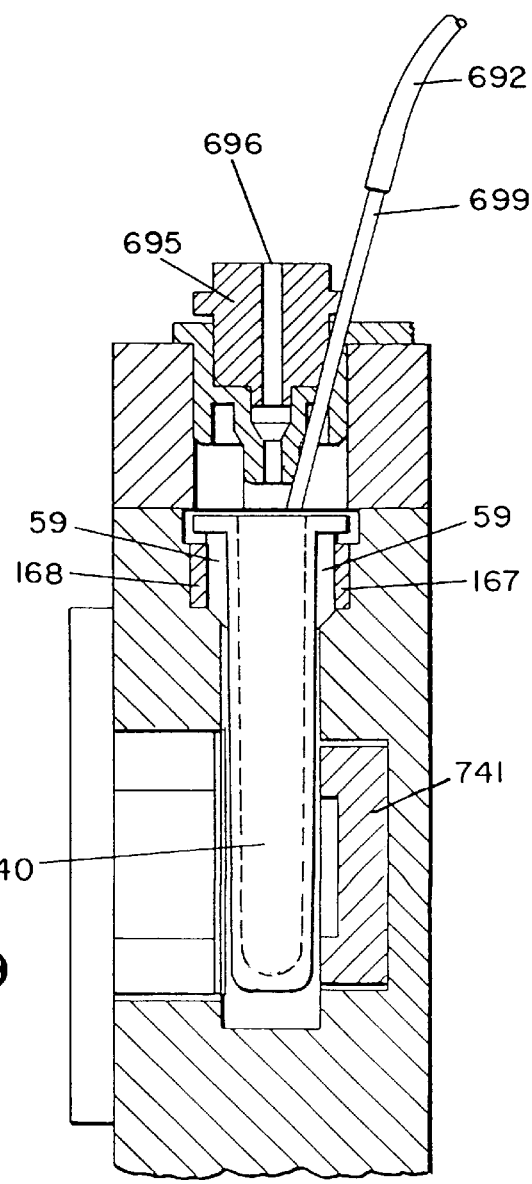
Fig. 80
Fig. 79

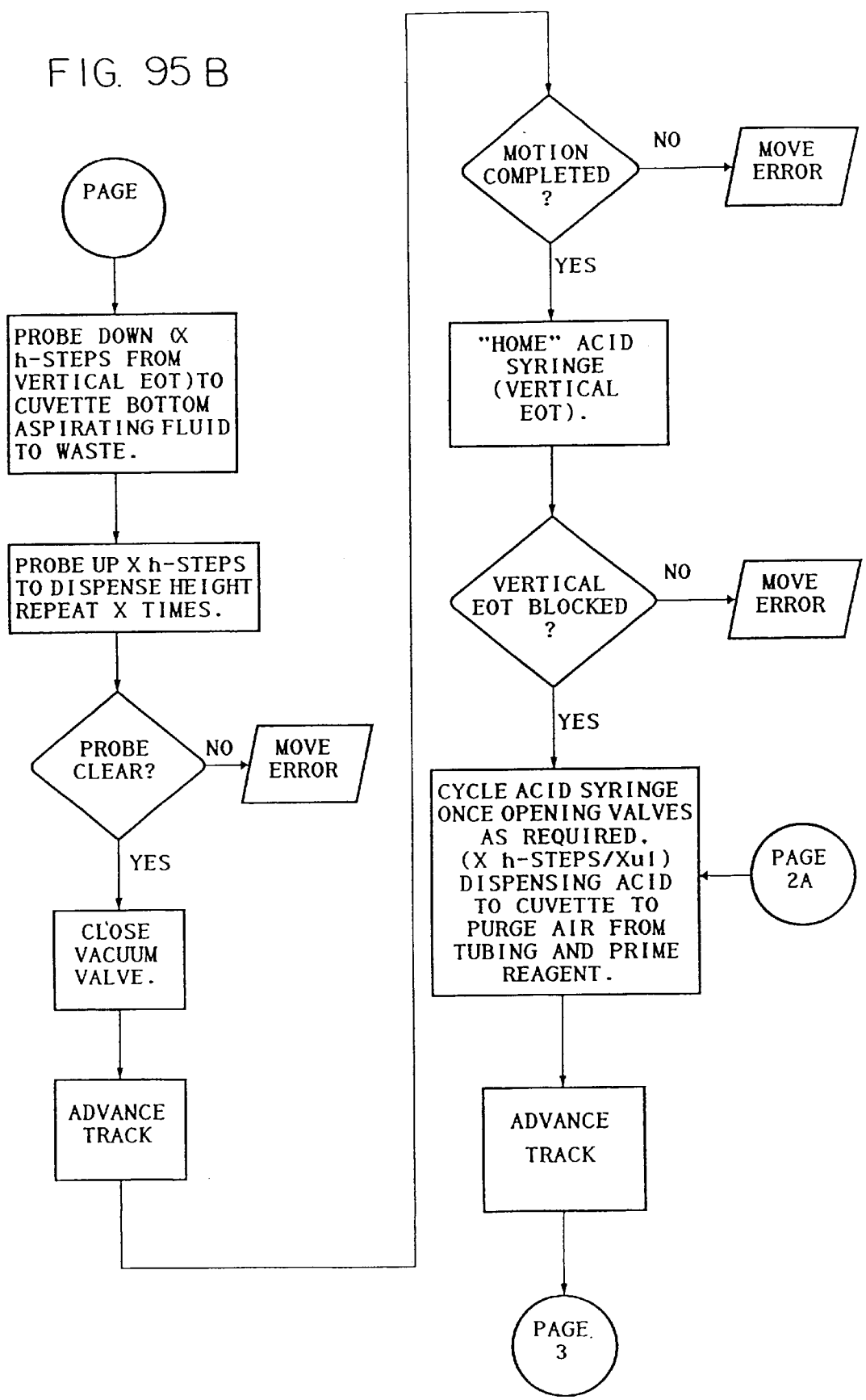

NOTE: CUVETTE IN LUMINOMETER IS ADVANCED TO PMT/BASE INJECTION POSITION FOR PRIMING THE BASE REAGENT LINES.

REAGENT CONTAINER FOR AUTOMATED ANALYZER

This is a divisional of copending application Ser. No. 08/222,559 filed on Apr. 1, 1994, which is a continuation of Ser. No. 07/665,196 filed Mar. 4, 1991, abandoned.

BACKGROUND OF THE INVENTION

The present invention is generally directed to an automated analyzer for conducting binding assays of various liquids, in particular biological fluids for substances contained therein.

The present invention is particularly directed to a machine for performing automated immunoassay testing, in particular heterogeneous immunoassays in which paramagnetic particles are the solid phase reagent and the labeled reagent (tracer reagent) includes a chemiluminescent label. The system can accommodate both. competitive and sandwich-type assay configurations. A chemiluminescent flash is initiated and its intensity measured as an indication of the presence or absence of an analyte in the test fluid which is being assayed. The analyzer can be selectively run in batch-mode or random access sequence.

Over the last several years, automated instrumentation has been developed for route testing in the clinical laboratory. Limited automation has been applied to the area of immunoassay testing. Although some instruments have been developed for limited immunoassay testing, many of the procedures are still performed manually. Test results are very often delayed because of the time factor and labor intensity for many of the manual steps, and long incubation or reaction times. These delays can be critical in many clinical situations. In addition, the manual procedures cause variations in test results and are quite costly. The causes of such variations include nonuniform testing protocols, technician experience skills and the precision of the apparatus/analyzer. These and other difficulties experienced with the prior art analyzer and manual testing systems have been obviated by the present invention.

It is, therefore a principal object of the invention to provide an automated analyzer for diagnostic immunoassay testing which is particularly applicable to heterogeneous immunoassay testing.

Another object of this invention is the provision of an analyzer which has a high degree of versatility, capable of performing a wide range of binding assay protocols for a wide range of clinical and non-clinical analytes.

A further object of the present invention is the provision of an automatic analyzer which is capable of handling a plurality of test protocols simultaneously, continuously and sequentially.

It is another object of the present invention to provide an automated analyzer which is capable of high sample throughput A still further object of the invention is the provision of an automated analyzer which greatly reduces the amount of time per assay or sample test It is a further object of the invention to provide an automated analyzer which provides consistent and reliable assay readings.

It is a further object of the invention to provide an automated analyzer which is self-contained and requires a minimal amount of space for complete sample processing.

A further object of the invention is to provide a constant luminescent light source for automatic monitoring of the luminometer calibration of an assay apparatus.

It is still a further object of the invention to provide an automated analyzer which can be selectively run in a bath-mode or random access sequence.

With these and other objects in view, as will be apparent to those skilled in the art, the invention resides in the combination of parts set forth in the specification and covered by the claims appended hereto.

SUMMARY OF THE INVENTION

In general, the automated analyzer of the present invention is a self-contained instrument which is adapted to be located on a suitable laboratory bench. It requires no external connections other than a standard power line and operates accurately within an ambient temperature range of 18° to 30° C. The functional units of the analyzer include a process track, a sample handling or transport system, a reagent handling or transport system, a separation and washing system, a detection system (luminometer) and data collection/processing system. The reagents and test samples are reacted in discreet, disposable cuvettes. The cuvettes are automatically and sequentially dispensed from a cuvette loader onto a linear process tract which moves each cuvette one cuvette space every twenty seconds. The temperature of the test reaction is controlled by a thermal system which preheats the cuvettes and reagents and maintains an environmental temperature of 37° C., plus or minus one degree, throughout incubation. Test samples are dispensed into the cuvettes by an aspirating and dispensing probe and reagents are added at so far are controlled intervals by means of three aspirating and dispensing reagent probes. The analyzer is particularly adapted for performing heterogeneous specific binding assays. The analyzer can be selectively ran in batch-mode or random access sequence.

BRIEF DESCRIPTION OF THE DRAWINGS

The character of the invention, however, may be best understood by reference to one of its structural forms, as illustrated by the accompanying drawings, in which:

FIG. 2 is a diagrammatic plan view showing the general organization of the subunits of the analyzer;

FIG. 3 is a diagrammatic plan view of a sequential series of cuvettes which are disposed on the preheater section and event conveyor;

FIG. 9 is a side elevational view of a container for holding reagent, specifically labeled reagent (tracer reagent);

Figure 20:
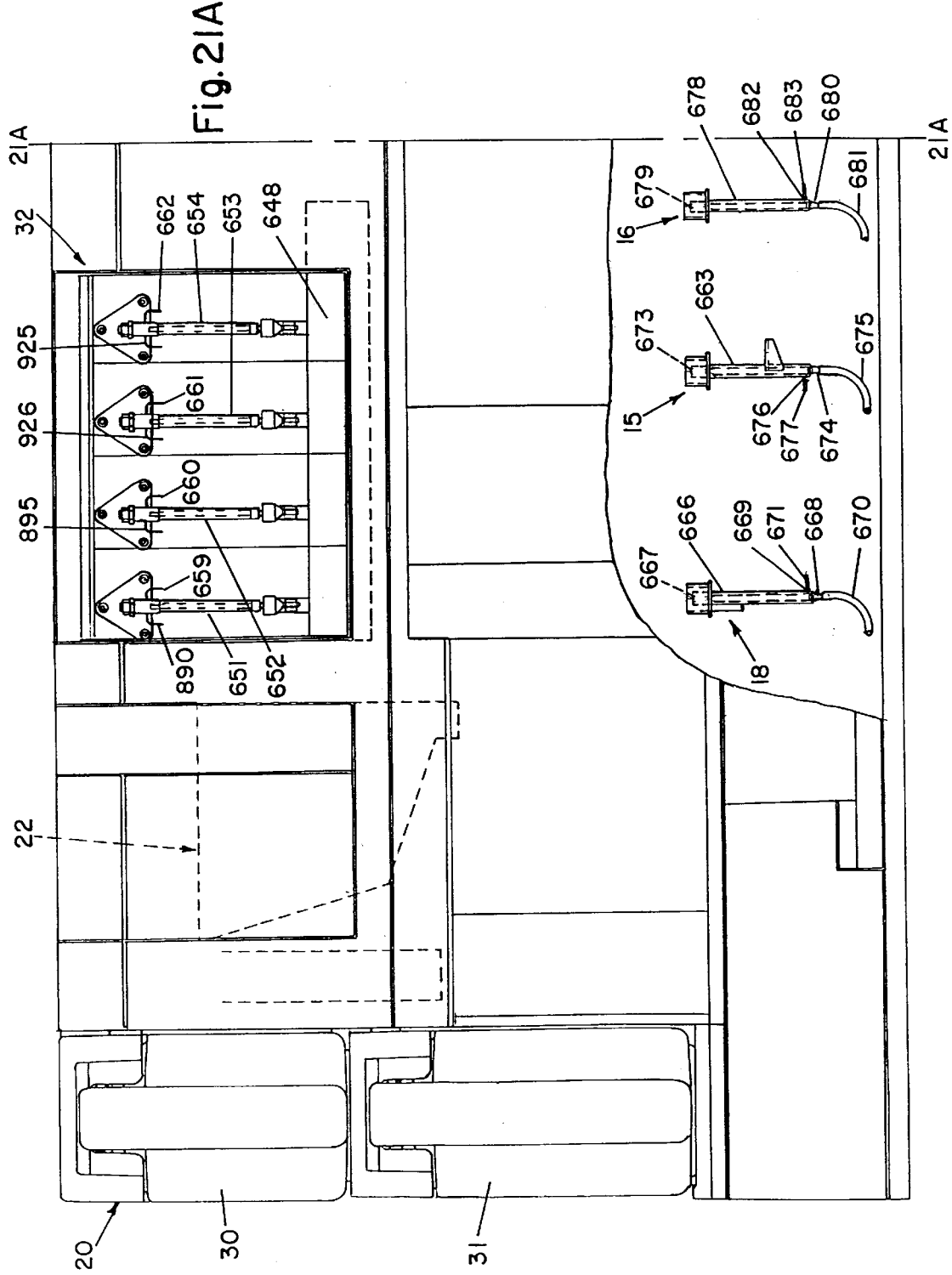
Figure 21:
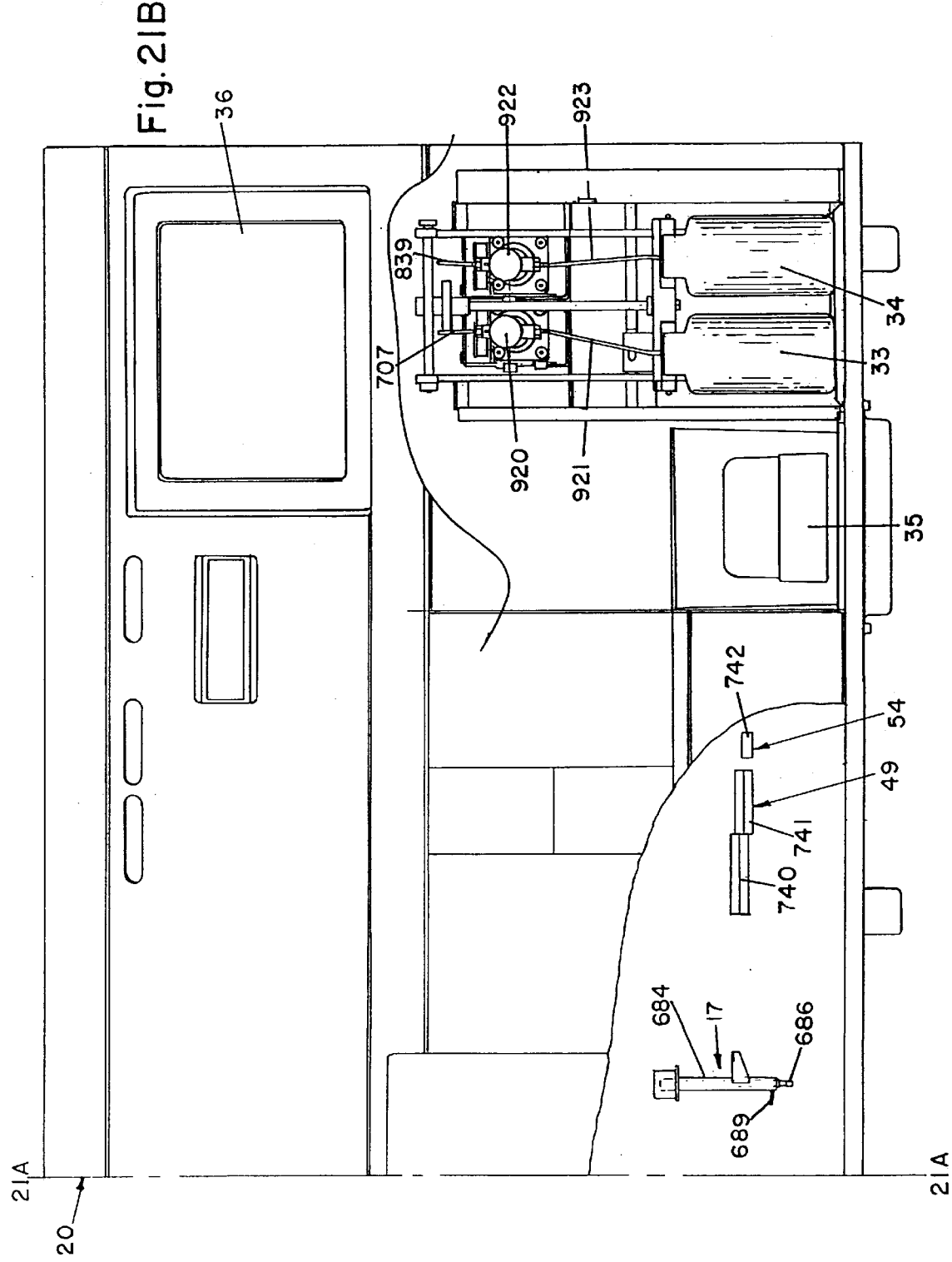
Figure 22:
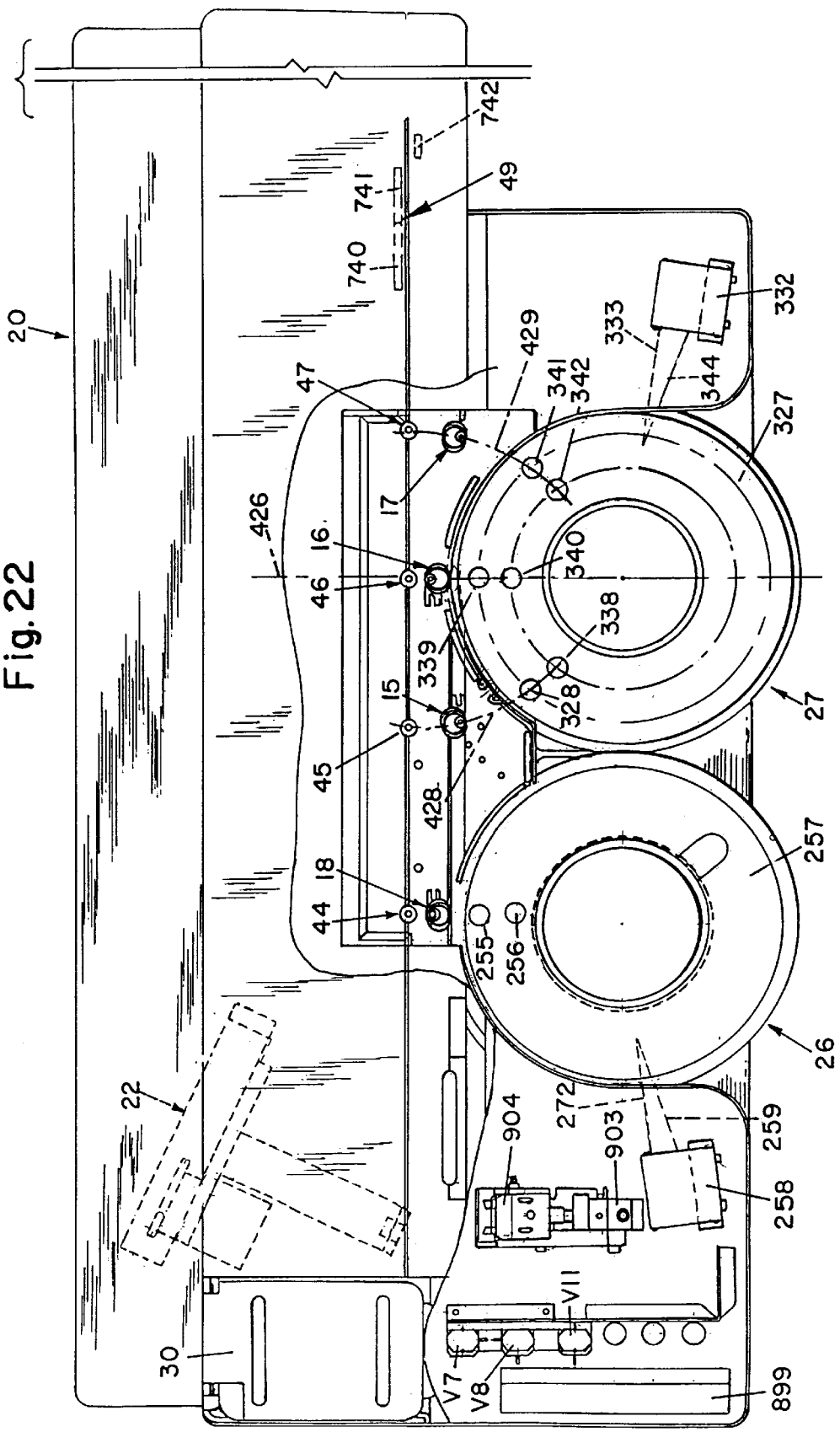
Figure 23:
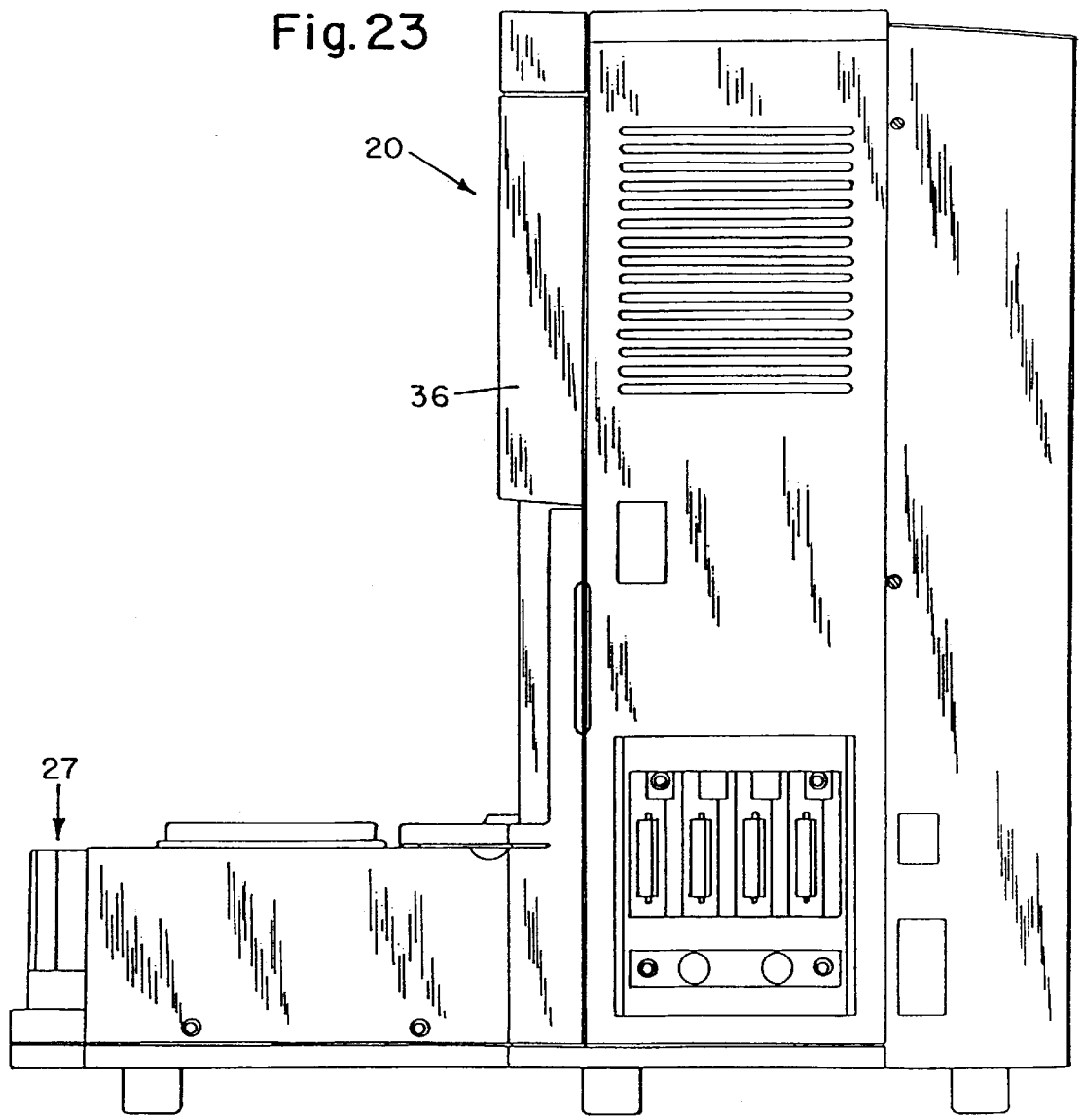
Figure 24:
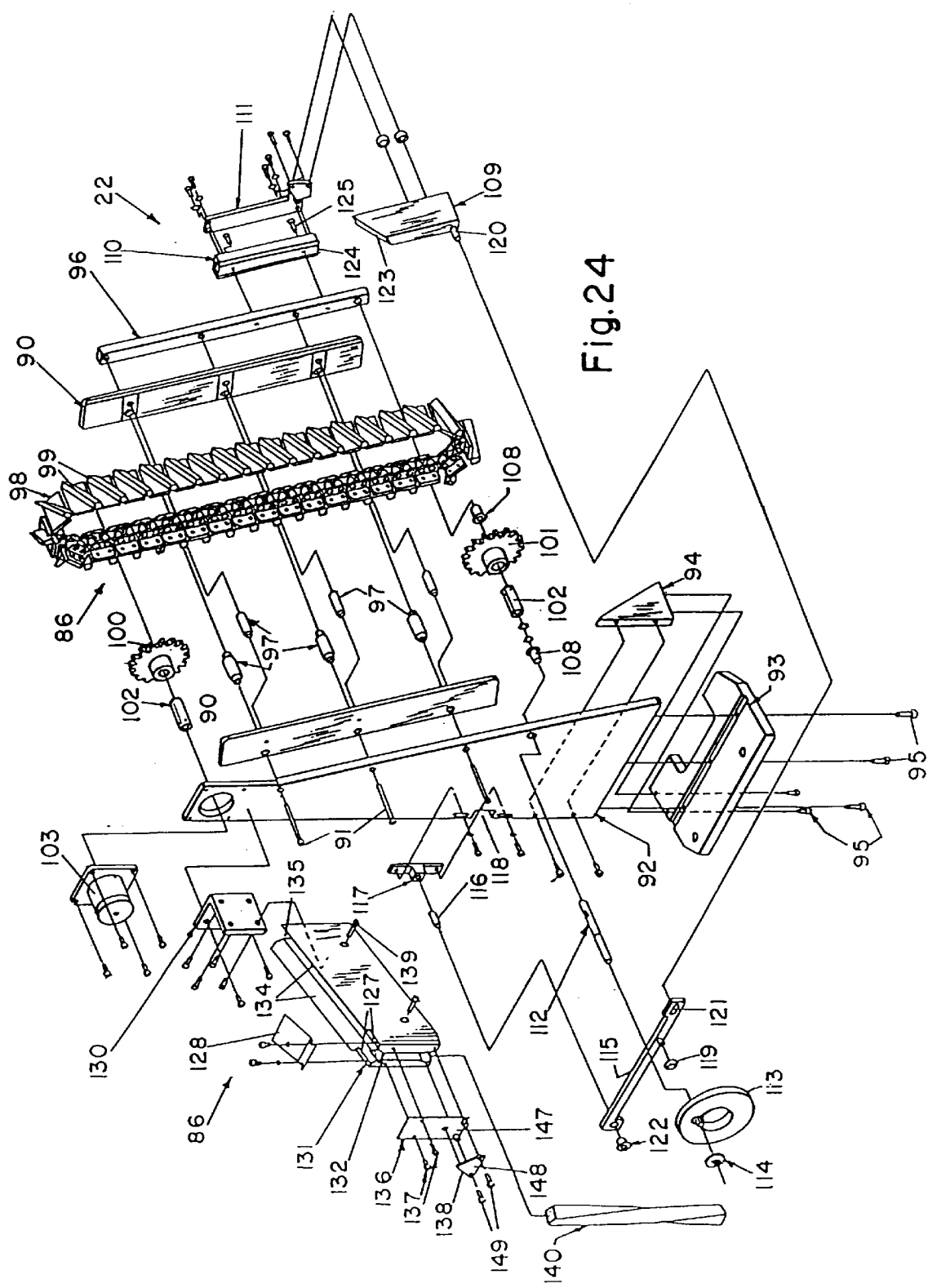
Figure 27:
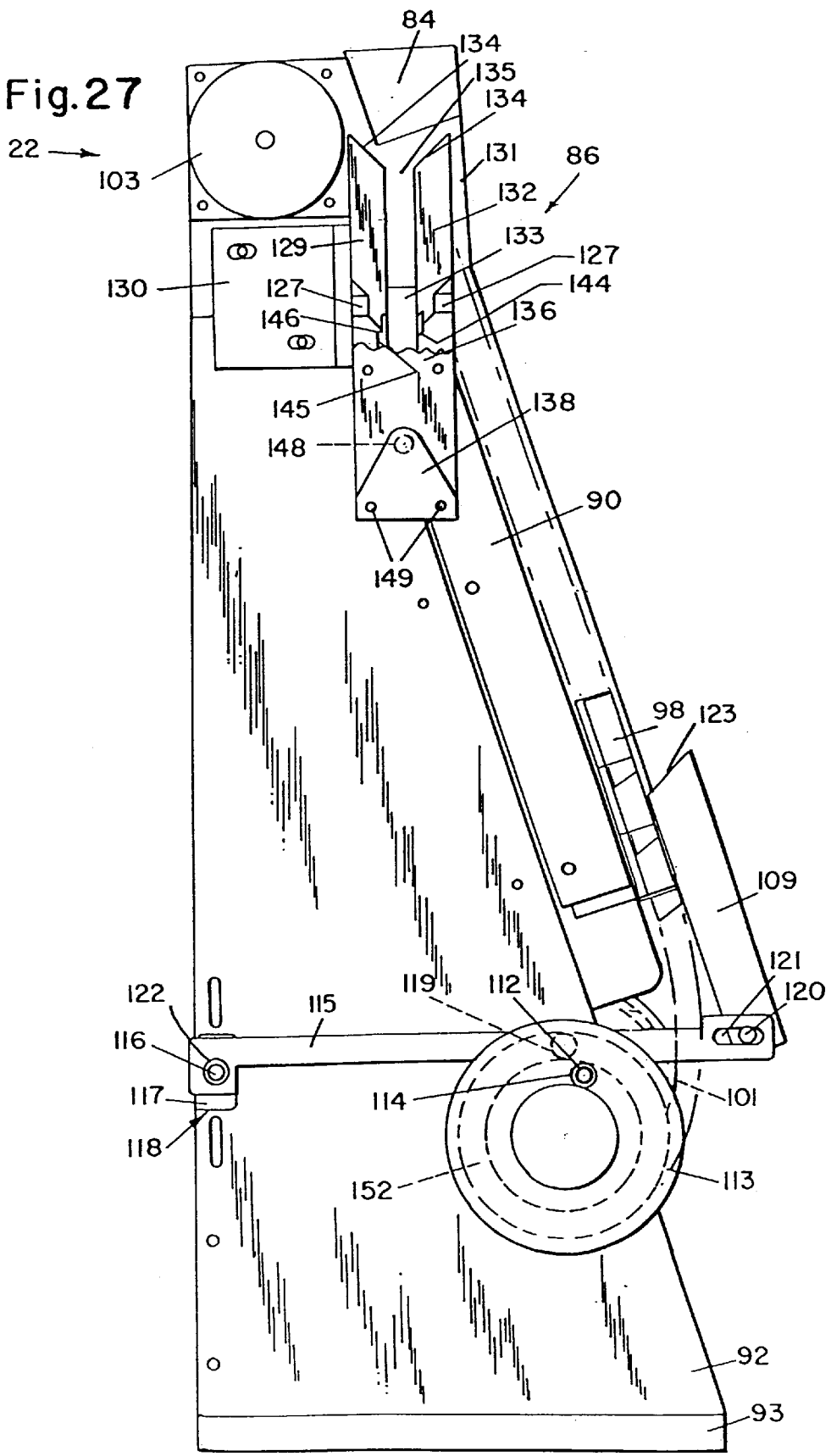
Figure 28:
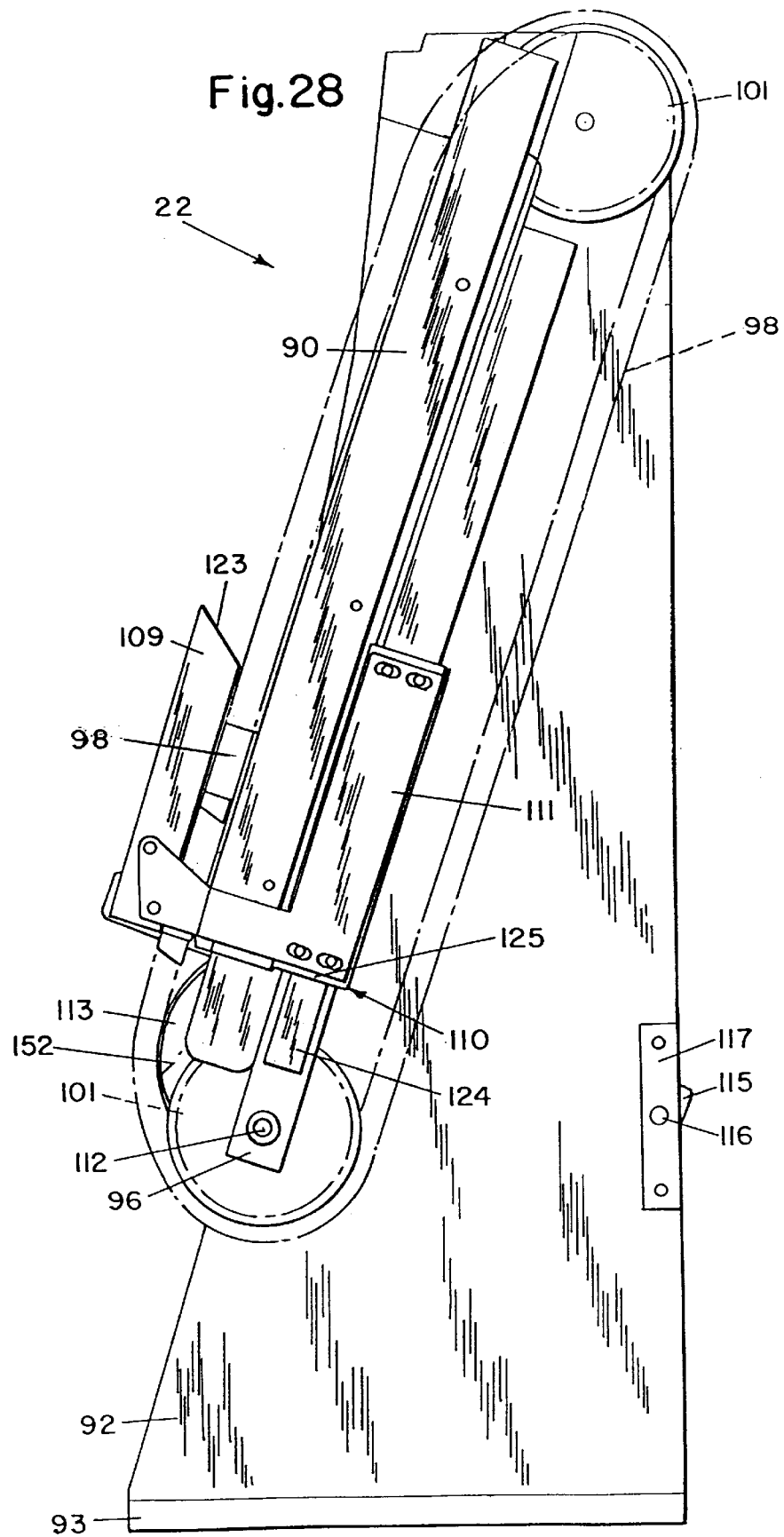
Figure 29:
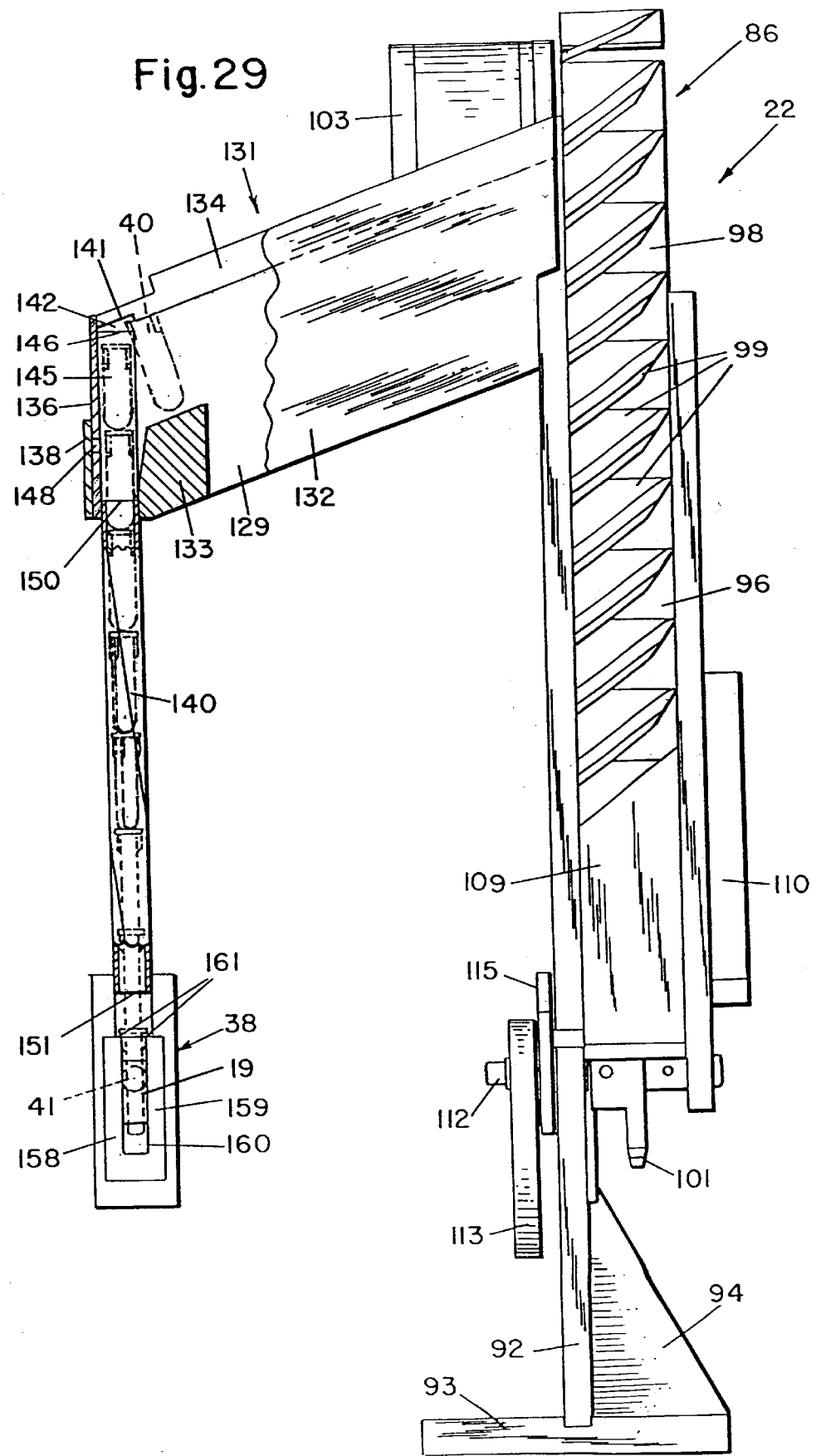
Figure 33A:
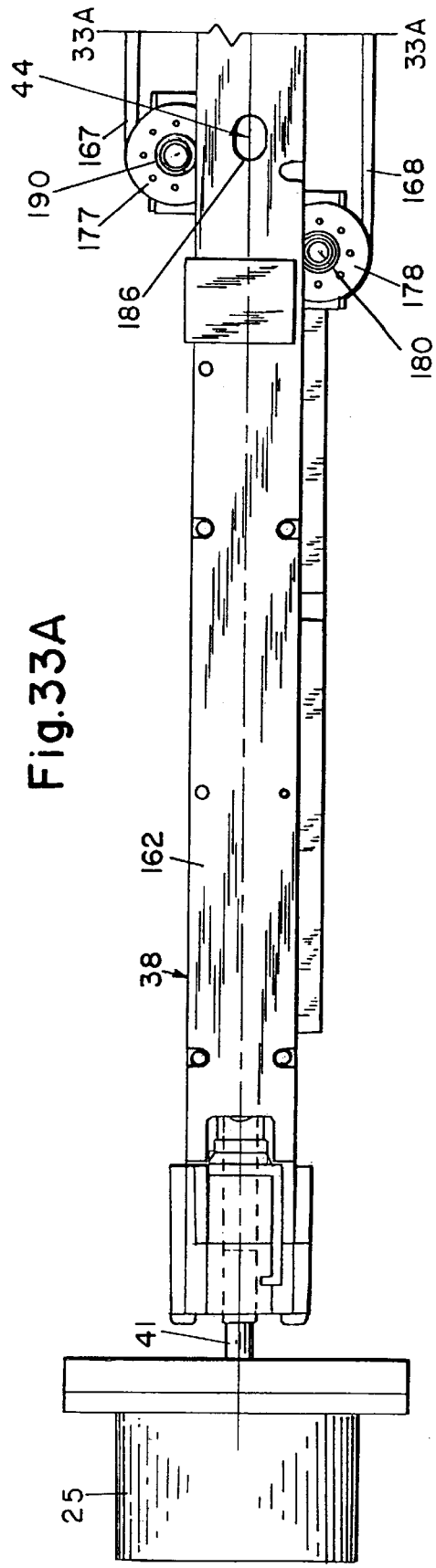
Figure 36:
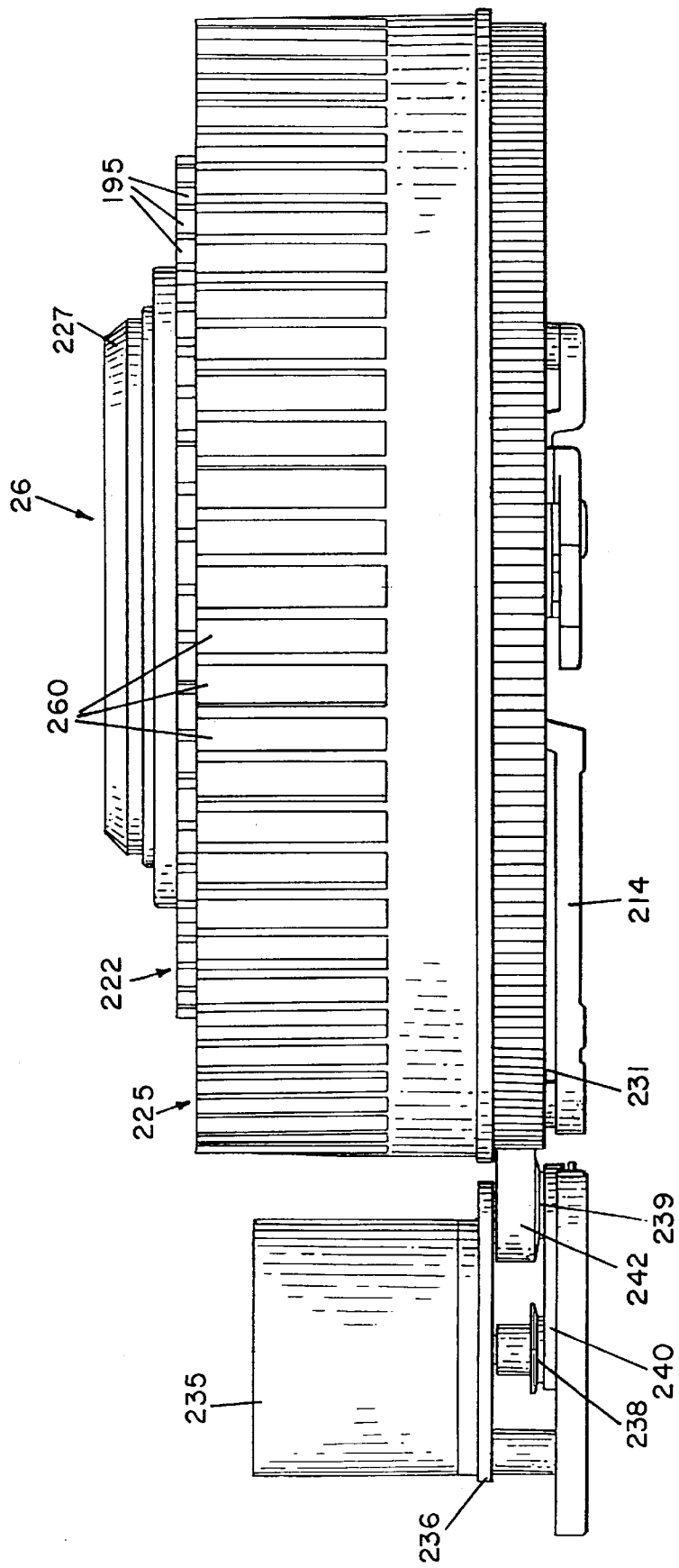
Figure 37:
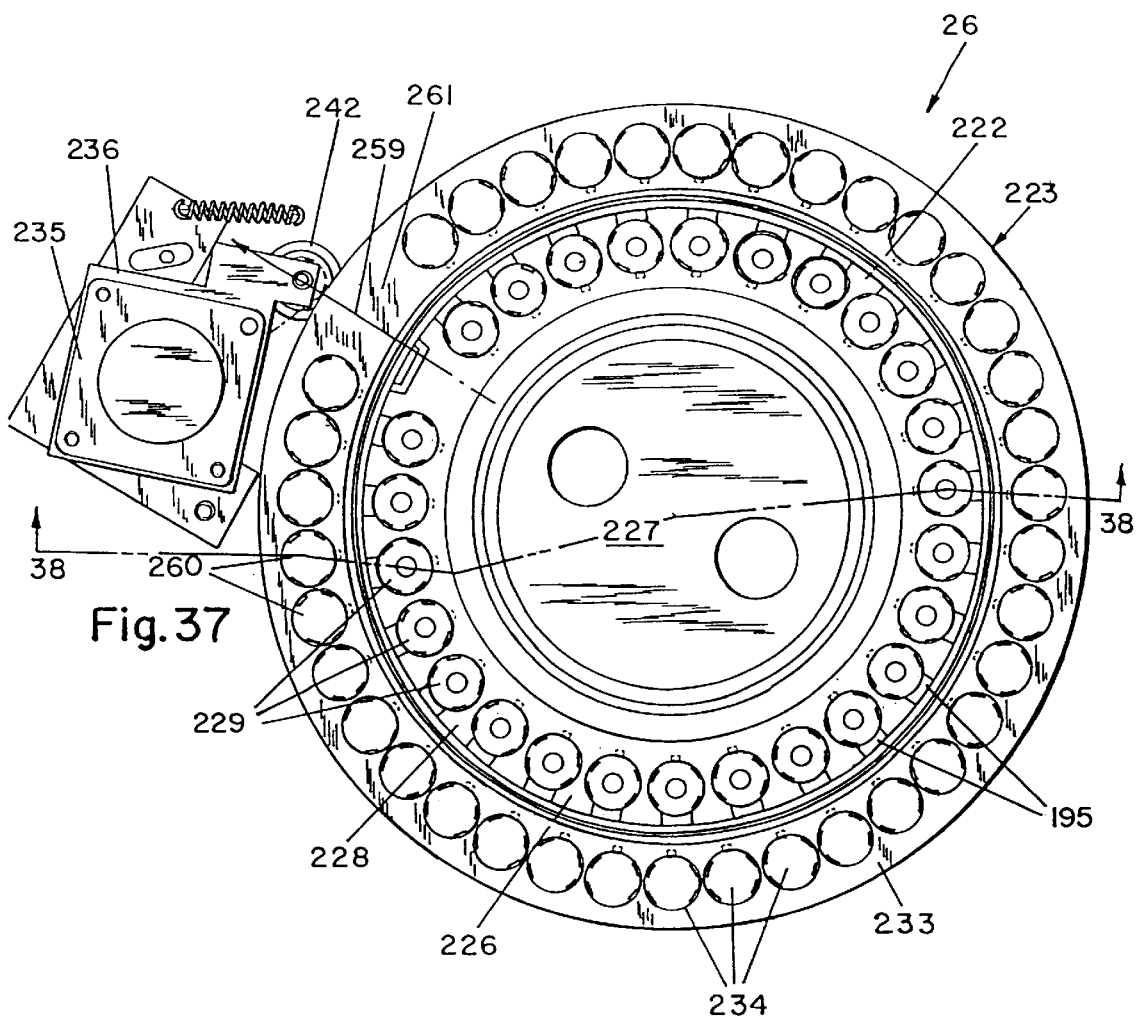
Figure 38:
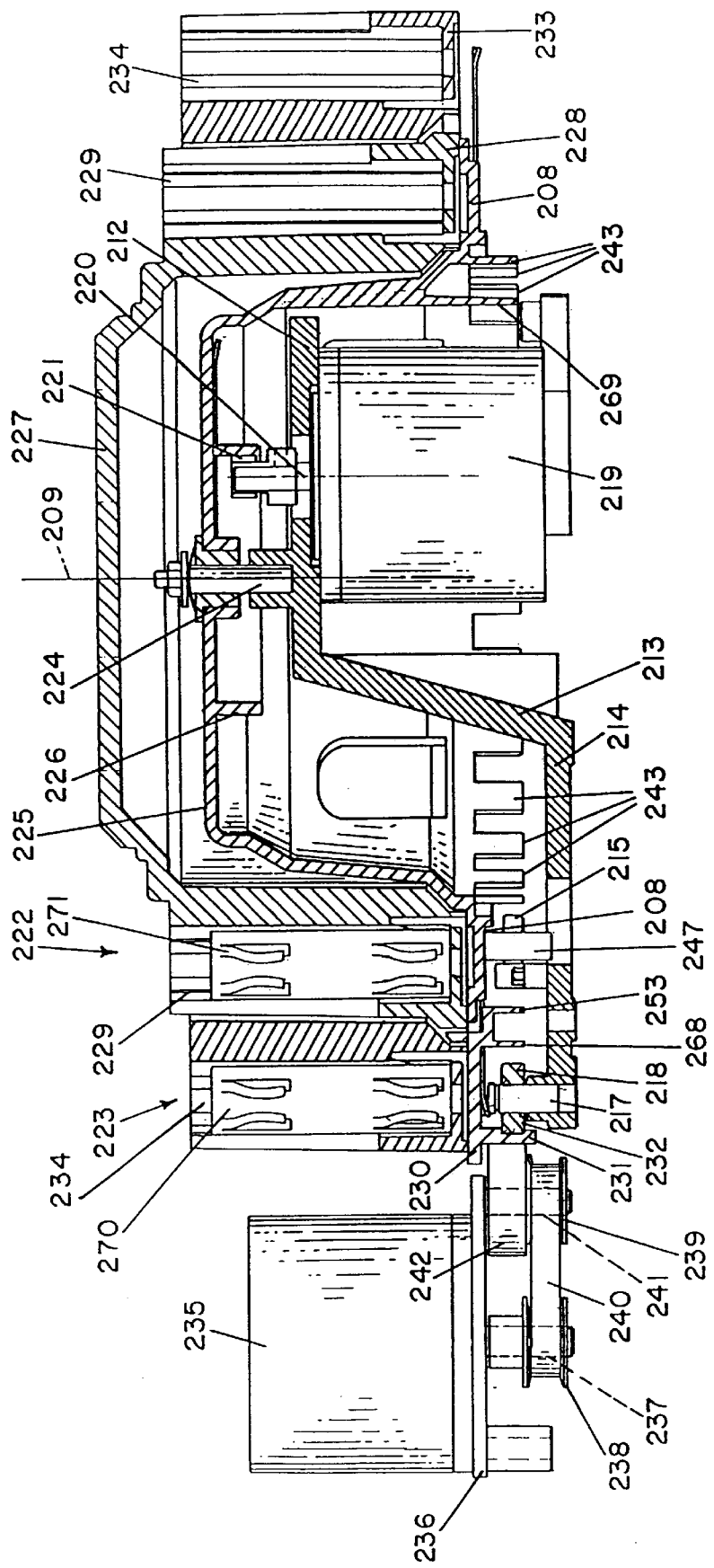
Figure 41:
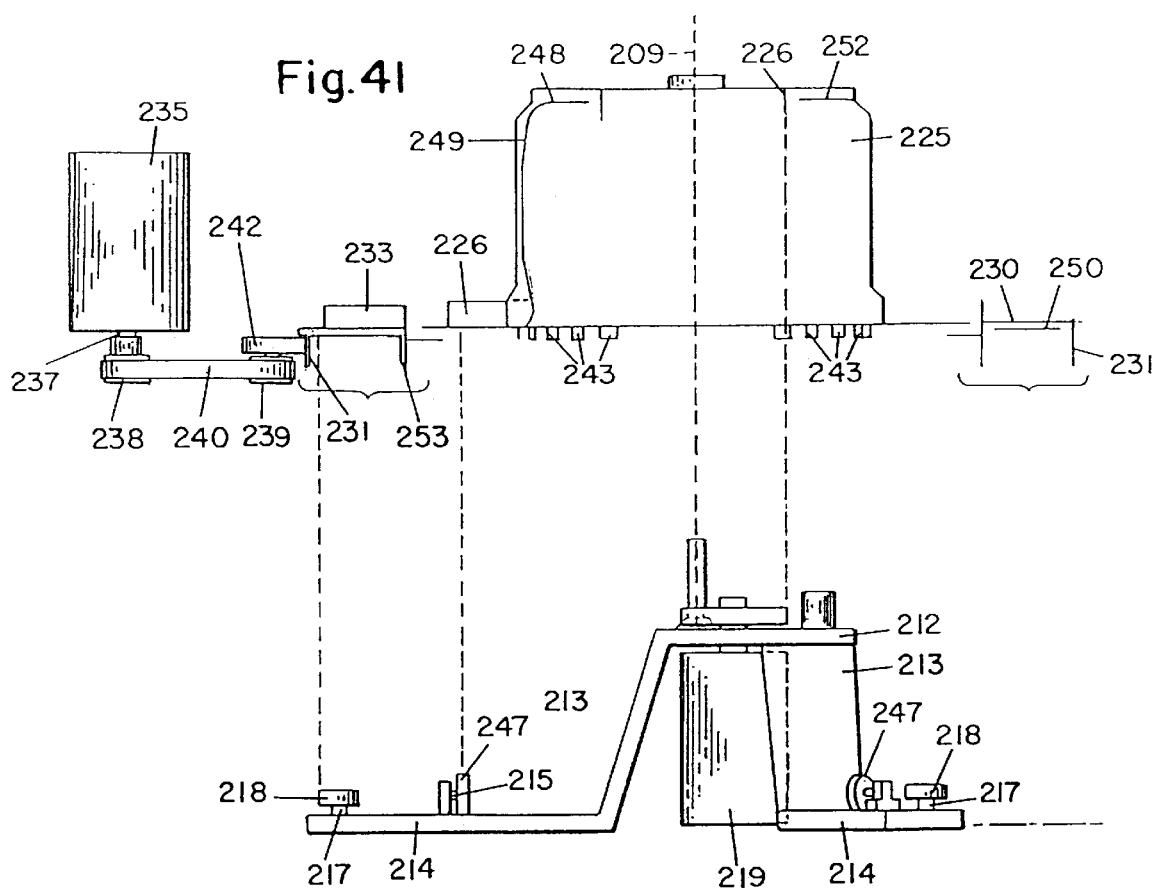
Figure 42:
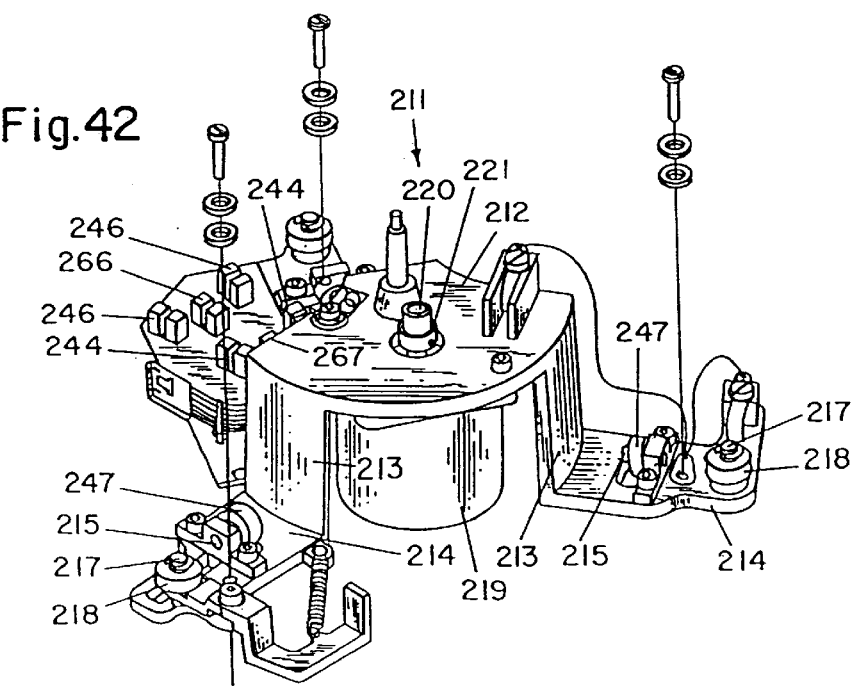
Figure 43:
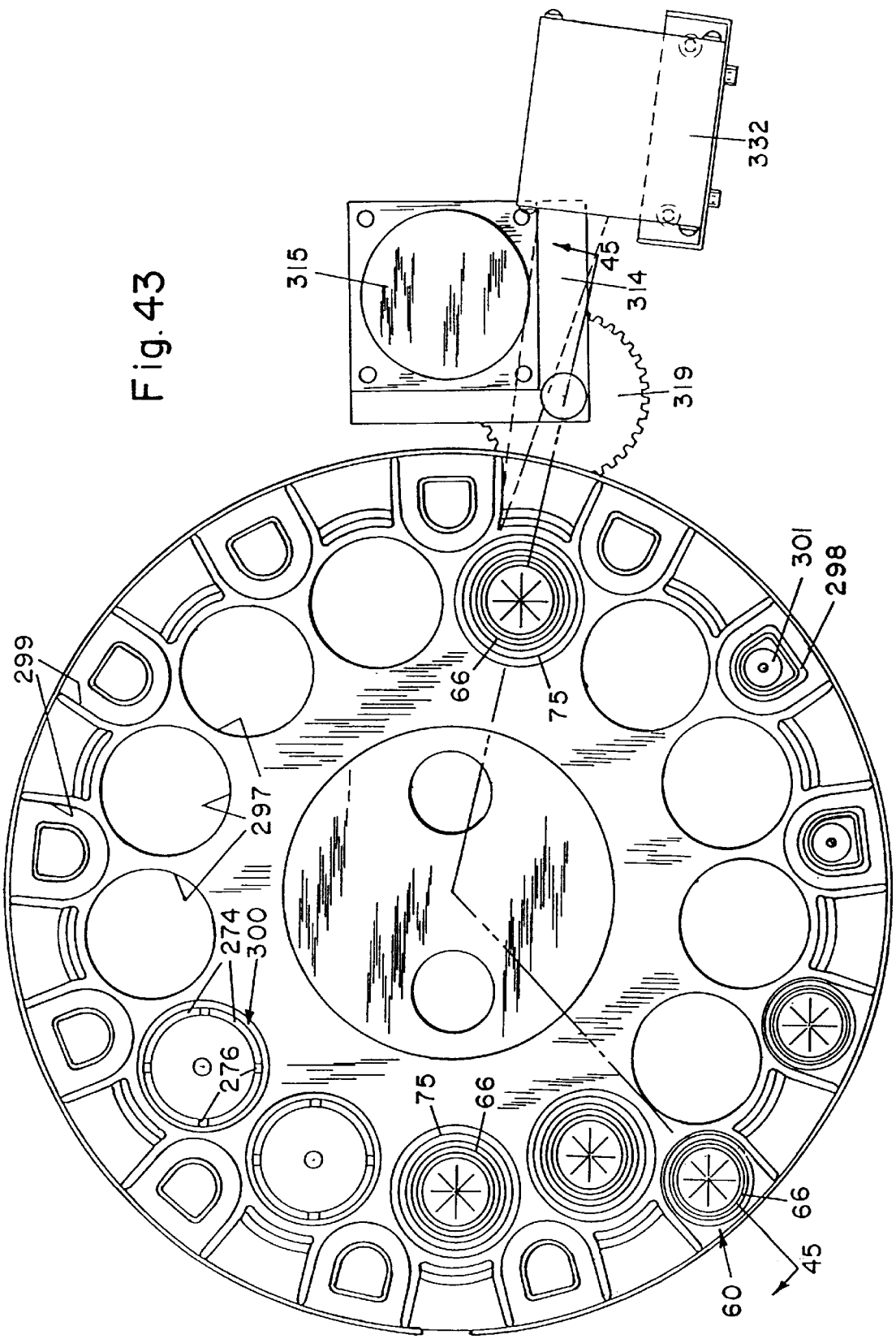
Figure 44:
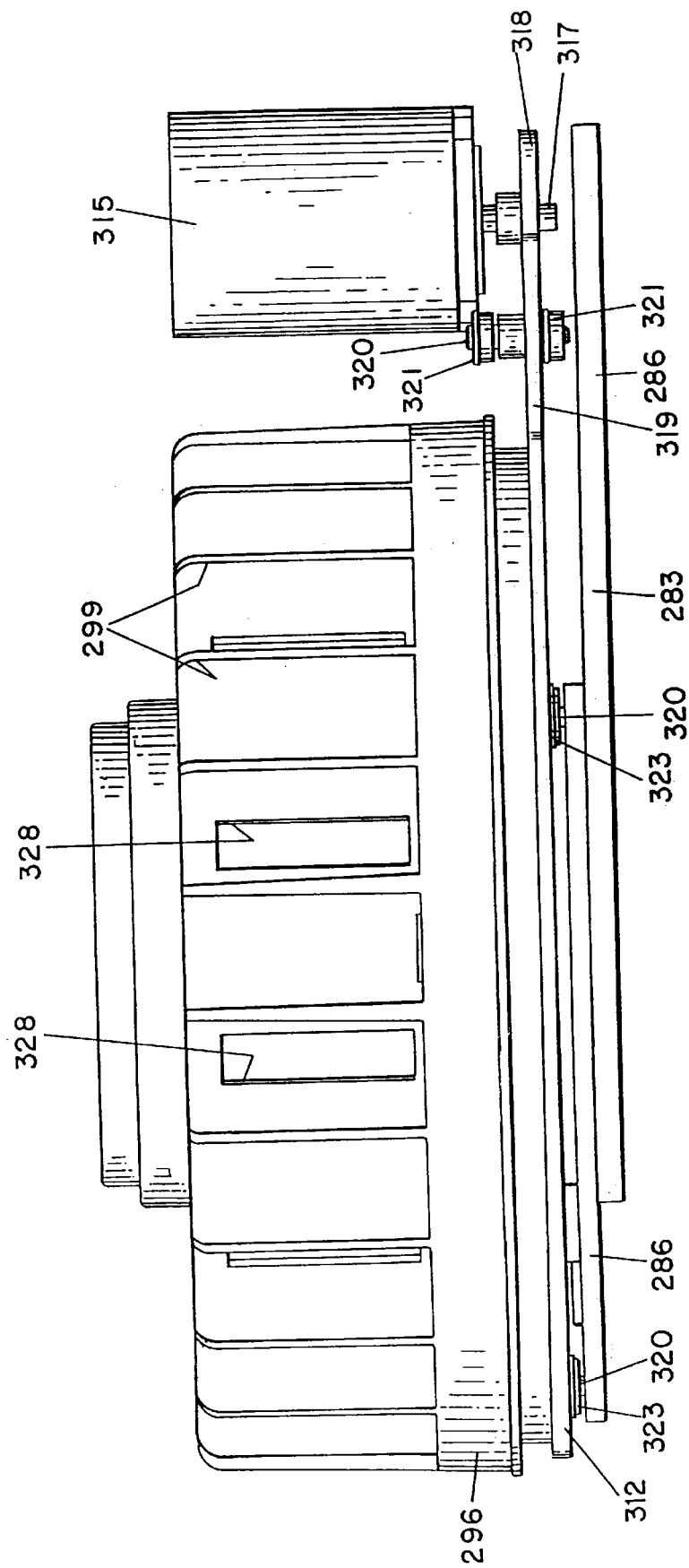
Figure 45:
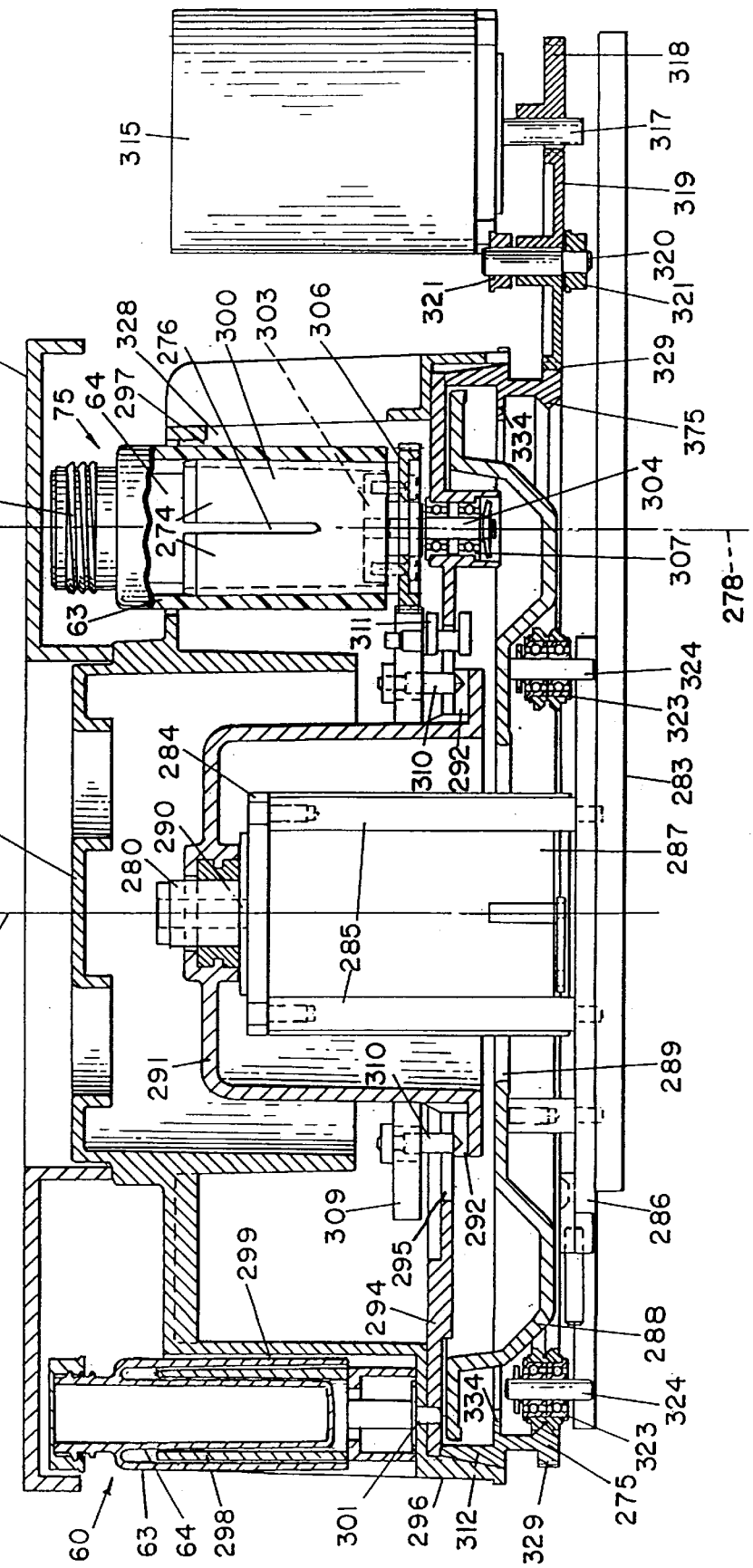
Figure 46:
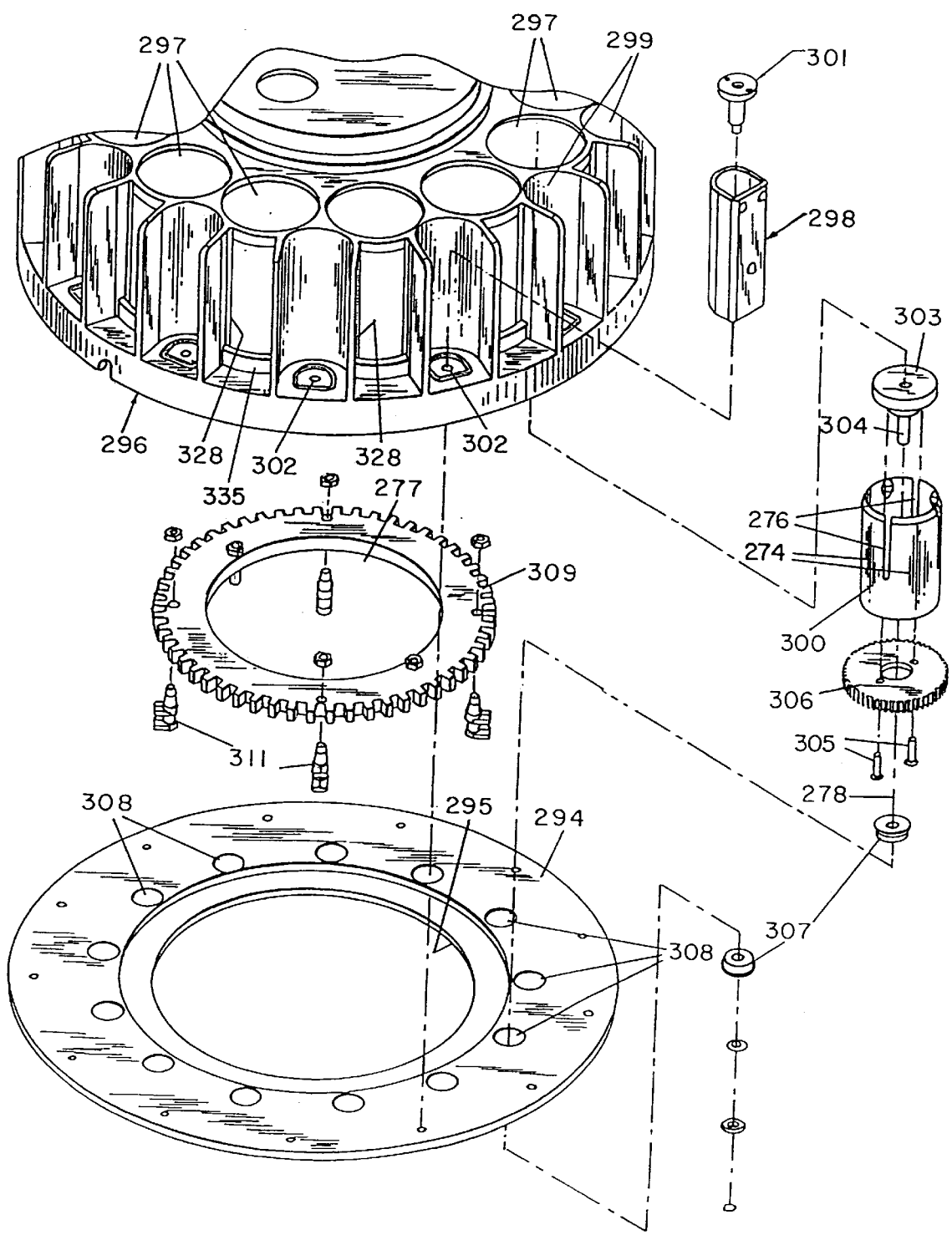
Figure 47:
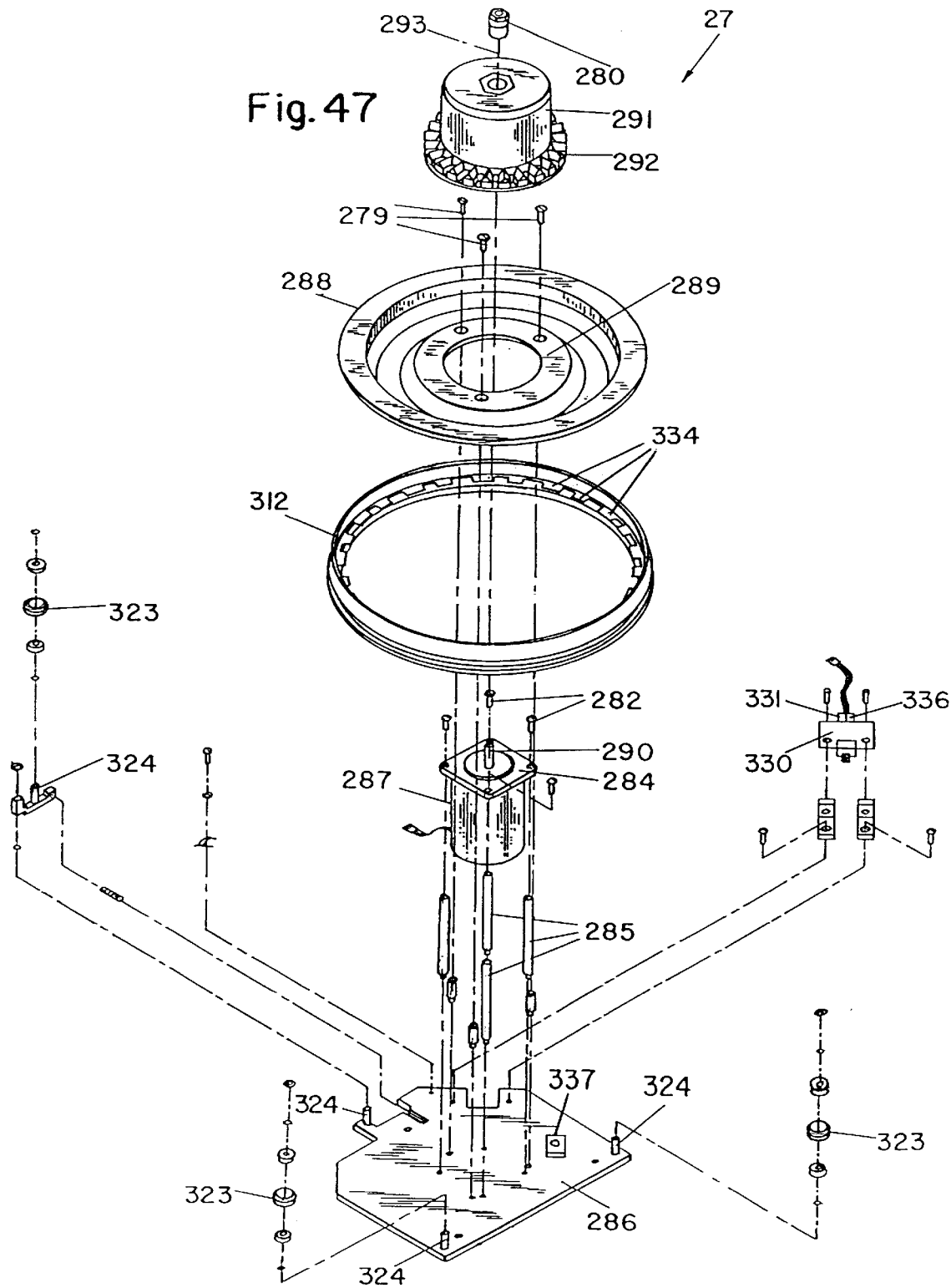
Figure 48:
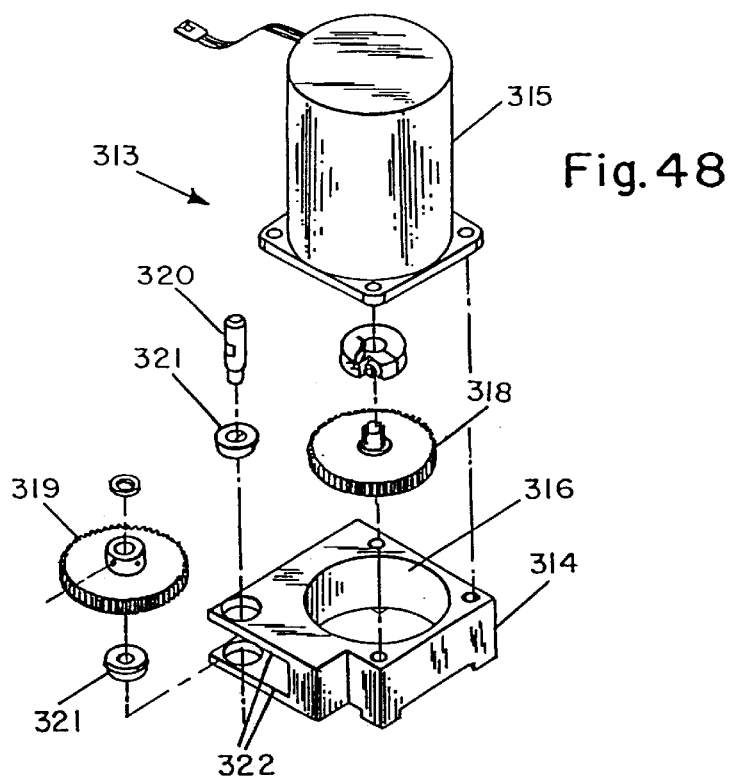
Figure 49:
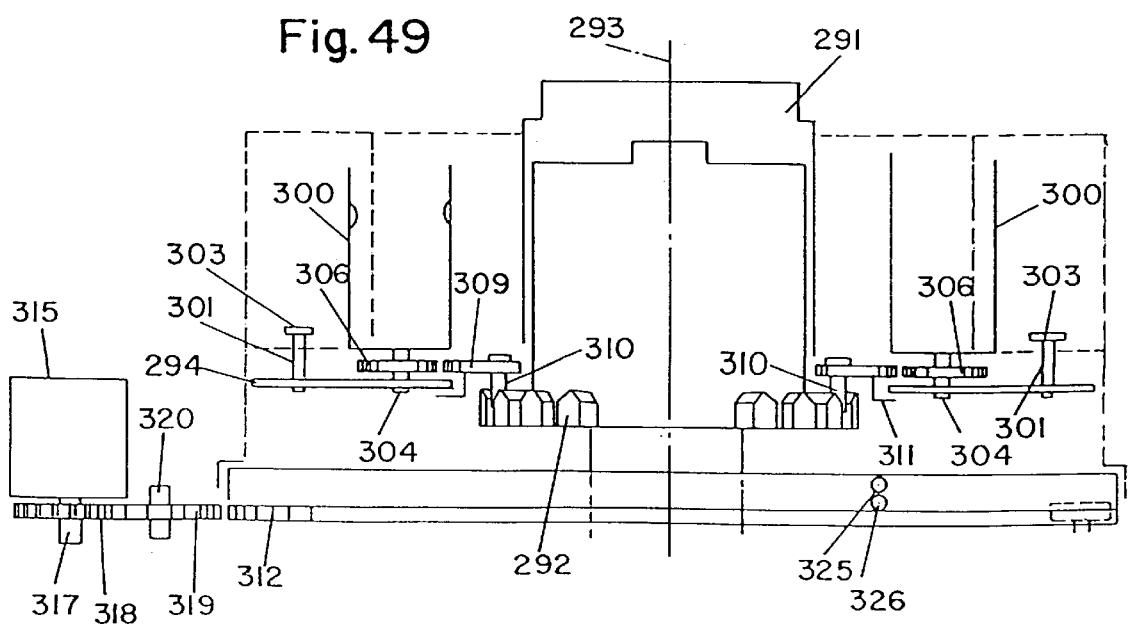
Figure 50:
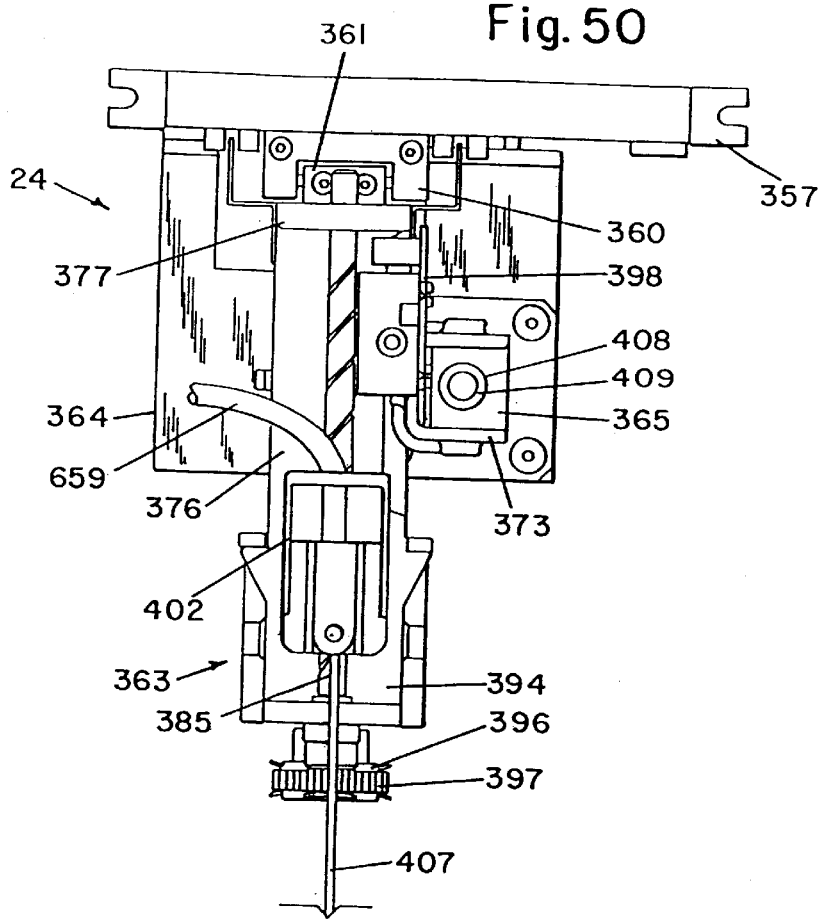
Figure 51:
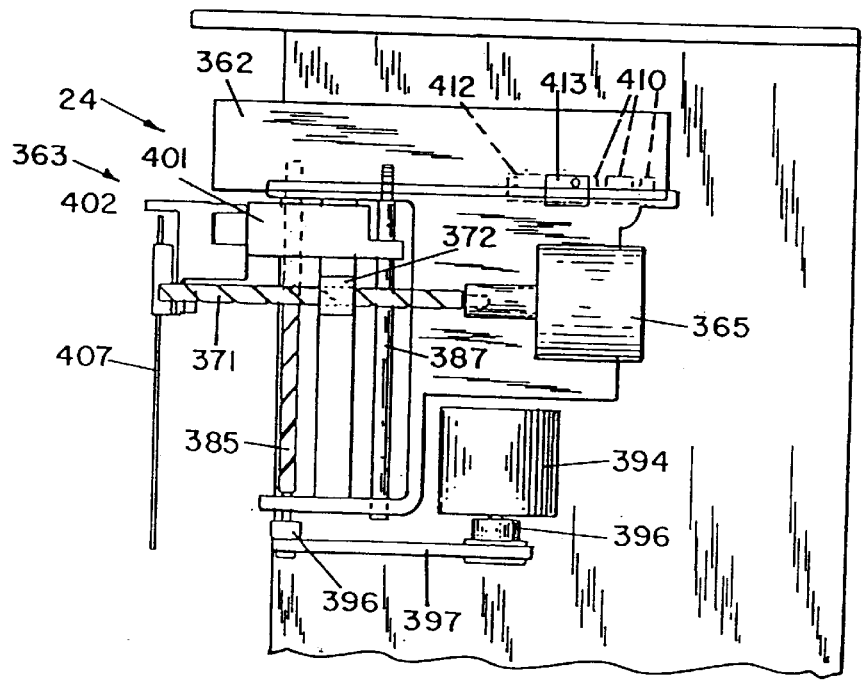
Figure 52:
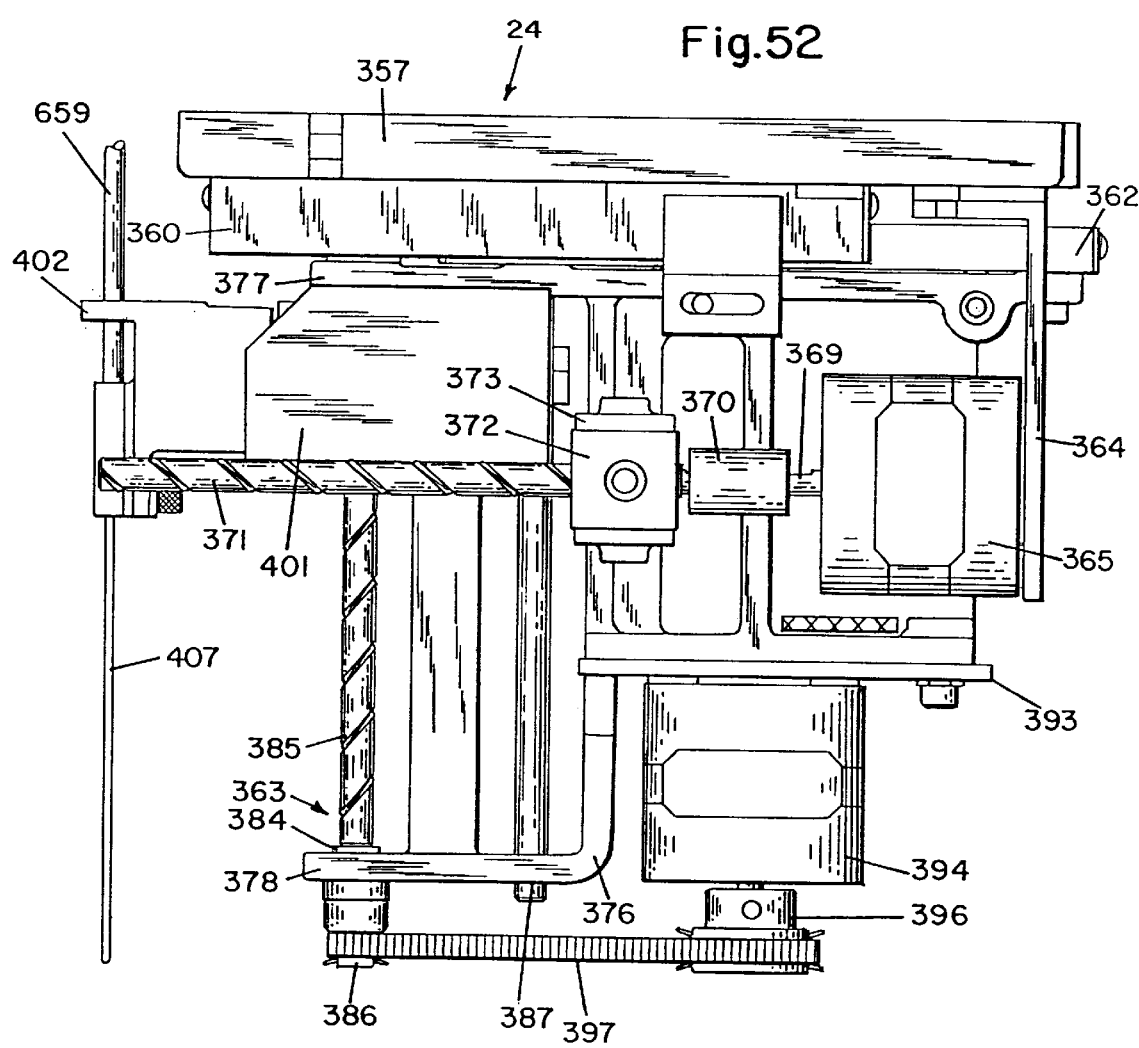
Figure 53:
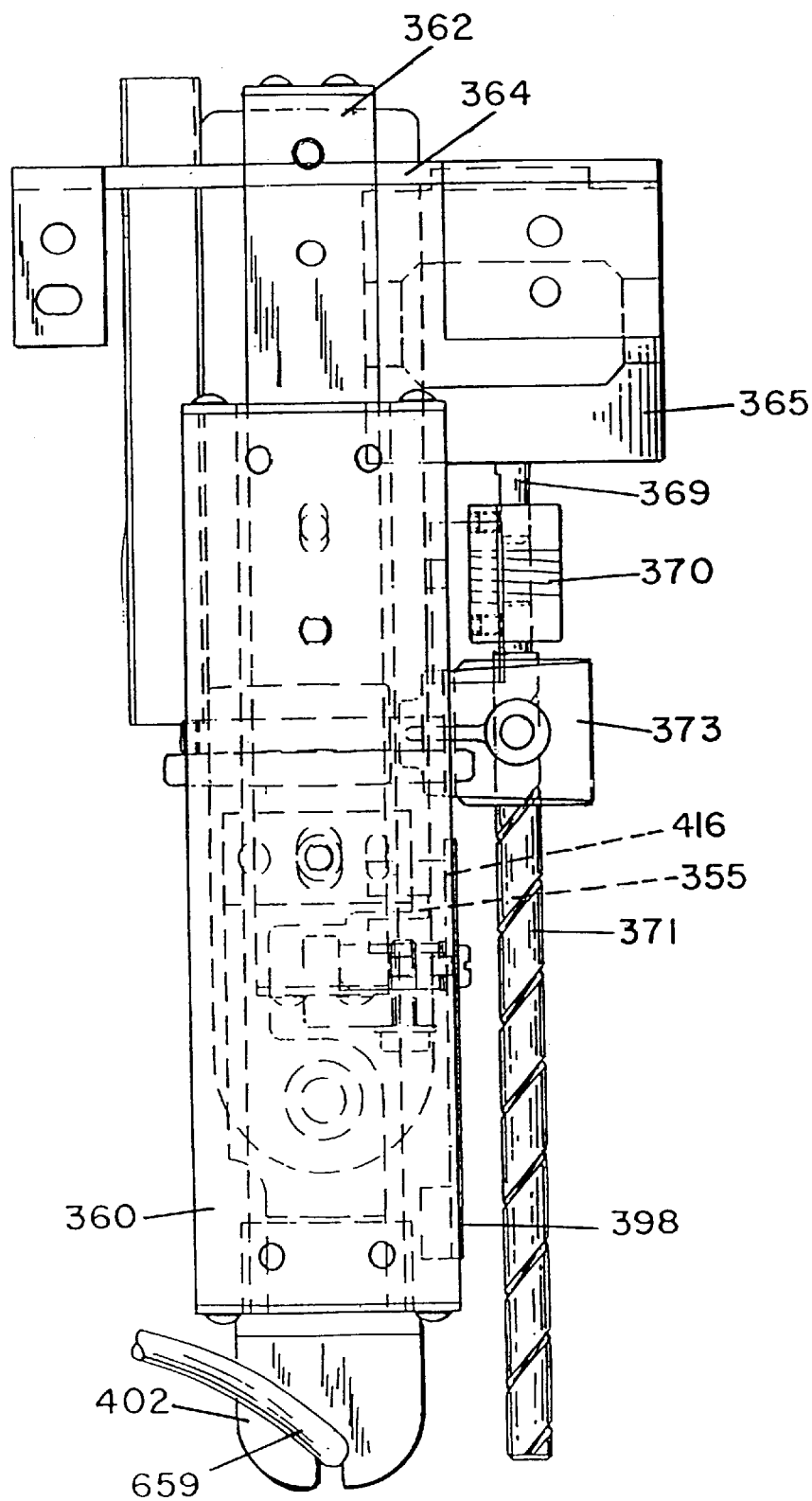
Figure 54:
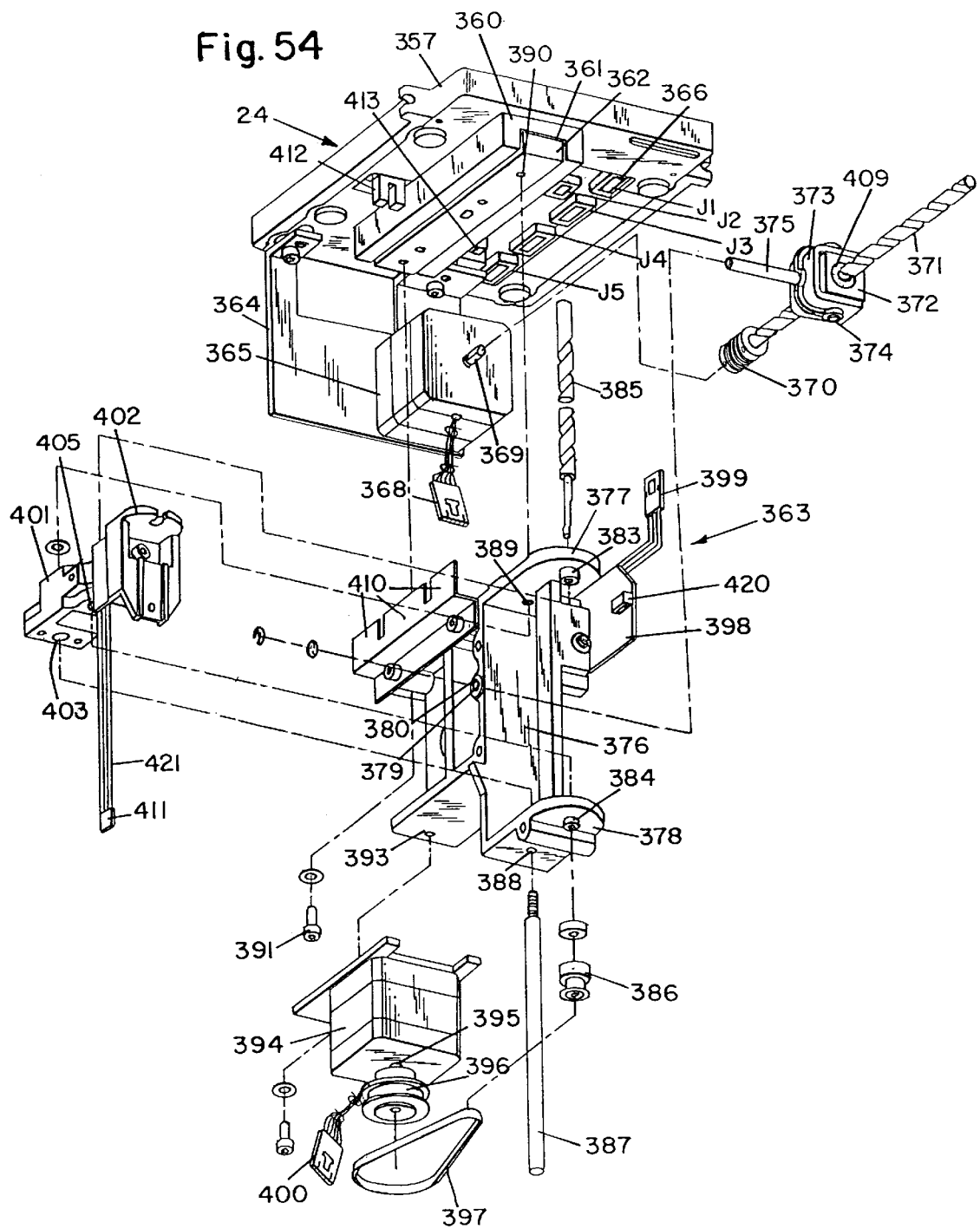
Figure 55:
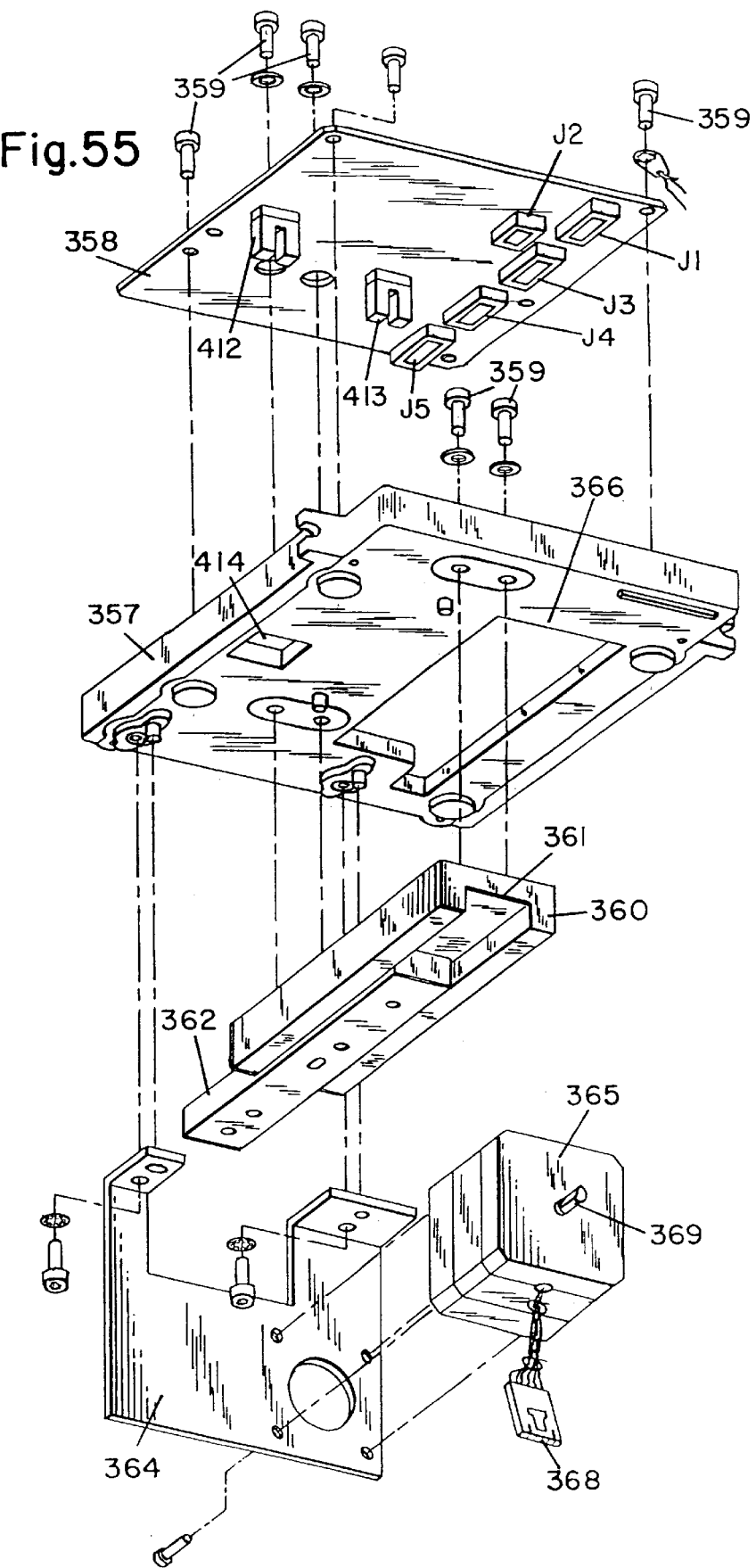
Figure 56:
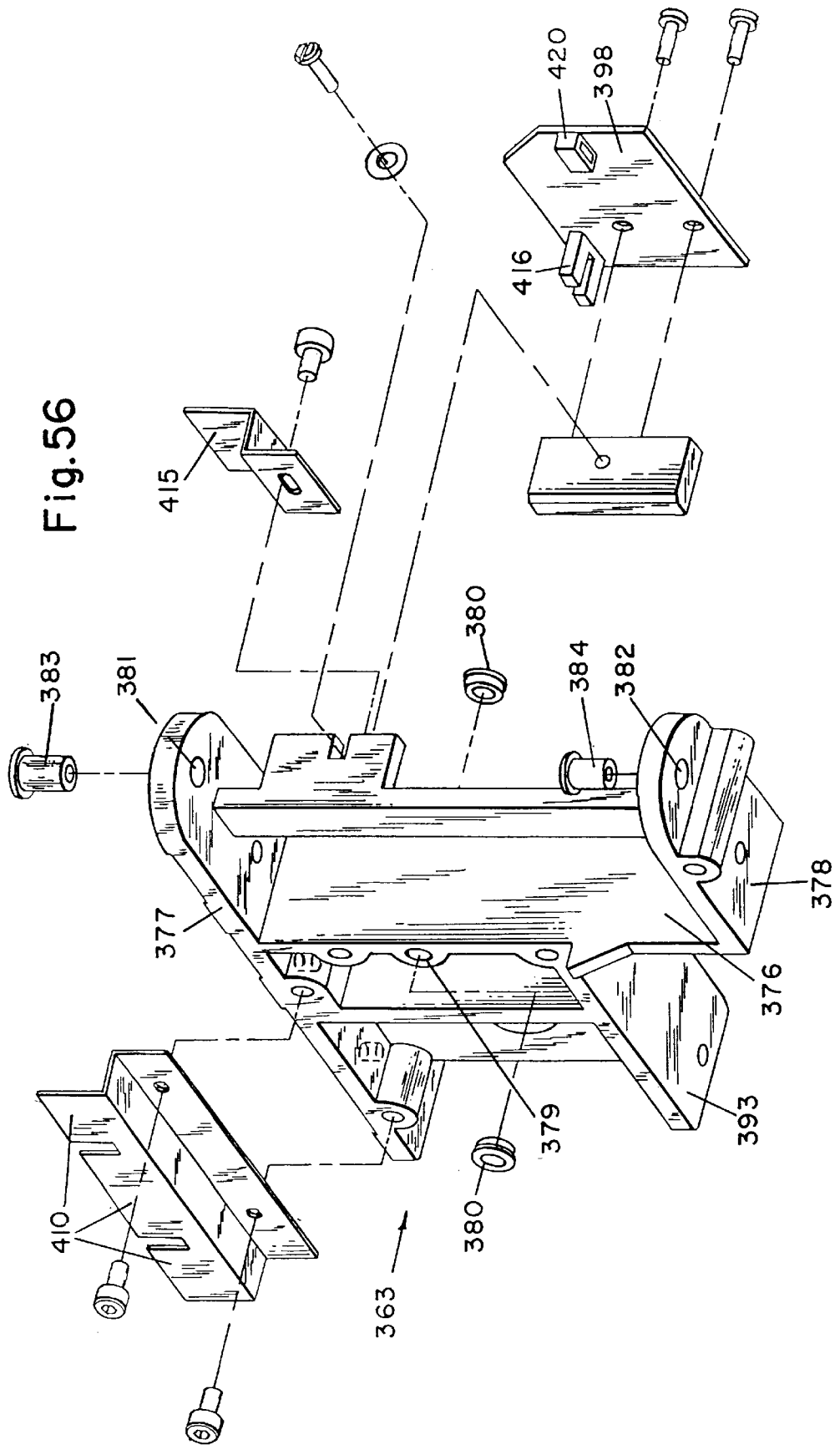
Figure 57:
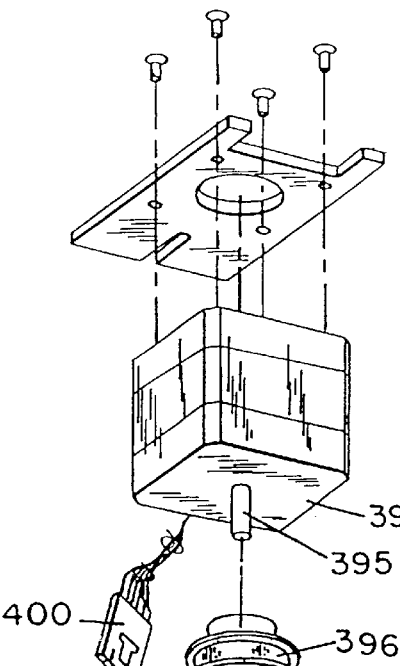
Figure 58:
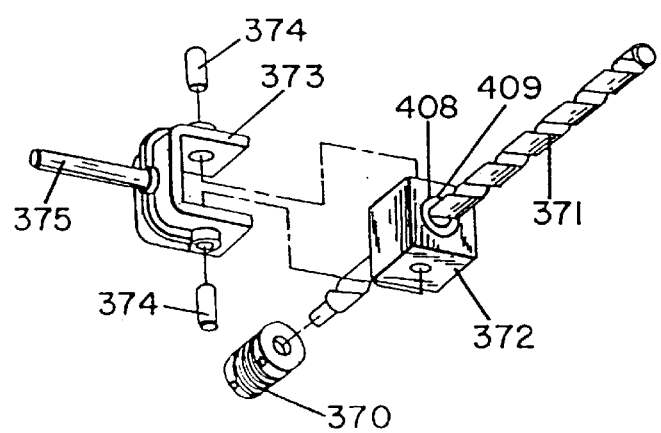
Figure 59:
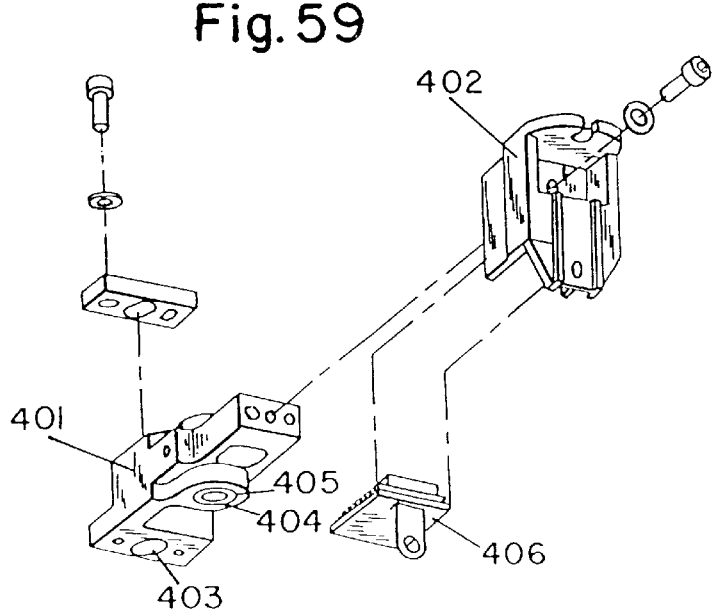
Figure 60:
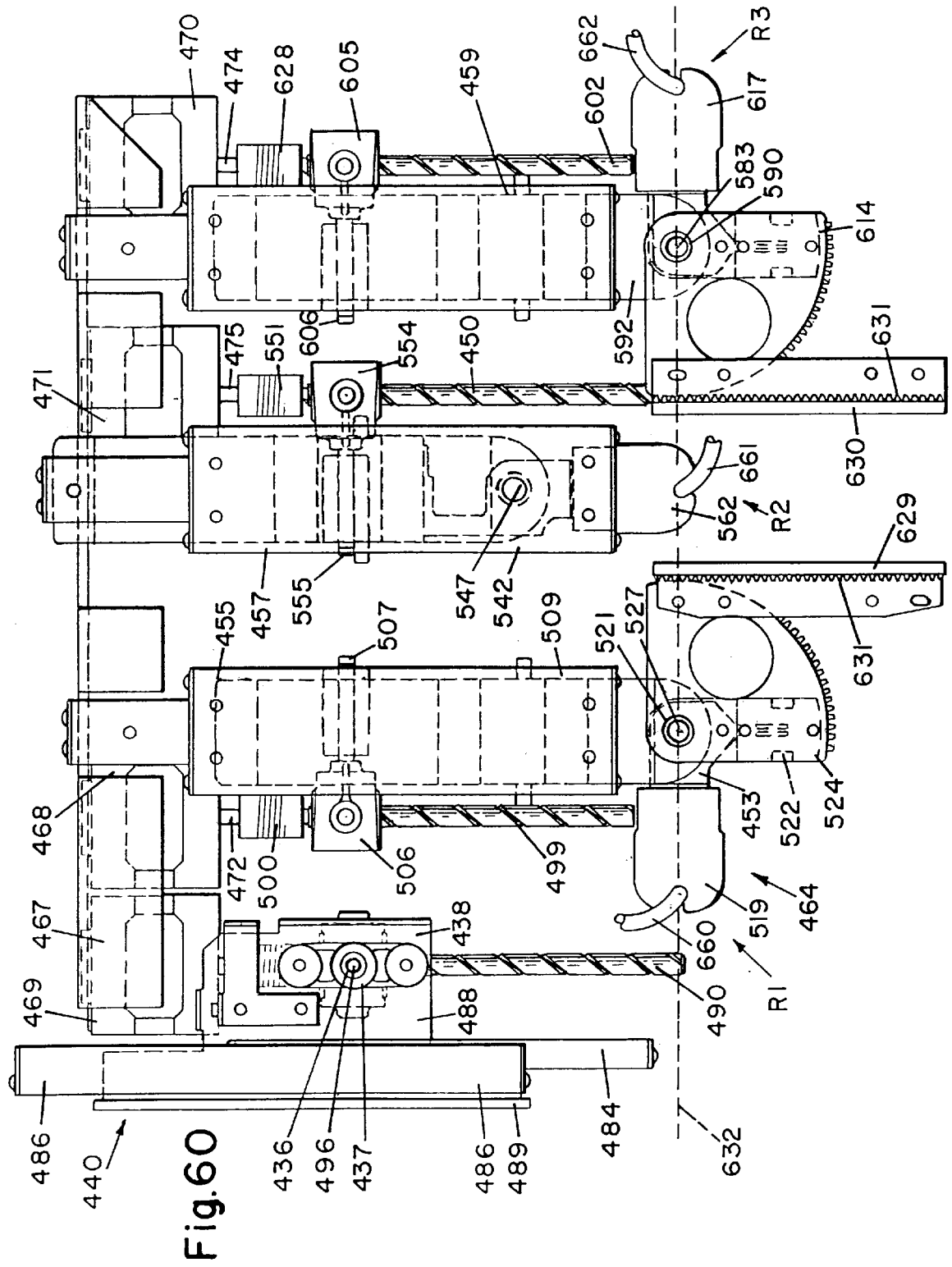
Figure 61:
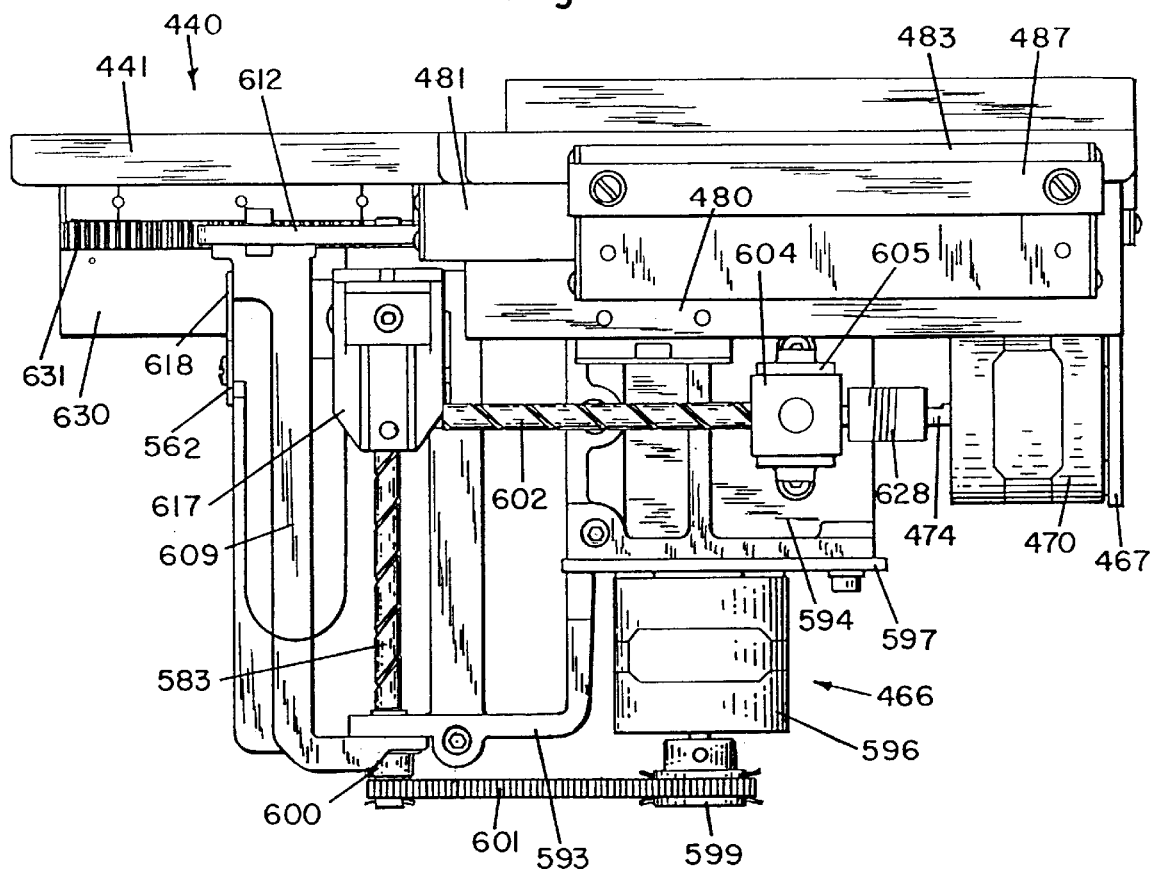
Figure 62:
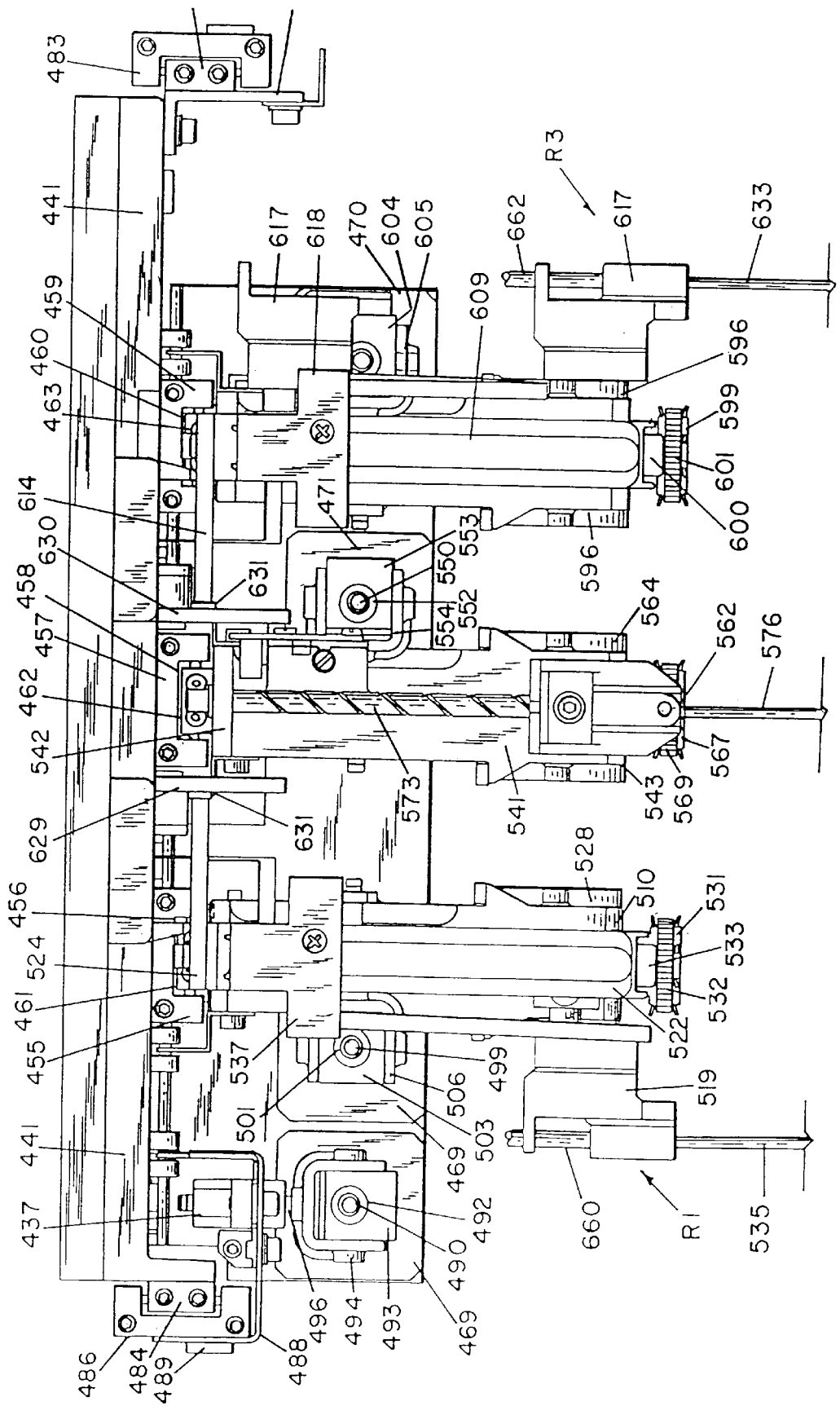
Figure 63:
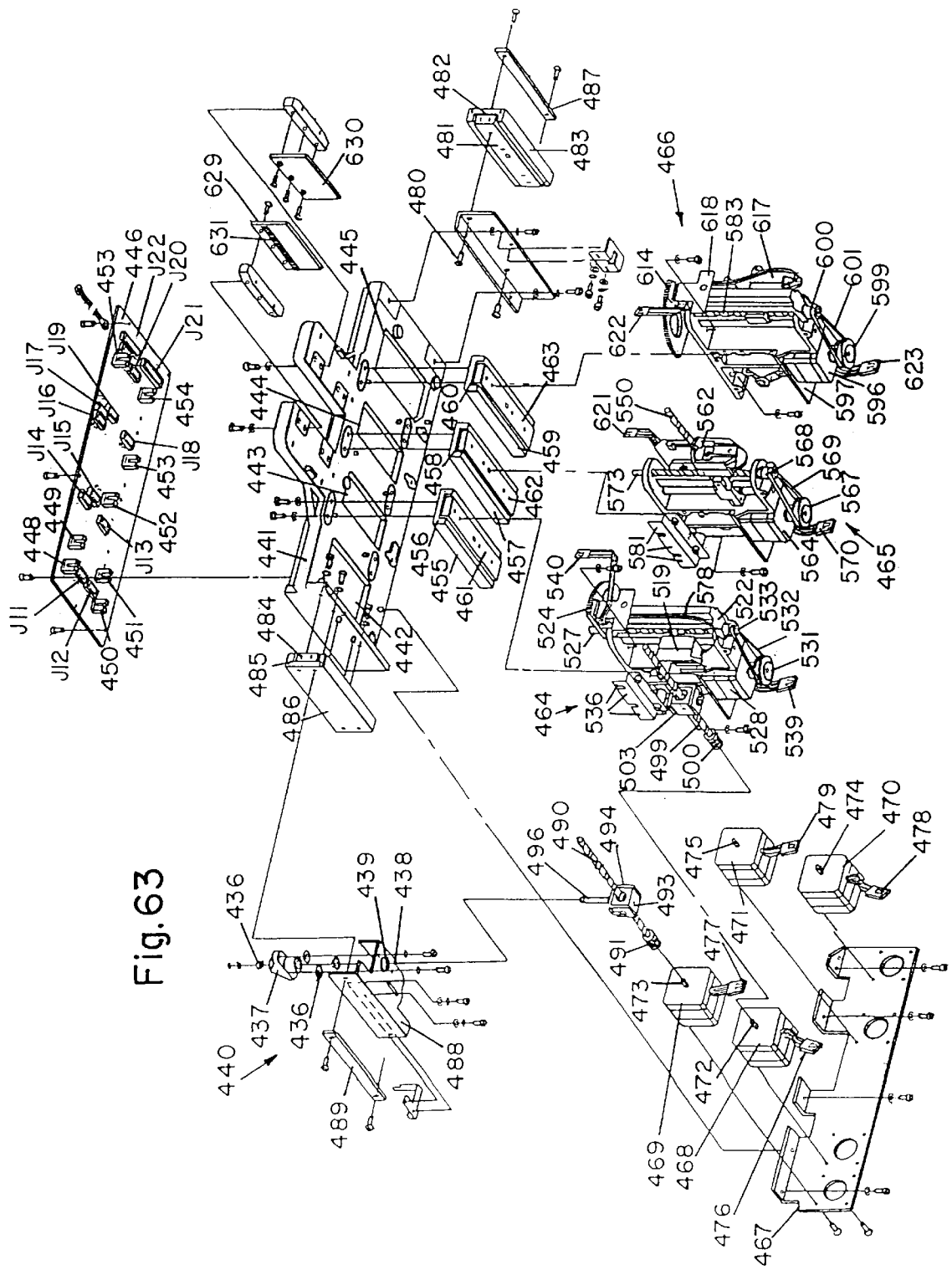
Figure 64:
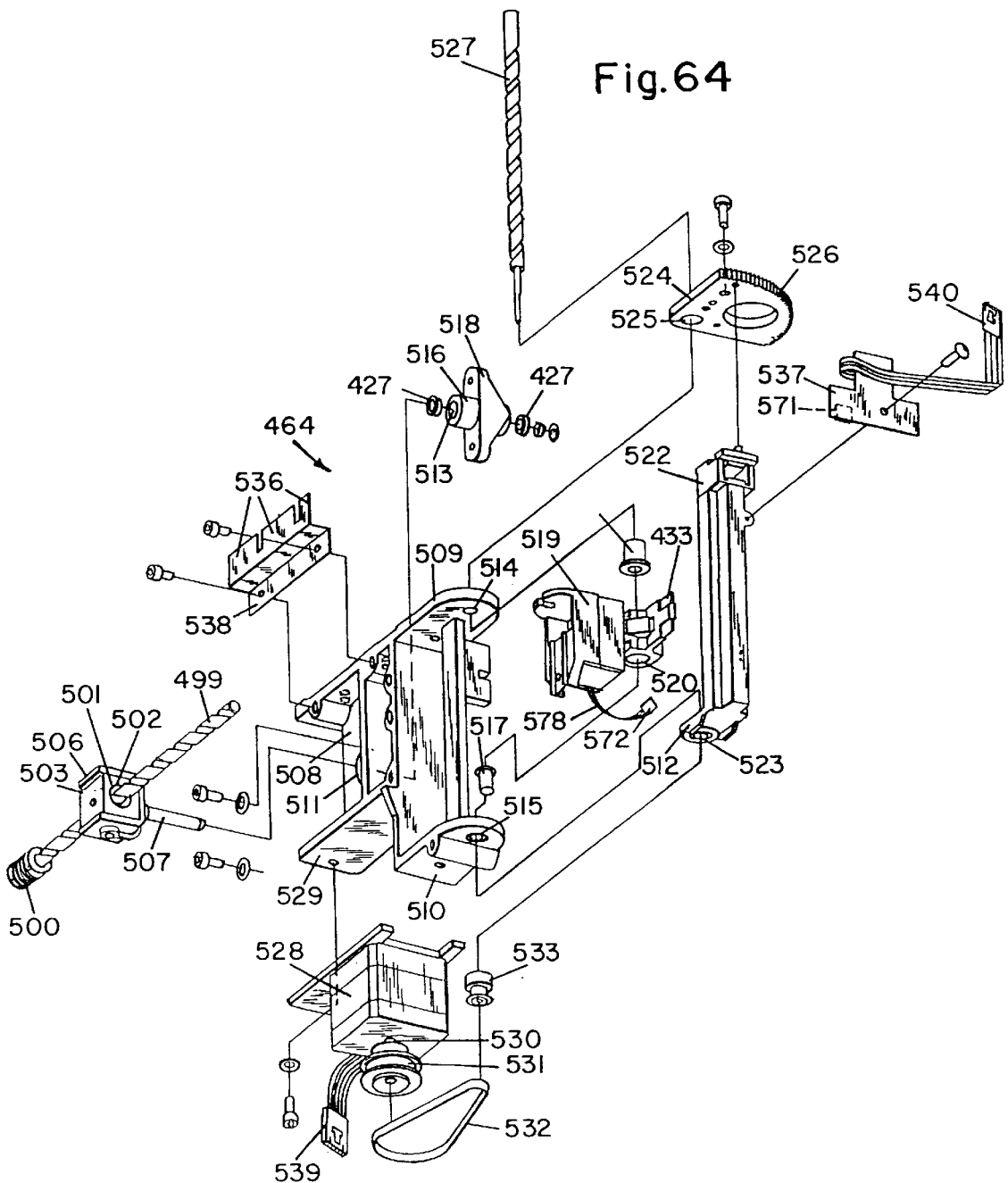
Figure 65:
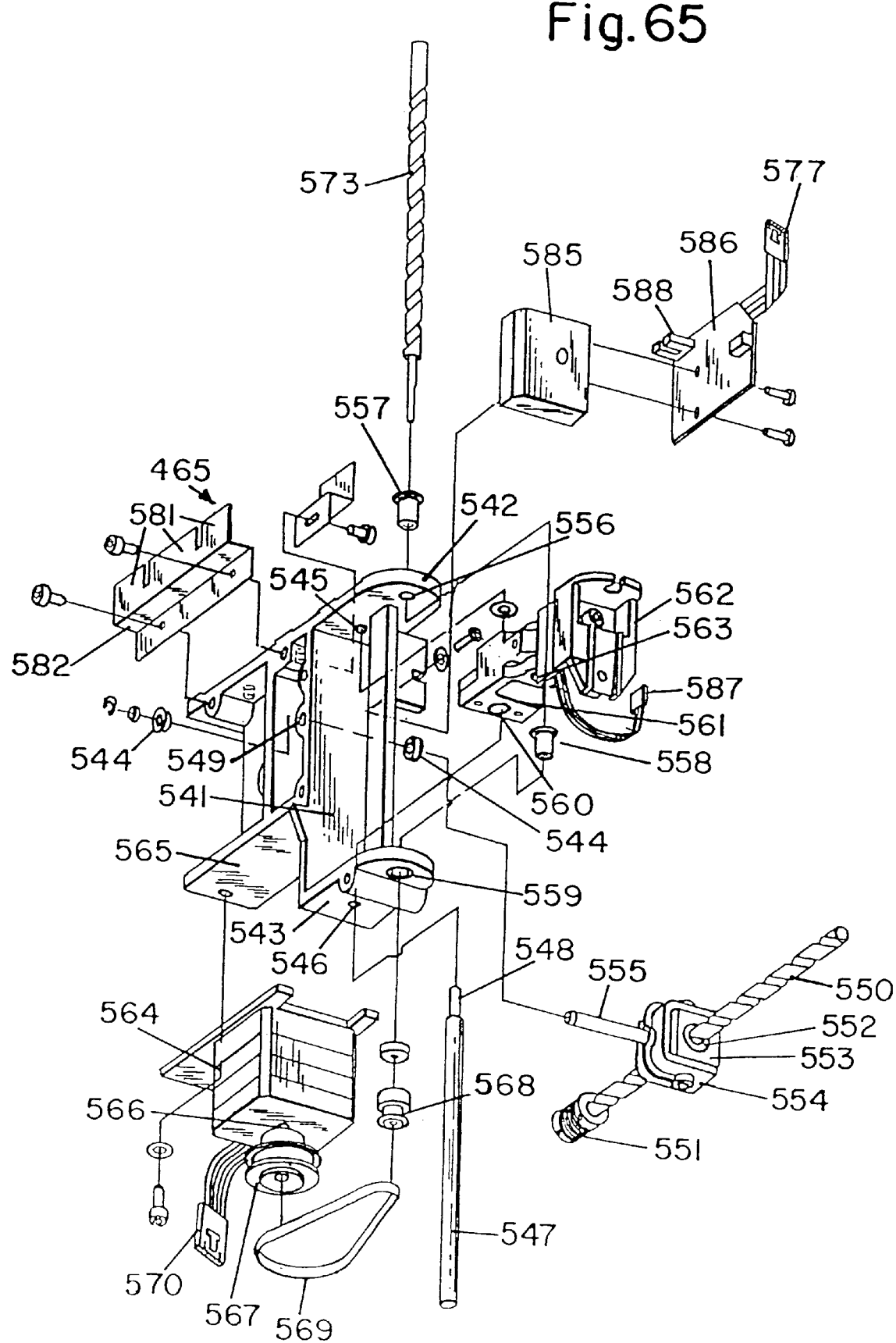
Figure 66:
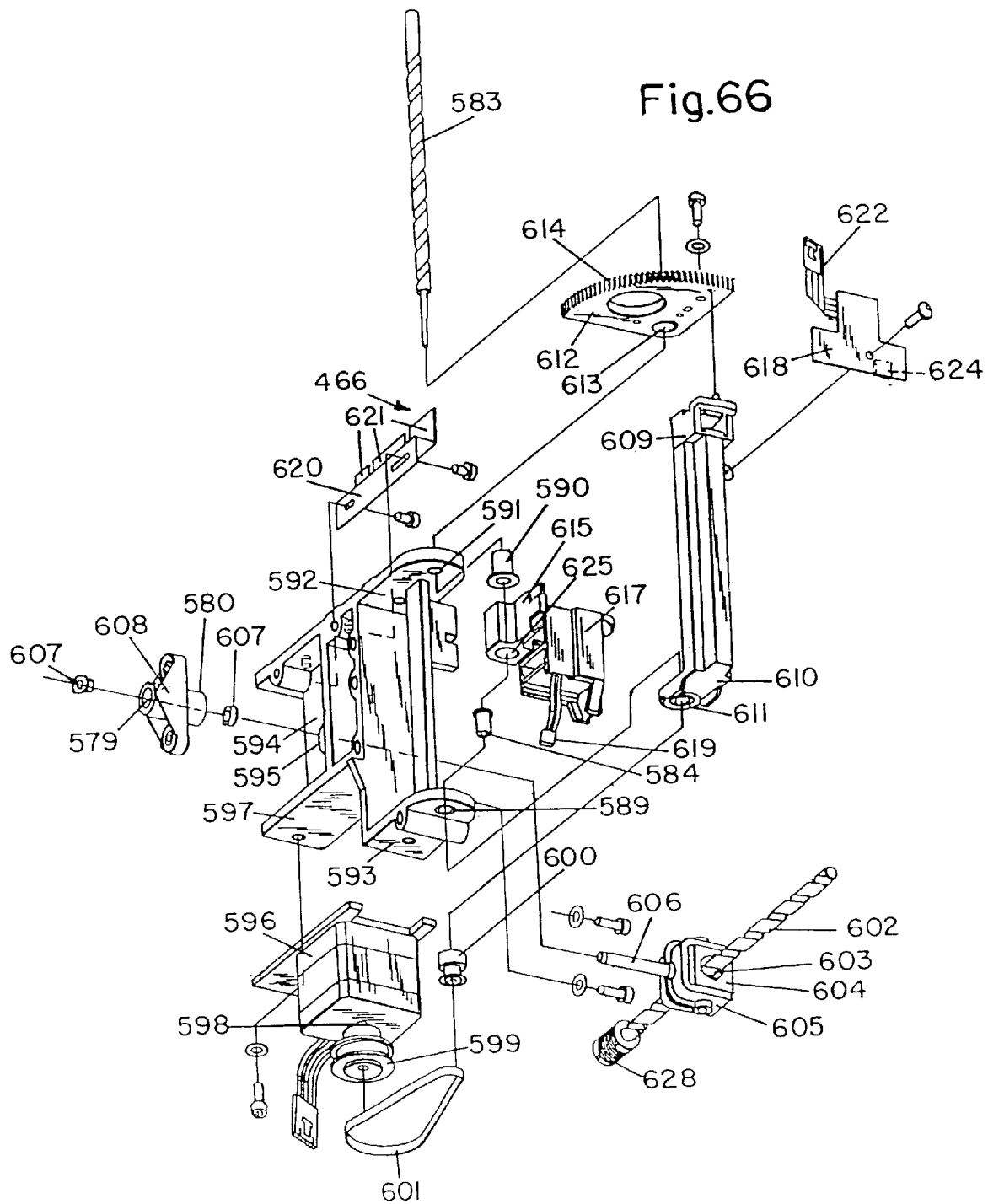
Figure 68:
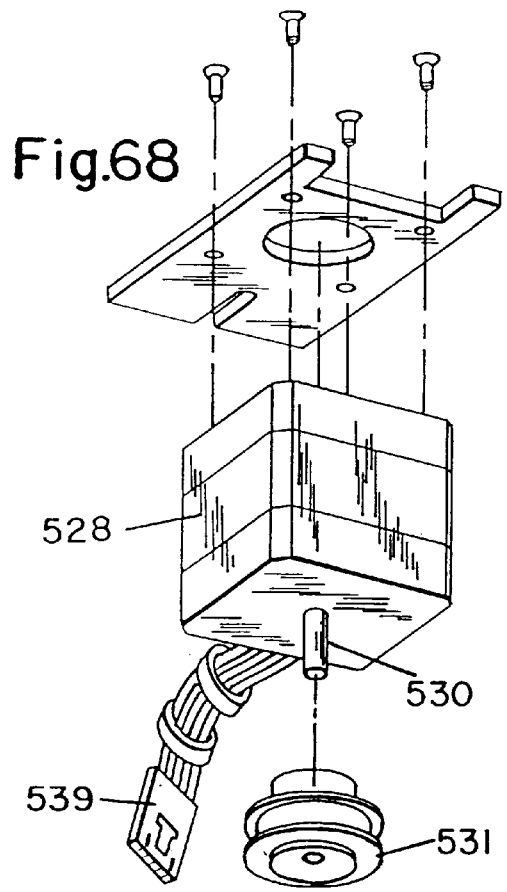
Figure 67:
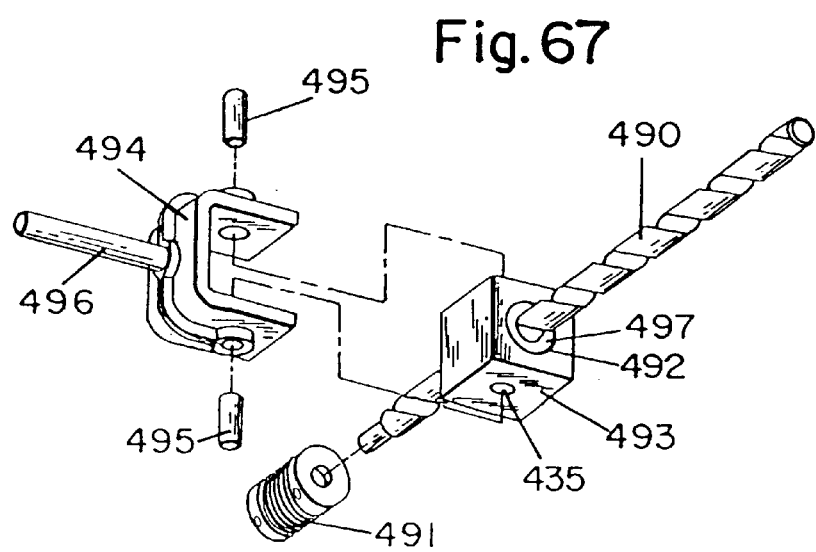
Figure 69:
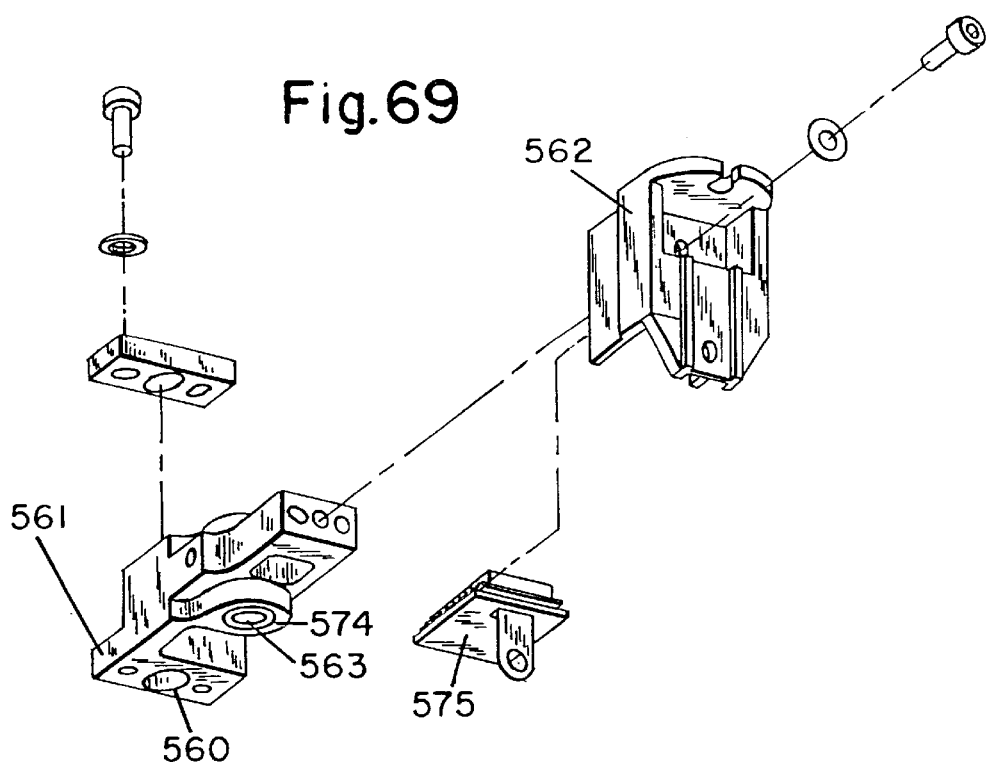
Figure 70:
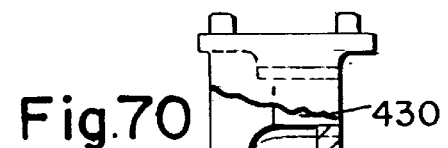
Figure 71:
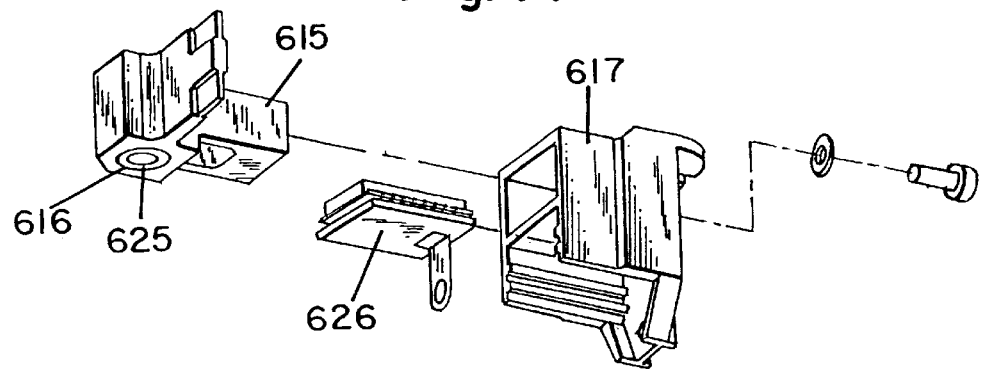
Figure 72:
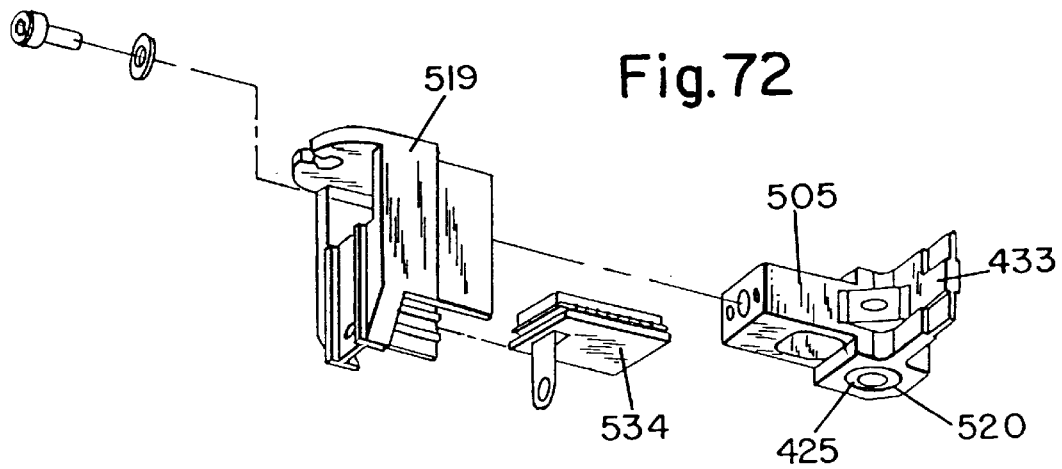
Figure 73:
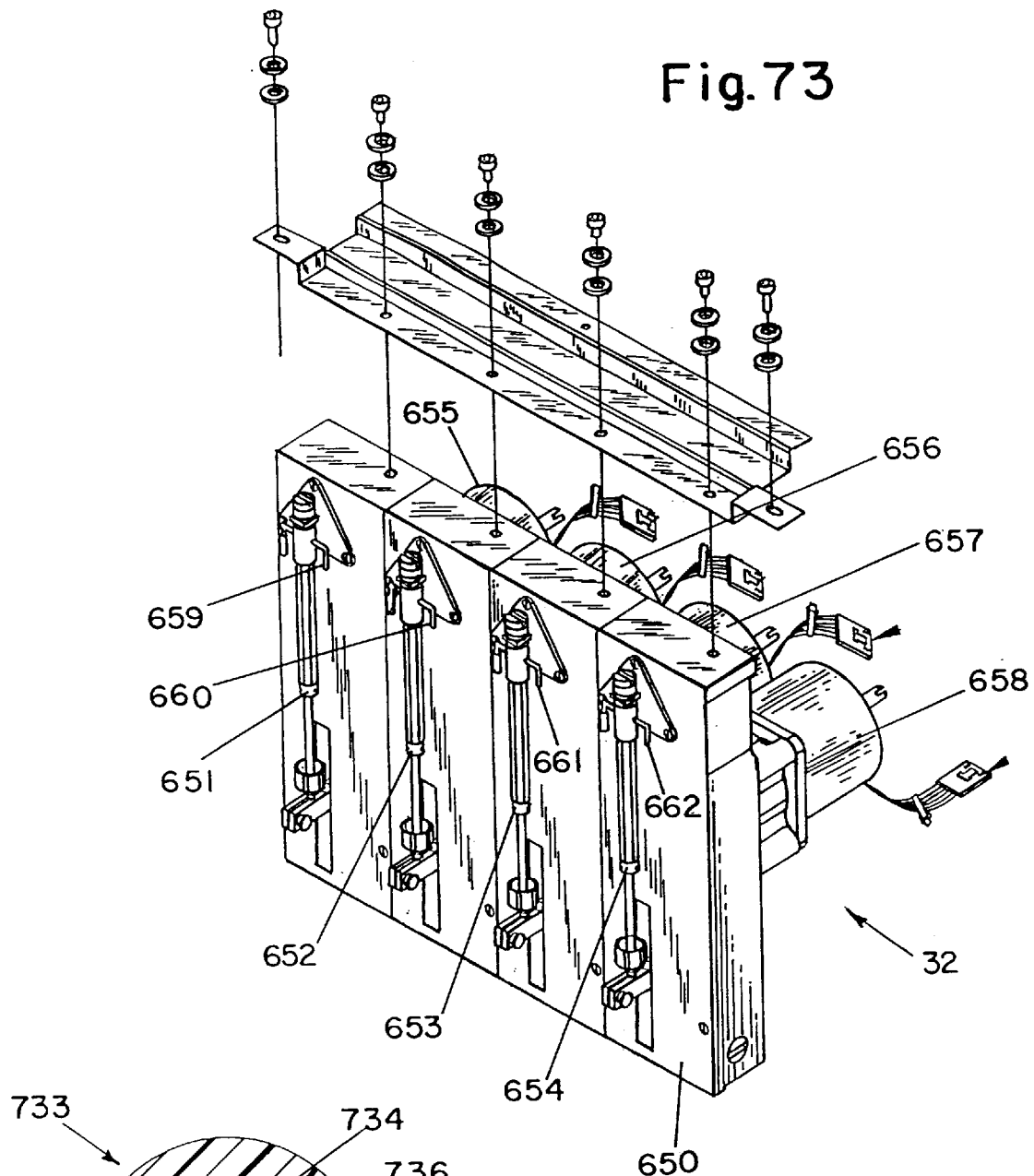
Figure 74:
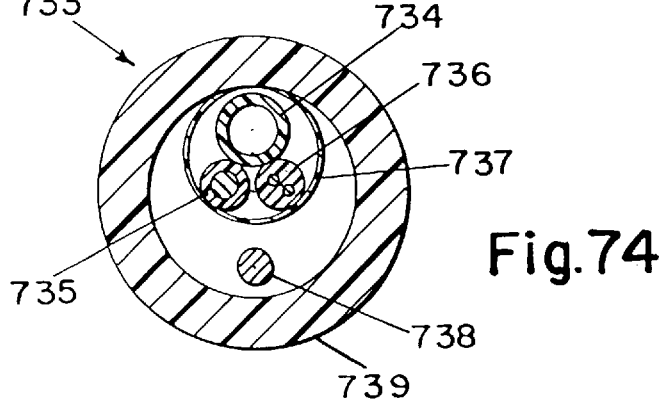
Figure 75:
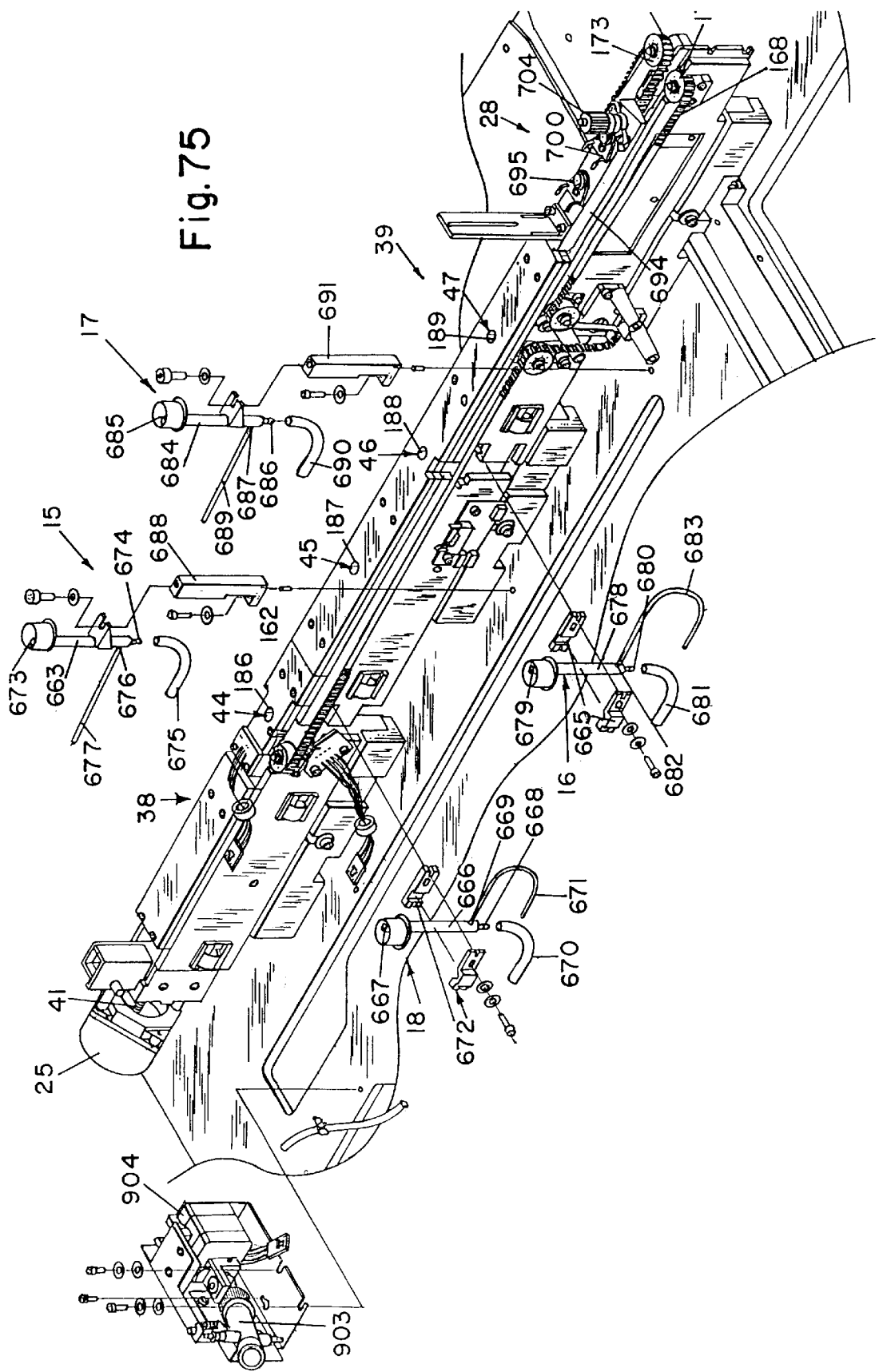
Figure 76:
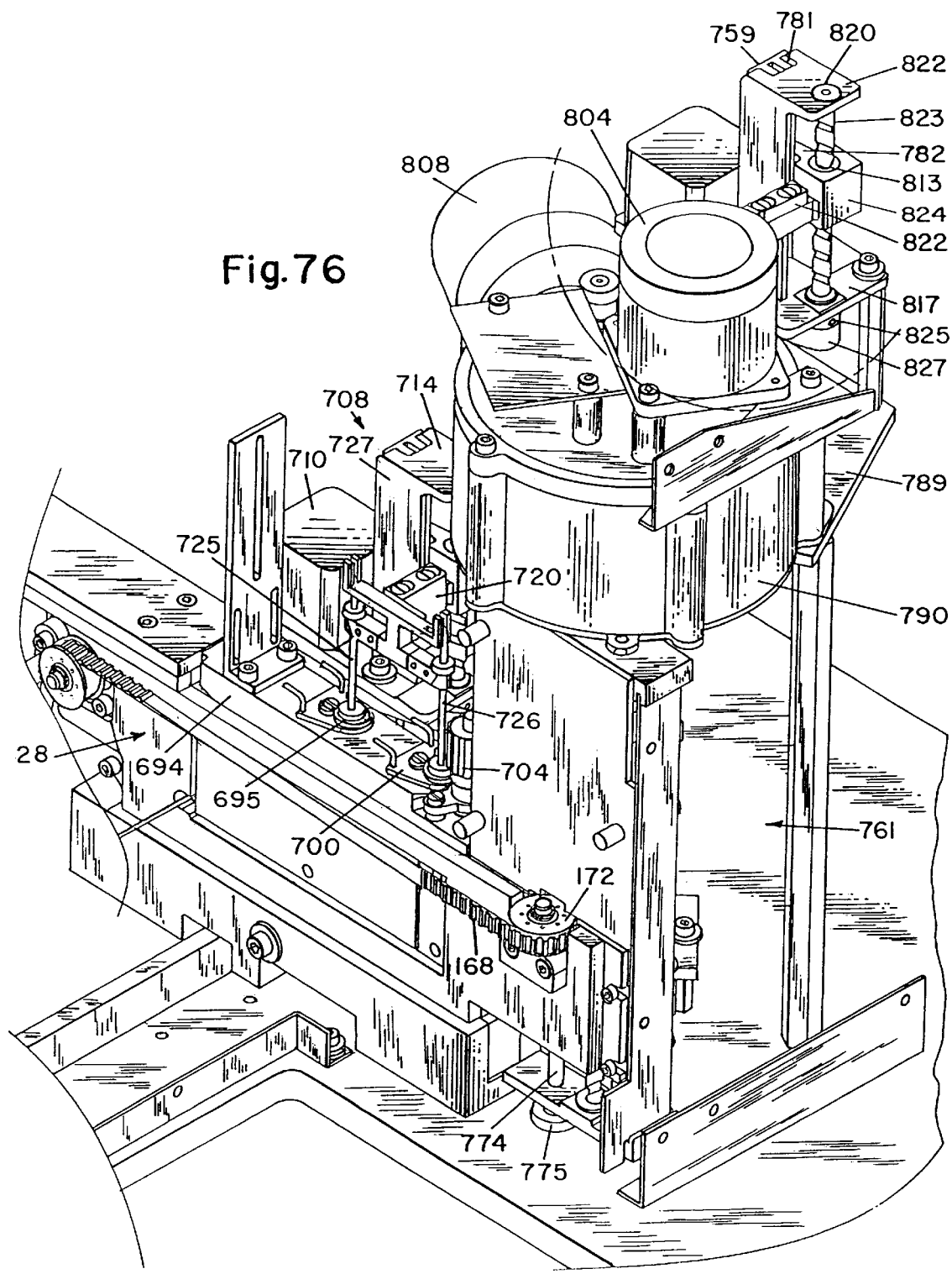
Figures 77, 78:
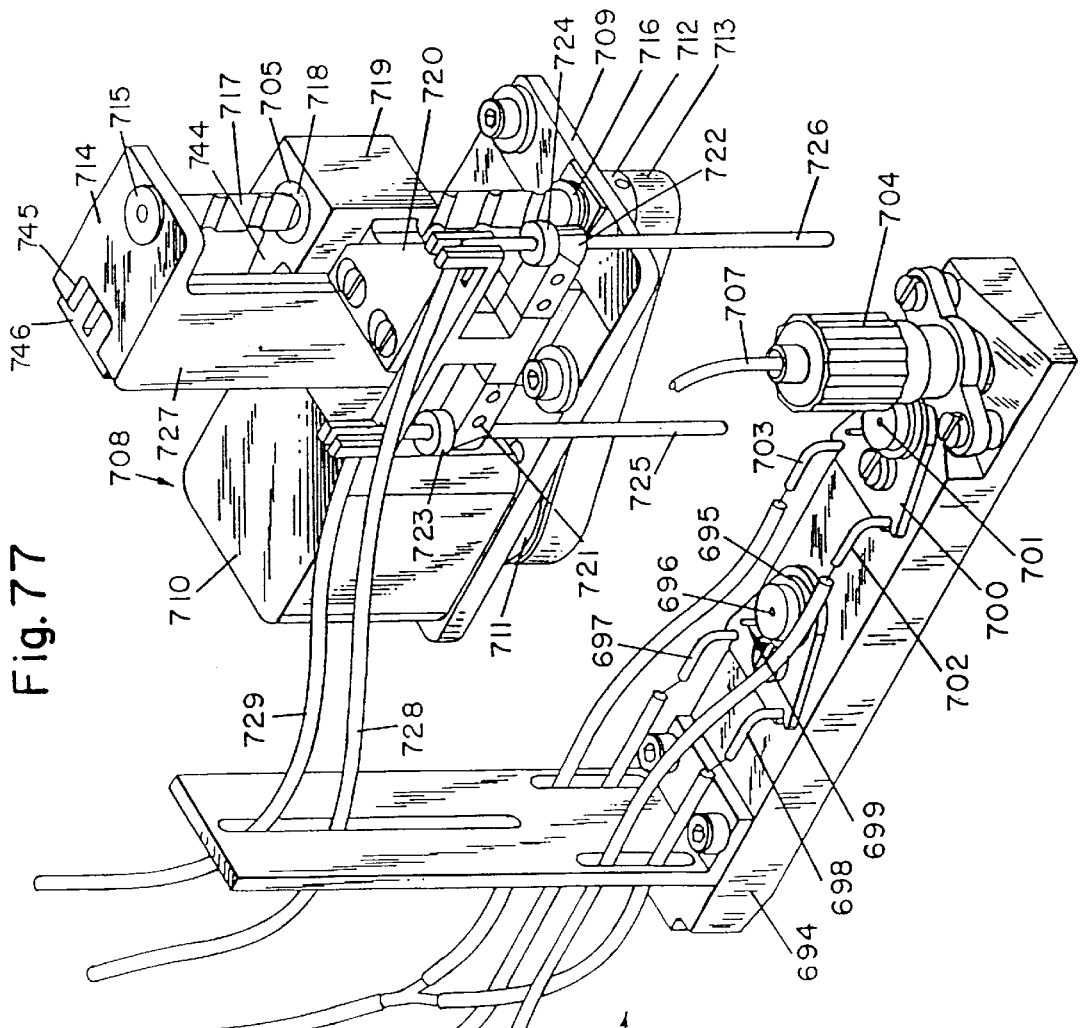
Figure 81:
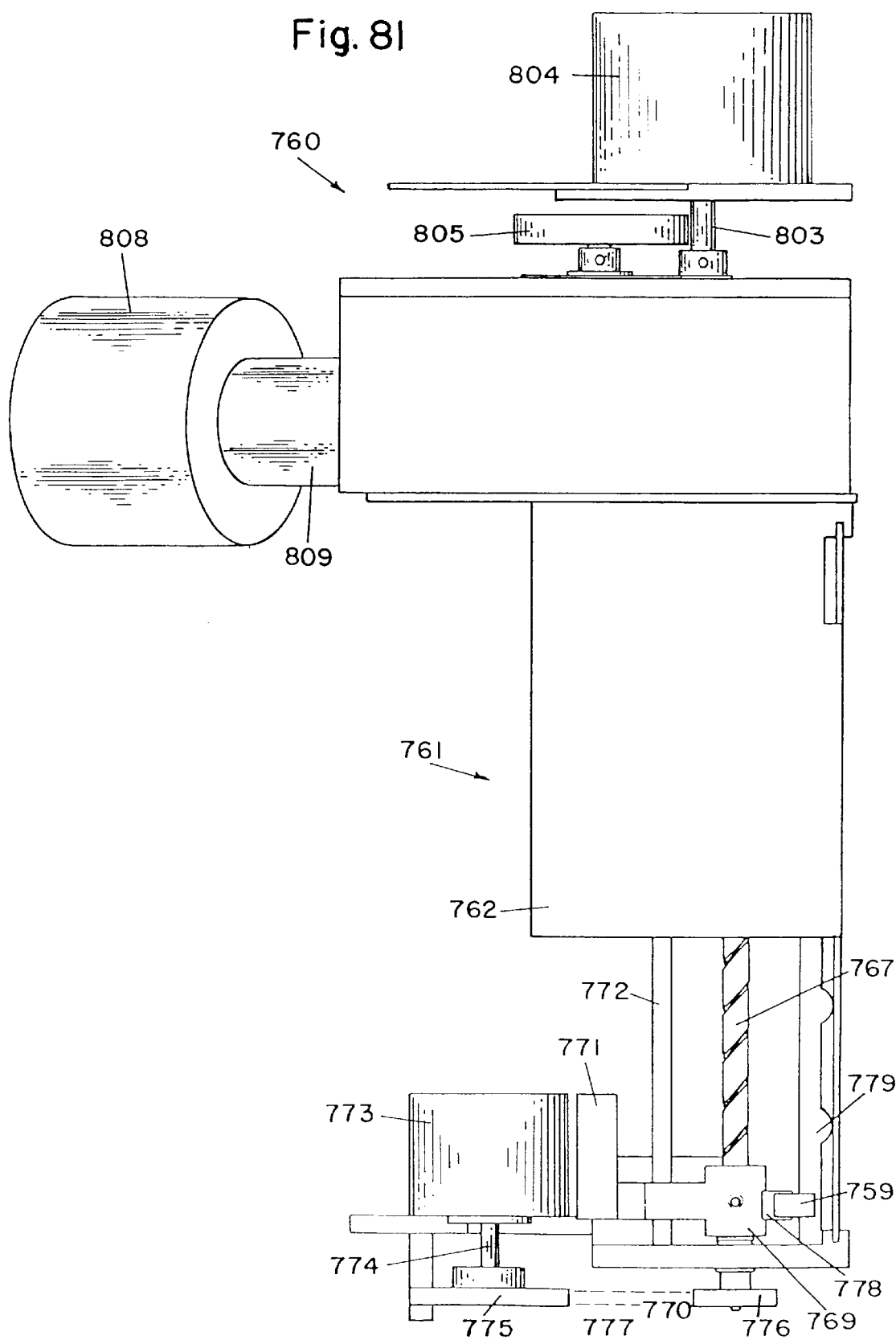
Figure 82:
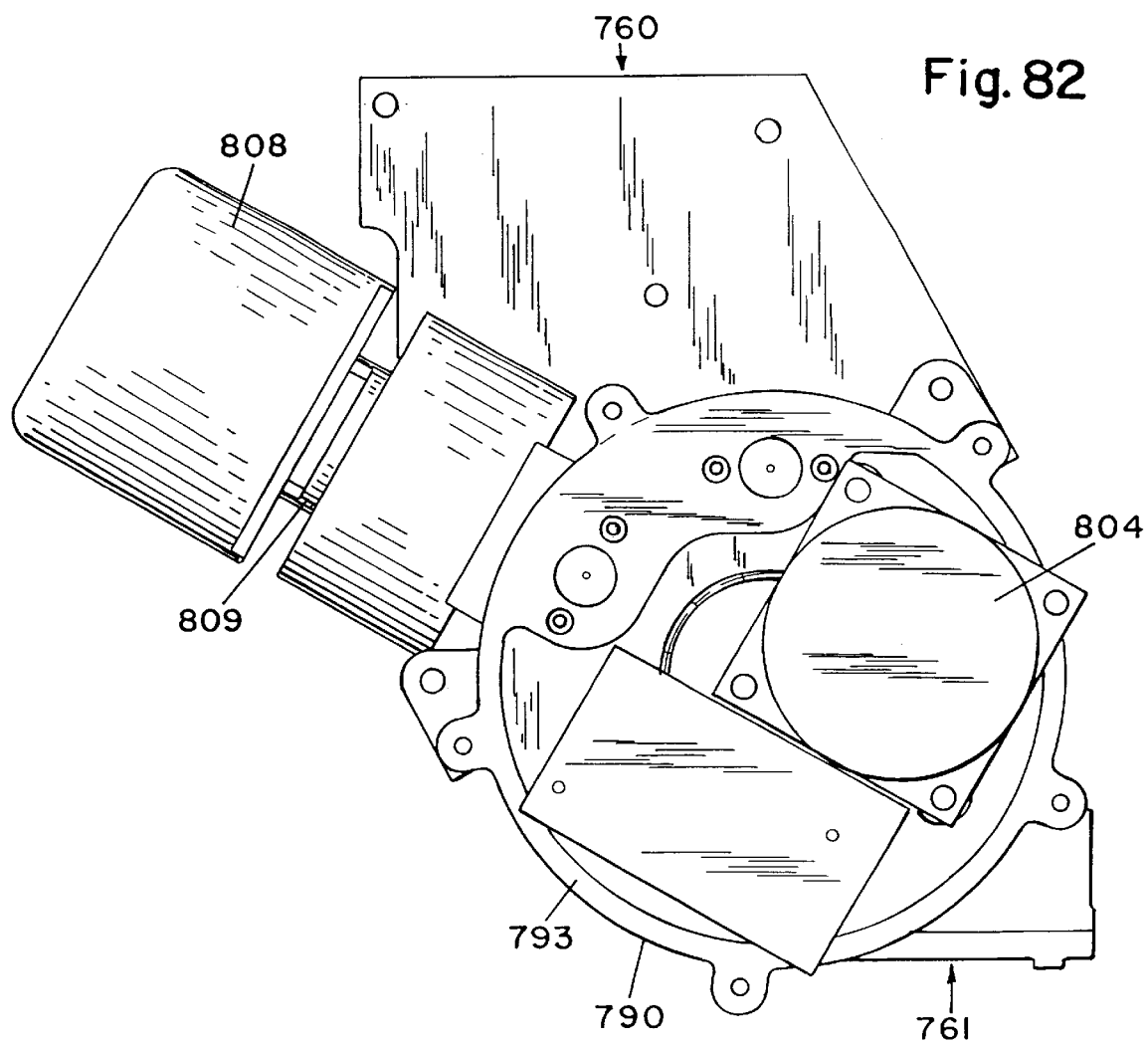
Figure 83:
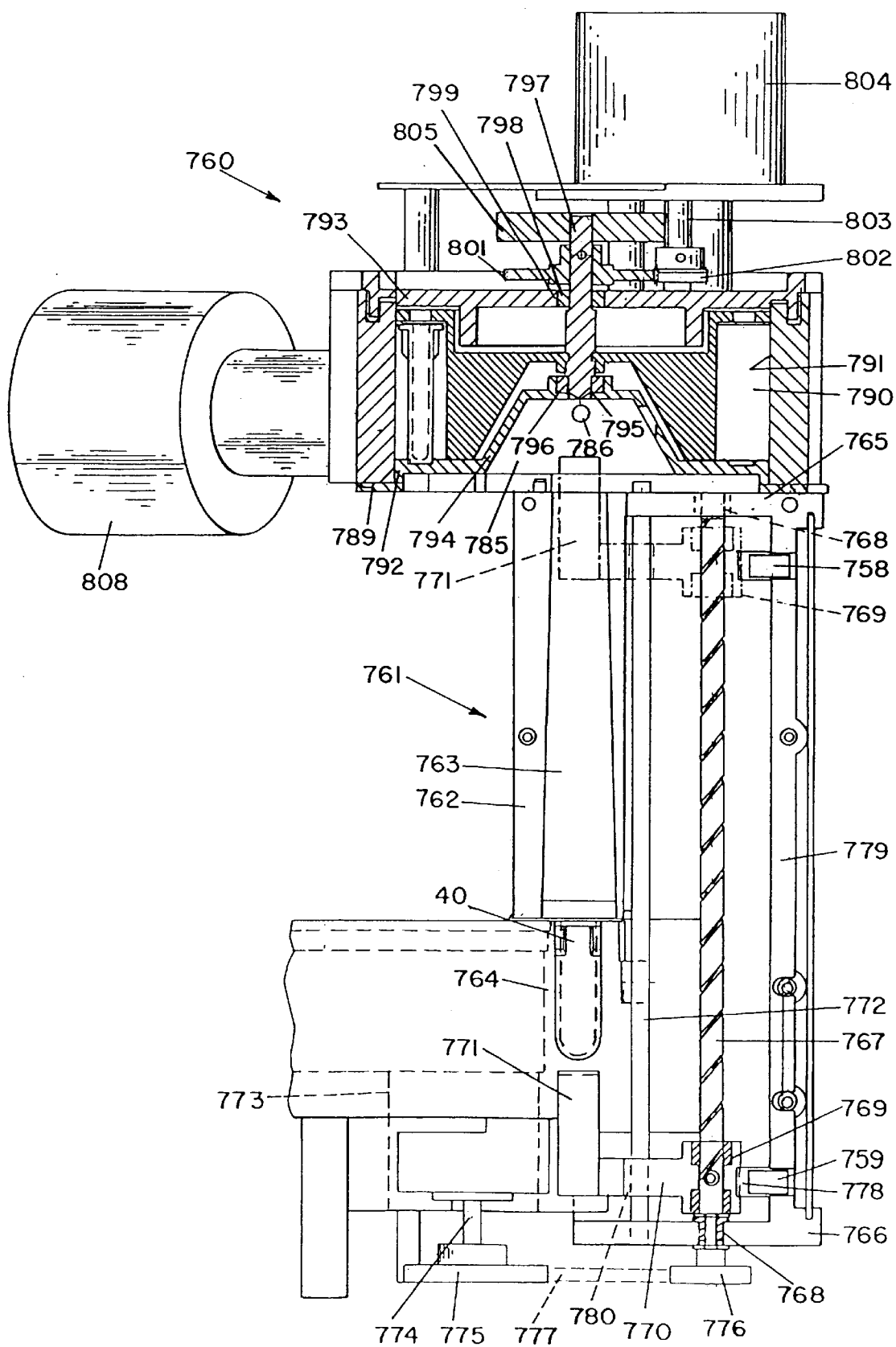
Figure 84:
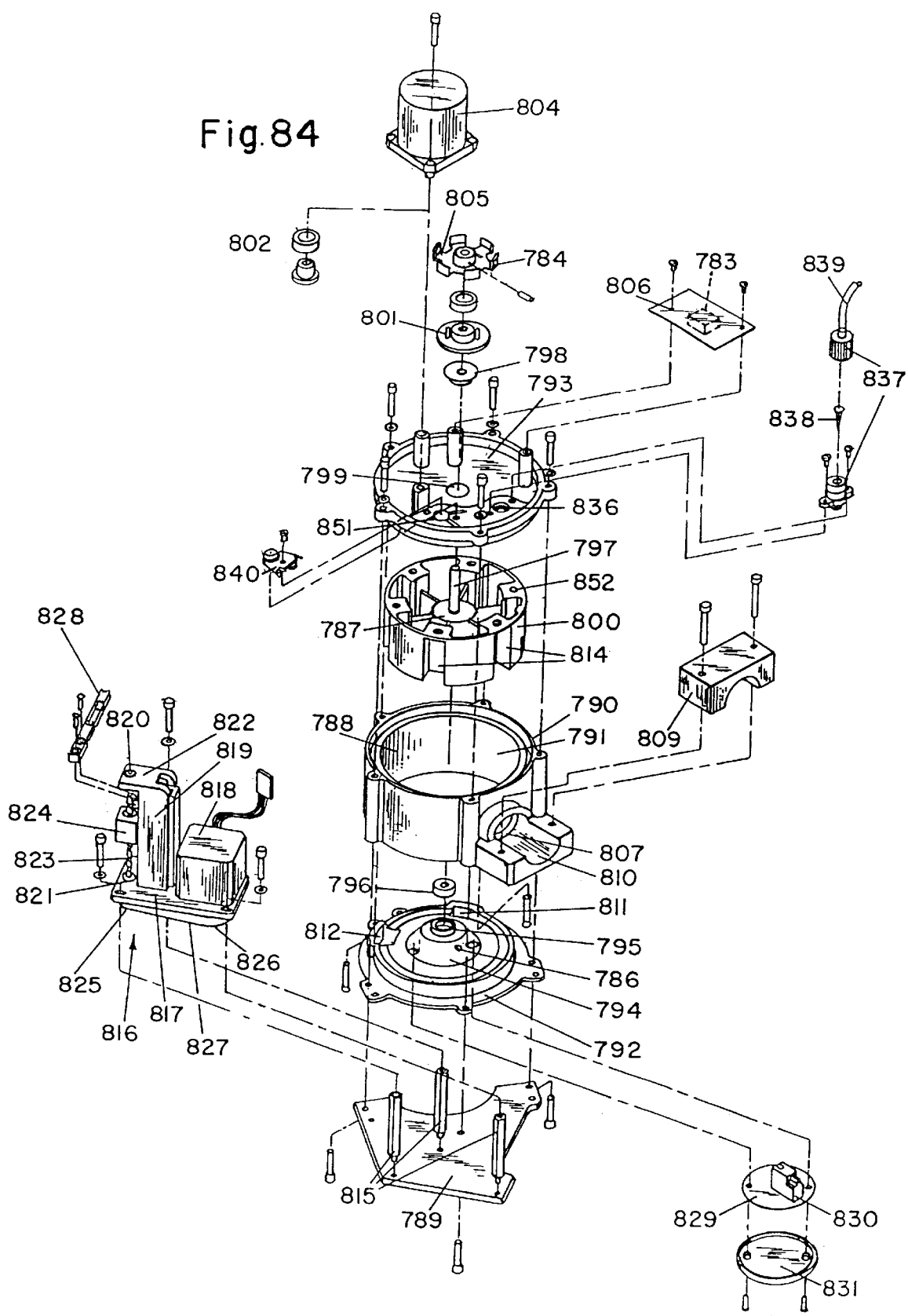
Figure 85:
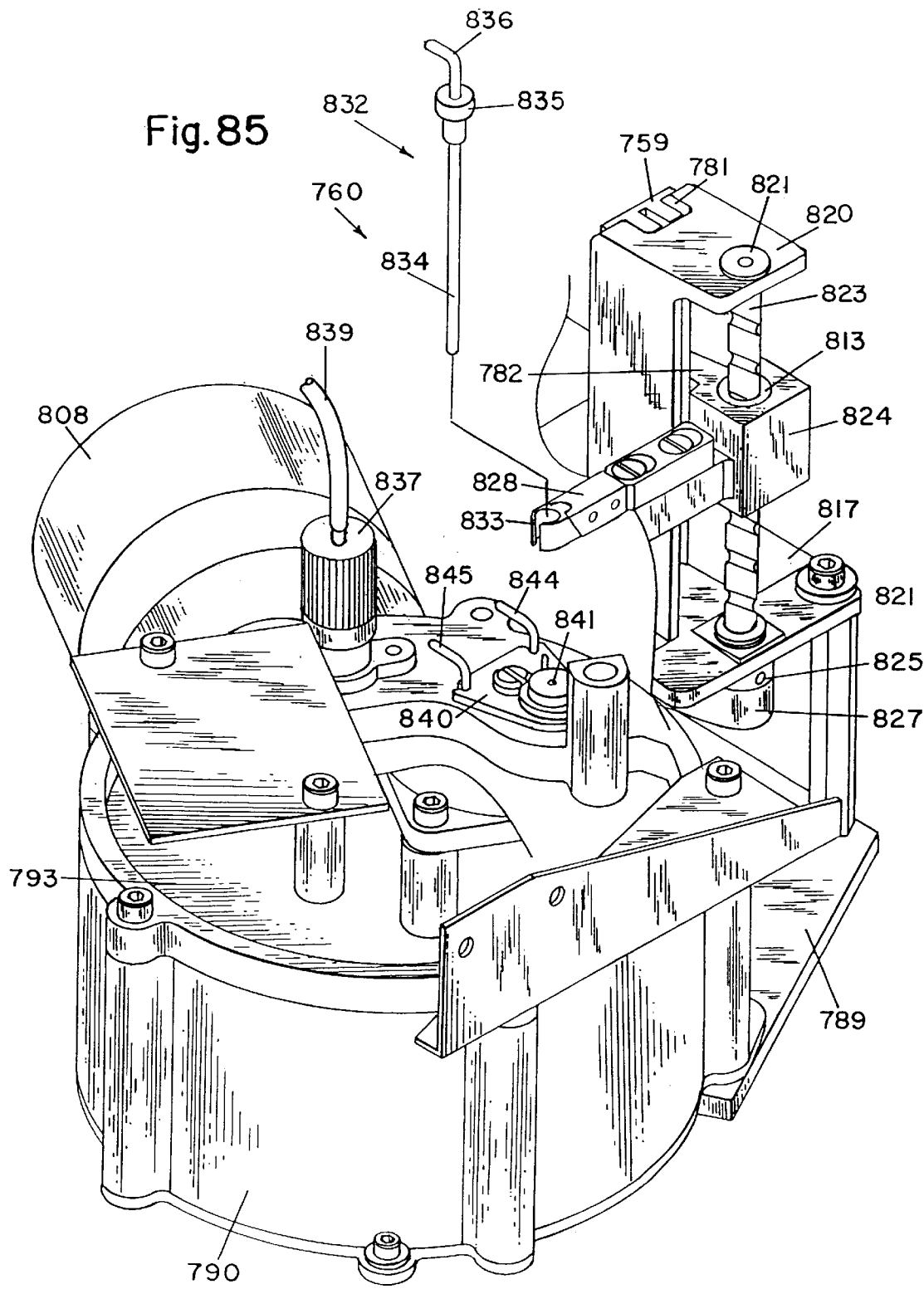
Figure 86:
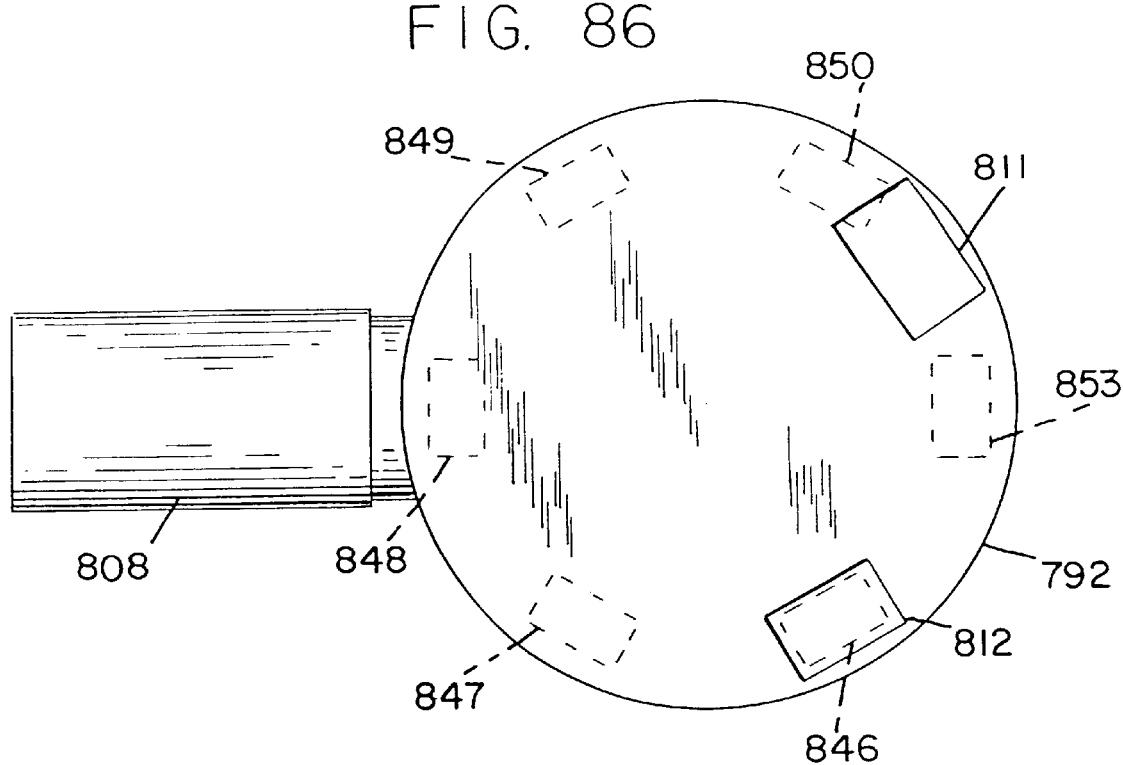
Figure 87A:
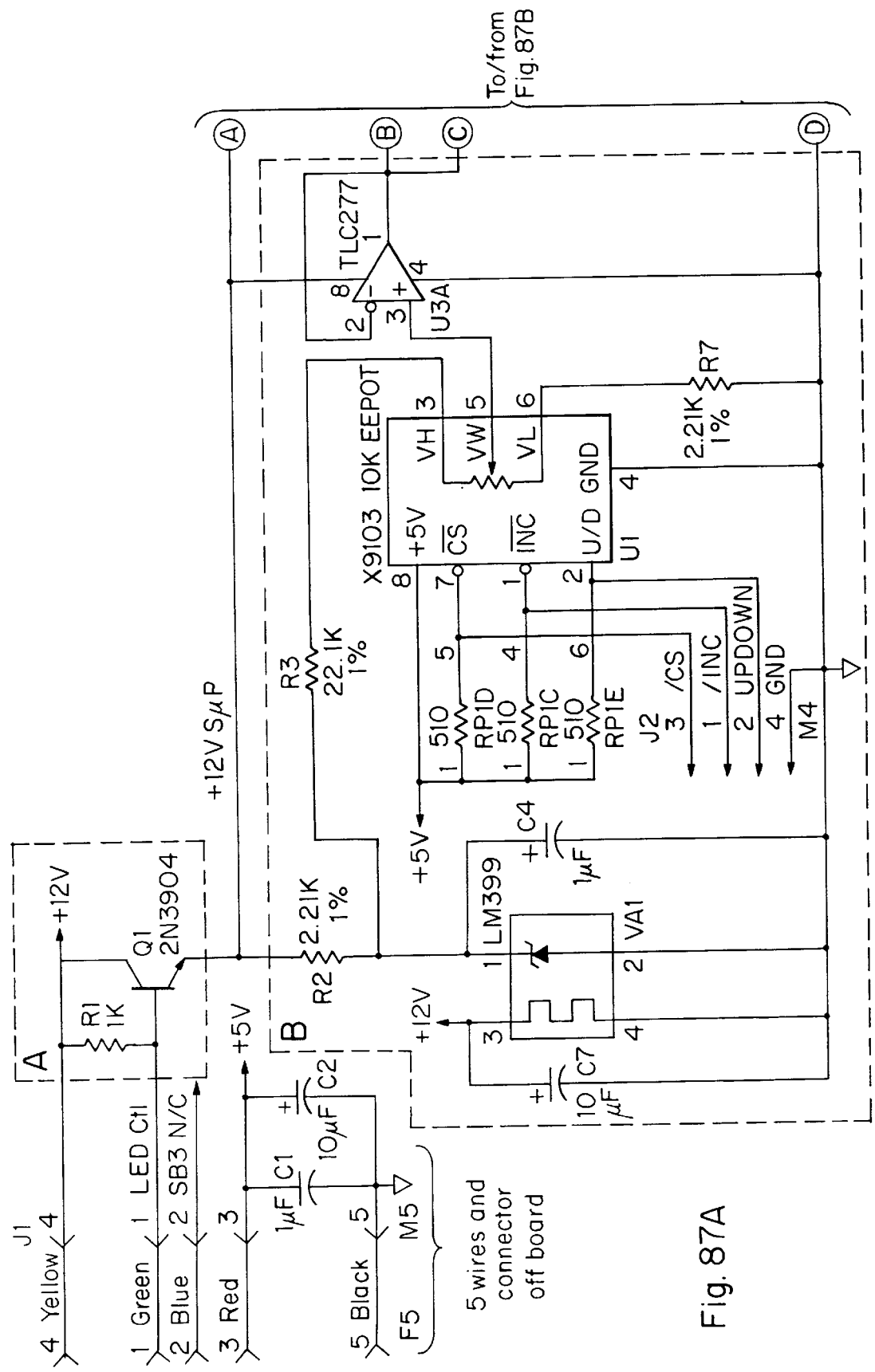
Figure 87B:
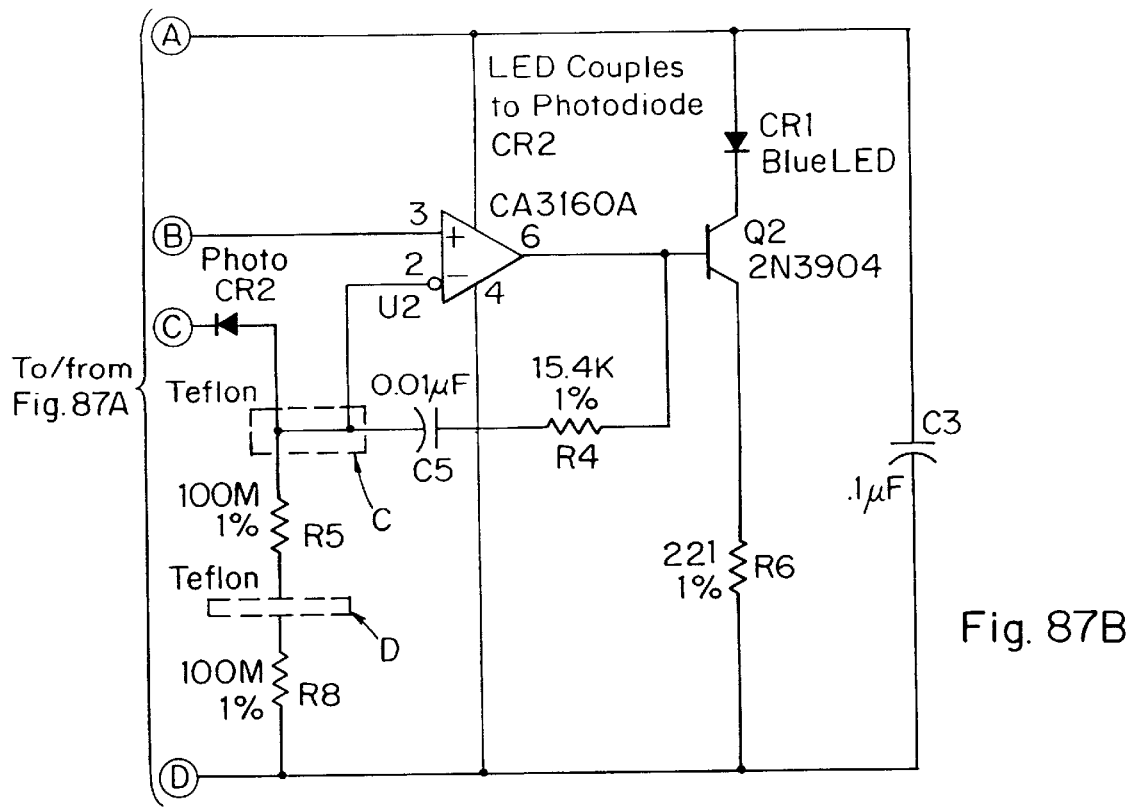
Figure 88:
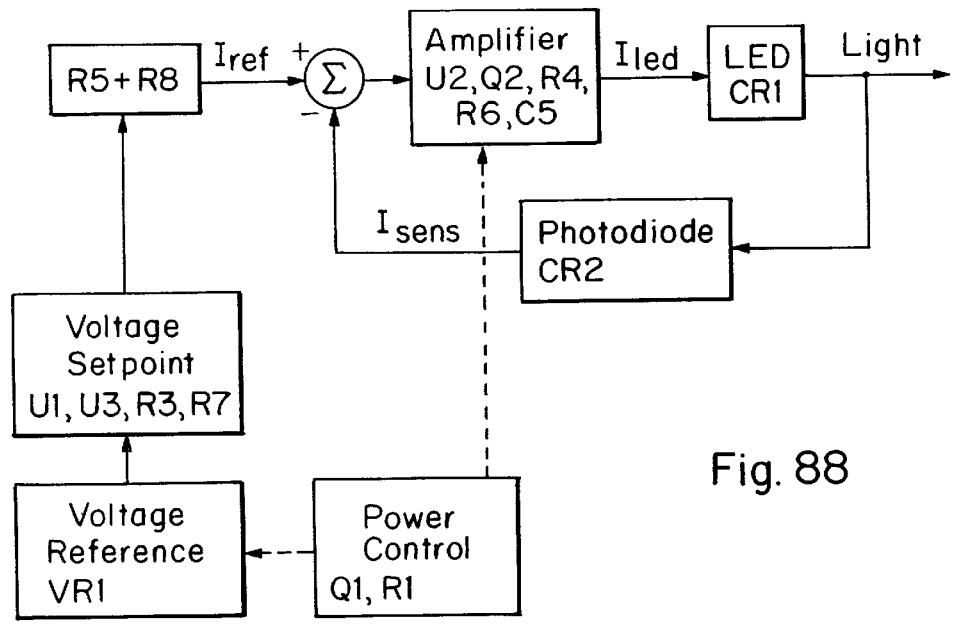
Figure 89:
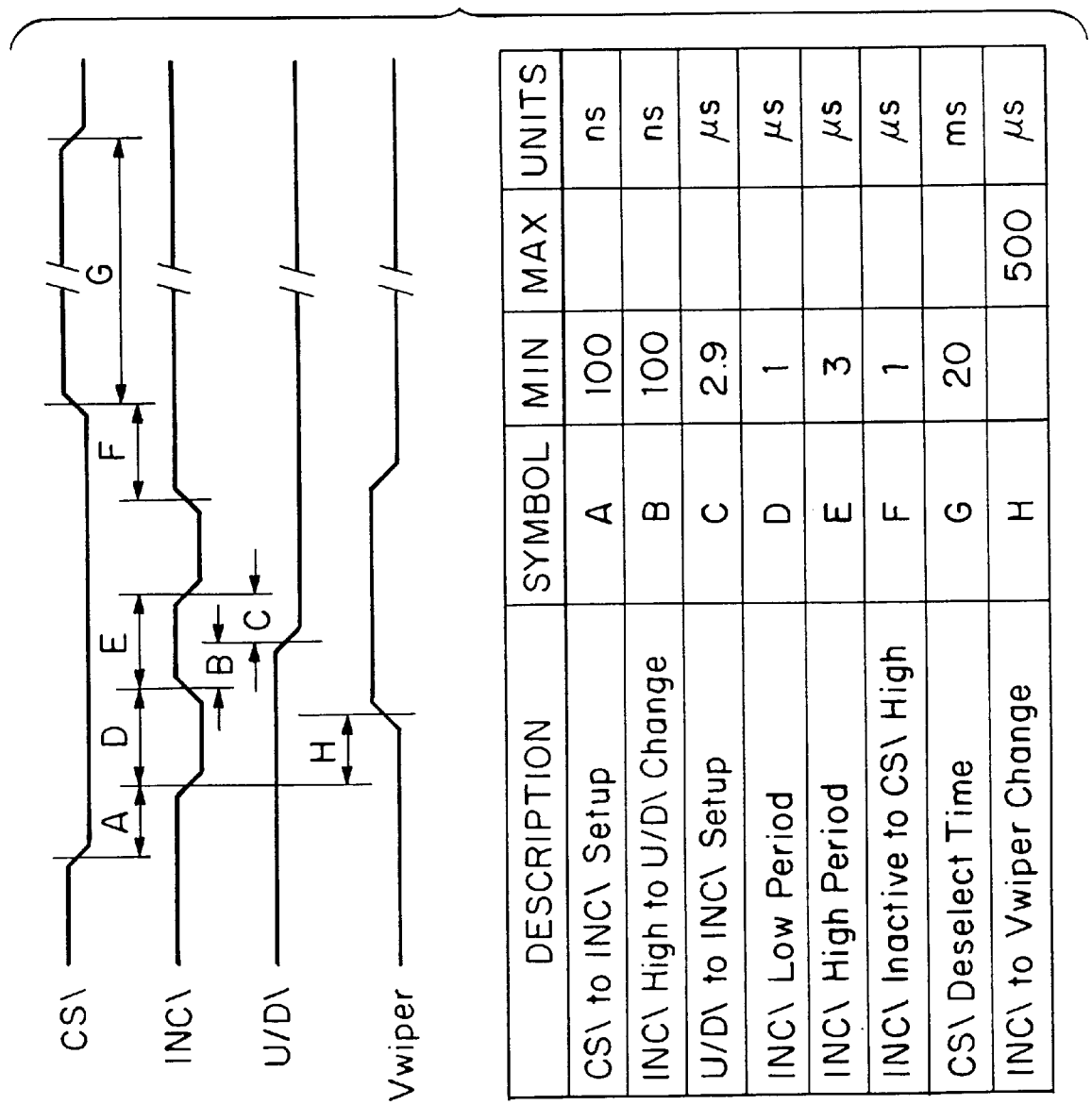
Figure 90:
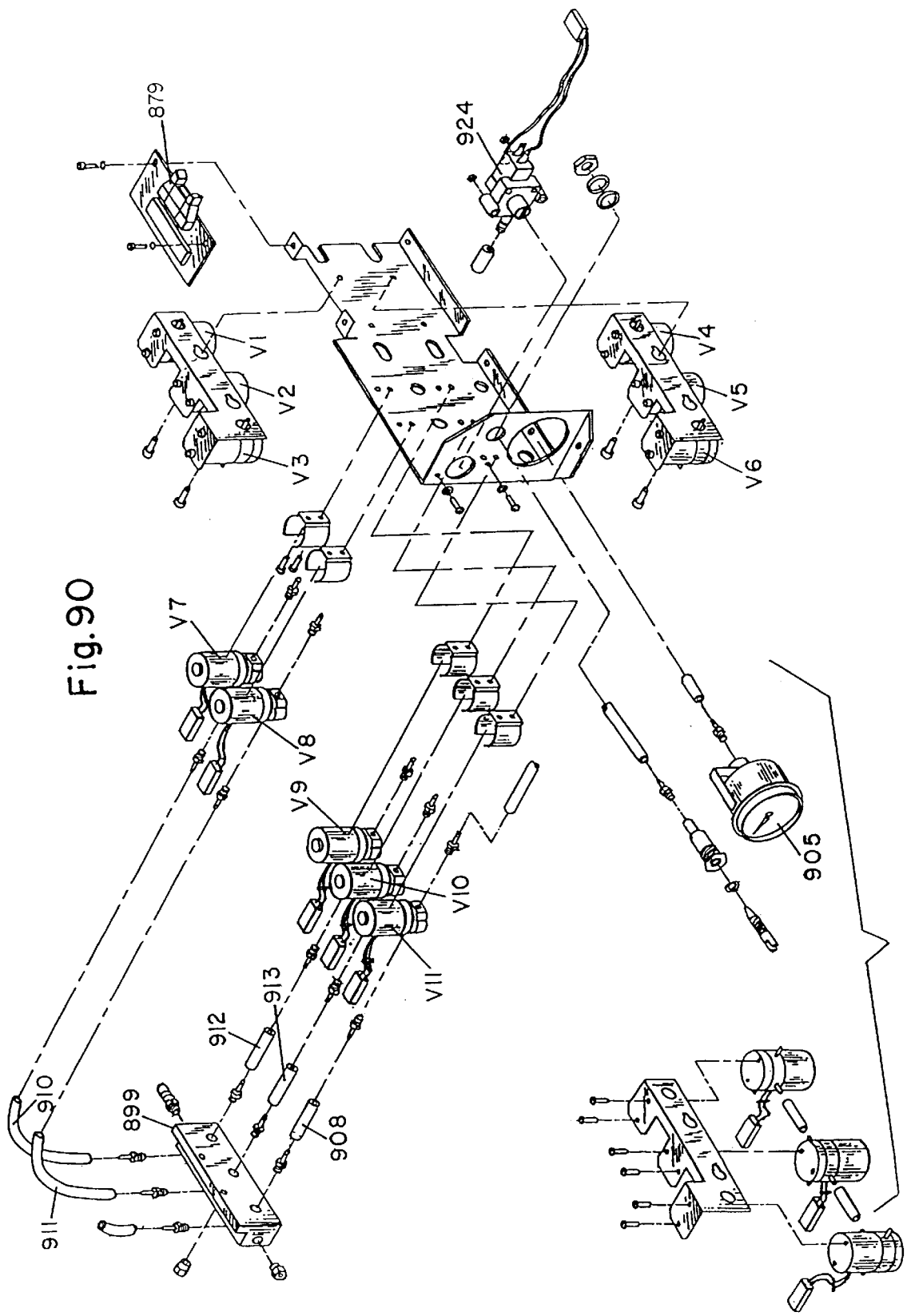
Figure 91:
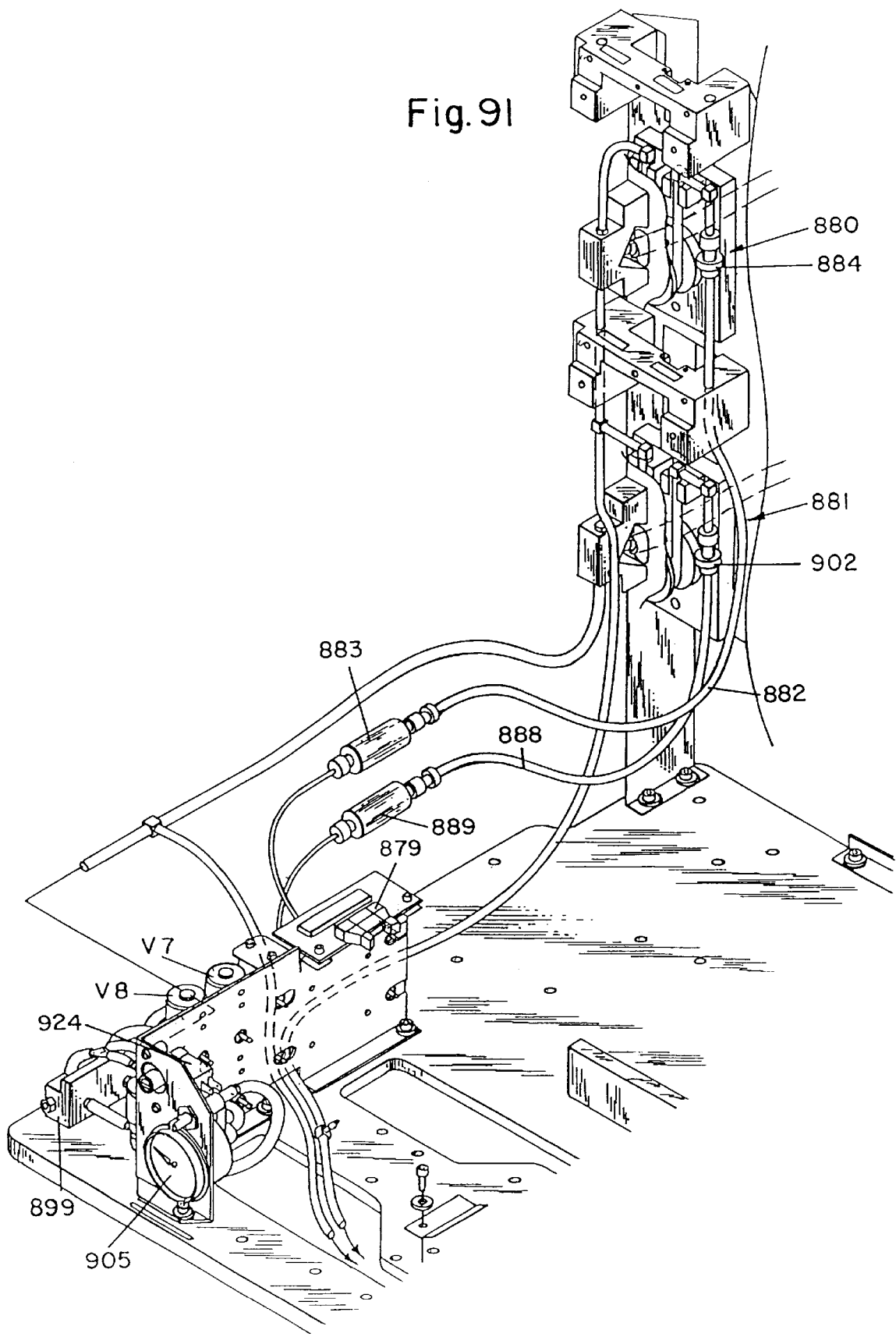
Figure 92:
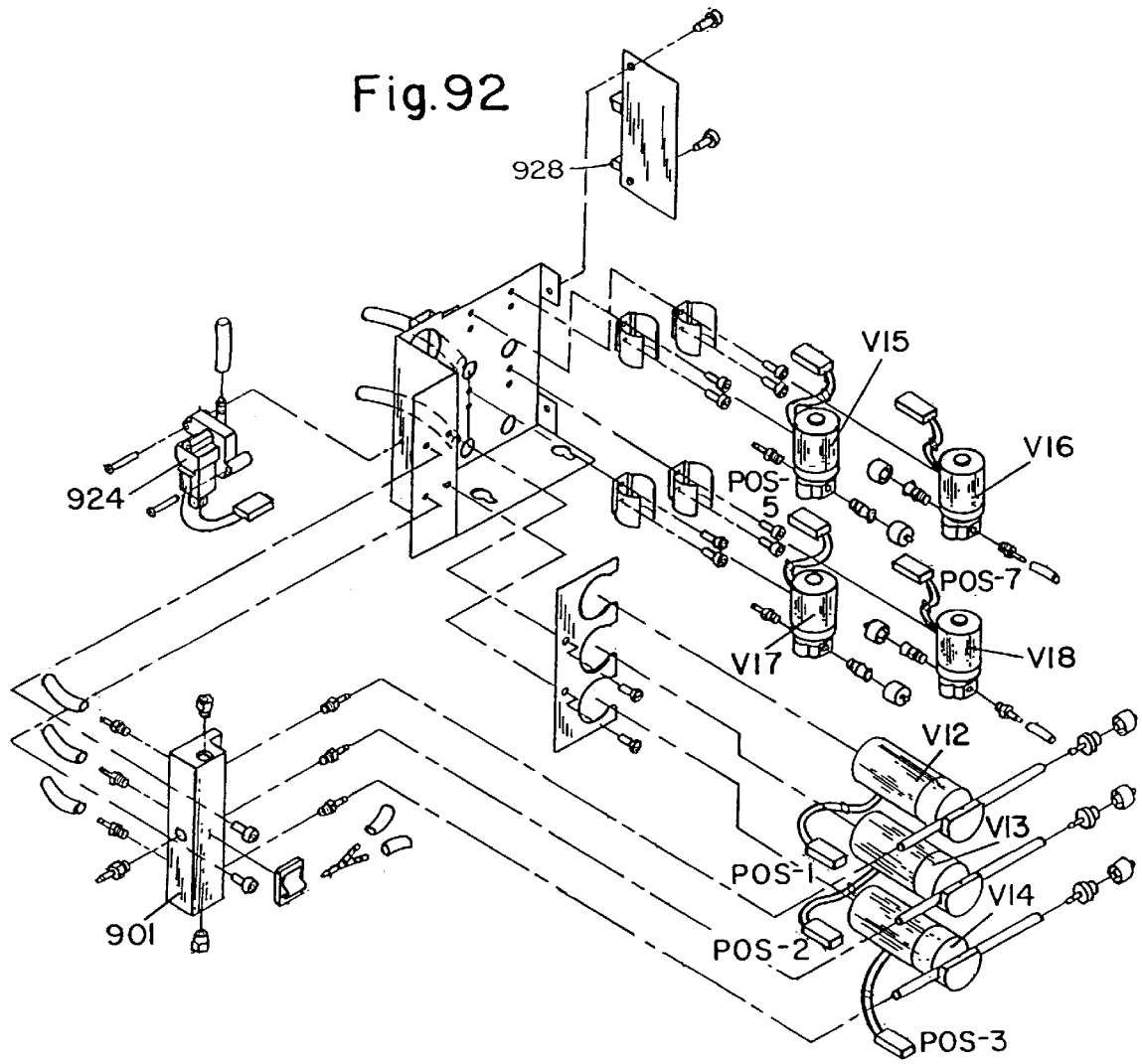
Figure 93A:
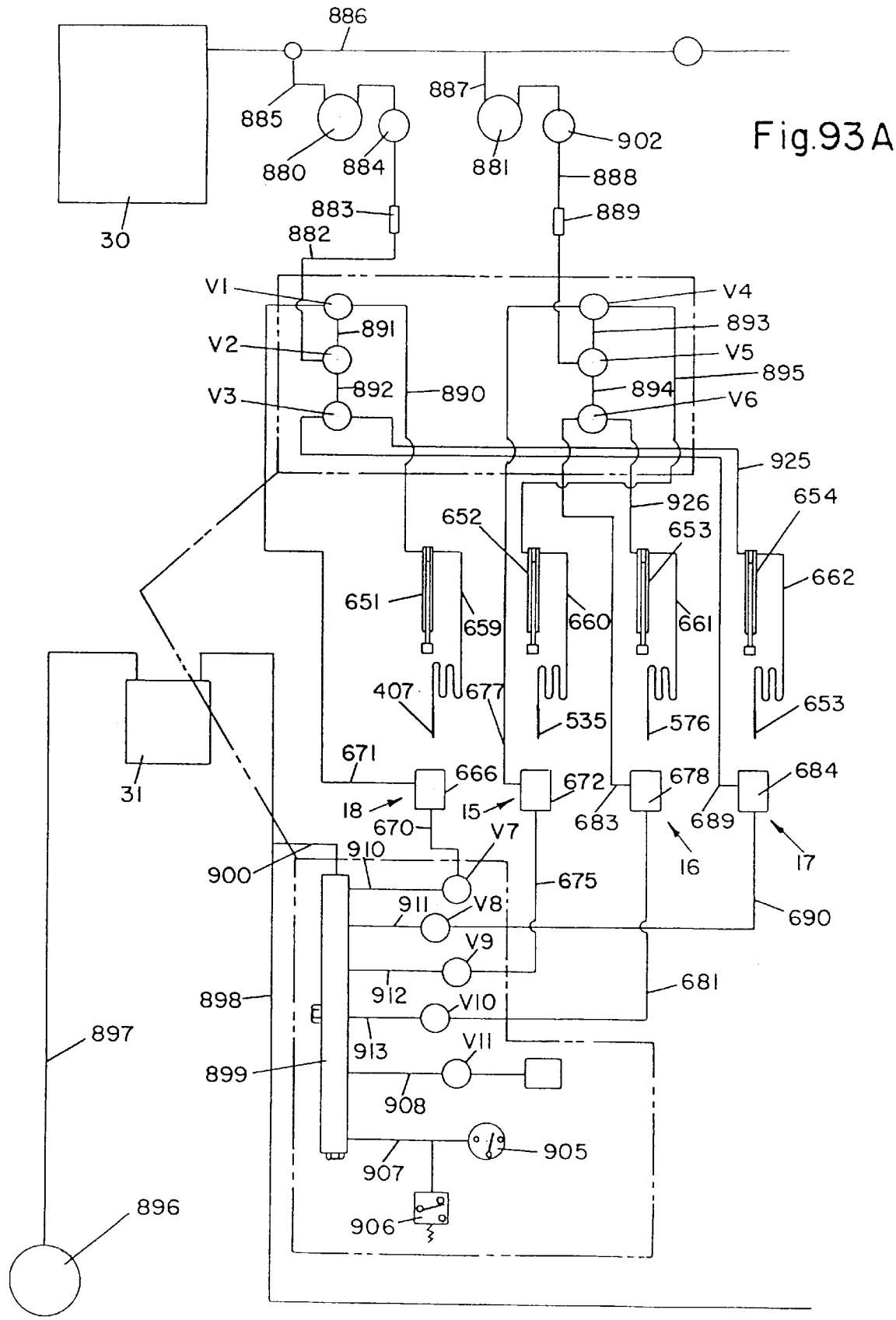
Figure 93B:
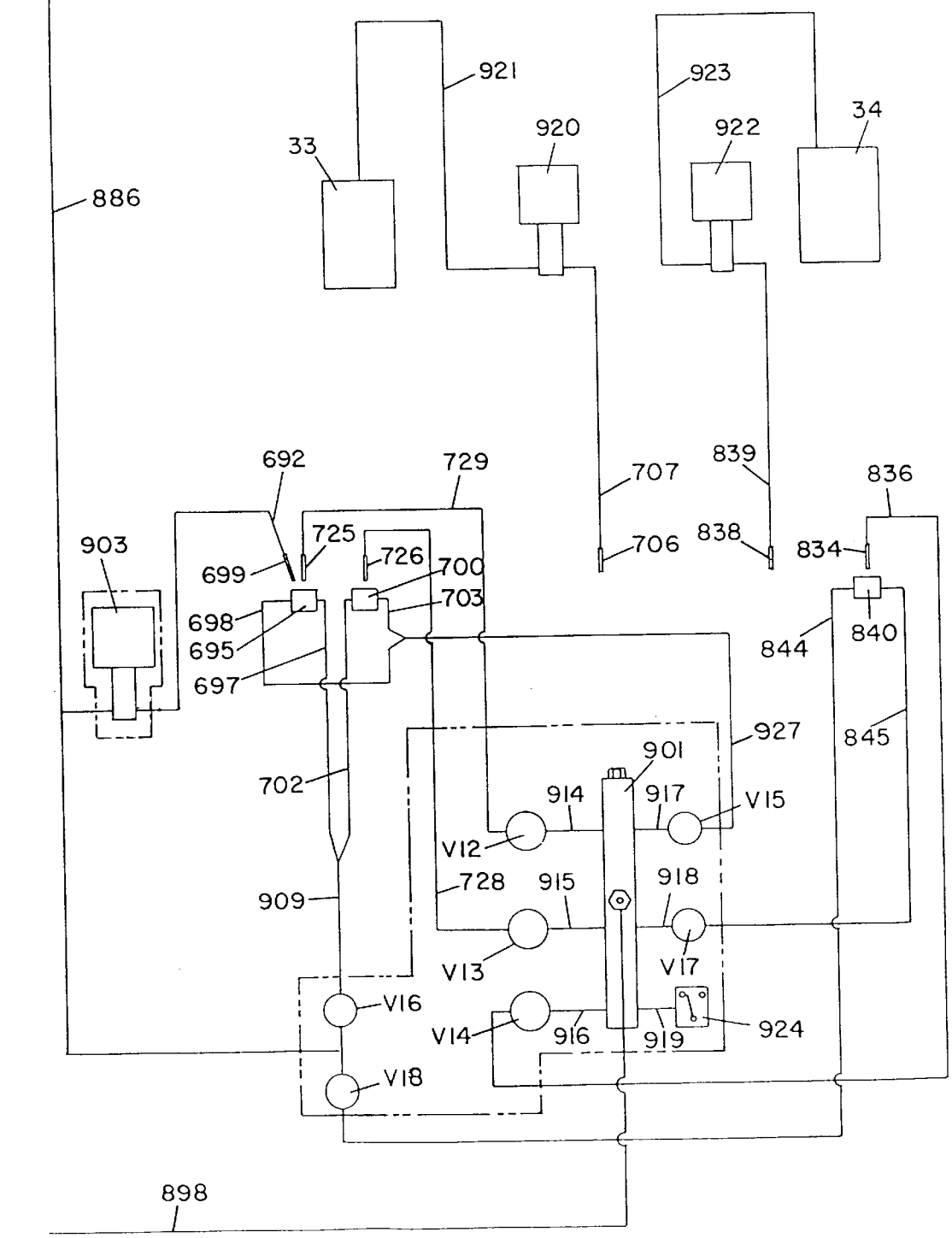

PIG. 10 is a top plan view of the container;

FIG. 11 is a bottom plan view of the container;

FIG. 12 is a perspective view of the container;

FIG. 13 is a vertical cross-sectional view of the container taken along the line 13—13 and looking in the direction of the arrows;

FIG. 14 is a bottom plan view of a cover for a container including the container which is shown in FIG. 9;

FIG. 15 is a vertical cross-sectional view of the cover taken along the line 15—15 and looking in the direction of the arrows;

FIG. 16 is a side elevational view of a reagent container, specifically for solid phase reagent;

FIG. 17 is a top plan view of the solid phase reagent container;

FIG. 18 is a bottom plan view of the reagent container;

FIG. 19 is a vertical cross-sectional view of the reagent container, taken along the line 19—19 of FIG. 17 and looking in the direction of the arrows;

FIG. 20 is a perspective view of the reagent container with portions broken away;

FIGS. 21A and 21B, when viewed together, is a front elevational view of the analyzer of the present invention, the sheets being joined along the line 21A;

FIG. 22 is a top plan view of the analyzer, with portions broken away;

FIG. 23 is an end view of the analyzer;

FIG. 24 is an exploded perspective view of a system for feeding cuvettes from a storage hopper;

FIG. 25 is a perspective view of a cuvette storage hopper;

FIG. 26 is an exploded perspective view of the cuvette feed system and hopper;

FIG. 27 is a front elevational view of the cuvette feed system;

FIG. 28 is a rear elevational view of the cuvette feed system;

FIG. 29 is a right side elevational view of the cuvette feed system, with portions broken away;

FIG. 30 is a plan view of the hopper and feed system;

FIG. 31 is a fragmentary view of a feed chute which forms part of the cuvette feed system, with portions broken away;

FIGS. 32A, 32B and 32C, when taken together, form a front view of a conveyor system for feeding cuvettes from the hopper feed system through the vent areas of the machine, the sheets being joined along the lines 32A and 32B;

FIGS. 33A, 33B and 33C, when viewed together, form a top plan view of the cuvette conveyor system the sheets being joined along the lines 33A and 33B;

FIG. 34 is a vertical cross-sectional view showing magnetic means for attracting paramagnetic particles from the test sample and reagent mire in a cuvette taken along the line 34A—34A of FIG. 33C and looking in the direction of the arrows;

FIG. 35 is a vertical cross-sectional view showing another aspect of the magnetic means for attracting the paramagnetic particles from the test sample and reagent mixture within a cuvette taken along the line 35A—35A of FIG. 33C and looking in the direction of the arrows;

FIG. 36 is a front elevational view of a sample transport system;

FIG. 37 is a top plan view of the sample transport system;

FIG. 38 is a vertical cross-sectional view of the sample transport system taken along the line 38A—38A of FIG. 37;

FIG. 39 is an exploded perspective view of some of the elements of the sample transport system;

FIG. 40 is an exploded perspective view of one of the drive mechanisms for the sample transport system;

FIG. 41 is an exploded diagrammatic elevational view of the sample transport system;

FIG. 42 is a perspective view of one of the drive elements of the sample transport system;

FIG. 43 is a top plan view of a reagent transport system;

FIG. 44 is a front elevational view of a reagent transport system;

FIG. 45 is a vertical cross-sectional view of the reagent sport system;

FIG. 46 is an exploded perspective view of some of the elements of the reagent transport system;

FIG. 47 is an exploded perspective view of additional elements of the reagent transport system;

FIG. 48 is an exploded perspective view of one of the drive elements for the reagent transport system;

FIG. 49 is a diagrammatic elevational view of the reagent transport system;

FIG. 50 is a front elevational view of a sample probe transport system;

FIG. 51 is a diagrammatic right side elevational view of the sample probe transport system;

FIG. 52 is a right side elevational view of the sample probe sport system;

FIG. 53 is a plan view of the sample probe transport system;

FIG. 54 is an exploded perspective view of some of the elements of the sample probe transport system;

FIG. 55 is an exploded perspective view of the horizontal drive components of the sample probe transport system;

FIG. 56 is an exploded perspective view of a sample probe supporting carriage which forms part of the sample probe transport system;

FIG. 57 is an exploded elevational view of one of the drive components for the sample probe transport system;

FIG. 58 is an exploded perspective view of one of the horizontal drive components for the sample probe transport system;

FIG. 59 is an exploded perspective view of one of the vertical drive components for the sample probe transport system;

FIG. 60 is a top plan view of a reagent probe transport system;

FIG. 61 is a right side elevational view of the reagent probe transport system;

FIG. 62 is a front elevational view of the reagent probe transport system;

FIG. 63 is an exploded perspective view of some of the elements of the reagent probe transport system;

FIG. 64 is an exploded perspective view of the components of the left hand reagent probe;

FIG. 65 is an exploded perspective view of the central reagent probe components;

FIG. 66 is an exploded perspective view of the right reagent probe components;

FIG. 67 is an exploded perspective view of one of the horizontal drive elements of the reagent probe transport system;

FIG. 68 is an exploded perspective view of one of the drive components for moving the left probe vertically;

FIG. 69 is an exploded perspective view of the probe supporting elements for the central probe of the reagent probe transport system;

FIG. 70 is an elevational view of a post which forms part of the mechanism for rotating the left probe about a vertical axis;

FIG. 71 is an exploded perspective view of the probe supporting elements for the right probe of the reagent probe transport system;

FIG. 72 is an exploded perspective view of the probe supporting elements for the left probe of the reagent probe transport system;

FIG. 73 is an exploded perspective view of the syringe bank for the sample and reagent probes;

FIG. 74 is a cross-sectional view of a heating system for a tube which extends from one of the reagent probes to its corresponding syringe;

FIG. 75 is an exploded perspective view of an event conveyor system and all of the wash stations for the sample and reagent probes;

FIG. 76 is a perspective view of the right hand end of the analyzer which illustrates the aspirate resuspend area of the event track and the luminometer;

FIG. 77 is an exploded perspective view of the aspirate resuspend components;

FIG. 78 is a cross-sectional view of one of the aspirating probes;

FIG. 79 is a vertical cross-sectional view of a cuvette wash apparatus which forms part of the aspirate resuspend section of the event conveyor taken along the line 79A—79A of FIG. 33C;

FIG. 80 is a vertical cross-sectional view of the acid resuspend mechanism taken along the line 80A—80A of FIG. 33C;

FIG. 81 is a right hand elevational view of a luminometer and elevator mechanism which conveys cuvettes to the luminometer at the end of the event conveyor;

FIG. 82 is a top plan view of the luminometer;

FIG. 83 is a vertical cross-sectional view of the luminometer and cuvette elevator;

FIG. 84 is an exploded perspective view of some of the elements of the luminometer;

FIG. 85 is a perspective view of the luminometer;

FIG. 86 is a diagrammatic plan view showing the path of the cuvettes within the luminometer;

FIGS. 87A–B is a schematic diagram of a preferred embodiment of a reference LED module;

FIG. 88 is a block diagram of the module;

FIG. 89 is a diagram of the preferred timing scheme of an electronically adjustable potentiometer in the reference LED module;

FIG. 90 is an exploded perspective view of the valve modules which are located at the left side of the analyzer;

FIG. 91 is a perspective view of the left side valve components and peristalic pumps;

FIG. 92 is an exploded perspective view of the valve components at the right hand side of the analyzer;

FIGS. 93A and 93B is a schematic view of all of the pneumatic and plumbing components for the analyzer;

FIGS. 94–102 are flow diagrams of the coordinated operation of the various subunits of the analyzer.

It is noted that the representations shown in the FIGS. may not indicate actual scales or ratios.

GLOSSARY

The following terms as used in this specification and claims are defined as follows:

ACID REAGENT:
  0.1 N $HNO_3$ with 0.5% peroxide; added to the magnetic particles after the wash cycle. The peroxide attaches to the acridinium ester at a low pH pH1). This reaction readies the acridinium ester for light emission.

ACRIDINIUM ESTER (AE):
  The chemical "label" responsible for the chemiluminescent flash when base reagent is added to the acidified magnetic particle/analyte/AE mixture in the cuvette. See U.S. Pat. Nos. 4,745,181, 4,919,192 and 4,946,95, which are incorporated by reference.

ANALTE:
  A substance of unknown concentration present or suspected of being present in a test sample.

ANTIBODY (Ab):
  1) a protein produced by the body in response to the presence of a foreign substance; part of the body's resistance to disease 2) proteins or carbohydrates containing proteins having the ability to combine with a specific antigen.

ANTIGEN (Ag):
  1) a substance foreign to the body which when introduced into the body stimulates the production of antibodies 2) under analysis conditions; a protein or non-protein compound capable of reacting with a specific antibody.

ASSAY:
  a diagnostic or analytical protocol for determining the presence and amount or absence of a substance in a test sample, said assay including immunoassays of various formats.

BASE REAGENT:
  0.25 N NaOH, pH 13, and ARQUAD; added to the magnetic particles suspended in acid when the cuvette is in the luminometer. When injected, the pH shift and accompanying electron excitation causes light emission at a specific wavelength (a flash). See U.S. Patent No. 4,927,769 which is incorporated by reference.

BUFFER:
  A solution used for pH maintenance; composed of a weak acid (or base) and its salt CALIBRATOR:
  A protein based solution (often human based) containing known concentrations of analytes providing a reference curve for converting measured signal into concentration.

CALIBRATION CURVE:
  A pair of calibrators are run as samples and the calibrator data is normalized against the stored Master Curve data for the tested analyte, compensating for current running conditions and instrument variability.

CHEMILUMINESCENCE:
  A chemical reaction in the production of light.

COMPETITIVE ASSAY:
  An Ab/Ag reaction where the unknown Ag in a sample and a labeled Ag in reagent compete for a limited amount of reagent labeled Ab.

CONTROL:
  A protein based product containing specific analytes within a predetermined concentration range; i.e., low, medium, high. Many controls are human serum based. Controls are used as a total system performance check.

COUNTS:
  The basic unit of measurement of PMT signal after processing by the PAD electronics.

COUNT PROFILE:
  Counts vs time; information is stored in files in system and can be plotted.

DARK COUNTS:
  The electronic noise of the PMT the absence of light

DILUENT (DIL):
   A protein based solution; used to dilute a patient sample when the original result is beyond the curve range.
FLASH:
   A short-lived burst of light produced from the immunoassay when the pH is rapidly changed from acidic to basic (with the addition of the base reagent).
HAPTEN:
   An incomplete antigen being incapable alone of causing the production of antibodies but capable of combining with specific antibodies.
IMMUNOASSAY:
   A chemical test involving an antibody/antigen reaction to determine the presence of and/or quantify a specific substance; the substance being assayed may be the antibody or antigen in the reaction.
LIGHT COUNTS:
   The electronic signal of the PMT in the presence of light, including dark counts.
MASTER CURVE:
   A ten point curve generated by Quality Control for each matched set of SP and Lite reagents, data is published in assay's package insert and programmed into instrument by operator; used by instrument as the master reference curve for converting measured signal into concentration.
NSB:
   non-specific binding—All tracer material which is present during the measurement phase but does not represent specific Ab binding. Tracer material may attach indiscriminately to cuvette wall or particles and does not wash away, resulting in signal that mimics an Ab/Ag reaction.
PAD:
   Electronics that amplify the Pi signal (pulse) and filter it for signal sot generated by photons.
PHOTON:
   A unit of right.
PMP:
   Para-magnetic particles; used in Solid Phase reagent
PMT:
   Photomultiplier tube—a vacuum (or gas-filled) phototube with a cathode, usually nine dynodes, and an anode. The cathode is capable of emitting a stream of electrons when exposed to light. The dynode arrangement provides, successive steps in amplification of the original signal from the cathode. The resulting signal produced is directly proportional to the amount of illumination.
PRE-TREATMENT AGENT (TRX):
   A solution mixed and incubated with sample to protect the analyte from releasing agent.
RELEASING AGENT (REL):
   A solution mixed with sample for the purpose of separating the analyte from another molecule and rendering it available for immuno-reaction.
RLU:
   Relative light units; used on the manual Magic® Lite analyzers. A unit of light measurement calibrated against a tritium source and unique for each instrument.
SANDWICH ASSAY:
   An Ab/Ag reaction where unknown Ag reacts with two forms of reagent labeled Ab; a solid phase or physical carrier reagent and a signal producing reagent, resulting in a Ab/Ag/Ab "sandwich".

SOLID PHASE REAGENT (SP):
   A physical carrier reagent coupled with antigen or antibody (as required by assay) in a buffer. See U.S. Pat. Nos. 4,554,088 and 4,672,040.
SYSTEM FLUID (system water, system diluent):
   All system syringes are water backed with D.I. water from the on-board supply; used to follow sample and reagent dispense to cuvette, wash all probes, wash magnetic particles in cuvette at aspirate/resuspend position in track.
TEST SAMPLE:
   A specimen for testing; including biological fluids, e.g. serum, urine, cellular products, controls, calibrators, etc., non biological fluids, e.g. chemical compounds, drugs, etc., and any other fluid of interest for which an assay protocol may be formatted.
TOTAL COUNTS:
   1) the area under the flash curve 2) counts per read interval.
TRACER REAGENT (Lite Reagent (LR)):
   Antibody or antigen (as required by assay) labeled with acridinium ester in a barbitol buffer (synonym—tracer).
TRITIUM:
   A radioactive light source in a sealed scintillation solution; it emits light and serves as a calibration reference for evaluating luminometer performance. (Los Alamos Diagnostics product insert; PN 71-002 & 61-006).

DESCRIPTION OF THE PREFERRED EMBODIMENT

General Organization of Machine Subunits

The analyzer requires on-board supplies of cuvettes, deionized water, and the acid and base reagents. Sensors monitor volumes of liquid supplies and indicate necessary refilling before the assay run is initiated. Additional cuvettes may be loaded at any time, even while the instrument is operating. Waste liquid is collected in an on-board removable reservoir, and used cuvettes are collected in a waste bin, after aspiration of all liquid waste. The analyzer advises the operator when either of these waste collectors are in need of emptying.

Figure 1:
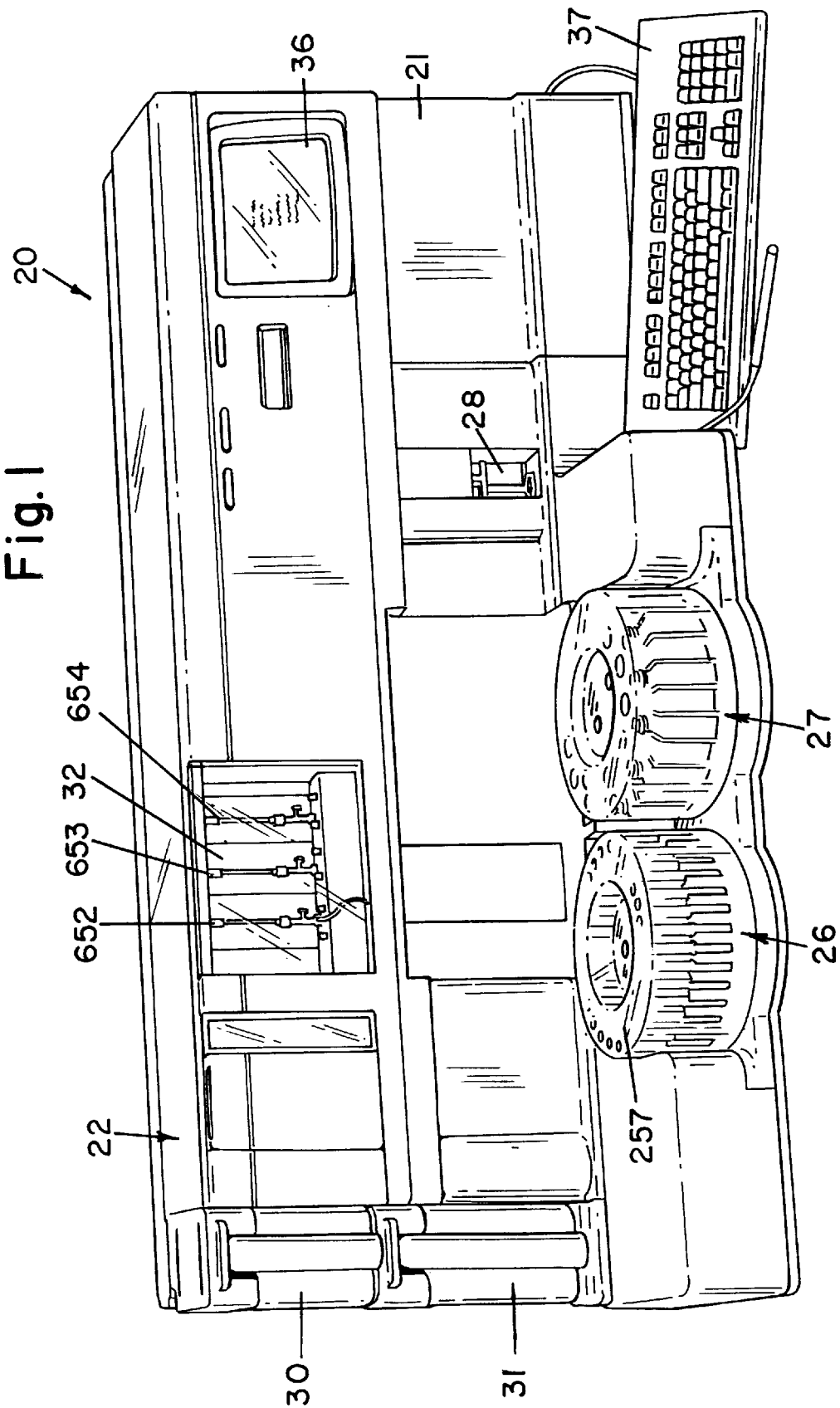
FIG. 1 is a front perspective view of the analyzer of the present invention.
Figure 5:
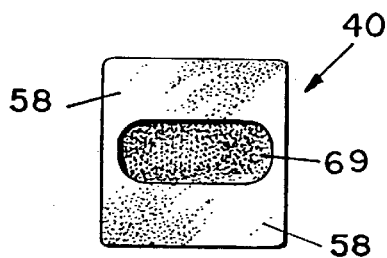
FIG. 5 is a top plan view of the cuvette.
Figure 4:
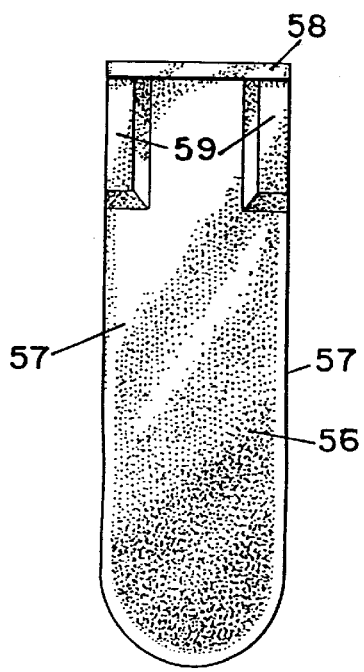
FIG. 4 is a front elevational view of a cuvette which is used with the automated analyzer of the present invention for holding sample and reagent.
Figure 7:
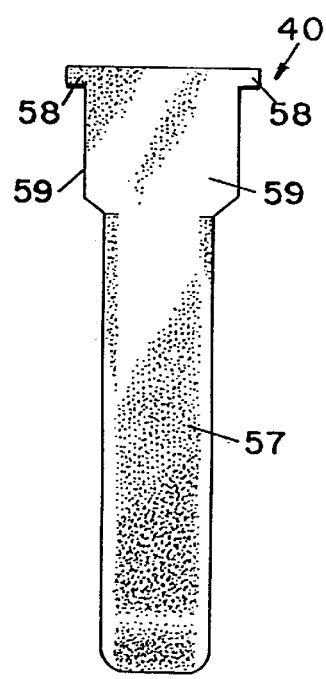
FIG. 7 is a side elevational view of the cuvette.
Figure 8:
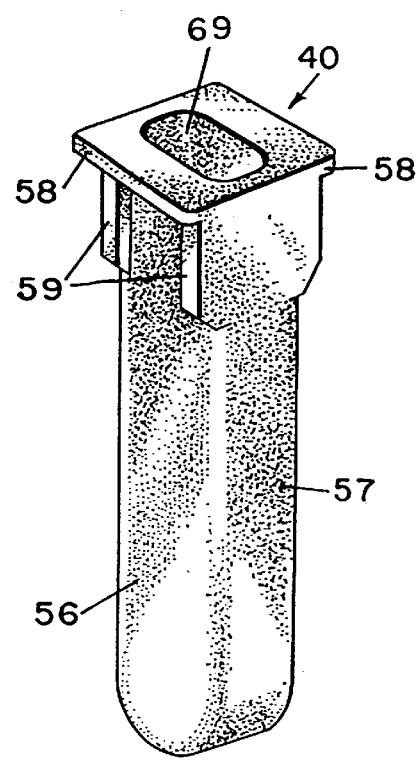
FIG. 8 is a perspective view of the cuvette.
Figure 6:
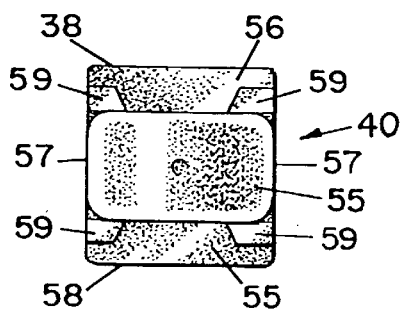
FIG. 6 is a bottom plan view of the cuvette.

Referring first to FIGS. 1, 2 and 3, the automated analyzer of the present invention and includes a housing 21 which contains or supports a plurality of subunits for performing the various steps for completion of a plurality of binding assays on fluid samples, e.g. blood serum. The analyzer is specifically adapted to perform heterogeneous immunoassays having various formats. The subunits include a cuvette hopper and feeder mechanism which is generally indicated by the reference numeral 22, a cuvette conveying system 23, a sample probe transport system 24, a plurality, of reagent probe transport systems R1, R2 and R3, a sample transport system which is generally indicated by the reference numeral 26, and a reagent transport system which is generally indicated by the reference numeral 27. A detection device 29 is located at the end of and above the conveyor system 23. The detection device of the preferred embodiment is a luminometer. Other devices, e.g. fluorimeter, isotope emitter counters, etc. are known in the arts. The uses of such other devices is determined by the type of label that is utilized in a test reaction. This system 20 also includes a syringe bank 32, a central processing unit (CPU). not shown, which is operably connected to a cathode ray tube (CRT) 36 and keyboard 37. The syringe bank 32 is operatively connected to the sample probe transport system 24 and reagent probe transport systems R1, R2 and R3.

A wash station for the sample aspirating and dispensing probe is located behind the sample transport system and is generally indicated by the reference numeral 18. Additional wash stations, generally indicated by the reference numerals 15, 16 and 17, for the reagent aspirating and dispensing probes are located behind the reagent transport system 27, see also FIGS. 21A, 21B and 22.

Referring particularly to FIG. 3, the conveyor system 23 is divided into two sections, a cuvette preheater section which is generally indicated by the reference numeral 38 and a cuvette dispense and incubation section which is generally indicated by the reference numeral 39. The cuvettes 40 are stored in a random manner in a hopper 22 and conveyed to the end of the preheater section 38 in an upright orientation. A plunger 19 is fixed to the end of a lead screw 41 which is driven horizontally by an electric motor 25 along its central longitudinal axis and the axis of the preheater section 38. The plunger 19 is moved from an outer retracted position to an extended position as shown in FIG. 3 to push a cuvette which has just been deposited on the preheater section 38 one cuvette space towards the incubation section 39. This advances all of the cuvettes 40 along the preheater section 38 so that the furthest cuvette is transferred onto the incubation section 39. The plunger 41 is then moved back to the retracted position to engage the next cuvette which will drop into the starting position. The lead screw 41 does not rotate about its axis. Cuvette sensors, generally indicated by the reference numeral 43, are positioned at the end of the preheat section 38 and at the beginning of the incubation section 39 to monitor the presence of cuvettes at these locations. The cuvettes 40 are conveyed along the incubation section 39 by conveyor means, described below, which is driven by a motor 42. As each cuvette reaches a sample dispense point 44 along the incubation section 39, a probe, described below, from the sample probe transport system 24 aspirates a predetermined amount of fluid to be analyzed from a container, described below, in the sample transport system 26 and deposits the sample in the cuvette at the sample dispense point 44. When the cuvette reaches any one of three predetermined positions 45, 46 or 47 adjacent the reagent transport system 27, a pair of reagents from the reagent transport system 27 is added to the fluid sample in the cuvette to initiate a test reaction for forming a detectable product by one or more of the reagent probes from the reagent probe systems R1, R2 or R3. The sequence of reagent addition into the cuvette is determined by the assay protocol selected for the test sample. Variation in reagent addition occurs for example when an incubation of test sample and one of the reagents is required. The reagents comprise a solid phase reagent and a labeled reagent (tracer reagent) which, in the preferred embodiment is of a luminescent compound.

The solid phase reagent in the preferred embodiment is paramagnetic particles having a binding substance coupled thereto. Alternate solid phase materials are known in the arts as well as separation techniques for isolating the said solid phase materials. The detectable product that is formed in the preferred embodiment is a complex that includes the solid phase reagent, analyte that is being assayed and the labeled reagent. The complex will vary depending on the format of the assay. Examples of binding assay formats which generate a detectable product include competitive and sandwich type reactions, each of which may be performed by the analyzer of the present invention. Thereafter, the cuvette passes an aspirate/resuspend area which is generally indicated by the reference numeral 28, which prepares the mixture for a "flash" or light emitting reaction in the luminometer 29. Referring particularly to FIG. 3, the aspirate resuspend area 28 of the preferred embodiment includes a magnetic apparatus 49. An aspirate/wash probe is located at point 50. An aspirate probe is located at point 51 and an acid resuspension probe is located at point 52.

When the cuvette reaches the end of the incubation section 39, it is lifted vertically by an elevator mechanism at point 53 to the luminometer 29. When the cuvette which contains the acid resuspended detectable product has been properly positioned within the luminometer, a base solution is added which results in a chemiluminescent detection reaction ("flash"). The "flash" effects a photomultiplier tube which counts photons from the "flash" and produces an electrical signal. The signal is processed by the central processing unit and an appropriate value reading is recorded. Deionized water is used for a system backing fluid and for many of the washing steps for typical assay protocols and is stored in a removable reservoir 30. A second removable reservoir 31 is located below the reservoir 30 for accepting all fluid waste. After each assay, the contents of the cuvette are aspirated from the cuvette and discharged into the fluid waste reservoir 31. The empty cuvette is then discarded into a waste receptacle 35. Acid reagent is stored in a reservoir 33 and base reagent is stored in a reservoir 34. An example of an acid reagent which is suitable for use with the present system is: 0.1 N. $HNO_3$,pH 1.0 with 0.5% peroxide. An example of a base reagent which is suitable for use with the present system is 0.25 N.,NaOH,pH 13, and ARQUAD. Variations in the concentration of the acid and base reagents may be required depending on the chemiluminescent label. The chemiluminescent label in the preferred embodiment is an acridinium ester.

Cuvette and Reagent Containers

Referring to FIGS. 4–8, the cuvette which is used as part of the automated analyzer of the present invention is generally indicated by the reference numeral 40. Cuvette 40 is generally rectangular in cross-section and consists of a bottom wall 55, a pair of opposite broad side walls 56 and a pair of opposite narrow sidewalls 57. The cuvette 40 has an interior chamber which is accessed from a top opening 69. A pair of flanges 58 extend outwardly from the broad sidewall 56 at the top of the cuvette. A pair of spaced teeth 59 extend outwardly from each broad sidewall 56 just below the flange 58. The flanges 58 and teeth 59 are instrumental in enabling the cuvette to be conveyed and transported trough the various subsystems of the machine 20, as will be described hereafter. The cuvette can be made of polypropylene or polyethylene which have been found to produce a more even light distribution during the subsequent-flash in the luminometer than other polymers which have been tested such as polystyrene. However, polypropylene has been found to be the preferred material for obtaining reliable results.

Referring to FIGS. 9–13, one of the two types of reagent containers which are utilized in the analyzer, is generally indicated by the reference numeral 60. The container 60 is utilized for carrying a labeled reagent (tracer reagent) which is specific for certain test protocols and comprises a main body portion 64 which has an inner chamber 61, a threaded neck portion 65 and a top opening 62 at the upper end of the neck portion 65 which opens into the chamber 61. A skirt 63 extends outwardly from a point below the neck 65 and extends downwardly to a point just below the main body portion 64. The skirt 63 is spaced from the main body portion 64 and consists of three flat sides and one rounded side. The skirt 63 enables the container 60 to be securely mounted on the reagent transport means, described below.

FIGS. 14 and 15 illustrate a cover for a container including the reagent container 60 which is generally indicated by the reference numeral 66 and includes a top wall 67 which has a plurality of slits 68 which cross at the center of the top wall 67. The cover 66 is made of an elastomeric material such as natural or synthetic rubber which enables the cover to engage the top of the neck portion 65 of the container 60. The cover 66 reduces evaporation of reagent from the container 60 and the slits 68 enable a reagent aspirating and dispensing probe to penetrate the top wall 67 to access the reagent fluid within the container. The slits 68 all intersect at the center of the top wall 67 to form a plurality of pie-shaped flaps which converge at the center of the cover and give way when pressure is applied to the center of the cover. The bottom of the cover 66 has an outer annular flange 70.

FIGS. 16–20 illustrate a second reagent container which is used with the analyzer and which is generally indicated by the reference numeral 75 for holding a solid phase reagent. The container 75 has a generally cylindrical main body portion 76 which has an inner chamber 77 which extends to a top opening 78 above a threaded neck portion 79. An annular skirt 80 extends outwardly from the main body portion 76 at a point just below the neck 79 and extends downwardly to a point below the main body portion 76, as shown most clearly in FIG. 19. A pair of fins 81 extend inwardly into the chamber 77 from the inner chamber wall as shown most clearly in FIGS. 17 and 20. The fins 81 are utilized for agitating the solid phase reagent within the container in a manner described below in connection with the reagent transport system 27. The top opening 78 is also sealed by the cover 66 by inverting the cover so that the top wall 67 extends below the top opening 78 and inside of the neck portion 79 so that the flange 70 of the cover rests on top of the neck portion 79.

Cuvette Feed and Orientation Mechanism

Referring to FIGS. 24–31, the cuvette feed and orientation mechanism 22 comprises a hopper which is generally indicated by the reference numeral 87, a feed conveyor which is generally indicated by the reference numeral 86, and an orientation chute which is generally indicated by the reference numeral 131. The hopper 87 is preferably made of an optically clear plastic material. This makes it easier for the operator to determine when the level of cuvettes in the hopper is low whereby the hopper requires additional cuvettes. In addition, the elements which are below the hopper, see FIG. 30 are visible.

Referring particularly to FIGS. 25, 26 and 30, the left side wall of the hopper has a vertical opening 88 and a pair of spaced outer flanges 89 which extend outwardly from the left side wall of the hopper on opposite sides of the opening 88, as shown most clearly in FIG. 25. An upper horizontal flange 83 extends outwardly from the left and rear side walls of the hopper. The forwardmost flange 89 has an opening 84 just below the top flange 83, as shown in FIG. 25. Referring also to FIG. 25, a pair of elongated reinforcing plates 82 are fastened to the outer surfaces of the outer flanges 89 by bolts 91. The bolts 91 are also utilized to fasten the hopper 87 to a pair of chain guide plates 90 which are mounted to a hopper feeder support 92 which is, in turn, mounted on a base plate 93 by means of bolts 95. The chain guide plates 90 are separated by a plurality of tubular spacers 97 through which the bolts 91 extend. A support bracket 94 is also mounted on the base plate 93 and is fastened to the side of the hopper feeder support 92 as shown in FIG. 24. A support bar 96 is also mounted to the outside of the rear most-plate 90 by the bolts 91. A ball slide assembly 110 is mounted to the support bar 96. A mixing bar mounting plate 111 is mounted to the ball slide assembly 110. An endless conveyor chain 98 is located at the vertical side opening 88 and extends around a lower idler sprocket 101 and an upper drive sprocket 100. The sprockets 100 and 101 are mounted on bushings 102 and are rotatively mounted on the hopper feeder support 92. The upper drive sprocket 100 is driven by a stepper motor 103 which is mounted on the support 92. One section of the conveyor chain 98 is guided along grooves in the outer longitudinal edges of the guide plate 90 and is located between the inner surfaces of the flanges 89 which define the opening 88. A plurality of spaced bars 99 are located on the outside of the conveyor chain 98 and slant downwardly and forwardly toward the event conveyor. The chain 98 travels upwardly from the bottom of the hopper 87 at an angle from the vertical. An idler sprocket shaft 112 extends through the bushing 102 and rotates with the idler sprocket 101, see FIGS. 26 and 27. The forward end of the shaft 112 is fixed to a cam wheel 113 so that the cam wheel 113 rotates with the idler sprocket 101 by means of a clamp 114. A lever arm 115 is pivotally mounted on a shaft 116 which is mounted in an adjusting fixture 117 which is located at a notch 118 in the left hand edge of the hopper feed support 92. The pivoted end of the lever arm 115 has a flanged bearing 122 which enables the lever to pivot freely on the shaft 116. The opposite end of the lever arm 115 has a slot 121 which receives a pin 120 of a slider mixing 109. The mixing block 109 is fixed to the mixing block mounting plate 111 and has an upper surface 123 which slants downwardly from back to front at the same angle as the bars 99. The mixing block 109 is parallel with the section of the conveyor 98 which travels upwardly along the vertical opening 88 of the hopper and is located adjacent the bars 99. A ball bearing follower 119 is rotatively mounted on the lever arm 115 and rides in a cam slot, not shown, on the rear side of the cam wheel 113. As the cam wheel 113 rotates with the idler sprocket 101, the lever arm 115 oscillates about the shaft 116. The right hand end of the lever arm 115 as viewed in FIG. 24, moves up and down and in turn causes the mixing block 109 to move up and down. The timing of the upper movement of the block 109 is such that the block moves upwardly at the same rate as the upward movement of the conveyor chain 98. The cuvettes are stored in the hopper 87 in a random manner. The mixing block 109 serves two functions. The first function is to agitate the cuvettes within the hopper 87, and the second function is to assist in guiding the cuvettes onto the bars 99, one cuvette per bar. As the cuvettes are carried upwardly by the bars 99, the ends of the cuvettes are guided by the inner surfaces of the flanges 89 to maintain the cuvettes in position on the bars 99. As each cuvette reaches the opening 84, it slides forwardly along its respective bar 99 trough the opening 84, see FIGS. 25 and 27, in the forwardmost flange 89 and falls into the orientation chute 131.

The orientation chute 131, as viewed in FIGS. 24, 27 and 30, consists of a left hand plate 129 and a right hand plate 132 which are connected together by screws 139 and held in a spaced parallel relationship by a pair of spacer blocks 133. Each plate 132 and 129 has an upper slide surface 134 which define, therebetween, a slot 135 toward the event conveyor The slide surfaces 134 extend at a downward angle from back to front and at a downward angle toward the slot 135. As each cuvette 40 falls through the opening 84 from the conveyor chain 98 to the orientation chute 131, the bottom end of the cuvette falls into the slot 135 and the flanges 58 are supported on the slide surfaces 134. This enables the cuvette 40 to slide down the surfaces 134 in a nearly upright orientation. The chute 131 is mounted to the hopper feeder support 92 by a chute support bracket 130. A chute end plate 136 is attached to the front edges of the plates 129 and 132 by screws 137. The plate 136 stops the downward slide of the cuvettes 40. The end plate 136 has a hole 147 for receiving a position sensor 148 which is mounted on a PC board 138. The PC board 138 is mounted on the plate 136 by fasteners 149. The forward end of each slide surface 134 has a flat upper surface 127 for receiving a flat spring 128 which helps to insure that the cuvette remains in the slot 135 when the cuvette strikes the end plate 136. The forward end of the slot 135 has a widened portion or access opening 141 which is slightly greater in width than the distance between the outer edges of flanges 58, see FIG. 30. The access opening 141 between the plates 129 and 132 enables the cuvette to fall between the plates into the orientation tube 140. The cuvette falls between a pair of opposed guide surface 142 and 143 along the inwardly facing surfaces of the plates 129 and 132, respectively. The guide surface 143 has an upwardly facing jutting surface 144. The guide surface 142 has a recessed portion 145 which forms a downwardly facing undercut surface 146. The undercut surface 146 is opposed to the jutting surface 144 of the plate 132. The orientation tube 140 has a top opening 150 and a bottom opening 151 and extends from the bottom of the orientation chute 131 to the top of the preheater section 38. When the cuvette falls into the access opening 141 at the end of the orientation chute, one of the flanges 58 of the cuvette sties the jutting surface 144. This deflects the cuvette laterally toward the recessed portion 145 of the left hand plate 129. As the cuvette shifts laterally, the opposite flange of the cuvette strikes the recessed portion 145 just below the downwardly facing undercut surface 146. This traps the flange of the cuvette below the undercut portion 146 and prevents the cuvette from accidentally flipping upside down when it reaches the end of the chute 131. The cuvette, thereafter, falls in an upright orientation along the guide surface 142 and 143 into the orientation tube 140 through the top opening 150 and through the bottom opening 151 into the preheater section 38. The orientation tube 140 has a helical twist which causes the cuvette to rotate approximately 90° about its vertical axis so that when the cuvette falls into the preheater section 38, the broad sides 56 of the cuvette are forward and back as welt as the flanges 58.

Referring to FIG. 29, the preheater section 38 comprises a pair of spaced horizontal bars 158 and 159 which define therebetween a vertical slot 160. Each of the bars 158 and 159 has a top edge 161. When a cuvette falls from the bottom of the orientation tube 140, the body of the cuvette falls into the slot 160 and the flanges 58 rest on the top edges 161. Plunger 19 is moved to its extended position into the slot 160 by the motor 25 from left to right as viewed in FIGS. 3, 32 and 33. The plunger 19 is moved from left to right a distance which is approximately or slightly more than a cuvette width which pushes all of the cuvettes in the preheater section toward the cuvette dispense and incubation section 39. The plunger 19 is then retracted by the motor 25 to allow a subsequent cuvette to fall from the orientation tube 140 into the preheater section 38. The motor 25 is activated to reciprocate the plunger 19 once every twenty seconds or when a test is request. The cuvettes are deposited into the orientation tube 140 at a faster rate than they are pushed along the preheater section 38 so that the tube 140 becomes full of cuvettes as generally shown in dotted lines in FIG. 29. The sensor 148 is a reflective object sensor which indicates the presence of a stationary cuvette when the tube is full. The sensor 148 forms part of the overall analyzer control system and is effective to stop the motor 103 when the sensor senses a stationary cuvette at the top of the orientation tube. The software which is used to control the instrument keeps track of the cuvettes as they are subsequently used out of the orientation tube and controls when the stepper motor 103 is reactivated. The preheater section 38 contains a thermistor for controlling a pair of solid state DC driven thermoelectric modules (TEMs) which maintain the temperature of the preheater section at a set temperature of 37° C. TEMs are also known as thermoelectric cooling couples which are used to maintain a predetermined temperature by transferring heat from one mass to another. The transfer of heat is reversed by reversing the direction of current flow. The machine framework provides a heat sink for the preheater section 38. When the temperature of the preheater section is below the set temperature, heat is transferred from the machine framework to the preheater section 38. When the set temperature of the pre-heater section is above the set temperature, as detected by the thermistor, the current through the TEMs is reversed and heat is transferred from the preheater section 38 to the machine framework. The cuvette dispense and incubation section 39 is also provided with a thermistor at two spaced strategic locations. Each thermistor controls a pair of thermoelectric modules (also strategically placed) for maintaining the cuvette temperature at 37° C. throughout the chemistry event line. In the particular embodiment shown, the preheater section 38 holds seventeen cuvettes and the cuvette dispense and incubation section 39 holds forty-five cuvettes.

Referring particularly to FIGS. 32 and 33, the track section 23 is shown in greater detail. The entire track section, including the preheater section 38 and the dispense and incubation section 39, is covered by a top plate 162 which has a plurality of access openings at the dispense points 44, 45, 46 and 47. The plate 162 has an opening 186 at the sample dispense point 44 as shown in FIG. 33A. The plate 162 has openings 187 and 188 for the reagent dispense points 45 and 46, respectively, as shown in FIG. 33B and an opening 189 for the reagent dispense point 47 as shown in FIG. 33C.

Referring particularly to FIG. 32A, the plunger 19 (not shown) has a tab 154 which extends horizontally toward the motor 25. When the plunger is in the outer or retracted position, it extends between a pair of spaced components of an interruption sensor 155. The sensor 155 has a photo transmitting portion which directs a beam toward a photo receiving portion. When the beam is interrupted bit the tab 154, a signal is transmitted to the CPU to indicate that the plunger is at the "home" position. (After a predetermined time period or when another test is requested), the stepper motor 25 is actuated for a predetermined number of steps to move the plunger 19 a predetermined distance out to the extended position. The motor is then reversed to bring the plunger back until the sensor 155 is interrupted by the tab 154 at the "home" position. All of the "interrupter" sensors described hereinafter are connect to the CPU through the machine controller board and operate in the same manner as the sensor 155. The cuvettes are pushed along the preheater section 38 and into the cuvette dispense and incubation section 39, at which point they are positively conveyed by a pair of conveyor belts 167 and 168. Each of the conveyor belts 167 and 168 has a plurality of teeth 164 on one side of the belt for engaging the teeth 59 of the cuvettes. A stepper motor 42 has a drive shaft 181 which is rotated in a clockwise direction when viewed from the front The belt 168 is driven by the motor 42 through the toothed drive pulley 170 which is located between and below a pair of idler pulleys 171 and 179. The belt 168 extends over the pulley 179 to and around an idler pulley 178 at the beginning of the incubation section 39. The belt 168 then travels along the front edge of the incubation section 39 to an idler pulley 172 at the end of the section 39 and then back over the idler pulley 171 to the drive pulley 170. The teeth 164 of the belt 168 face upwardly as the belt 168 extends around the drive pulley 170 and the idler pulleys 171 and 179 so that the teeth 164 of the belt engage the teeth of the drive pulley 170. As the belt travels to the pulley 178, it gradually assumes a vertical orientation so that the teeth. 164 face forwardly. As the belt extends around the pulley 178 and travels along the front edge of the dispense and incubation section 39, the teeth 164 face rearwardly and, thereby, engage the flanges 58 of the cuvettes. The belt 168 continues in a vertical orientation around the idler pulley 172 and gradually reassumes its horizontal orientation as it reaches the idler pulley 171. The pulleys 179 and 171 are rotatably mounted on horizontal shafts 182 and 183, respectively. The pulleys 178 and 172 are rotatably mounted on vertical shafts 180 and 184, respectively. The drive belt 167 is located on the rear side of the dispense and incubation section 39 and is driven longitudinally by a drive pulley 175 which is fixed to the drive shaft 181. The drive pulley 175 has external teeth 191 and is located between and below idler pulleys 174 and 176. The belt 167 extends over the idler pulley 176 which is rotatively mounted on the horizontal shaft 182 and around an idler pulley 177 which is rotatively mounted on a vertical shaft 190. The belt 167 then extends along the back side of the cuvette dispense and incubation section 39 to and around an idler pulley 173 which is rotatively mounted on a vertical shaft 185. The belt 167 then extends over the idler pulley 174 which is rotatively mounted on the horizontal shaft 183 and back to the drive pulley 175. The belt 167 has a plurality of teeth 193 on one side of the belt. The teeth 164 on the belt 167 face upwardly as the belt 167 extends over the idler pulley 174 and under the drive pulley 175 and back up around the idler pulley 176. The teeth 193 of the belt 167 are in drive engagement with the teeth 191 of the drive pulley 175. When the belt 167 travels between the pulley 176 and the pulley 177 it gradually assumes a vertical orientation so that the teeth 193 face forwardly as the belt travels along the aspiration and incubation section 39 to the idler pulley 173. As the inner sections of the belts 167 and 168 travel from left to right as viewed in FIGS. 32 and 33, the rearwardly facing teeth of the belt 168 and the forwardly facing teeth of the belt 167 engage the flanges 58 of the cuvettes 40 to advance the cuvettes along the event track or dispense and incubation scion 39 for a predetermined time period during the twenty second system cycle.

Sample Transport System

The sample transport system consists of a sixty position sample tray for receiving sample containers containing test samples, calibrators, controls, and diluents; a laser bar code reader; and a digital diluter. The sample tray consists of two concentric rings, each capable of holding a mixed population of various tubes and sample containers. The outer ring can accommodate this four sample containers, the inner rig twenty-six sample containers. Each position has a spring clip so that different sizes of sample containers can be accommodated. The bar code reader recognizes six versions of bar code language, and recognizes the identity of each bar coded sample and the identity of the bar coded tray. The operator may program the analyzer to automatically repeat any sample whose initial test result exceeds a selected range. Also, for most assays, the system will automatically dilute and re-assay any sample above the range of the standard curve, if desired. Various dilution ratios are selectable, based upon sample size. The sample aspirating and dispensing probe is specially coated and has capacitance level sensing in order to recognize the surface of the sample. This insures that liquid is present in a sample container before aspirating, as well as minimizing immersion into the test sample. After each aspiration and dispensing cycle, the inner and outer surfaces of the probe are thoroughly washed with deionzed water at a wash station to minimize sample carryover.

The sample transport system 26 is shown in FIGS. 36–42. Referring first to FIGS. 38, 39 and 41, the sport system 26 includes a fixed base which is generally indicated by the reference numeral 211 and which is mounted in a fixed position on the machine framework in front of the cuvette dispense and incubation section 39. The fixed base 211 includes an upper horizontal plate 212 and three descending legs 213, each with a horizontally and outwardly extending foot portion 214. Each foot portion 214 supports a roller 247 which is rotatively mounted on a horizontal shaft 215 for rotation about a horizontal axis. Each foot 214 also supports a roller 218 which is rotatively mounted on a vertical shaft 217 for rotation about a vertical axis. An electric stepper motor 219 is fixed to the bottom of the upper plate 212 and has a drive shaft 220 which extends through a hole 216 in the upper plate 212. A friction drive wheel 221 is fixed to the outer end of the shaft 220 for rotation therewith. An inner tray, generally indicated by the reference numeral 222, and an outer tray, generally indicated by the reference numeral 223, are rotatively mounted on the base 211 for rotation independently of one another about a vertical axis 209.

The inner tray 222 includes an inner hub portion 225 which is rotatively mounted on a vertical shaft 224 which is fixed to the upper plate 212 and which extends along the vertical axis 209, see FIG. 38. The inner hub portion 225 has a downwardly ending annular flange 226 which is in fictional engagement with the drive wheel 221. When the motor 219 is actuated, the drive wheel 221 is rotated by the shaft 220 which, in turn, rotates the inner hub portion 225 about the axis 209 due to the frictional engagement of the roller 221 against the inner surface of the annular flange 226. The inner hub 225 has an outwardly extending circular flange 208 at the bottom of the hub. The flange 208 is rotatably supported on the rollers 247. The inner tray 222 also includes an outer hub 227 which has an outer annular flange 223 which supports a plurality of receptacles 229 for supporting a plurality of sample containers, see FIG. 37. The receptacles 229 are arranged in an inner circle which is concentric with the axis 209. Each receptacle 229 has an outwardly facing opening 195.

The outer tray 223 includes a drive ring 230 which has an outer downwardly extending annular flange 231. The annular flange 231 has an inwardly facing annular groove 232 for receiving the rollers 218 which support the drive ring 230 for rotation about the axis 209. The drive ring 230 supports an outer ring 233 which contains a plurality of upwardly extending receptacles 234 for supporting a plurality of sample containers. The receptacles 234 are arranged in a circle which is concentric with the axis 209 and is located outside of the circle of receptacles 229 as shown in FIG. 37. Each receptacle 234 has an outwardly facing opening 260. Each of the receptacles 229 and 234 is at least partially lined with a metal plate 270 which has a plurality of inwardly protruding resilient fingers 271. The fingers provide a snug fit for a test tube or sample container and enable test tubes of different diameters to be used and held securely. The plates 270 and fingers 271 also provide a ground connection to the metallic machine framework to provide one component of a capacitance level sensing system to be described in a later section entitled: "SAMPLE PROBE TRANSPORT SYSTEM". The outer tray 223 is rotated independently of the inner tray 222 by means of a stepper motor 235 which is fixed to a mounting plate 236 which is, in turn, supported on the framework of the machine. The stepper motor 235 has a drive shaft 237 which is fixed to a drive pulley 238. A pulley 239 is fixed to a vertical shaft 241 which is mounted for rotation on the plate 236. The pulley 239 is driven from the pulley 238 by a timing belt 240. A drive wheel 242 is fixed to the pulley 239 and is in frictional engagement with the outer surface of the flange 231. When the motor 235 is activated, the roller 242 is rotated about the axis of the shaft 241 which, through its fictional engagement with the outer surface of the flange 231, causes the drive ring 230 to rotate about the a 209. This rotation is totally independent of the rotation of the inner tray 222 by the stepper motor 219.

Referring to FIGS. 40 and 42, a PC board 245 is mounted to the machine bar adjacent the sample transport system 26. The PC board 245 supports a plurality of interrupt sensors for the inner and outer trays. The sensors are arranged in two groups, an outer group for the outer ring, and an inner group for the inner ring. The outer group includes a pair of spaced outer sensors 246 and an inner home sensor 266. The inner group includes a pair of inner sensors 244 and an inner home sensor 267. The outer ring 230 has a single downwardly descending home tab 253 which interrupts the beam of the home sensor 266 to determine a starting position for the outer ring at the beginning of a test or a series of tests. A plurality of tabs 268 extend downwardly from the drive ring 230 of the outer tray 223 outside of the home tab 253 and extend in a circle about the axis 209. As the outer ring rotates about the axis 209, the tabs 268 pass through both sets of sensors 246. There is a tab 268 for each sample position of the ring 230 so that each time that the ring is rotated one position, the beam in each of the sensors 246 is interrupted to provide a signal to the CPU to indicate that the outer tray 223 has moved one position. The distance between the two sensors 246 differs from the spacing between two adjacent tabs 268 so that the sensors are not interrupted simultaneously. This enables the control electronics to determine the direction of rotation of the ring 230. To position a particular bottle or sample container about the axis 209, a command is given to the stepper motor 235 to move a number of steps in a certain direction and acceleration. The optical interrupt sensors 246 count the number of positions moved by the drive ring 230 to determine the final desired position of the ring. When the correct number of transitions have occurred, the stepper motor 235 will move a calibrated number oil steps past the transition point and stop. This will be the final container positioning point. The CPU is programmed to move the ring 230 and outer tray 223 in whichever direction will result in the smallest amount of rotation of the ring for each new sample container position. A single "home" tab 269 extends downwardly front the inner tray 222 for interrupting the beam of the home sensor 267 to determine the starting or "home" position of the inner tray. A plurality of tabs 243 each downwardly from the tray 222 outside of the "home" tab 269 and extend in a circle which concentric with the axis 209. The tabs 243 interact with the interrupt sensors 244 for controlling the stepper motor 219 and selectively positioning the inner tray 222 in the same manner as the tabs 268 and sensors 246 are utilized to selectively position the outer tray 223. The inner and outer trays are moved selectively and independently to position a specified predried sample container to a predetermined pickup position for aspiration by the sample aspirating and dispensing probe 24. Referring to FIG. 22, the pickup position for the outer tray is located at the opening 255 in the outer cover 257. The pickup position for the inner tray is located at the opening 256 in the outer cover 257. A bar code label is affixed to the outer wall of each sample container. The label has a specific bar code which identifies the test sample within the container. All of the information relating to the sample, such as the name of the patient and the tests which are to be performed with the sample, are stored within the memory of the central processing unit Referring to FIG. 22, a bar code reader 258 is located adjacent the sample transport system 26 and has two lines of sight which are indicated by the dotted lines 259 and 272. Prior to a run of tests, the receptacles in the inner and outer trays are charged with sample container. each containing its own spec bar code which cm be viewed through the openings 260 in the outer parts of the receptacles 234 and the clear plastic cover 257. The outer tray 223 is rotated about the axis 209 so that each sample container passes through the lines of sight 272 and 259 relative to the bar code reader 258 so that the bar code on each sample container can be read by the bar code reader. The energy beam from the transmitting portion of the bar code reader 258 passes along the line of sight 272 and the beam is reflected back from the bar code label on the sample container along the line of sight 259 to the beam receiving portion of the bar code reader. The vertical openings 260 and the transparency of the outer cover 257 enable the bar codes on the samples to be "seen" by the bar code reader. This enables the identity of each sample container to be correlated with the position of the outer tray relative to a home position. After all of the sample containers have been read by the bar code reader, the outer tray 223 is positioned so that a gap 261 in the circle of receptacles 234 is aligned with the lines of sight 259 and 272. This enables tee bar codes on the sample containers in the inner tray 222 to be exposed through openings 195 in the outer portions of the receptacles 229 to the bar code reader 258. The inner tray 222 is rotated so that each sample container in the inner tray passes through the lines of sight 259 and 272 so that the specific bar code of each sample in the inner tray 222 is read by the bar code reader. This information is utilized by the central processing unit to correlate the position of each sample container in the inner tray 222 relative to the home position of the inner tray.

Referring particularly to FIGS. 39 and 41, a contact ring 250 is fastened to the drive ring 230 by a screw 262 which also mounts a positioning key 263 to the drive ring 230. A contact ring 252 is fastened to the upper wall of the hub 225 by a screw 264. Positioning key 265 is fixed to the hub 225 at the base of the flange, 226. The metal grounding wire 248 is connected to the contact ring 252 and connected to the keys 265 and 263 by a connecting wire 249. These elements form part of the grounding system for grounding the fingers 271 to the machine framework.

The bar code-labeled sample containers may be loaded in any order in the sample tray. The analyzer will read all bar codes automatically, and identify the sample and its position in the tray. If bar code labels are not used, a worklist printout is utilized, which directs placement of samples in specific sample tray positions.

Reagent Transport System

The reagent sport system or tray provides a carrier for twenty-six reagent bottles or containers, sufficient for up to thirteen different assays. The inner portion is made to specifically accept the solid-phase reagent containers, and periodically agitates these containers to maintain homogeneity of the solid phase reagent This mixing action is aided by the design of the reagent bottles, which have agitator fins molded into their inner walls. The tracer or labeled reagent bottles are also specially shaped to automatically orient the identifying bar code label affixed to the container, and are loaded into the outer positions on the reagent tray. Reagents are bar code labeled. A reagent laser bar code reader records the loaded position of each specific reagent, including identity and lot number, making random loading permissible. Reagents may be loaded directly from refrigerated storage, since they are warmed to 37° C. before dispensing. The three reagent aspirating and dispensing probes have capacitance level sensing and may be programmed to make an initial reagent level, check before starting an assay run to insure that adequate reagent volumes have been loaded to complete the scheduled worklist stored in the CPU. Reagent volumes used range from 50–450 uL, depending on the assay, and specific reagents may be added to the sample in the cuvette by each of the three reagent probes, with incubation times of 2.5 to 7.5 minutes, depending on optimal condition for specific assays. Reagent probes, like the sample probes, are thoroughly washed with deionized water between dispensings.

Referring to FIGS. 43–49, the reagent transport system is generally indicated by the reference numeral 27. The reagent transport system 27 comprises a fixed supporting base 286 which is fixed to the machine framework 283 and an electric stepper motor 287 which is fixed to the supporting base 286 by fasteners 282 and connecting rods 285. The stepper motor 287 has a drive shaft 290 which is fixed to a motor hub 291 by a trantorque clamp 280. The drive shaft 290 is rotated about a vertical drive axis 293. The base of the motor hub 291 consists of a ring of upwardly facing gear teeth 292. The circular spill tray 288 has a central circular opting 29 and is fixed to the supporting base 286 by a plurality of fasteners 279 so that the stepper motor 287 extends upwardly through the opening 289. Referring to FIGS. 45 and 46, a support ring 294 is located concentrically of the central vertical axis 293 and has a central circular opening 295 and a plurality of smaller openings 308 which are arranged in a circle which is concentric with the axis 293. A reagent tray 296 is mounted on the support ring 294 and contains a ring of inner pockets 297 and a ring of outer pockets 299. The pockets 297 and 299 are arranged in inner and outer concentric circles, respectively, about the axis 293. Each outer pocket 299 contains a tubular outer bottle or reagent container holder 298 which is fixed to the pocket by a fastening disc 301. The connector 301 extends through an aperture 302 at the base of the pocket to the support ring 294 for fastening the reagent tray 296 to the ring 294. When a container 60 of labeled or tracer reagent is placed in the pocket 299, the tubular holder 298 extends between the skirt 63 and the main body portion 64 as shown in FIG. 45.

Each inner pocket 297 contains an inner container holder 300. A fastening disc 303 bears against the bottom wall of the holder 300 and has a vertical shaft 304 which extends through an opening in the bottom wall of the holder. The fastening discs 301 and 303 are metallic and are grounded to the machine framework. The discs 301 and 303 provide one component of a capacitance level sensing system which is described in a following section entitled "REAGENT PROBE TRANSPORT SYSTEM". A gear 306 is fastened to the bottom of the holder 300 by a pair of screws 305 which also effectively clamp the fastening disc 303 and the gear 306 against the bottom wall of the holder 300. The bottom of the shaft 304 extends below the gear 306 and into a pair of flanged bearings 307 which are mounted in one of the apertures 308 of the support ring 294. This enables each holder 300 and its respective gear 306 to rotate about its own central longitudinal secondary axis 278. The gears 306 extend about a ring gear 309 and are in driving engagement with the outer teeth of the ring gear, see FIG. 46. The ring gear 309 has a large central opening 277. A pair of pins 310 are fixed to the gear 309 and extend below the gear into driving engagement with the teeth of the ring gear 292, see FIG. 45. Actuation of the stepper motor 287 causes the hub 291 in the ring gear 292 to rotate about the axis 293. This causes rotation of the ring gear 309 through the drive pins 310. The ring gear 309, in turn, drives all of the satellite gears 306 for rotating each bottle holder 300 about its respective secondary axis 278. The ring gear 309 is fully supported by the satellite gears 306. A plurality of retainers 311 are fixed to the ring gear 309 and extend below the gear 309 for straddling the inner edge of the support ring 294. The bottle holder 300 holds a solid phase bottle or reagent container 75. The side walls of the holder 300 has a plurality of vertical slots 276 which form a plurality of resilient fingers 274 which extend between the main body 76 and the skirt 80 of the reagent bottle or reagent container 75 for holding the reagent container 75 in a friction fit. The stepper motor 287 is reversible and controlled by the central processing unit to oscillate the drive shaft 290 at predetermined intervals. Each of the bottle holders 300 is adapted to receive a solid phase reagent container 75. The oscillations of the holder 300 provide the necessary motion to the reagent container 75 for enabling the fins 81 to agitate the solid phase reagent solution the bottle 75 and, thereby, maintain a uniform concentration of the solid phase elements within the solution. Each of the bottle holders 298 is adapted to receive a labeled reagent container 60 which does not require agitation. Referring particularly to FIGS. 45 47, a ring gear 312 encircles the spill tray 288 and is mounted for rotation on the supporting base 286 about the axis 293. The lower part of ring gear 312 has an inwardly facing V-shaped bead 275 which engages a plurality of V-guide wheels 323 which support the ring 312 for rotation about the axis 293. Each wheel 323 is rotatively mounted on a vertical shaft 324 which is fixed to the base 286. The ring gear 312 supports the support ring 294 and the reagent tray 296. Referring also to FIGS. 48 and 49, part of the ring gear 312 has an annular flange which is opposite the V-shaped beads 275 and contains a ring of outwardly facing gear teeth 329 which are in driving engagement with an idler gear 319 which is keyed to a vertical shaft 320. The shaft 320 is rotatively mounted in flanged bearings 321 which are supported on flanges 322 of a motor mount 314. The motor mount 314 has a circular bore 316 which contains a drive gear 318 which is fixed to the drive shaft 317 of a stepper motor 315. The stepper motor 315 is fixed to the motor mount 314. The wall of the bore 316 of the motor mount 314 has a lateral opening which enables the drive gear 318 to engage the idler gear 319. Actuation of the motor 315 causes the drive gear 318 to dive the ring gear 312 through the idler gear 318 about the vertical axis 293. The inner and outer pockets 297 and 299, respectively, are enclosed within, a clear stationary plastic covers 327. The cover 327 has a plurality of openings 328, 338, 339, 340, 341, and 342 which provide access to the bottles within the pockets 297 and 299 by reagent aspirating and dispensing probes to be described in a later section, see FIG. 22.

Referring to FIG. 47, a PC board 330 contains a pair of interrupter sensors 331 and 336 and a photo reflector sensor, not shown, which is located beneath then sensors 331 and 336. The optical reflector sensor has a beam transmitting portion and beam receiving portion. If a beam from the transmitting portion strikes a reflective surface, the beam is reflected back to the receiving portion of the sensor. When the beam is not reflected back, the sensor generates a signal to the CPU. The PC board 330 is mounted to the base plate 286 so that the sensor optical reflector faces outwardly toward the ring 312. The beam from the transmitting portion of the beam reflector sensor strikes the ring 312 and is reflected back to the beam receiving portion of the sensor. The ring 312 has an aperture 326, see FIG. 49, which is at the same level as the beam from the photo reflector sensor. At the beginning of a testing sequence, the ring 312 is rotated about the axis 293 until the beam of the photo reflector sensor is aligned with the aperture 326. When this occurs, the beam passes through the aperture and is not reflected back to the sensor. The absence of the reflected beam initiates a signal to the CPU to indicate the "home" or string position of the reagent tray at the beginning of a series of tests. Referring to FIG. 47, the ring 312 has a plurality of tabs 334 which extend inwardly from the ring 312 and which pass between the two spaced elements of each interrupter sensor 331 and 336 for interrupting a beam from each optical sensor which provides feedback to the control electronics for reagent bottle positioning. There is a tab for each reagent bottle position in the tray 296 so that each time that the ring is rotated one position, the beam in each of the sensors 331 and 336 is interrupted to provide a signal to the CPU to indicate that the tray has moved one position The distance between the two sensors is less than the spacing between two adjacent tabs 334 so that the sensors 331 and 336 are not interrupted simultaneously. This enables the CPU to determine the direction of rotation of the reagent tray. To position a particular bottle or container to a reagent probe pickup or aspiration position, a command is given to the stepper motor 315 to move a fixed number of steps in a certain direction. This causes the reagent tray 296 to rotate along with the tabs at the bottom of the drive ring 312. The sensors 331 and 336 counts the number of tab transitions and determines the, position of the reagent tray 296. When the correct number of transitions have occurred, the stepper motor 315 will move a calibrated number of steps past the transition point and stop. The bottle containing the designated reagent will thereby be positioned at the predetermined pickup point for one of the reagent probes.

A photo reflective sensor 337 is mounted on the plate 286 and directs a light beam upwardly. The motor hub 291 has a bottom reflective surface which has a plurality of spaced apertures. As the hub 291 oscillates, the beam from the sensor 337 is alternately reflected back to the sensor by the bottom reflective surface of the hub and absorbed by the apertures in the bottom surface. This provides appropriate signals to the CPU to indicate that the hub is being oscillated at predetermined intervals.

Each reagent container has a bar code label affixed to its outer skirt portion. The label contains a specific bar code which identifies the reagent within the container. The information relating to all of the reagents in the bar codes associated with the reagents are stored within the memory of the central processing unit Referring to FIGS. 43 and 22, a bar code reader 332 is located adjacent the reagent transport system 27. The bar code reader 332 transmits an energy beam along a line of sight which is indicated by the dotted line 333. The beam is reflected back go the bar code reader 332 from he bar code label along a line of sight which is indicated by the dotted line 344. The return beam along the line of sight 344 is received by the beam receiving portion of the bar code reader. The bar code in the preferred embodiment is printed on the label for each reagent bottle in a vertical direction The inner pockets 297 and outer pockets 299 are staggered with respect to each other. As the reagent tray 27 is rotated about the axis 293 by the stepper motor 315, the inner and outer pockets alternately pass through the lines of sight 333 and 334 of the bar code reader 332. The stepper motor 287 is also utilized during the initial reading of reagent container bar codes prior to a run of tests. Referring to FIGS. 43 and 46, there is a relatively large space between each outer pocket 299. Each inner pocket 297 is horizontally aligned with the space between two adjacent pockets 299. A vertical wall 335 which separates the inner and outer pockets 297 and 299, respectively, has a relatively large opening 328 at each space between outer pockets 299 so that each reagent container is exposed to the line of sight of the bar code reader when the container is rotated about the axis 293 by the stepper motor 315. As the reagent tray 27 is rotated about the axis 293, each reagent container or bottle in the ring of inner pockets 297 is given one and one-half revolutions per pass of a reagent container 75 through the lines of sight 333 and 334 to insure that the bar code is exposed to the reader. The bar codes on the bottles in the inner and outer pockets can be read by the bar code reader 332 through the clear plastic cover 327.

The operator loads required assay reagents, in original bar code-labeled bottles, into the reagent tray in any order, solid-phase reagents on the inner bottle holders 300, labeled or tracer reagents on the outer bottle holders 298. Due to the design of the reagent bottles, it is not possible to mis-load reagents. The analyzer will read all bar codes before initiating a run identifying each reagent, its position, its lot number and expiration date. If greater than 50 tests of a specific assay has been requested in the worklist, multiple bottles of the necessary reagents may be loaded on the reagent tray and the analyzer will access them sequentially, as needed.

Sample Probe Transport System

Referring to FIGS. 50–59 and first to FIGS. 54 and 55, the sample probe transport system 24 comprises a fixed upper horizontal support plate 357, and a sample probe supporting carriage, generally indicated by the reference numeral 363, which is mounted for horizontal back and forth movement relative to the supporting plate 357. The support plate 357 has an opening 366. A PC board 358 is fixed to the upper surface of the plate 357 by screws 359. The under surface of the PC board has a plurality of electrical junctions J1, J2, J3, J4 and J5 which extend into the opening 366. A vertical bracket 364 is fixed to the underside of the plate 357 at the rear end of tie plate. An electrical stepper motor 365 is fixed to the forward side of the bracket 364 and has a drive shaft 369 which is rotatable about a horizontal axis. A lead screw 371 is fixed to the drive shaft 369 through a drive coupling 370 and extends through a roll nut 409 which is fixed within a bore 408 of a block 372. (See also FIG. 58.) The block 372 is mounted in a yoke 373 between a pair of upper and lower dowel pins 374. The dowel pins 374 enable the block 372 to pivot about a vertical axis to compensate for slight misalignments between the block 372 and the lead screw 371. The block 372 has a laterally extending horizontal shaft 375 which is mounted to the carriage 363 in a manner described herein below.

A guide bracket 360 is fixed to the underside of the plate 357 by the screws 359 and has a downwardly facing horizontal groove 361. A carriage supporting bar 362 is slidably mounted in the groove 361. The carriage 363 is fixed to the sliding bar 362 by a screw 391 and an anti pivot rod 387 which has a threaded upper end. The carriage 363 includes a forwardly facing vertical wall 376, a top horizontal wall 377 and a lower horizontal wall 378. The top wall 377 has an aperture 389 and the bottom wall 378 has an aperture 388. The anti pivot rod 387 extends freely through the apertures 388 and 389 and is threaded into the block 362. Referring also to FIG. 56, the wall 376 has a horizontal bore 379 which has a bearing 380 at each end of the bore. The shaft 375 of the yoke 373 extends through the bore 379 within the bearings 380. A vertical lead screw 385 is rotatably mounted in upper and lower bearings 383 and 384, respectively, in the upper and lower walls 377 and 378, respectively. The lower end of the lead screw 385 extends below the bottom wall 378 and is fixed to a pulley 386. An electrical stepper motor 394 is fixed to the underside of a rearwardly extending horizontal flange 393 of the carriage 363. The stepper motor 394 has a vertical drive shaft 395 which is fixed to a pulley 396, see also FIG. 57. The pulley 396 is drivingly connected to the pulley 386 through a ting belt 397. The inner surface of the timing belt 397 has a plurality of teeth for engaging corresponding teeth on the drive pulleys 396 and 386, (teeth not shown). A lead screw follower 401 is positioned between the walls 377 and 378 and has a vertical bore 403 and a vertical bore 404 which contains a roll nut 405 (see also FIG. 59). The anti pivot rod 387 extends freely through the bore 403 and the lead screw 385 extends through the roll nut 405. The roll nut 405 is fixed relative to the follower 401 so that as the lead screw 385 is rotated about its vertical axis, the follower 401 moves along the central longitudinal axis of the lead screw 385 relative to the walls 377 and 378. A probe holding arm 402 is fixed to the forward end of the follower 401 and carries an aspirating and dispensing sample probe 407.

A PC board 398 is fixed to the carriage 363 and has an electrical connector 399 which is connected to the electrical junction 12. The stepper motor 394 has a connector 400 which is connected to the electrical junction J4. The stepper motor 365 has a connector 368 which is connected to the junction J5, The probe supporting arm 402 has a PC board 406 which is connected to a connector 411 through a flexible ribbon 421. The connector is connected to junction 420 of the PC board 398.

The stepper motor 365 is reversible. When the lead screw 371 is rotated in one direction, the carriage 363 moves rearwardly along the central longitudinal axis of the lead screw 371 toward the flat bracket 364. This causes the carriage 363 and the sample probe 407 to move from a forward position to a rearward position relative to the sample tray. When the stepper motor 365 is reversed, the lead screw 371 is rotated in the opposite direction. This causes the carriage 363 to move forwardly and, thereby, move the sample probe 407 from its rearward position to one of two forward pickup positions above the sample tray. The sample probe 407 can also be positioned in intermediate positions between rearward and forward positions, as for example, above the wash station 18. The motor 394 is also reversible. Rotation of the lead screw 385 in one direction causes the follower 401 and the arm 402 to move upwardly. Rotation of the lead screw 385 in the opposite direction, causes the follower 401 and the arm 402 to move downwardly. The sample aspirating and dispensing probe 407 is moved forwardly when it is in the upper position until it reaches one of the sample pickup or aspiration positions above the sample tray and is then moved downwardly to pick up a volume of a sample. The probe 407 is them moved to the upper position and returned to a point above the wash station, whereupon it is moved downwardly again for a wash cycle, or to its rearward position above one of the cuvettes, whereupon it is lowered into the cuvette for depositing the sample volume into the cuvette. The stepper motors 394 and 365 are capable of making very precise step-by-step motions for very precise horizontal and vertical positioning of the sample probe 407.

Referring to FIGS. 54 and 56, a plurality of spaced tabs 410 extend upwardly from the carriage 363 from front to back on one side of the carriage. A single "home" tab 415 extends upwardly from the carriage 363 on the opposite side of the carriage. When the carriage 363 reaches its rearward "home" position, the tab 415 passes between the elements of an interrupt sensor 413 which extends downwardly from the support plate 357. The tab 415 interrupts a light beam between the two elements of the sensor 413 which initiates a signal to the CPU that the carriage has reached its "home" position and the sample probe 407 is directly above a cuvette at the sample dispense point 44. The upper portion of the probe carrying arm 401 is determined by an interrupt sensor 416 which is fixed to the PC board 399. The PC board is fixed to the carriage 363 so that it extends horizontally toward the probe carrying arm 401, see FIGS. 50 and 56. The follower 401 has a tab 355 which extends toward the sensor 416. The tab 355 cannot be seen in FIGS. 54 and 56 since it is located on the hidden side of the follower 401, but is indicated by dotted lines in FIG. 53. When the follower 401 reaches the upper position, the tab 355 passes between the two elements of the sensor 416 and interrupts a light beam. The interruption of the light beam provides a signal to the CPU to indicate that the follower 401 and the probe 407 have reached the upper position. This insures that the carriage 363 can be safely moved to a new horizontal position at a predetermined point of time in the operating cycle, whereupon the motor 365 is given pulses for a predetermined number of half steps. At the appropriate time, the motor 394 its activated to move the arm 401 and the probe 407 downwardly. For each sample pickup cycle, the motor 365 is actuated for a predetermined number of half steps to move the carriage forwardly with the probe 407 in the upper position from the home position until the probe 407 is above the wash station 18. The motor 394 is actuated for a predetermined number of half steps to lower the probe 407 into the wash station 18 for a wash cycle. The probe 407 is then raised by reversing the stepper motor 394 for a predetermined number of half steps. The motor 365 is actuated for a predetermined number of half steps to move the carriage 363 forwardly until the probe 407 is above the opening 255 or the opening 256 in the outer cover 257 of the sample tort system. The motor 394 is actuated to move the follower 401, together with the arm 402 downwardly to lower the probe 407 into tee sample container which is located beneath whichever of the openings 256 or 255 which is vertically aligned with the probe 407. The lower position of the sample probe 407 is determined by a capacitance fluid sensing system. The capacitance fluid sensing is a function of a signal change occurring through two conductive materials such as the metal probe 407 and ground fluid and one non-conductive material such as air or plastic/glass sample container. When the probe is in-the upper position, the probe's reference current is measured, as the probe moves downwardly seeking fluid, an increase in signal indicates the presence of fluid When fluid is detected, the motor 394 is actuated for a predetermined number of half steps to move the probe 407 a predetermined distance below the meniscus of the fluid This distance is determined by the amount of fluid to be aspirated, a large volume requiring a deeper penetration of the probe than a smaller volume. After aspiration of a volume of sample by the probe 407, the probe is raised to its upper position, whereupon the motor 365 is actuated for a predetermined number of half steps to move the carriage 363 rearwardly to its "home" position so that the probe 407 is directly above the sample, dispense point 44. The motor 394 is actuated for a predetermined number of half steps to lower the probe 407 in the cuvette which is located beneath the dense point. 44. The quantity of sample is then dispensed by the probe 407 into the cuvette. The probe 407 is raised to its upper position to begin another cycle. As the carriage moves between the "home" and forward positions, the tabs 410 pass between the elements of an interrupt sensor 412. The tabs 410 are positioned so that when the carriage stops at a forward position for a sample pickup or a wash cycle, none of the tabs 410 will interrupt the light beam which passes from one element of the sensor 412 to the other. The light beam will pass through one of the spaces between the tabs 410 or outside of the outer edge of one of the tabs when the probe is properly positioned. If the probe is not properly positioned, due to a malfunction in the system, one of the tabs 410 will interrupt the light beam and a signal will be sent to the CPU to stop the machine. This will prevent the lowering of an improperly positioned probe and subsequent breaking of the probe.

For most test protocols, the sample probe will make one forward stop after the wash cycle to pick up a volume of sample from either the outer tray or the inner tray. In some cases, the sample probe stops at both of the openings 255 and 256 to pick up a volume of diluent as well as a volume of sample. The diluent is generally a protein based solution which is used to dilute a patient sample when an original test result is beyond a test curve range. The type of diluent used should correspond to the type of assay being performed by the analyzer. Diluent solutions are normally placed in the inner tray. The sample probe picks up the diluent before picking up the test sample as to avoid contaminating the diluent with sample. Other treatment liquid materials which are sometimes picked up with a sample solution are pre-treatment agents and releasing agents. A releasing agent is sometimes mixed with the sample for the purpose of separating the analyte from another molecule and rendering it available for reaction. A pre-treatment agent is a solution which is mixed and incubated with the test sample to protect the analyte from a releasing agent Reagent Probe Transport System The reagent probe transport system is shown in FIGS. 60–72. Referring first to FIGS. 60–63, the reagent probe transport system is generally indicated by the reference numeral 440 and includes the reagent probe transport systems R1, R2 and R3. The system 440 comprises an upper horizontal support plate 441 which has openings 442, 443, 444 and 445. A PC board 446 is fixed to the upper surface of the plate 441 and has a plurality of interrupter sensors on tee undersurface of the PC board which extend into the openings 442, 443, 444 and 445. Interrupter sensors 448, 449, 450 and 451 extend into the opening 442. Interrupter sensor 452 extends into the opening 443. Interrupter sensor 453 extends into the opening 444 and interrupter sensors 454 and 453 extend into the opening 445. A plurality of electrical junctions are also mounted on the other side of the PC board 446 and are accessible through the openings 442, 443, 444 and 445. Junctions J11 and J12 are accessible through the opening 442. The junctions J13, J14 and J15 are accessible through the opening 443. Junctions J16, J17, J18 and J19 are accessible through the opening 444. Junctions J20, J21 and J22 are accessible trough the opening 445. Three horizontal guide brackets 455, 457 and 459 are fixed to the underside of the support plate 441. The guide brackets 455, 457 and 459 have elongated horizontal grooves 456, 458 and 460, respectively. Elongated carriage supporting guide bars 461, 462 and 463 are slidably mounted in the grooves 456, 458 and 460, respectively. The guide bar 461 is fixed to a reagent probe supporting carriage which is generally indicated by the reference numeral 464 and which forms part of the reagent probe transport system R1. The carriage supporting slide bar 462 is fixed to a reagent probe supporting carriage which is generally indicated by the reference numeral 465 and which forms part of the reagent probe transport system R2. The carriage supporting slide bar 463 is fixed to a reagent probe supporting carriage which is generally indicated by the reference numeral 466 and which forms part of the reagent probe transport system R3. Slide bars 461, 462 and 463 enable the carriages 464, 465 and 466 to move forwardly and rearwardly relative to the support plate 441.

A flat vertical rear bracket 467 is fixed to the back end of the support plate 441 and extends downwardly from the under surface of the support plate. A plurality of stepper motors 468, 469, 470 and 471 are fixed to the front side of the plate 467. The stepper motors 468, 469, 470 and 471 have forwardly extending and horizontal drive shafts 472, 473, 474 and 475, restively. The motors 468, 469, 470 and 471 have electrical connectors 476, 477, 478 and 479, respectively, which are connected to the electrical junctions J10, J12, J20 and J18, respectively, on the PC board 446. A bracket 480 is connected to the right side of the support plate 441 as viewed in FIG. 63 and fixedly supports a horizontal slide bar 481 which is slidably mounted in the horizontal groove 482 of a guide bracket 483. The guide bracket 483 is fixed to a guide rail 487 which is fixed to the framework of the machine. A horizontally extending slide bar 484 is fixed to the left side of the support plate 441 as viewed in FIG. 63 and is slidably mounted in a horizontal groove 485 in a guide bracket 486. The guide bracket 486 is fixed to an upwardly extending arm of a U-shaped bracket 488 which is fixed to a guide rail 489. The guide rail 489 is, in turn, fixed to the machine framework. Brackets 483 and 486 are fixed relative to the machine frame and the slide bars 484 and 481 are fixed to the support plate 441. The support plate 441 is able to move forwardly and rearwardly between the guide brackets 486 and 483, along with the carriages 464, 465 and 466 which are supported from the underside of the support plate 441.

The forward and backward motion of the support plate 441 is provided by the stepper motor 469. The drive shaft 473 of the motor 469 is fixed to a horizontally extending lead screw 490 through a coupling 491 (See also FIG. 67). The lead screw 490 extends trough a roll nut 497 which is located in a bore 492 of a block 493. The block 493 is pivotally mounted between the parallel arms of a yoke 494 by means of a pair of upper and lower dowel pins 495 which extend into a bore 435 of the block 493. The roll nut 497 is fixed to the block 493 so that as the lead screw 490 is rotated, the block 493 moves along the central longitudinal axis of the lead screw. The pivoting motion of the block 493 along the longitudinal axis of the bore 435 within the yoke 494 compensates for any possible misalignments between the block 493 and the lead screw 490. The yoke 494 has a shaft 496 which extends upwardly through a tubular follower guide 437 which is located in an aperture 439 in a bottom wall 438 of the U-shaped bracket 488, see FIG. 63. The shaft 496 rides in a pair of bearings 436 at opposite ends of the follower guide 437. When the lead screw 490 is rotated upon actuation of the motor 469, there is relative motion between the block 493 and the lead screw 490 along the longitudinal axis of the lead screw. Since the block 493 is fixed relative to the machine framework, this motion causes the lead screw 490 and the motor 9 to move relative to the machine framework, which, in turn, causes the support plate 441 to move forwardly or backwardly, depending upon the rotation of the lead screw 490.

The forward position of the plate 441 is the normal operating position for the reagent probe transport systems R1, R2 and R3 which are carried by the plate 441. In this normal operating position, the reagent aspirating and dispensing probes for each of the systems R1, R2 and R3 move forwardly and rearwardly between a rearward "home" position in which the probe is above a corresponding reagent dispense point and a forward aspirating position in which the probe is above a corresponding opening in the cover 327 of the reagent transport system. The plate 441 is moved to the rearward position between test runs in order to position the guard which extends in front of the reagent probe transport systems in back to the cover 327 of the reagent trays to enable the cover to be removed for replacement of the reagent containers. The forward and rearward positions of the plate 441 are determined by the sensors 448 and 450 and a tab 431 which extends upwardly from the bracket 488. When the plate 441 reaches its rearward position, the tab 431 passes between the elements of the sensor 450 to interrupt a light beam and provide a signal to the CPU that the plate 441 is properly positioned at the rearward position of the plate. When the plate 441 is in its forward position, the tab 431 is located between the elements of the sensor 449 so that the beam which passes from one element to the other is interrupted to provide an electrical signal to the CPU that the plate is properly positioned in its forward position.

Referring particularly to FIGS. 63 and 64, the carriage 464 of the reagent probe transport system R1 includes a rear vertical wall 508 which has a horizontal bore 511, a top wall 509, which has a vertical bore 514 and a bottom wall 510 which has a vertical bore 515. A bearing 517 is located in the bore 515 and a bearing 521 is located in the vertical bore 514. A follower mounting guide 518 is fixed to the wall 508 and has a cylindrical portion 516 which extends into the bore 511. A horizontal bore 513 extends through the mounting guide 518 and there is a pair of bearings 427 at each end of the bore 513. A lead screw 499 is fixed to the drive shaft 472 of the motor 468 by a coupling 500. The lead screw 499 extends through a roll nut 501 in a bore 502 of a block 503. The block 503 is pivotally mounted between a pair of parallel arms of a yoke 506 in the identical manner as the mounting of the block 493 in the yoke 494 as shown in FIG. 67. The yoke 506 has a laterally extending shaft 507 which is supported within the bearings 427 and extends through the bore 513 of the follower mounting guide 518. Since the roll nut 501 is fixed to the block 503, rotation of the lead screw 499 upon the actuation of the motor 468, causes the block 503 to move axially along the lead screw 499. This causes the carriage 464 to move forwardly or rearwardly relative to the support plate 441, depending on the direction of rotation of the lead screw 499.

Referring also to FIG. 72, a probe holding arm 519 is mounted to a follower guide 505. The follower guide 505 has a horizontal bore 520 which contains a roll nut 425 which is located between and in axial alignment with the bearings 521 and 517 in the upper and lower walls 509 and 510, respectively, see FIG. 64. The lead screw follower 505 has a tab 433 which is slidably mounted in a vertical groove 432 of a vertical post 522, see FIGS. 64 and 70. The post 522 has a lower horizontal flange 512 which is located below the bottom wall 510. The flange 512 has a bore 523 which is vertically aligned with the bore 515. The upper end of the post 522 is fixed to a gear segment 524 which has a bore 525. The gear segment 524 has gear teeth 526 which extend radially about the center of the bore 525. The gear segment 524 is located above the top wall 509 so that the bore 525 is in axial alignment with the bore 514. The teeth of the gear segment 524 are in driving engagement with the teeth 631 of a horizontal plate 629 which is fixed to the plate 444 as shown in FIG. 60. When the carriage 464 is in its rear position, the probe holding arm 519 faces to the left as viewed in PIG. 60. As the carriage 464 moves forwardly, the gear segment 524 rotates about the vertical axis of the lead screw 527. This causes the probe supporting arm 519 to rotate approximately 90° from the leftwardly facing position as shown in FIGS. 60 and 62 to a forwardly facing position. Referring to FIG. 22, this causes the probe 535 to move along a curved path which is indicated by the dot and dash line 428. The line 428 intersects the vertical axes of the dispensing point 45, wash station 15 and the openings 329 and 338 in the clear plastics cover 327 of the reagent tray as shown in FIG. 22.

A stepper motor 528 is fixed to a rearwardly Ending horizontal flange 529 of the carriage 464. The motor 528 has a downwardly extending drive shaft 530 which is fixed to a pulley 531. A vertical lead screw 527 is rotatably mounted within the bearings 425 and 517 and is drivingly engaged with the roll nut 521 of the follower 505. The lead screw 527 extends through the bores 523 and below the flange 512. The lower end of the lead screw 527 is fixed to a pulley 533, which is drivingly connected to the pulley 531 through a timing belt 532. The inner surface of the timing belt 532 has a plurality of teeth which engage corresponding teeth on the pulleys 533 and 531 to provide a precise predetermined degree of rotation of the pulley 533 for each driving step of the stepper motor 528 (teeth not shown). When the stepper motor 528 is actuated for rotating the lead screw 527 in one direction, the probe holding arm 519 is moved upwardly. When the lead screw 527 is rotated in the opposite direction, the probe holding arm 519 is moved downwardly relative to the upper and lower walls 509 and 510 and the post 522.

An interrupt sensor 571 is located at the top of the groove 432. When the probe holding arm 519 is moved to its upper position, a beam in the sensor 571 is interrupted to provide an electrical signal to the CPU that the probe 535 is properly positioned in its upper position. The sensor 571 is mounted on a PC board 537 which is attached to the post 522, see FIG. 64. A connector 540 connects the PC board 537 to the junction 115 of the PC board 537.

Referring to FIG. 72, a PC board 534 is fixed to the probe holding arm 519. The arm 519 also supports a first reagent probe 535, see FIG. 62. Referring to FIG. 64, a bracket 538 is fixed to the upper wall 509 of the carriage 464 and has a plurality of upwardly extending tabs 536 for interacting with interrupt sensors 451 and 449 on PC board 446. The sensor 451 is a "home" sensor which provides a signal to the CPU when the rearmost tab 536 interrupts a beam between the two elements of the sensor when the carriage is in its "home" or rearward position. When the carriage is in the "home" position, the probe 535 is directly over a cuvette at the reagent dispense point 45. The tabs 536 also interact with the interrupt sensor 449 to insure that the probe 535 is located precisely at each of its forward positions. If the probe 535 is properly positioned, at any of the forward positions, the beam of the sensor 449 will be aligned with a space between two adjacent tabs or to the outside of one of the tabs. If the probe is not properly positioned, the beam will be interrupted by one of the tabs and a signal will be sent to the CPU to stop the machine.

The forward positions of the probe 535 include the wash station 15 and the openings 328 and 338 of the outer cover 327 of the reagent tray 27. For each reagent pickup cycle, the motor 468 is actuated for a predetermined number of half steps to move the carriage 464 forwardly with the probe 535 in the upper position from the home position until the probe 535 is above the wash station 15. The motor 528 is actuated for a predetermined number of half steps to lower the probe 535 into the wash station 18 for a wash cycle. The probe 535 is then raised by reversing the stepper motor 528 for a predetermined number of half steps. The motor 468 is actuated for a predetermined number of half steps to move the carriage 464 forwardly until the probe 535 is above the opening 328 or the opening 338 in the outer cover 327. If the test protocol requires that the tracer or labeled reagent and the solid phase reagent arm to be picked up by the probe 535, the probe is moved to each of the openings 328 and 338 in succession. At each position 328 or 338, the probe 535 is lowered by the motor 529. The lower position of the probe 535 is determined by a capacitance fluid sensing electronics as described for the aspirating step for the sample probe 407. After aspiration of a volume of reagent, the probe 535 is raised to its upper position, whereupon the motor 528 is actuated for a predetermined number of half steps to move the carriage 464 so that the probe 535 is above the other reagent opening or moved rearwardly so that the probe 535 is above the reagent dispense point 45. The reagent aspirating and dispensing probe is then lowered into a cuvette which is beneath the point 45. The volume of reagent is then dispensed into the sample solution in the cuvette. The probe 535 is then raised to its upper position and moved to the wash station 15 for a wash cycle which is described in detail in following section of the description. After washing of the probe, the probe is ready to begin another aspirating and dispensing cycle. The speed of the motor 564 is controlled by the CPU in accordance with the operating program. The probe 535 is lowered to a point just above the surface of the sample in the cuvette and then raised at a predetermined rate while reagent is dispensed into the cuvette. The probe 535 is raised at a rate which maintains the tip of the probe just above the rising surface of fluid in the cuvette. This provides maximum uniform mixing of the sample and reagent and minimizes splashing of fluids. This procedure also minimizes the introduction of air bubbles into the reaction mixture. This procedure is followed for the reagent probe systems R2 and R3 which are described hereinafter. A connector 572 is connected to the PC board 534 of the arm 519 through a flexible lead 578 and is connected to the PC board 537. The metallic probe 535 is electrically connected to the connector 572 and forms part of the capacitance level sensing system.

Referring more specifically to FIGS. 63, 65 and 69, the carriage 465 of the reagent probe system R2 includes a vertical forwardly facing wall 541, a top horizontal wall 542 and a bottom horizontal wall 543. The wall 541 has a horizontal bore 549 with a bearing 544 at each end of the bore. The top wall 542 has a bearing 557 which is located in a vertical bore 556. The bottom wall 543 has a bearing 558 which is located in a vertical bore 559. The bores 556 and 559 are vertically aligned. The wall 542 also has a vertical bore 54 which is vertically aligned with a vertical bore 546 in the bottom wall 543. An anti pivot rod 547 is located in the bores 546 and 545 and has an upper threaded end 548 which is threaded into the carriage supporting slide bar 462. A lead screw 550 is connected to the stepper motor 471 through a coupling 551 and extends through a roll nut 552 in a block 553. The block 553 is mounted in a yoke 554 in the same manner as the mounting of the block 493 in the yoke 494 as shown in FIG. 67. Since the roll nut 552 is fixed within the block 553, rotation of the lead screw 550 upon actuation of the stepper motor 471 causes the block 553 to move along the longitudinal axis of the lead screw 550. The yoke 554 has a shaft 555 which is mounted within the bearings 544 and extends through the horizontal bore 549. As the block moves forwardly and rearwardly along the longitudinal axis of the lead screw 550, it causes the entire carriage 465 to move forwardly and rearwardly relative to the support plate 441, depending on the direction of rotation of the lead screw 550 by the reversible stepper motor 471. A follower guide 561 is located between the upper and lower walls 542 and 543, respectively, and has a vertical bore 560 through which the anti pivot rod 547 extends. Referring to FIG. 69, the follower guide 561 also has a vertical bore 574 which contains a roll nut 563. The follower 561 is fixed to a probe carrying arm 562 which carries a reagent probe 576, see FIG. 62. A PC board 575 is connected to the arm 562, see FIG. 69. A vertical lead screw 573 is located within the roll nut 563 and is rotatably mounted within the bearings 557 and 558. The bottom end of the lead screw 573 extends below the bottom wall 543 and is fixed to a pulley 568. An electric reversible stepper motor 564 is fixed to a lower and rearwardly extending horizontal bracket 565 of the carriage 465 and has a downwardly extending drive shaft 566. A pulley 567 is fixed to the shaft 566 and is drivingly engaged with the pulley 568 through a timing belt 569. The interior surface of the timing belt 569 has teeth which engage corresponding teeth on the pulleys 567 and 568, (teeth not shown). When the lead screw 573 is rotated in one direction by the stepper motor 564, the follower guide 561 moves upwardly relative to the support plate 441 along with the reagent probe 576. The reagent probe 576 is moved downwardly with the follower guide 561 when the motor 564 is reversed to rotate the lead screw 573 in the opposite direction. An electrical connector 570 extends from the stepper motor 564 and is connected to the junction J13 on the PC board 446. A bracket 582 is fixed to the top wall 542 and has a plurality of upwardly extending tabs 581 which interacts with the interrupter sensor 452 for insuring that the probe 576 is properly positioned at the several forward positions. If one of the tabs 581 interrupts a beam in the sensor 452 as any one of the forward positions of the probe 576, a signal is transmitted to the CPU that the probe is improperly positioned. A "home" tab 634 extends upwardly from the carriage 465 and interacts with the interrupt sensor 453. When the carriage 465 reaches its rearward "home" position, the tab 634 interrupts the beam of the sensor 453 which transmits a signal to the CPU that the carriage is properly positioned at the "home" position in which the probe 576 is positioned over the reagent dispensing point 46.

The stepper motors 471 and 564 are selectively controlled by the CPU to move the carriage vertically and horizontally to position the probe 576 in the same aspirating and dispensing sequence as described for the probe 535 except that the probe 576 is moved in a straight forward to back line 426, see FIG. 22, which intersects the vertical axes of the reagent dispensing point 46, the wash station 16, and the holes 339 and 340 in the cover 327 of the reagent transport system 27. Depending on the test protocol, the probe 576 will be moved forwardly to pick up or aspirate a labeled or tracer reagent at the opening 339 or a solid phase reagent at the opening 340. The test protocol may also require that a labeled reagent and a solid phase reagent are to picked up by the probe 576. The probe 576 is lowered by the motor 564 at each position 339 and 340. The lower position of the probe 576 is determined by a capacitance fluid sensing electronics as described for the sample probe 407. After aspiration a volume of reagent the probe 576 is moved to its upper position, whereupon the motor 471 is actuated for a predetermined number of half steps to move the probe above the other reagent opening or rearwardly so that the probe 576 is above the reagent dispense point 46. The probe is then lowered into a cuvette which is beneath the point 46. The aspirated reagent is then dispensed into the sample solution in the cuvette. The probe 576 is then raised to its upper position and moved to the wash station 16 for a wash cycle, whereupon it will be ready to begin another aspirating and dispensing cycle.

Referring to FIGS. 22, 63, 66 and 71, the carriage 466 of the reagent probe system R3 includes a rearwardly extending vertical wall 594, a top horizontal wall 592 and a bottom horizontal wall 593. The vertical wall 594 has a bore 595 which contains the cylindrical portion 580 of a guide 608 which has a bore 579. A bearing 607 is located at each end of the bore 579. The top horizontal wall 592 has a bearing 590 which is located in a bore 591. The bottom wall 593 has a bearing 584 which is located in a bore 589. A lead screw 583 is rotatably mounted in the bearings 590 and 584 and extends from the top wall 592 to the bottom wall 593. The bottom of the lead screw 583 extends below the bottom wall 593 and is fixed to a pulley 600. A reversible stepper motor 596 is fixed to a lower horizontally and rearwardly extending bracket 597. The motor 596 has a downwardly extending drive shaft 598 which is fixed to a pulley 599. The pulley 600 is drivingly connected to the pulley 599 through a timing belt 601. The inner surface of the belt 601 has teeth which engage corresponding teeth on the drive pulleys 599 and 600 (teeth not shown). A reagent probe carrying arm 617 has a tab 627 which extends into a vertical slot in the rear side of the post 609 is fixed to a lead screw follower 615 which has a roll nut 625 within a bore 616. The lead screw 583 is drivingly engaged with the roll nut 625 for moving the probe carrying arm 617 vertically up or down depending on the direction of rotation of the lead screw by the stepper motor 596. A vertical post 609 is located between the upper wall 592 and the lower wall 593, and has a lower rearwardly extending horizontal flange 610. The flange 610 extends below the lower wall 593 and has a bore 611 which is vertically aligned with the bore 589 so that the post is mounted on the bearing 584 for rotation about the central longitudinal axis of the lead screw 583. The rear side of the post 609 has a vertical slot which is identical to the slot 432 of the post 522. The reagent probe carrying arm 617 has a tab 627 which extends horizontally into the vertical slot of the post 609. This enables the post 609 to rotate with the gear segment 612 about the longitudinal axis of the lead screw 583 for changing the angular position of the third reagent probe 633 relative to the carriage 466. A PC board 618 is fixed to the post 609 and has an interrupter sensor 624. An electrical connector 622 extends from the PC board 618 and is connected to the junction J16 of the PC board 446. When the probe carrying arm 617 reaches its upper position, the tab 627 interrupts a beam on the sensor 624 which initiates a signal to the CPU which indicates that the probe is properly positioned in its upper position. The back and forth motion of the carriage 466 is provided by the stepper motor 470 which has a drive shaft 474. The shaft 474 is fixed to a lead screw 602 by a coupling 628. The lead screw 602 is engaged with a roll nut 603 in a block 604. The block 604 is mounted in a yoke 605 in the same manner as block 493 which is mounted in the yoke 494 as shown in FIG. 67. The yoke 605 has a shaft 606 which is mounted in the bearing 607 and extends through the bore 579 of the follower guide 608. Rotation of the lead screw 602 causes the block 604 to move along the central longitudinal axis of the lead screw.

When the stepper motor 596 is rotated in one direction, the carriage 466 moves forwardly relative to the plate 441. When the stepper motor 596 is reversed, the carriage 466 is moved rearwardly relative to the plate 441, A bracket 620 is fixed to the upper wall 592 of the carriage 466 and has a plurality of upwardly extending tabs 621 which interact with the interrupt sensors 453 and 454. The sensor 454 is a home sensor. When the carriage 466 is in its rearward position so that the probe 633 is located above the reagent dispensing point 17, the rearmost tab 621 interrupts a beam in the sensor 454 which initiates a signal to the CPU that the probe is in its "home" position. The tabs 621 interrupt a beam in the sensor 453 when the probe 633 is improperly positioned in any one of its forward aspirating or wash positions as described for the reagent probe systems R1 and R2. A PC board 618 is fixed to the post 609 and has an electrical connector 622 which is connected to the electrical junction 116 of the PC board 446. Referring to FIG. 71, a PC board 626 is fixed to the probe supporting arm 617 and is connected to the PC board 618 by an electrical connector 619.

The upper end of the post 609 is fixed to a gear segment 612 which has a bore 613. The gear segment 612 has gear teeth 614 which extend radially about the center of the bore 613. The gear segment 612 is located above the top wall 592 so that the bore 613 is an axial alignment with the bore 613. The teeth of the gear segment 612 are in driving engagement with the the 631 of a horizontal plate 630 as shown in FIG. 60. When the carriage 466 is in its rear position, the probe holding arm 617 faces to the right as viewed in FIG. 60. As the carriage 466 moves forwardly, the gear segment 612 rotates about the vertical axis of the lead screw 583. This causes the probe supporting arm to rotate approximately 90° from the rightwardly facing position as shown in FIGS. 60 and 62 to a forwardly facing position. This causes the probe 633 to move along a curved path which is indicated by the dotted dot and dash line 429 as shown in PIG. 22. The line 429 intersects the vertical axes of the dispensing point 46, wash station 17, and the openings 341 and 342 in the cover 327 of the reagent tray 27 as shown in FIG. 22.

Depending on the test protocol, the reagent aspirating and dispensing probe 633 will be moved forwardly to pick up or aspirate a labeled or tracer reagent at the opening 341 or a solid phase reagent at the opening 342, see FIG. 22. Although the probe 633 is capable of picking up labeled and solid phase reagent, the probe 633 is normally used for picking up a single reagent The probe 633 is utilized for picking up a reagent which compliments the single reagent which was picked up and dispensed into a cuvette by a preceding probe in accordance with a particular test protocol. At each position 341 and 342, the probe 633 is lowered by the motor 596. The lower position of the probe 633 is determined by a capacitance fluid sensing electronics as described for the sample probe 407. After aspiration of a volume of reagent, the probe 633 is moved to its upper position, whereupon the motor 470 is actuated for a predetermined number of half steps to move the probe above the other reagent opening or rearwardly so that tee probe 633 is above the reagent dispense point 47. The probe is then lowered into a cuvette which is beneath the point 47. The aspirated reagent is then dispensed into the sample solution in the cuvette. The probe 633 is then raised to its upper position and moved to the wash station 17 for a wash cycle, whereupon it will be ready to begin another aspirating and dispensing cycle.

The lower position of each reagent probe is determined by a capacitance fluid sensing system as described for the reagent probe systems R1 and R2.

In the preferred embodiment, the solid phase reagent and the labeled reagent are arranged in two separate concentric circles which maximizes the number of reagent pairs that can be used with the analyzer. This means that each of the reagent probes must have two reagent aspirating positions in order to pick up either of the reagents. It is possible to place the labeled reagent in the same type of container as the solid phase reagent and to place the container on the inner circle of holders with the solid phase reagents. If a test protocol calls for both reagents of a pair to be picked up by a probe, the probe would be raised after aspirating one of the reagents This would allow the reagent tray to position the second reagent of the pair beneath the probe. The second reagent would then be picked up by the probe.

Fluid Aspirating and Dispensing Apparatus

Referring to FIG. 73, the means for aspirating and dispensing fluid through the sample reagent probes includes the syringe bank 32 which includes a housing 650 and a plurality of stepper motors 655, 656, 657, and 658 which are mounted to the back of the housing 650. A plurality of syringes 651, 652, 653, and 654 are mounted to the front of the housing and are actuated by the stepper motors 655, 656, 657, and 658, respectively, the drive mechanism between each stepper motor and its respective syringe is a frictional rack and pinion drive which is shown and described in U.S. Pat. No. 4,539,854 to Bradshaw et al. and incorporated herein by reference. Each syringe can be controlled to aspirate or dispense a small amount of fluid by controlling the signals to the corresponding stepper motor from the CPU in accordance with the machine control program. The syringe 651 is operatively connected to the sample aspirating and dispensing probe 407 through a tube 659. The syringe 652 is operatively connected to the reagent aspirating and dispensing probe 531 of the reagent probe system R1 through a tube 660. The syringe 653 is operatively connected to the reagent aspirating and dispensing probe 576 of the reagent probe system R2 by means of a tube 661. The syringe 654 is operatively connected to the reagent aspirating and dispensing probe 633 of the of the reagent probe system R3 by a tube 662. Each tube which connects a reagent probe to its corresponding syringe passes through a heated fluid bath 648. Each reagent probe aspirates a predetermined volume of reagent and after the probe has been raised out of contact with the reagent solution the corresponding syringe is operated for a predetermined draw of air which also draws the aspirated reagent into the fluid bath 648. The fluid bath 648 maintains the reagent at a predetermined operational temperature, preferably 37° C. A portion of the tube which is in the fluid bath is coiled so that the entire quantity of reagent solution is equilibrated to the operational temperature before the reagent is dispensed into the appropriate cuvette. The air which has been drawn in behind the reagent is dispensed until the reagent reaches the tip of the probe prior to dispensing of the reagent into the cuvette.

Referring to FIG. 75, wash stations 15, 16, 17, and 18 are shown mounted in front of the cuvette dispense and incubation section 39. Station 18 comprises a tubular housing 666 which is mounted to the machine framework by a clamp 665. The housing 666 has a top opening 667, a bottom outlet nipple 668 and a side port 669 which is located near the bottom opening 668. A tube 670 is connected to the nipple 668 and a tube 671 is connected to the side port 669. The wash station 15 comprises a tubular housing 663 which is mounted to the machine framework by a post 688. The housing 663 has a top opening 673, a bottom outlet nipple 674 and a side port 676 which is located near the bottom opening 674. A tube 675 is connected to the nipple 674. A tube 677 is connected to the side port 676. The wash station 16 comprises a tubular housing 678 which is mounted to the machine framework by a clamp 665. The housing 678 has a top opening 679, a bottom opening 680, and a side port 682 which is located near the bottom outlet nipple 680. A tube 681 is connected to the nipple 680 and a tube 683 is connected to the side port 682. The wash station 17 comprises a tubular housing 684 which is fixed to a post 691 which is fixed to the supporting base of the machine framework. The housing 684 has a top opening 685, a bottom outlet nipple 686, and a side port 687. A tube 690 is connected to the bottom opening 686 and a tube 689 is connected to the side port 687.

Water supply to the wash stations from the reservoir 30 will be described below.

The wash stations function to wash the various probes of the present invention between aspiration and dispense cycles. Deionized water is utilized as the wash solution in the preferred embodiment. Wash solution is discarded in waste container 31 after the wash cycle, as will be described below.

Separation/Wash/Resuspend System

The reaction kinetics of the assays performed by the analyzer of the present invention are maximized by the elevated temperature and the very efficient binding afforded by the large surface area of the paramagnetic solid-phase particles. Each assay sample undergoes the same total incubation time of seven and one, half minutes. When a cuvette reaches the end of this total incubation time, it enters a section of the process track or incubation section where separation and washing is accomplished. Powerful permanent magnets of neodymium-boron are mounted on the process track at tis point, and the paramagnetic particles are rapidly pulled to the back wall of the cuvette. Liquid is aspirated from the cuvette by a vacuum probe which consistently seeks the bottom of the cuvette, the liquid being held in a waste reservoir for later disposal. Washing of the cuvette and particles is accomplished by forceful dispensing of deionized water, followed by rapid magnetic separation and aspiration. One or two washes may be performed, based upon the specific assay, yielding non-specific binding of less than 0.1%. After completion of the wash cycle, the particles are resuspended in an acid containing 0.5% hydrogen peroxide in a weak nitric acid, added from a fixed port above the cuvette.

Referring to FIGS. 76–80, the aspirate resuspend area 28 includes a block 694 which is mounted above the cuvettes and the aspirate resuspend area at the downstream end of the cuvette dispense and incubation section 39. A pair of spaced plumbing fixtures 695 and 700 are mounted in the block 694. The fixture 695 has a bore 696 which extends completely through the block 694 to the cuvette and two tubes 697 and 698, which communicate with the bore 696 and a nozzle 699 which extends through the fixture 695 in a fixed angular position. The nozzle 699 is connected to a tube 692 which is operatively connected to the reservoir 30 of deionized water. The nozzle 699 is positioned to direct a stream of deionized water against the front wall of the cuvette as shown in FIG. 79. The fixture 700 has a bore 701 which extends completely through the block 694 to the cuvettes and two tubes 702 and 703 which communicate with the bore 701. An acid dispense fixture 704 is mounted to the block 694 downstream of the fire 700. As shown in FIG. 80, a nozzle 706 is mounted in an angular fixed position in the fixture 704 so that the end of the nozzle 706 is located just above the top opening of the cuvette which is positioned just beneath the fixture 704. As shown in FIG. 80, the nozzle 706 is connected to a tube 707 which is operatively connected to the acid reservoir 33, see FIG. 21B. The probe 106 is positioned at an angle to the vertical so that the stream of acid which is dispensed from the end of the nozzle is directed against the back wall of the cuvette 40 for a purpose to be described.

Referring to FIG. 77, an aspirating unit which is generally indicated by the reference numeral 708 is mounted on the fixed position behind the block 694. The aspirating unit 708 comprises a fixed horizontal supporting plate 709. A stepper motor 710 and a bracket 727 which are mounted on the plate 709. The bracket 727 has an upper horizontal flange 714. A lead screw 717 is rotatably mounted in bearings 715 and 716 in the flange 714 and the base 709, respectively. The lead screw 717 extends through a roll nut 718 which is fixed within a bore 706 of a follower 719. The lower end of the lead screw 717 extends below the base 709 and is fixed to a pulley 712. The drive shaft of the stepper motor 710 extends below the base 709 and is fixed to a pulley 711. The pulley 712 is driven from the pulley 711 through a timing belt 713 which engages corresponding teeth on the pulleys 711 and 712, (teeth not shown). A forwardly extending arm 720 is fixed to the follower 719 and has a pair of laterally extending arms 721 and 722. Referring also to FIG. 78, a probe 725 extends freely through the arm 721 and a housing 723 which is fixed to the arm 721 and 725 has a protuberance 730 within the housing 723 which limits the upward movement of the probe relative to the housing 73. The probe 725 is biased in the downward position by a spring 731. A probe 726 extends freely through the arm 722 and a housing 724 which is identical to the housing 723 to limit the upward movement of the probe 726 relative to the arms 722 and the housing 724 and to bias the probe 726 downwardly. The probes 725 and 726 are vertically aligned with the bore 696 and 701 respectively. Actuation of the motor 710 causes the lead screw 77 to rotate about its vertical longitudinal axis which causes the follower 719 to move upwardly or downwardly depending on the direction of rotation of the drive shaft of the stepper motor 710. The vertical motion of the follower 719 causes the probes 725 and 726 to move from an upper position in which the probes are above the top openings of the cuvettes and a lower position in which the bottom tips of the probe s extend down to the bottom of the cuvettes. The arm 720 is moved downwardly a distance which is slightly more than that which is required to enable the probes 725 and 726 to reach the bottom of the cuvettes. When the probes 725 and 726 strike the bottoms of their reeve cuvettes, the additional slight movement of the arm 720 causes the probes to move upwardly relative to the arms 721 and 722, respectively, against the bias of the springs 731. This grantees that the bottom ends of the probes 725 and 726 will always be at the bottom of each cuvette for complete aspiration of the fluid in the cuvette. The follower 719 has a laterally extending horizontal tab 744 which rides in a vertical slot 745 in the post 727. This prevents rotation of the follower about the longitudinal axis of the lead screw 717. An interrupter sensor 746 is located at the top of the slot 745. When the follower 719 reaches its upper position, the, tab 744 interrupts a light beam between the two elements of the sensor 746 which initiates an electrical signal to the CPU to indicate that the probes 725 and 726 have reached their upper predetermined positions. At a designed time in the machine operation sequence, the motor 710 is energized for a predetermined number of half steps to lower the probes 725 and 726 to their lower positions.

Referring to FIG. 74, there is shown a cross-section of a heated tube configuration which is generally indicated by the reference numeral 733. This configuration forms a portion of the tubing which connects each reagent probe to its corresponding syringe that extends between the probe and the heated fluid bath 648. The heated tube configuration 733 comprises a teflon tube 734 through which the reagent flows, an insulated heater wire 735 which is spirally wound around the tube 734 and a thermistor 736. The tube 734, the heater wire 735 and the thermistor 736 are all enclosed within a shrink-wrap tube 737. The heater wire 735 is a nickel-chromium wire which has a return lead 738 outside of the shrink-wrap tube 737. The shrink-wrap tube 737 and the return lead 738 are, in turn, enclosed in a polyvinyl chloride tubing 739. The function of the heated tube 733 is to maintain the temperature of the reagent at 37° C. after it is transferred from the heated fluid bath 648 to the reagent aspirating and dispensing probe. The CPU controls energization of the heater coil 735.,in accordance with electrical signals which are received from the thermistor 736 which functions to maintain the temperature of the tube 734 at 37° C., plus or minus one degree. Although the heated fluid bath 6 is effective in heating the reagent to the desired predetermined temperature, i.e., 37° C., experience has shown that the temperature of the reagent drops below the predetermined set temperature as it passes back from the heated fluid bath 648 to the reagent probe. The reason that this occurs is that the section of tubing between the reagent probe amid the heated fluid bath is chilled by the reagent as it is aspirated from its container, particularly if the reagent is colder than room temperature, which sometimes occurs at the beginning of the initial setup of a run of tests. The pre-chilling of this section of the tube causes the tube to act as a heat-sink and absorb heat from the reagent when it passes back from the heated fluid bath A. The heated tube configuration 733 maintains the tube at the set temperature and prevents this chilling effect This insures that the temperature of the reagent remains the same as it was in the heated fluid bath 648. The entire structure of the heated tube configuration 733 is flexible to compensate for the vertical movement of the reagent probe. The wall thickness of the teflon tube 734 is very important for the satisfactory operation of the heated tube configuration 733. The wall thickness of the teflon tube 734 is between and including 0.006 and 0.010 inches. If the wall thickness is below the lower value, the breakage frequency of the tube is considered unacceptable. If the thickness is greater than 0.010 inches, the efficiency of heat transfer from the heater wire 735 to the reagent fluid as it passes through the tube 734, is significantly reduced, thereby making it difficult to maintain the reagent at the set temperature.

The tube 734 is made of a fluoroplastic material, specifically PTFE (polytetfluorethylene). PTFE has exceptional resistance to chemicals and heat and is used for coating and to impregnate porous structures. The relative stiffness or rigidity of PTFE renders it generally unsuitable for fluid us. However, for the optimum thickness range of the tube 734, PTFE is sufficiently flexible and yet provides superior heat transfer and chemical resistant qualities to the tube.

Referring also to FIGS. 34 and 35, the aspirate/resuspend area 28 also includes three magnets 740, 741 and 742 which are located beneath the cuvette conveyor along the back wall of a channel 743 through which the cuvettes pass as they are card by the drive belts 167 and 168. Each of the magnets 740 and 741 is elongated and extend horizontally, see also FIG. 21B. The magnet 741 extends from he end of the 740 on the downstream side and is located at a slightly lower level than the magnet 740 as shown in FIGS. 34 and 35. Each magnet 740 and 741 creates a magnetic field having a vertical north-south polarity. The magnet 742 is located on the front wall of the channel 743 and extends downstream from the end of the magnet 741. The magnet 742 creates a magnetic field having a north-south polarity which is below the magnetic field of the magnet 741. As a cuvette enters the aspirate/resuspend area 28, the paramagnetic particles from the solid phase reagent are attracted toward the magnet 740 and migrate to the back wall of the cuvette. As the cuvette continues to travel along the magnet 740, the paramagnetic particles begin to concentrate more towards the center of the magnet 740. As the cuvette passe beneath the bore 696, the liquid in the cuvette is aspirated by the probe 725 and delivered to the waste fluid reservoir 31, while deionized water from the reservoir 30 is introduced into the cuvette through the nozzle 699. The aspiration of the liquid from the cuvette effectively removes all of the unbound labeled reagent and unbound, test sample from the sample reagent mixture. This process isolates the detectable, product that is formed by the test reaction, i.e. the complex including the paramagnetic particles. The deionized water from the nozzle 699 is directed against the front wall of the cuvette to minimize any disturbance of the paramagnetic particles against the back wall of the cuvette. As the cuvette advances from the position beneath the bore 696 to the position beneath the bore 701, the paramagnetic particles continue to concentrate into a progressively tightening mass or "pellet" against the back wall of the cuvette. The magnet 741 is located in this area and since it is lower than the magnet 740, the paramagnetic particles tend to congregate at a lower point in the cuvette. This locates the concentrated mass of particles in an area which is below the level of the acid solution which is added in a subsequent step. When the cuvette stops at the point beneath the bore 701, the probe 726 descends to the bottom of the cuvette and aspirates the wash solution of deionized water which is delivered to the fluid waste reservoir 31. When the cuvette is next positioned beneath the bore 705 of the fixture 704, the nozzle 706 dispenses a volume of an acid solution such as hydrogen peroxide from the acid reservoir 33. Because of the angle of the probe 706, the acid is delivered against the back wall of the cuvette just above the concentration of paramagnetic particles. This effectively washes the particles away from the back wall and resuspends them in the acid solution. As the cuvette moves away from the bore 705, it passes along the front magnetic 742 which helps to pull some of the paramagnetic particles away from the rear part of the cuvette toward the front. This helps to distribute the particles evenly within the acid solution. Since the probes 725 and 726 are linked into the same actuating-mechanism, they are lowered into the bore 696 and 701, respectively, simultaneously. While the probe 725 aspirates a sample reagent solution from a cuvette beneath the bore 696, the probe 726 aspirates a wash solution from a cuvette which is located beneath the bore 701. At the same time, the probe 706 dispenses a volume of acid solution to a cuvette which is located downstream of the cuvette which is located beneath the bore 701. The cuvette which is beneath the acid probe 706 is then advanced toward the elevator mechanism to the luminometer which is described in the next section.

Luminometer System

The luminometer includes a rotary housing with six wells. A detector includes a photomultiplier tube (PMT) which is mounted in front of the housing. A cuvette enters one of the wells in the housing from the entrance opening and is moved in increments to the exit opening. At the third position from the entrance opening, the cuvette is aligned with the PMT. This design effectively eliminates ambient light from the measuring chamber prior to initiating the chemiluminescent reaction. With the cuvette positioned in front of the PMT, a base solution, containing dilute sodium hydroxide, is injected into the cuvette. For one particular assay, for example, this causes the oxidation of an acridinium ester label and results in the emission of light photons of 430 nm wavelength. This emission is a sharp spike within one second and has a duration of 34 seconds. The intensity of the emission is measured over a 5 second interval by the PMT, which operates in the photon-counting mode. "Dark counts" are measured before the light emission, and are subtracted automatically.

The luminometer system is shown in FIGS. 76 and 81–86 and comprises a luminometer assembly which is generally indicated by the reference numeral 760 which is mounted on top of an elevator assembly which is generally indicated by the reference numeral 761. The elevator assembly 769 comprises a housing 762 which has a vertical bore 763 which ends from a chamber 764 at the end of the event conveyor to the luminometer assembly. Referring particularly to FIG. 83, the elevator assembly 761 also includes a top plate 765 and a lower plate 766. A lead screw 767 is rotatably mounted in bearings 768 in the lower and upper plates 766 and 765, respectively. A follower 769 is mounted on the lead screw 767 for movement along the central longitudinal axis of the lead screw upwardly or downwardly depending upon the direction of rotation of the lead screw. Plunger 771 is located below the chamber 764 and is fixedly connected to the follower 769 by a horizontal arm 770. A vertical anti-pivot rod 772 is fixed to the bottom plate 766 and the upper plate 765 and extends freely through an aperture 780 in the arm 770. The lower end of the lead screw 767 extends below the bottom plate 766 and is fixed to a sprocket 776. A stepper motor 773 is mounted to the lower end of the elevator assembly 761 and has a downwardly extending drive shaft 774 which is fixed to a sprocket 775. The sprocket 776 is driven from the sprocket 775 through a drive chain 777, see FIG. 81. The motor 773 is reversible. When the lead screw 767 is rotated in one direction the follower 769 is moved from the lower position shown in full lines to the upper position shown in dotted lines in FIG. 83. This causes the plunger 771 to move from tee lower full line position to the upper dotted line position as shown in FIG. 83. When the lead screw 767 is rotated in the opposite direction, the follower 769 and the plunger 771 move downwardly from the dotted line position to the full line position. The cuvettes 40 are conveyed along the event conveyor at twenty second intervals. Every twenty seconds a cuvette 40 is deposited into the chamber 764 from tee event conveyor while the plunger 771 is in the lower full line position. The motor 773 is actuated for rotating the lead screw 767 so that the plunger 771 moves to the upper position carrying the cuvette 40 which is in the chamber 764 to the luminometer assembly 760. The follower 769 has a horizontally extending tab which interacts with upper and lower interrupter sensors 758 and 759. When the follower is at the lower position shown in full lines in FIG. 83, the tab 778 interrupts a light beam between the two elements of the sensor 759 which initiates a signal to the CPU that the plunger 771 is properly positioned at the lower position. At a predetermined time in the overall machine sequence, a cuvette 40 is delivered by the event conveyor to a point above the plunger 771 as shown in full lines in FIG. 83 and the motor 773 is energized for a predetermined number of half steps to raise the plunger 771 to the dotted line position which delivers the cuvette 40 to a starting position within the luminometer assembly 760. When the follower 769 reaches its upper position, the tab 778 interrupts a light beam between the two elements of the sensor 758 which initiates a signal to the CPU that the plunger 771 is properly positioned at its upper position. The motor 773 is then reversed for a predetermined number of half steps to return the plunger 771 to its lower position.

Referring particularly to FIGS. 83 and 84, the luminometer assembly 760 comprises a bottom support plate 789 which is supported on the top plate 765 of the elevator assembly. A luminometer housing 790 includes a cylindrical vertical wall 788, a bottom wall 792 and a top wall 793. The housing 790 has a large circular chamber 791 which contains a carrousel 800. The luminometer housing 790 is supported on the bottom support plate 789. The bottom plate 792 has a central uplifted portion 794 which has an aperture 795 which contains a bearing 796. The top wall 793 has an aperture 799 which contains a bearing 798. A vertical shaft 797 is rotatably mounted in the bearings 796 and 798 and is fixed to a hub 787 of the carrousel 800. The upper end of the shaft 797 extends above the top wall 793 and is fixed to a gear 801. A stepper motor 804 is mounted on the top wall 793 and has a downwardly descending drive shaft 803 which is fixed to a gear 802. The gear 802 is in driving engagement with the gear 801 for rotating the shaft 797 which causes the carousel 800 to rotate about the central longitudinal axis of the shaft 797. An encoder wheel 805 is fixed to the top end of the shaft 797 above the gear 801. A luminometer sensor board assembly 806 is fixed to the top wall 793. The encoder wheel 805 has a plurality of spaced upwardly extending tabs 784 which interacts with an interrupt sensor 783 which extends downwardly from the PC board 806. In the embodiment shown in FIG. 84, there are six tabs 784 which correspond to six external cavities or wells 814 in the outer wall of the carousel 800. The carousel 800 is indexed to a new position every twenty seconds by the stepper motor 804 through the gears 801 and 802. The stepper motor 804 is given an input signal from the CPU which causes the carousel 800 and the encoder wheel to rotate about the axis of the shaft 797. The carousel continues to rotate until the edge of one of the tabs 784 interrupts a light beam between the elements of the interrupt sensor 783. When this occurs, the motor 804 is de-energized for a predetermined time period, whereupon the motor will be energized to move the carousel 800 to the next position. A side opening 807 is located in the cylindrical vertical wall 788 and opens into a tunnel 810 of a connector arm 809 which connects the luminometer housing 790 to a photo-multiplier tube 808. The bottom wall 792 has an entrance opening 811 and an exit opening 812. The entrance opening 811 is vertically aligned with the vertical bore 763 of the elevator assembly 761. The exit opening 812 is vertically aligned with a waste receptacle 35 for the cuvettes, see FIG. 21B. The six cavities 814 in the outer surface of the carousel 800 are sequentially vertically aligned With the openings 811 and 812 as the carrousel 800 is rotated about the axis of the shaft 797. Each cavity 814 has an outer opening which is closed by the cylindrical wall 788 of the hub 780 and a bottom opening which is closed by the bottom wall 792. The upper wall of each cavity has a small access opening 852 which leads to the cavity. The access openings 852 are covered by the top wall 793 except when they are vertically aligned with a pair of holes 836 and 851 in the top wall 793 for a purpose to be described. Referring to FIG. 86, as the carousel rotates about the central vertical axis of the shaft 797, relative to the housing 790, each cavity 814 is maintained light tight from light from the outside except where the cavity is aligned with one of the openings 812 and 811. Each cuvette is delivered by the elevator 761 into a cavity 814 which is aligned with the opening 812. The carousel is rotated 60° every twenty seconds. The cuvette is carried in a circle about the axis of the shaft 797 until it reaches the opening 811 and falls into the waste receptacle 35. Every twenty seconds, a new cuvette is delivered into a cavity 814 and a processed cuvette is dropped through the opening 811. The central uplifted portion 794 forms a downwardly facing cavity 785. The uplifted portion 794 has an aperture 786 which faces the side opening 807. A reference LED (light emitting diode) 830 is mounted on a PC board 829. The PC board 829 is fixed to the bottom wall 792 so that the reference LED 830 extends into the cavity 785. The LED 830 is periodically energized to emit a beam of light and is positioned so that the beam of light passes through the aperture 786 to the photomultiplier tube 808. The bottom opening of the cavity 785 is closed by a cover 831 so that light cannot enter the cavity from the outside. The amount of light from the LED is substantially greater tin the light from a test flash and is beyond the normal operating range of the photomultiplier tube 808. A light filtering means, not shown, is positioned between the LED and the photomultiplier tube 808 to alter or reduce the amount of light which reaches the PMT from the LED.

Referring particularly to FIGS. 84 and 85, a wash/waste tower assembly 816 is fixed to the tops of a plurality of vertical posts 815 which are in mm fixed to the bottom support plate 889. The assembly 816 comprises a support plate 817 which is fixed to the posts 815, a stepper motor 818 and a post 819 which is fixed to the top of the plate 817. The post 819 has a laterally extending upper arm 820. A vertical lead screw 823 is rotatably mounted in bearings 821 in the arm 820 and the plate 817. A follower 824 is mounted on the lead screw 823 for movement along the central longitudinal axis of the lead screw. The lead screw is drivingly engaged with a roll nut 813 which is mounted within the follower 824. The stepper motor 818 has a downwardly extending drive shaft which is fixed to a pulley 826. The lower end of the lead screw 823 extends below the plate 817 and is fixed to a pulley 825. The pulley 825 is driven from the pulley 826 through a timing belt 827. The inner surface of the timer belt 827 has teeth which engage corresponding teeth on the pulleys 825 and 826 (teeth not shown). Rotation of the stepper motor 818 in one direction causes the follower 824 to move upwardly along the lead screw 823 while rotation of the stepper motor in the opposite direction causes the follower 824 to move downwardly along the lead screw 823. A probe retainer arm 828 is fixed to the follower 824 and extends forwardly and horizontally therefrom. The forward end of the arm 828 has a bore 833 which holds a probe assembly 832. The probe assembly 832 includes a housing 835 which is fixed to the arm 828 with the bore 833 and an aspirating probe 834. The probe 834 is mounted in the housing 835 for limited vertical movement and is biased in the downward position in the same manner as the probes 725 and 726 as illustrated in FIG. 78. The upper end of the probe 834 is fixed to a tube 836 which is operatively connected to the waste fluid reservoir 31. The follower 824 has a laterally extending arm 782 which rides in a vertical groove 781 in the post 819 as the follower 824 moves vertically relative to the lead screw 823. The tab 782 prevents the follower 824 from rotating about the central longitudinal axis of the lead screw. A plumbing fixture 837 is mounted to the top wall 793 above the hole 836. The fixture 837 has a nozzle 838 which extends into the hole 836 and is connected to a tube 839 which is operatively connected to that base solution reservoir 34. A plumbing fixture 840 is fixed to the top wall 793 just above the hole 851 and has a bore 841 which extends down to the hole 851. The probe 834 is vertically aligned with the bore 841 so that when the probe is moved to its lower position, it enters the bore 841 and extends through the hole 851 and through the access opening 852 of one of the cavities 814 which is vertically aligned with the hole 851. The fixture 840 also has a pair of tubes 844 and 845 which are operatively connected to the bore 841. The tube 844 is operatively connected to the deionized water reservoir 30 and the tube 845 is operatively connected to the waste fluid reservoir 31. The upper end of the probe 834 is located in a housing 835 which is identical to the housing 723 which is shown in FIG. 78. The probe 834 is programmed to be lowered to the bottom of a cuvette which is located beneath the bore 841 and slightly beyond. When the probe 834 reaches the bottom wall of the cuvette, it is forced upwardly relative to the housing 835 against the bias of the spring within the housing. This insures that the probe will always reach the bottom of the cuvette for complete aspiration of fluid within the cuvette.

FIG. 86 is a diagrammatic representation of the bottom wall 792 and the photomultiplier tube 808. The cuvette 40 is delivered by the elevator 761 through the opening 812 in the bottom wall 792 to one of the cavities 814 which is aligned with the opening 812 and which is identified in FIG. 86 as position 846. The cuvette is moved every twenty seconds in 60° increments in a circle about the axis of the shaft 797. The cuvette is moved from position 846 to position 847 and then to position 848 in front of the opening 807. In this position, the nozzle 838 delivers a predetermined volume of a basic solution 0.25 N. NaOH to the acid solution, eg. 0.1 N. $HNO_3$ with 0.5% $H_2O_2$, which is already in the cuvette. This causes the generation of a chemiluminescent signal. The signal is detect over a five second interval by the PMT which operates in a photon-counting mode. A chemiluminescent signal or flash produces a flash profile which is compared to a stored standard curve to determine the analyte concentration in the sample. A master dose-response curve is generated for each lot of reagents. This information is put into the analyzer by keyboard or bar code. The information is calibrated by measuring two standards, whose values are used to adjust the stored master curve. The recommended data of reduction methods are selected from a spline fit, or four or five parameter logistic curve fits, and are preprogrammed for each assay. The cuvette is next moved to position 849 which is beneath the bore 841. The probe 834 is lowered to the bore 841, the opening 851 and into the cuvette, which is beneath this position, through the access opening 852. All of the fluid contents in the cuvette are aspirated by the probe 834 whereupon the probe 834 is raised to its upper position The cuvette is moved to position 850 and then moved toward position 853. When the cuvette reaches the opening 811, it falls through the opening and into the cuvette waste receptacle 35.

Corrected counts am used to calculate analyte concentration in the sample using a stored master curve. At the time of manufacture of each lot of reagents, a master dose-response curve is generated using multiple assay runs on multiple instruments. This lot-specific dose-response curve data is supplied with the reagents and input into the CPU memory using an integral bar code-reading wand, or through the keyboard. The stored master curve is recalibrated by assaying two calibrators, whose values are predetermined and provided to the software. Multi-analyte calibrators are provided for this purpose, and weekly recalibrations are recommended for most assays.

Reference LED Module for Chemiluminescence Assay

FIGS. 87A–B, schematically illustrated the analyzer's LED module. The reference LED utilizes optical feedback to provide a constant light output which can be presented to the PMT.

The light output level may be set by adjusting an electronically adjustable potentiometer (EEPOT). This EEPOT is used to adjust the light output for manufacturing and component variances. The EEPOT may be set with a specific sequence of control signals, and is not designed for field adjustment.

Advantageous features of the reference LED board are:

o—Compact packaging fits under the luminometer o—Optical feedback yields constant 470 nm. calibration for the photomultiplier tube signal o—Compensated voltage reference for added stability o—Electronically adjustable light output allows easy factory calibration o—May be powered on/off from machine controller board The power requirements of the preferred embodiments are:

for the Logic +5.00 V +/−5% (75 mA max.);

for the Analog +12.0 V +/−10% (300 mA max.).

The unit is preferably configured as a 2.1" diameter two-sided board, with a ground plane on bottom side. The following connectors should be provided:

a 5 pin pigtail connector to mate with the machine controller and power source, connection to luminometer home sensor board, and a 4 pin header to facilitate programming of the EEPOT. The Power Connector pigtail, J1, shown as in FIGS. 87A–B has the following pin assignments:

| Pin | Name |
|---|---|
| 1 | LEDCTL (from machine controller, 0 = off, 1 = on) |
| 2 | SB3 (from machine controller, not used) |
| 3 | +5 V |
| 4 | +12 V |
| 5 | GND |

The EEPOT header Connector, J2 shown as in FIG. 87, has the following pin assignments:

| Pin | Name | |
|---|---|---|
| 1 | /INC | EEPOT wiper increment line |
| 2 | UP/DOWN\ | EEPOT direction select line |
| 3 | /CS | EEPOT chip select |
| 4 | GND | |

The preferred embodiment of the reference LED circuitry is further detailed in FIGS. 87A–B. Because stray light from the LED-could affect the photomultiplier tube reading during sample analysis, the reference LED can be turned off via a control line on the luminometer machine controller board. $Q_1$ and $R_1$ form the power control logic. (A in FIGS. 87A–B) Bringing LED CTL low (0 volts) turns off all op-amps and the LED; returning LED CTL high turns the LED power on.

The closed loop that derives the LED uses a voltage as a command input (see FIG. 88). VR1, U1, U3A and R2, R3, and R7 comprise an adjustable voltage reference. (B in FIG. 87) VR1 provides a temperature-compensated zener reference of 6.9 V +/−5%. The heater, to VR1 is on at all times to allow faster responses after instrument warm-up. R3, the EEPOT wiper resistance (10 K), and R7 form a voltage divider. With the nominal values of these components, the EEPOT wiper has a voltage range of 0.5–2.5 V. Op-amp U3A buffers the reference voltage to provide a low-impedance source for the control loop.

An optical feedback loop is used to control the LED's light output CR1 (blue LED, 470 nm wavelength) is a diffused bezel LED mounted in a housing such that its light is incident upon the surface of CR2, a blue-sensitive photodiode. CR2 faces CR1 and is preferably positioned at 45° off CR1's optical axis. The positioning of CR1 and CR2 is controlled by the LED mounting block. (Alternately a beam splitter may be provided to bring a portion of the LED output to $CR_2$). $CR_2$ is used in current mode (virtual short circuit across its terminals) to eliminate dark noise in the reference.

Q2 and R6 are used to drive current through the LED; this current is limited to 50 mA by the values of the circuit components and the upper voltage rail of U2. U2 alone cannot drive the LED at 50 mA.

FET-input op amp U2 can tolerate inputs down to ground and can swing it; output from ground to about 3 volts off the positive rail. This ground output capability is important for operating the LED at low light levels. The FET-input capability was chosen to minimize effects of input current (Iin<30 pA) on the summing junction.

U2 works to maintain 0 volts between its input pins. This will force the voltage across the series combination of R5 and R8 to be virtually equal to the reference voltage applied by U3A. The reference voltage across R5+R8 yields a reference current of 2.5–12.5 nA. In steady state, CR2's current will equal the reference current; if CR2's current is constant, the light from CR1 causing that current is also constant.

In the event that the light output from CR1 fluctuates, the circuit's negative feedback will correct the error. For example, if CR1 outputs too much light, CR2's current will increase. This increase in current will flow through R4 and will drive Q2's base voltage down, causing the CR1's current to decrease. Similarly, too little light from CR1 causes U2 to output a higher voltage, yielding more current through CR1 and more light output The response time of the circuit is limited by the combination of C5 and R4. C5 functions as an integrator to prevent any instantaneous fluctuation of the output, in effect averaging the error signal. R4 and C5 filter off any high frequency noise that would be superimposed on the right output of CR1.

Because the current flowing through the reference resistors R5 and R8 is on the order of 10 nA, board leakage currents caused by flux and oils can have a detrimental effect. To prevent leakage currents from disturbing the circuit, the summing junction of the op-amp should be given special consideration. A teflon solder post C is provided to tie R5, CR2's anode, Us's summing input (pin 2), and C5 together. Another teflon post D is provided to join R5 and R8. Also, C5 should be a high insulation respace (>30000 Megohm) capacitor to minimize shit leakage through the feedback path around U2. A third, non-insulated, solder post is used to provide a connection point for CR2's cathode. Finally, the entire assembly is cleaned very thoroughly and then hermetically sealed to prevent deposits from forming.

In experimental testing, the circuit has shown that a short interval is necessary to allow the circuit voltages and currents to stabilize. A one-minute interval should be allowed between energization and observation to ensure that the light output will be stable.

Test requirements:

In addition to the short circuit and open circuit test performed by the in circuit tester, the following additional tests must be performed:

A. Power logic

With +12 V and +5 V applied to J1 pins 4 and 3 respectively, drive J1 pin 1 to ground. Verify that no current flows through R6 and that the voltage at U3 pin 1 is at ground potential. Now apply +12 V to J1 pin 1. Verify that the voltage at pin U3 pin 1 is between 0.4 and 2.8 V.

B. EEPOT logic

If the EEPOT'S non-volatile memory has a limited number of write cycles, varying this pot should only be done once during testing.

Bring the CS\pin to TTL (0 V).

Next, apply pulses to the EEPOT'S INC\ pin and verify that the wiper moves in the direction of the U/D\ pin. Vary the U/D\ level and verify EEPOT operation Also, verify that the current flowing through R6 changes with the value of the EEPOT setting. Timing information for the EEPOT'S control lines in the preferred embodiment is shown in FIG. 89.

C. Control loop

Because the summing junction carries such small currents, measurement at this point is to be avoided. During the calibration of the LED and PMT module, the optical operation of the module will be verified.

Hydraulic and Pneumatic Controls

The hydraulic and pneumatic controls for the subunits of the analyzer are shown in FIGS. 90–93. All of the valves described herein are electrically actuated via the CPU. Referring first to FIGS. 90, 91, 93A and 93B, a pair of three way diverter valves V2 and V5 are connected to a main water line 886 by a pair of flexible tubes 882 and 888, respectively. The main water line 886 is connected to the de-ionized water reservoir 30. A peristaltic pump 880 is operatively engaged with the tube 882 for drawing water from the reservoir 30 to the valve V2 A peristaltic pump 881 is operatively engaged with the tube 888 for pumping water from the reservoir 30 to the diverter valve V5. The valve V2 is connected to a three way diverter valve V1 by a tube 891 and to a three way diverter valve V3 by a tube 892. The diverter valve V5 is connected to a three way diverter valve V4 by a tube 893 to a three way diverter valve V6 by a tube 894. The valve V2 dive water from the tube 882 to the valve V1, or the valve V3. The valve V2 is normally closed to the valve V1 and normally open to the valve V3. The valve V5 diverts water from the tube 888 to the valve V4 or to the valve V6. The valve V5 is normally closed to the valve V6 and normally open to the valve V4. The diverter valve V1 diverts water to the syringe 651 through a tube 890, or through the tube 671 to the housing 666 of the wash station 18, see FIG. 75. The valve V3 diverts water to the syringe 654 through a tube 925, or to the housing 694 of the wash station 17 through the tube 689. The valve V5 diverts water from the tube 888 to the valve V4, or to the valve V6. The valve V4 diverts water to the syringe 652 through a tube 895 or to the housing 672 of the wash station 15 through the tube 677. The valve V6 diverts water to the syringe 653 through a tube 926, or to the housing 678 of the wash station 16 through the tube 683. The valve V1 is normally closed to the tube 890 and normally open to the tube 671. The valve V3 is normally closed to the tube 925 and normally open to the tube 689. The valve V4 is normally closed to the tube 895 and normally pen to the line 677. The valve V6 is normally closed to the tube 926 and normally open to the tube 683. A check valve 884 and a filter 883 is located in the tube 882. A check valve 902 and a filler 889 is located in the tube 888.

The waste fluid reservoir 31 is maintained at a sub-atmospheric pressure by a vacuum pump 896 which is connected the waste fluid reservoir by an air line 897. A main air line 898 extends from the reservoir 31 and is connected to a manifold 899 by a tube 900. A plurality of valves V7, V8, V9, V10 and V11 are connected to the manifold 898 by tubes 910, 911, 912, 913, and 908, respectively. A vacuum gauge 905 is also connected to the manifold 898 by a tube 907. The valve V11 is a bleeder valve which is opened and-closed by a switch 906 which is, in turn, controlled by the gauge 905. When the pressure in the manifold 899 exceeds a predetermined set pressure, as detected by the gauge 905, the switch 906 is closed to open the bleeder valve V11 to release air and lower the pressure in the manifold 899 to the set pressure. When the set pressure is reached, the gauge 905 opens the switch 906 to close the valve V11. The valves V7, V8, V9 and V10 are on/off valves which are operatively conned to the wash stations 18, 15, 16, and 17, respectively. The valve V7 is connected to the bottom of the housing 666 of the wash station 18 by a tube 670. The valve V8 is connected to the bottom of the housing 684 of the wash station 17 by a tube 690. The valve V9 is connected to the bottom of the housing 672 of the wash station 15 by the tube 675. The valve V10 is connected to the bottom of the housing 678 of the wash station 16 by the tube 681.

A wash-dispense pump 903 is connected to the main water line 886 and to the nozzle 699 by a tube 692. The pump 903 is a displacement pump which is actuated by a motor 904. The pump 903 extends at an angle to the drive shaft of the motor 904 and is connected to the drive shaft by a universal coupling. The motor 904 is energized to rotate its drive shaft one complete revolution which produces a displacement cycle for the valve 903. The amount of displacement is determined by the angle of the valve relative to the drive shaft of the motor. When the motor 904 is actuated for a single displacement cycle, water is pumped from the reservoir 30 to the nozzle 699 of the fixture 695 for a wash cycle.

The main water line 886 is connected to a pair of on/off valves V16 and V18. The valve V16 is connected to a tube 909 which splits into the tubes 702 and 697, which are connected to the fixtures 700 and 695, respectively. The valve V18 is connected to the tube 844, which ends from the fixture 840 at the luminometer assembly. The main vacuum line 898 is connected to a manifold 901 and on/off valves V12, V13, V14, V15 and V17 are connected to the manifold 901 by tubes 914, 915, 916, 917 and 918, respectively. The valve V12 is connected to the tube 729 which leads to the probe 725. The valve V13 is connected to the tube 728 which leads to the probe 726. The valve V14 is connected to the tube 836 which leads to the aspirating probe 834. The valve V15 is connected to a tube 927 which splits into the previously described tubes 703 and 698 to the fixtures 700 and 695, respectively. The valve 17 is connected to the tube 845 which extends to the fixture 840. A low pressure switch 924 is connected to the manifold 901 by a tube 919. When the pressure in the manifolds 901 and 899 falls below a predetermined minimum value, the switch 924 sends a signal the CPU to stop the machine.

A pump 920 is connected to the acid reservoir 33 by a tube 921 and to the tube 707 which leads to the acid dispensing probe 706. A pump 922 is connected to the base solution reservoir 34 by a tube 923 and to the tube 839 which extends to the base dispensing probe 838. Energization of the pump 920 dispenses a predetermined volume of acid from the reservoir 33 through the nozzle 706. Energization of the pump 922 dispenses a predetermined volume of base solution through the nozzle 838. Referring particularly to FIGS. 93A and 93B, a single cuvette 40 will be followed as it travels along the event conveyor and through the luminometer. A sample solution is obtained by positioning the sample aspirating and dispensing probe 407 above one of the openings 255 and 256 of the sample transport system 26. The probe 407 is lowered into the sample container and the syringe 651 is actuated with the valve V1 in the closed position with respect to the tube 890. This enables a volume of sample solution to be aspirated by the probe 407. The probe 407 is then positioned over the sample dispense point 44 and lowered into a cuvette which is positioned below the point 44. The syringe 651 is then actuated to dispense the aspirated sample solution into the cuvette. Valves V1 and V2 are actuated to divert water to the syringe 651 for dispensing a small amount of water into the cuvette to insure that all of the sample is dispensed. If the test protocol calls for the addition of a diluent or pretreatment solution, the housing 666 of the wash station 18 is filled with water from the tube 671. The probe aspirates the diluent or pretreatment solution, moves to the wash station 18 and is dipped into the water filled housing 666. The probe is then positioned over the selected test sample solution for lowering into the sample and aspirating a volume of sample. The probe is then moved to the sample dispense point 44 for dispensing the aspirated sample and diluent pretreatment solution into the cuvette. The cuvette then proceeds along the event conveyor toward the point 45. The sample probe 407 is then moved above the wash station 18 as water from the peristaltic pump 880 is diverted from the valve V2 to the valve V1 which diverts the water to the tube 890 which passes through the syringe 651 to the tube 659 and is dispensed through the probe 407 for cleaning the inside of the probe and then diverted by the valve V1 through the tube 671 into the housing 666 for washing the outside of the probe 407. The washing solution which is introduced into the housing 666 by the probe 407 and the tube 671 is aspirated from the bottom of the housing through the tube 670 by opening of the valve V7. The initial dispensing of water through the probe 407 fills the housing 666 which effectively cleans the outside of the probe as well. This water is aspirated from the bottom of the housing and the water from the tube 671 provides a final cleaning to the outside of the probe. The water is also aspirated from the bottom of the housing. The aspirated fluid passes through the tube 910 into the manifold 899 and eventually to the wastewater reservoir 31 through the tubes 900 and 898.

After the cuvette 40 has been filled with sample at the sample dispenser point 44 it travels along the event conveyor to one of the reagent dispense pouts 45, 46, or 47, depending on the protocol of the test. Each reagent aspirating and dispensing probe is capable of picking up or aspirating traces or labeled reagent from the outer ring and a solid phase reagent from the inner ring or only one of the reagents. Any combination is possible. For example, for a particular cuvette, a labeled reagent may be picked up by the reagent probe system R1 while the solid phase reagent is picked up by the reagent probe system R2 or R3 when the cuvette is approximately positioned at either of these systems. On the other hand, the reagent probe system R1 can pick up a solid phase reagent while the labeled reagent is added by either the reagent probe systems R2 or R3. As a practical matter, the reagent probe systems R1 and R2 are used primarily for protocols which require the aspiration and dispensing of both reagent solutions by a single probe. Although the reagent probe system R3 is capable of aspirating both reagents, less incubation time is available so that the system is used primarily for adding a reagent solution to a cuvette which contains a single reagent that had been added by the reagent probe system R1 or R2.

If the test protocol calls for the aspiration of one or both reagents by the reagent probe system R1, each reagent solution is aspirated by the actuation of the syringe 652 with the valve B4 closed with respect to the tubes 895. The reagent or reagents are drawn into the coiled section of the tube 660 which lies in the heated fluid bath 648 by drawing air into the probe 535 when the probe is out of contact with the reagent solution. When the probe is positioned above the cuvette which contains the corresponding sample to be tested, the syringe is actuated to first displace the air which is in the tube 660 and thereafter to dispense the reagent solution into the cuvette. The probe 535 is then positioned over the wash station 15 and then lowered into the wash station. The valve V4 is actuated to divert water to the tube 895. The water flows through the probe 535 for flooding the housing 672 and, simultaneously, washing the inside and outside of the probe 535. At the same time, the valve V9 is opened to aspirate the waste fluid from the bottom of the housing 672 through the tube 675 which eventually finds its way to the waste fluid reservoir 31. The valve V4 is then returned to its normal state to divert water through the tube 677 into the housing 672 for a final washing of the outside of the probe 535. This valve V5 is in its normally open state with respect to the valve V4 for the washing cycle of the probe 535. If the test protocol calls for aspirating and dispensing of reagent by the reagent probe system R2, reagent is aspirated by the probe 576 by actuating the syringe 653 while the tube 926 is closed with respect to the valve V6. The reagent is dispensed into the cuvette which is located at the dispense point 46 by the syringe 653 using the same procedures as for the reagent probe system R1. The valve V5 is actuated to divert water to valve V6 and valve V6 is actuated to divert water through the tube 926 to the probe 576 when the probe is positioned within the housing 678 of the wash station 16. When the valve V6 is returned to its normally opened state to divert water through the tube 683 for a final outside wash of the probe. The valve V10 is opened for aspirating all of the waste fluid from the housing 678 through the tube 681.

If the test protocol calls for the introduction of a reagent by the reagent probe system R3, reagent is aspirated by the probe 653 by actuation of the syringe 654 with the valve V3 in its normally closed position with respect to the tube 925. After dispensing of the reagent into the cuvette by the probe 653 so the probe is positioned within the housing 684 of the wash station 17 for a wash cycle. With the valve V2 in its normally open position with respect to valve V3, the valve V3 is actuated to divert water through the tube 925 to the reagent probe 653 for the initial washing step as described for the reagent probe systems R1 and R2. Thereafter, the valve V3 is returned to its normal state so that it is open with respect to the tube 689 for the final washing step. All of the waste fluid is aspirated from the bottom of the housing 684 by opening of the valve V8.

The cuvette continues to be advanced along the event conveyor until it is positioned beneath the bore 696 of the fixture 695. After the probe 725 has been lowered, the probe 725 is lowered into the bore 696 so that it extends all the way to the bottom wall of the cuvette whereupon the valve V12 is open for aspirating all of the liquid within the cuvette. The paramagnetic particles are drawn against the back wall of the cuvette by the magnets 740 and remain in the cuvette during aspiration of the liquid. The liquid includes unreacted labeled reagent and unreacted test sample. The pump 903 is actuated to dispense the deionized water from the main line 886 through the nose 699 against the front wall of the cuvette. If the test protocol calls for a second wash cycle, the deionized water from the first wash cycle is aspirated through the probe 725 by again opening the valve V12. The pump 903 is actuated for a second time to introduce deionized water from the main water line 886 through the nozzle 699 for a second wash cycle. The liquid from the second wash cycle or the first wash cycle if only one wash cycle is required, remains in the cuvette until the cuvette is located beneath the port 701 of the fixture 700. When the probe 726 is lowered through the bore 701 to the bottom of the cuvette, the valve V13 is opened to aspirate all of the wash liquid from the cuvette. At this point all of the paramagnetic particles are held against the back wall of the cuvette by the magnets 741. When the cuvette arrives at a point beneath the acid dispense fixture 704, the pump 920 is actuated to dispense a predetermined volume of acid from the acid reservoir 33 through the tube 707 and through the nozzle 706 against the back wall of the cuvette which dislodges all of the paramagnetic particles from the back wall and resuspends them into the acid solution.

After the addition of acid solution into the cuvette, the cuvette is advanced along the event conveyor to the luminometer conveyor 761, whereupon the cuvette is raised to the luminometer 760. The cuvette is advanced by the carousel 800 to the position 848 in line with the opening 807 which leads to the photomultiplier tube 808, see FIG. 86. With the cuvette in this position, the pump 922 is actuated to dispense a predetermined volume of base solution from the base reservoir 34 through the nozzle 838. This produces a detection reaction "flash" which is read by the photomultiplier tube 808 as described previously. When the cuvette arrives at position 848 in the luminometer beneath the bore 841, the probe 834 is lowered into the bore 841 to the bottom of the cuvette. The valve V14 is opened to aspirate the liquid in the cuvette through the probe 834 and through the tube 836 to the manifold 901. The liquid is then drawn into the waste fluid reservoir 31. The valve 18 is then opened to introduce water into the bore 841 while the valve V17 is opened. Continued aspiration of water through the probe 834 cleanses the inside of the probe while aspiration of water through the tube 845 helps to cleanse the outside of the probe. When the cuvette is advanced to the opening 811 it falls through the opening into the waste receptacle 35.

All of the valves and pumps are controlled by the central processing unit in coordination with the operation of all of the machine subunits which are associated with the valves and pumps. All of the valves and other electrical components on the right side of the machine are connected to a connector 92 by a ribbon cable FIG. 92). The connector 928 is operatively connected to the CPU. All of the valves and electrical components on the left side of the machine are connected to a connector 879 by a ribbon cable (FIGS. 90 and 91). The connector 879 is operatively connected to the CPU.

Software Capabilities

The software system for the analyzer is capable of multi-tasking operation. At any time, the operator may access test results by sample or by test, pending results by sample or by test, results history, calibration status, QC statistics, operating status, maintenance schedule, or service history.

Test Definitions are custom programmable, including selection of reporting units, number of decimal places in reported results, number of replicates, normal range, precision allowances, calibration interval, and automatic repeat with or without sample dilution.

Control Definitions are also programmable, including identity of control, selection of tests per control, and upper and lower limits per test, which will trigger flagging of out of range result. A plurality of specific test profiles may be defined and accessed. When a profile is requested, all assays selected in that profile are automatically performed.

Description of Flow Diagrams

Figure 94A:
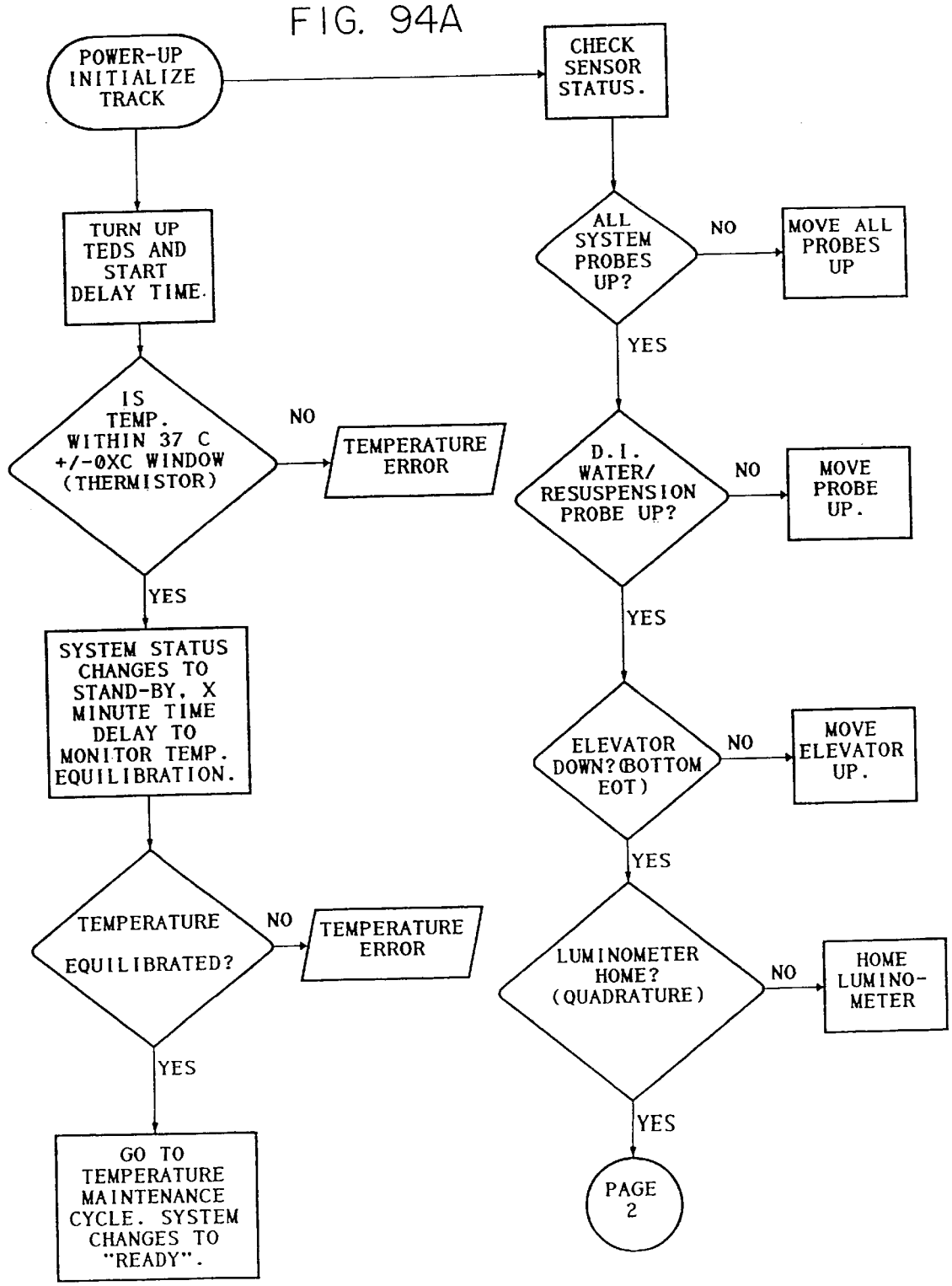
Figure 94B:
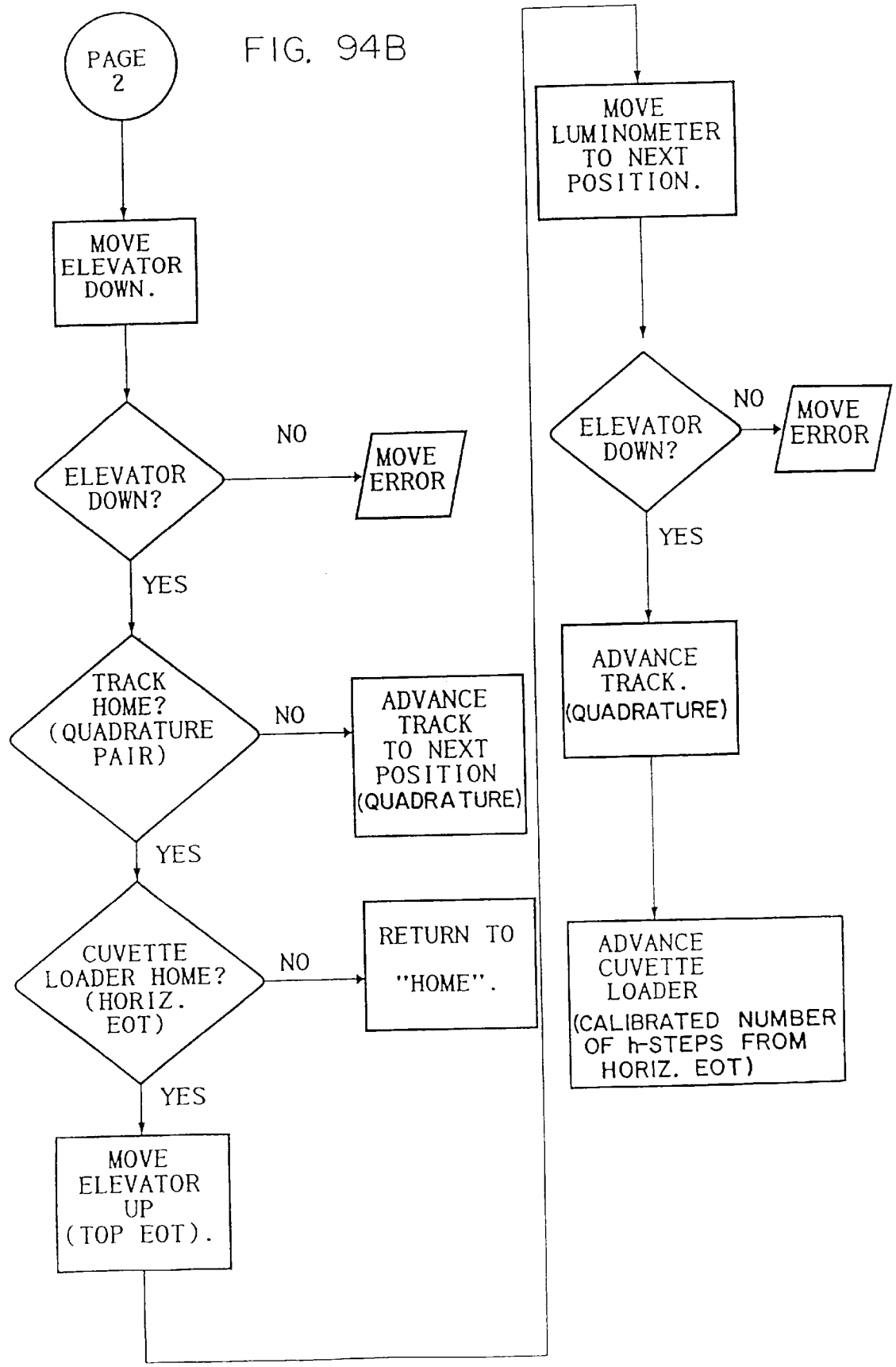

FIGS. 94A and 95B constitute a single flow diagram and are connected by the common symbol "PAGE 2". The diagram of FIGS. 94A and 94B is a time line which illustrates the coordinated movements of the elements which advance the cuvettes from the supply hopper to the detection point in the luminometer at the beginning of a test run. The diagram also depicts the coordinated "home" or upper positioning of the probes and temperature checks. The designation "track" refers to the event conveyor and the "cuvette loader" refers to the mechanism for advancing the cuvettes along the preheater section to the event conveyor.

Figure 95A:
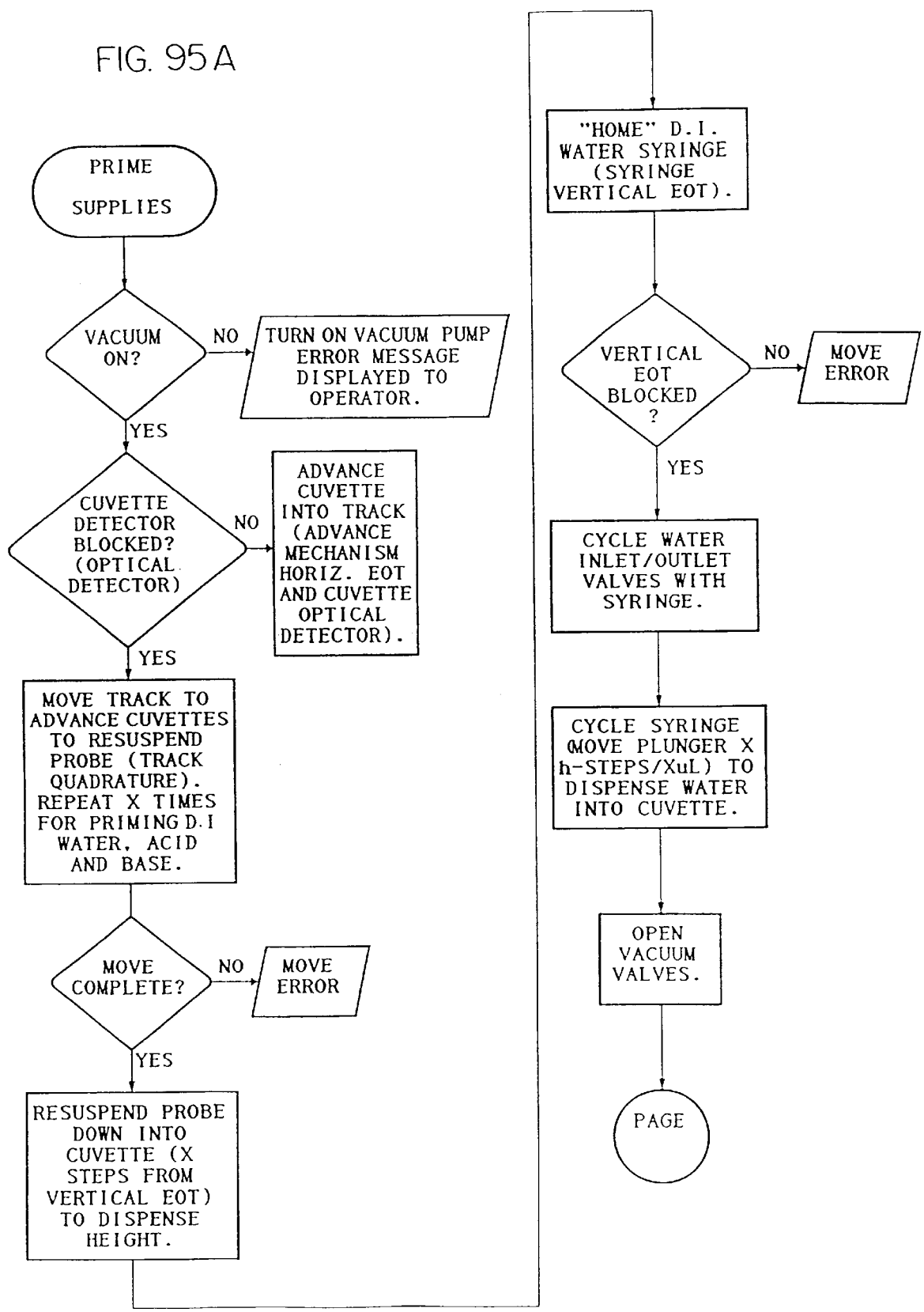
Figure 95C:
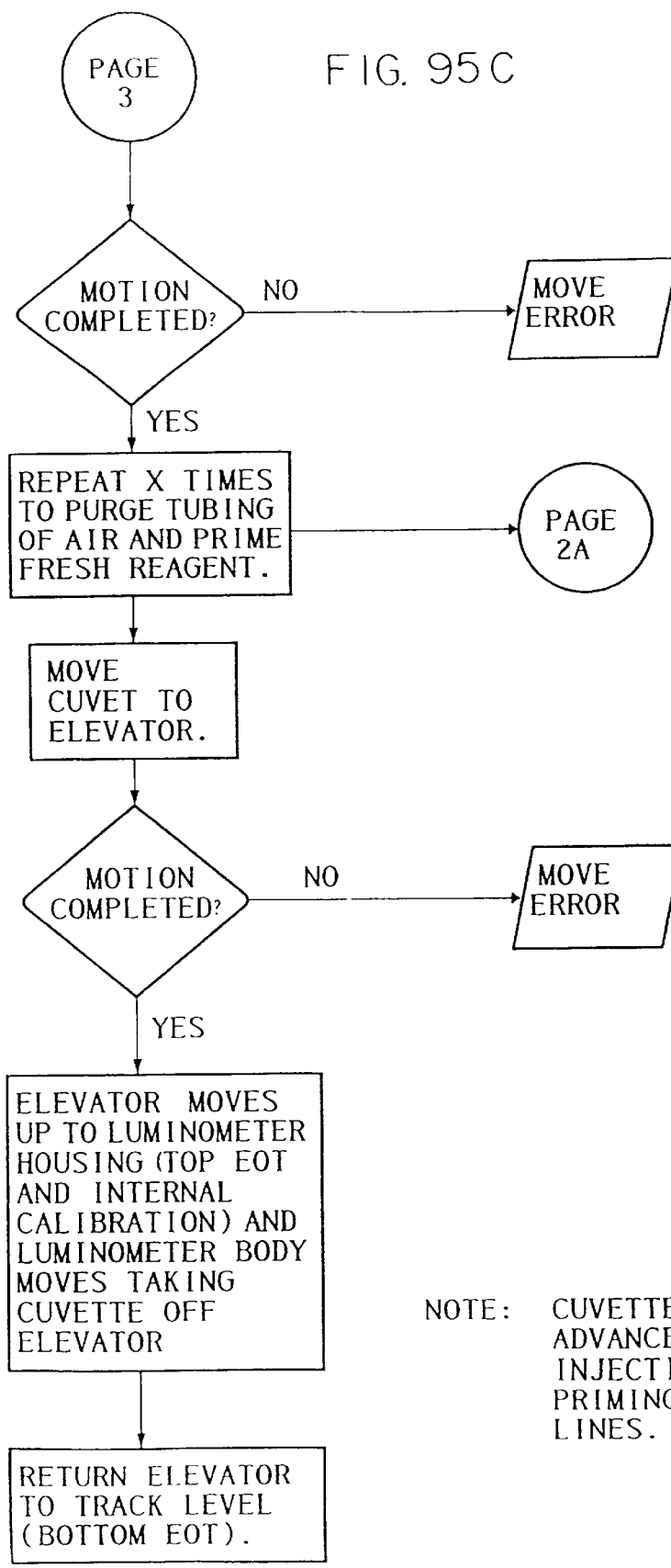

FIGS. 95A, 95B and 95C constitute a single flow diagram. FIGS. 95A and 95B are connected by their common symbol "PAGE". FIGS. 95B and 95C are connected by their common symbol "PAGE 3" AND "PAGE 2A". The diagram of FIGS. 95A, 95B and 95C is a time line which illustrated the coordinated movements of the mechanisms which advance the cuvettes and the coordinated movements and functioning of the probes along the event conveyor or "track.

Figure 96A:
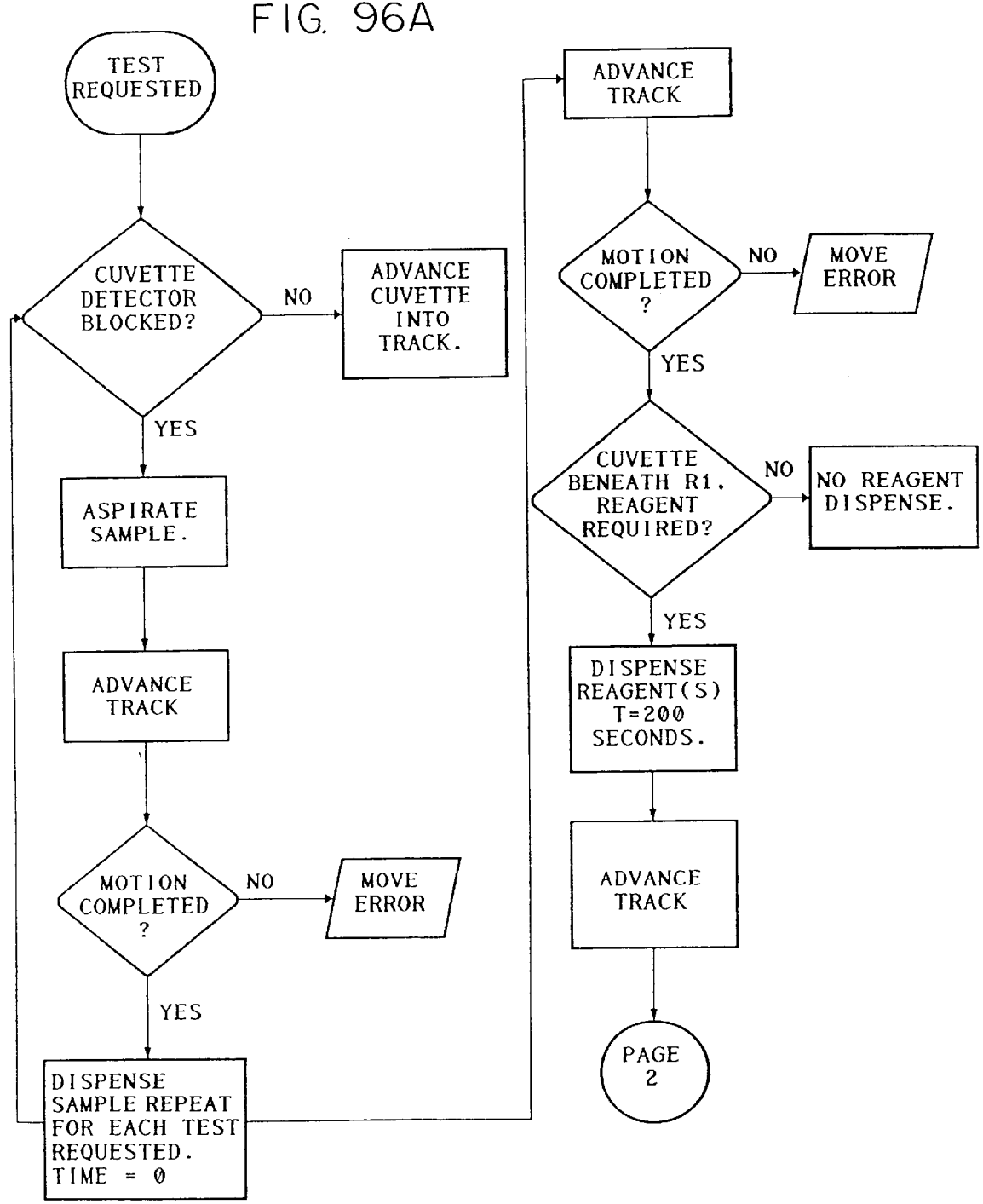
Figure 96B:
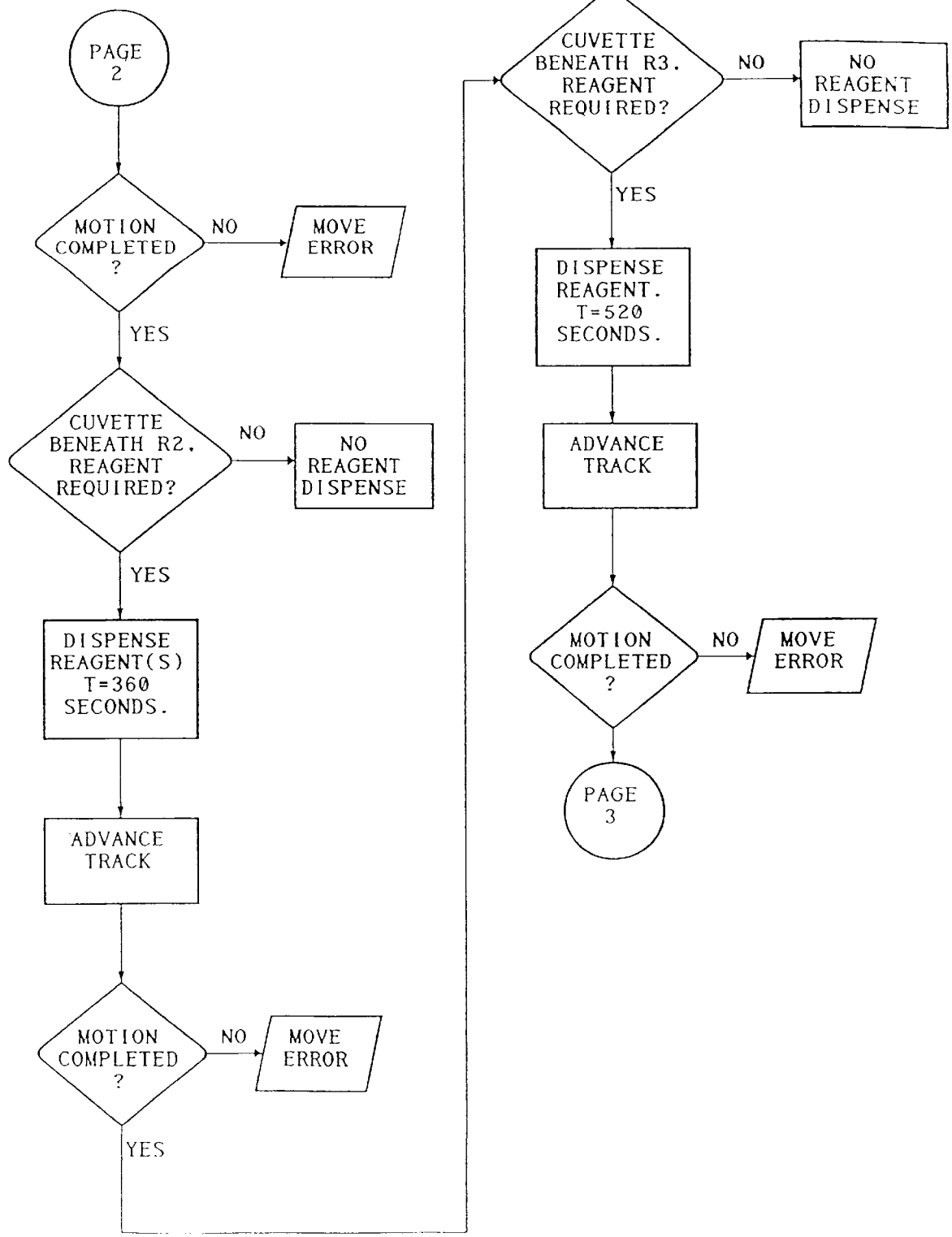
Figure 96C:
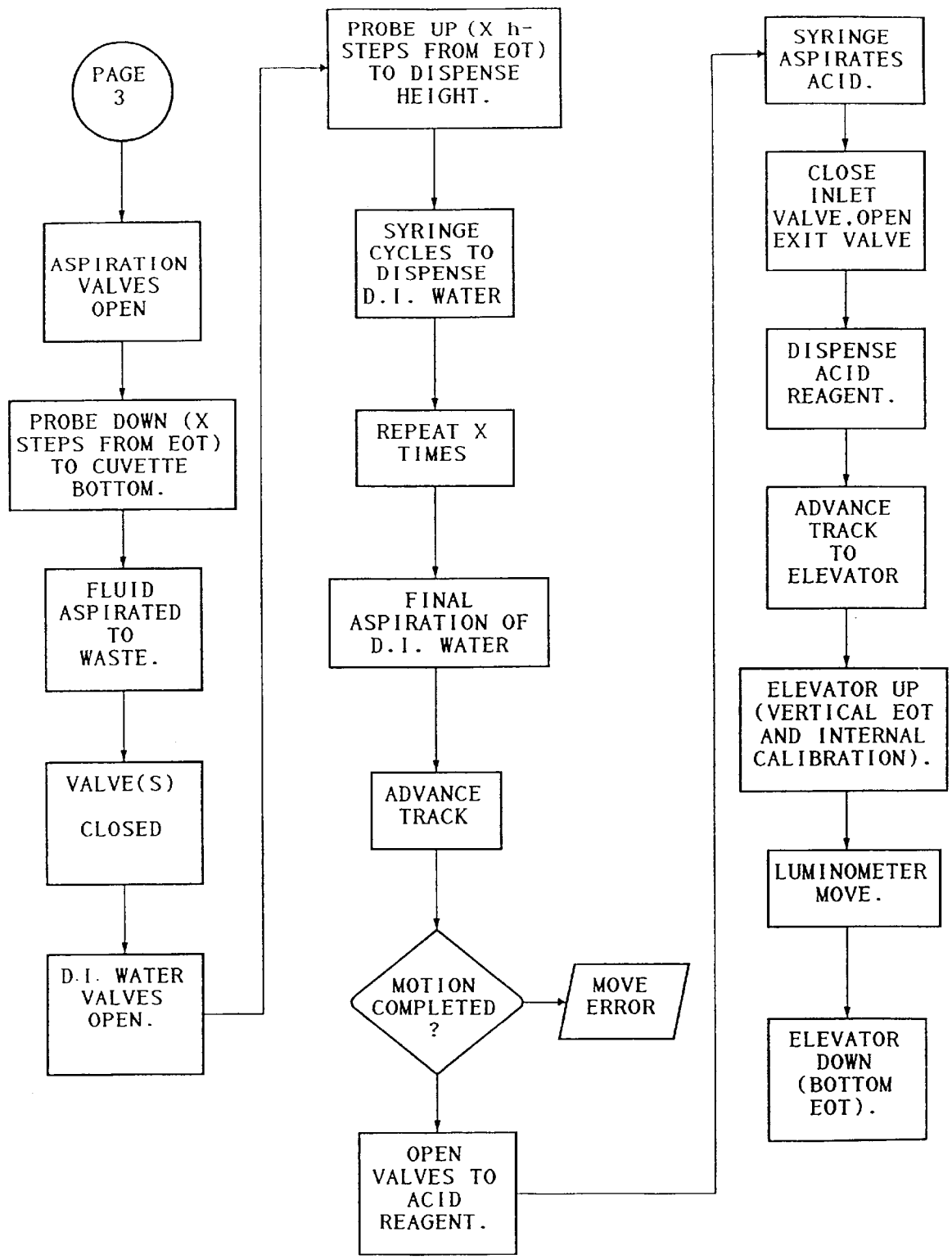

FIGS. 96A, 96B and 96C constitute a single flow diagram. FIGS. 96A and 96B are connected by their common symbol "PAGE 2". FIGS. 96B and 96C are connected by their common symbol "PAGE 3". The diagram of FIGS. 96A, 96B, and 96C is a time line diagram which depicts the coordinated movements of the elements which advance the cuvettes and the coordination of the movements of the cuvettes with the dispensing of sample and reagent into the cuvettes.

Figure 97:
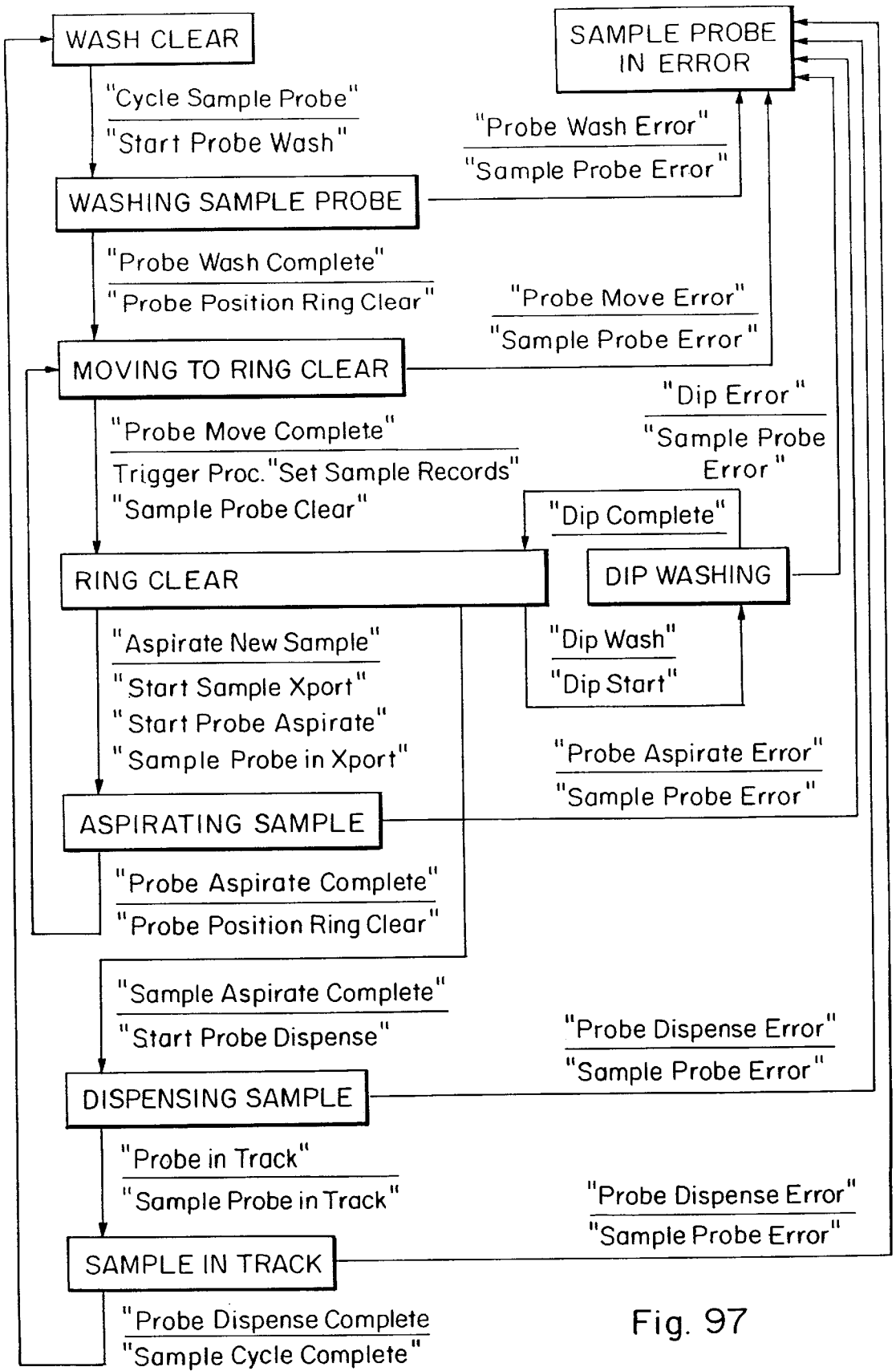

FIG. 97 is a time line which depicts the coordination of the movements of the sample probe and the aspirating, dispensing and washing of the sample probe.

Figure 98:
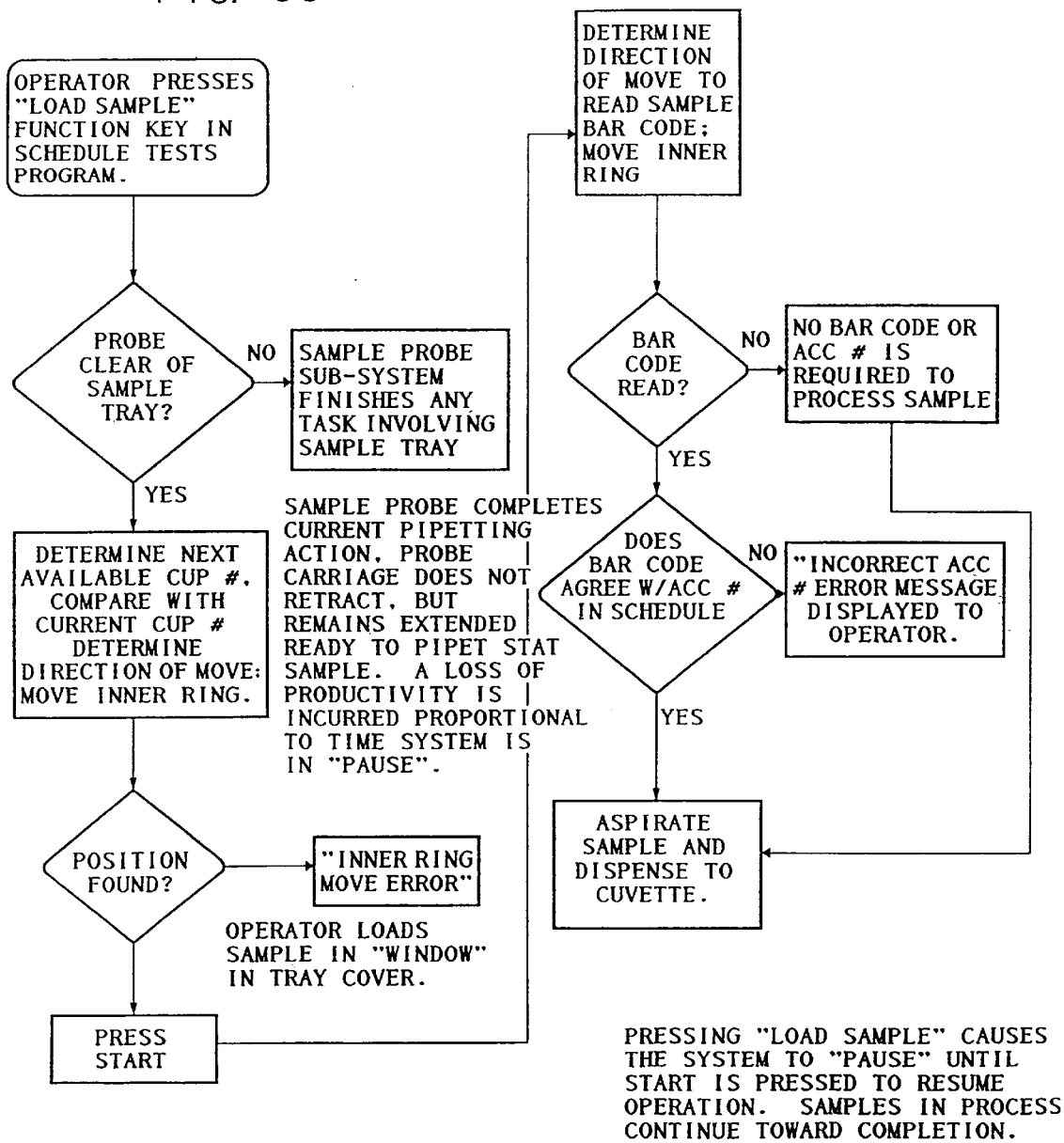

FIG. 98 is a time line diagram which depicts the coordinated movements of the inner ring of the sample transport system and the sample probe when a sample container or "cup" is added to the inner ring during a run of tests.

Figure 99:
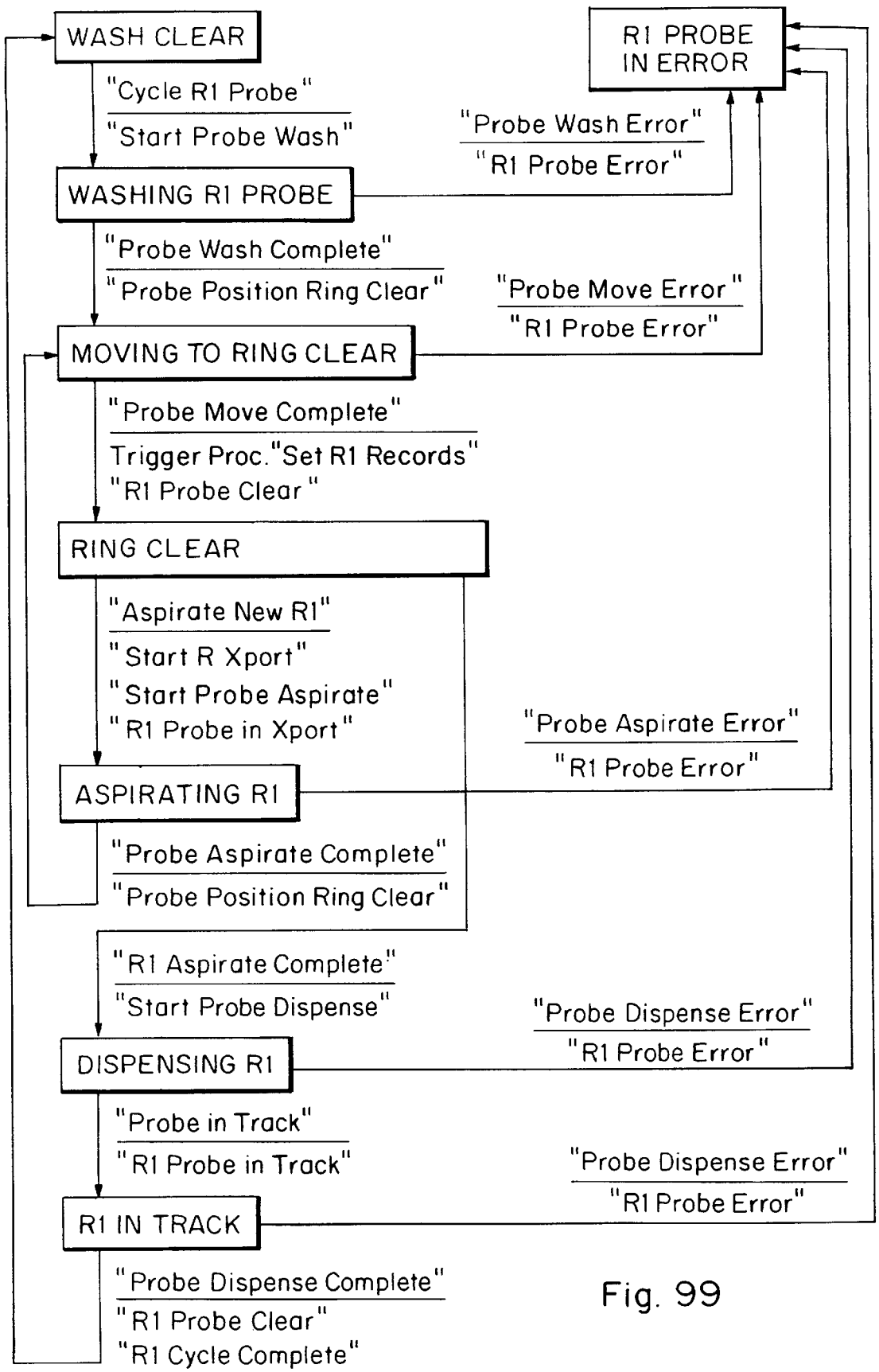

FIG. 99 is a time line diagram which depicts the movements of the probe transport system R1 in coordinating the functions of the probe for the R1 probe transport system.

Figure 100:
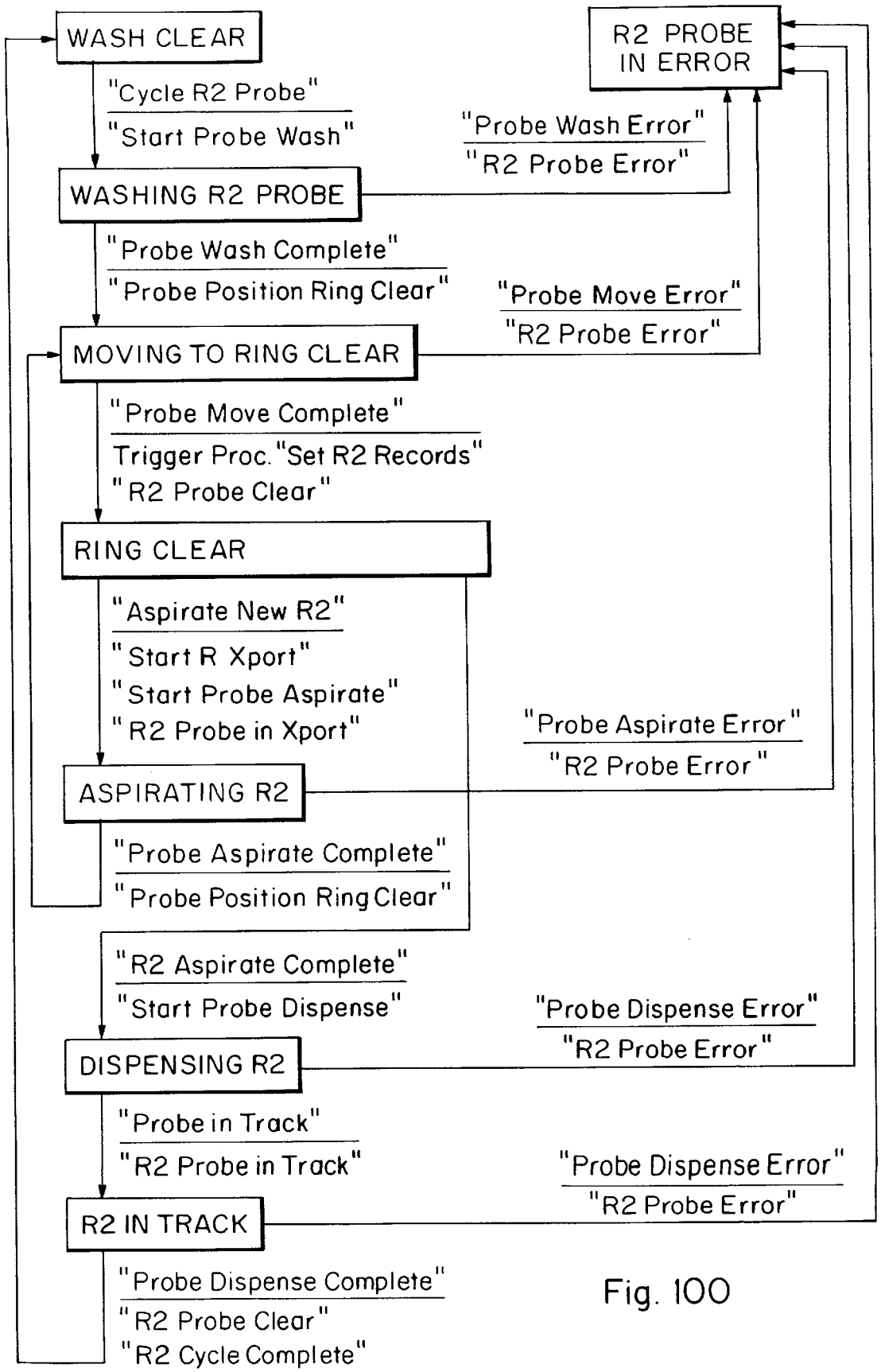

FIG. 100 is a time line diagram which depicts the movements of the probe transport system R2 in coordination with the functions of the probe for the R2 probe transport system.

Figure 101:
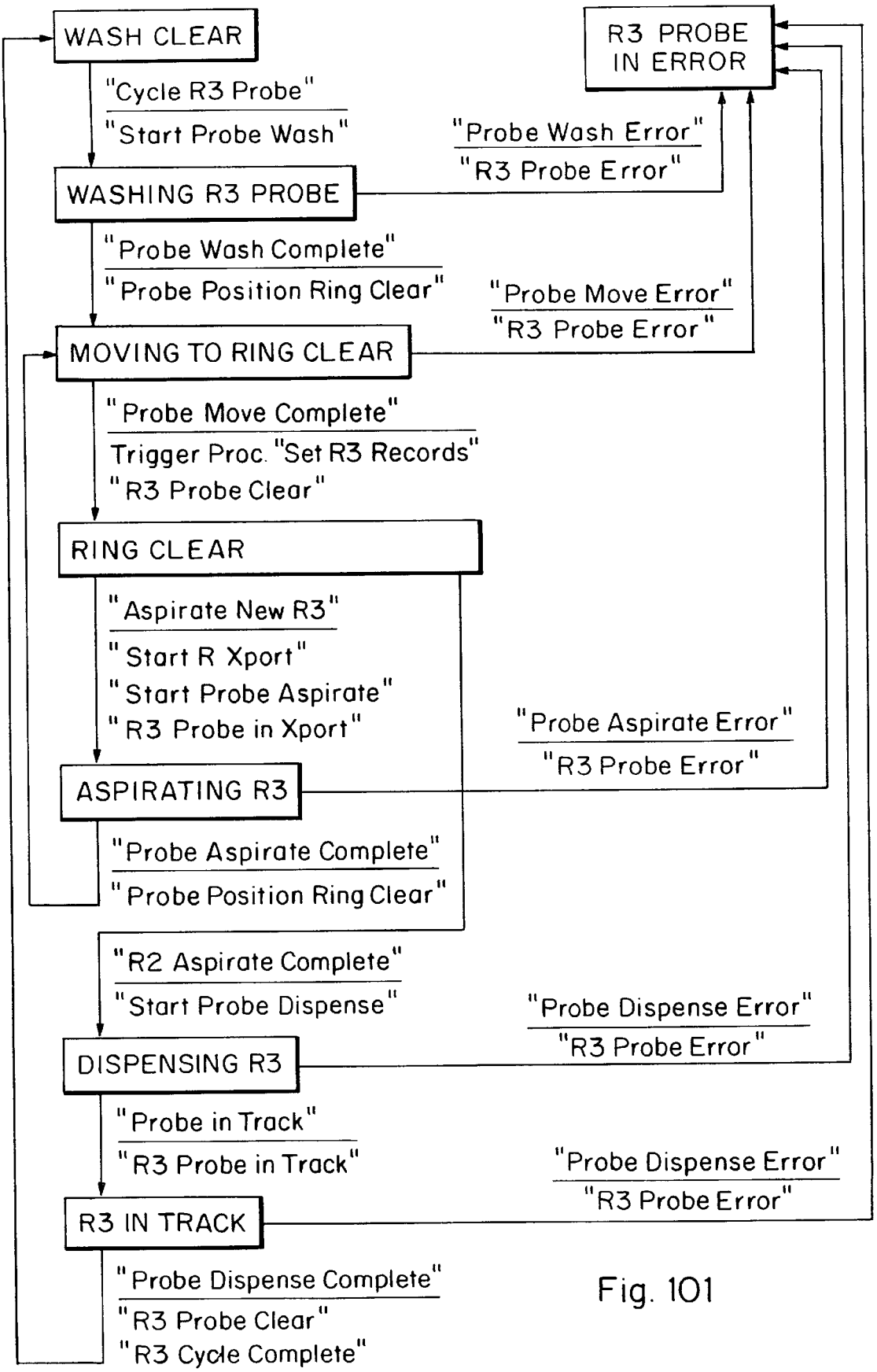

FIG. 101 is a time line diagram which depicts the movements of the probe transport system R3 in coordination with the functions of the probe for the R3 probe transport system.

Figure 102:
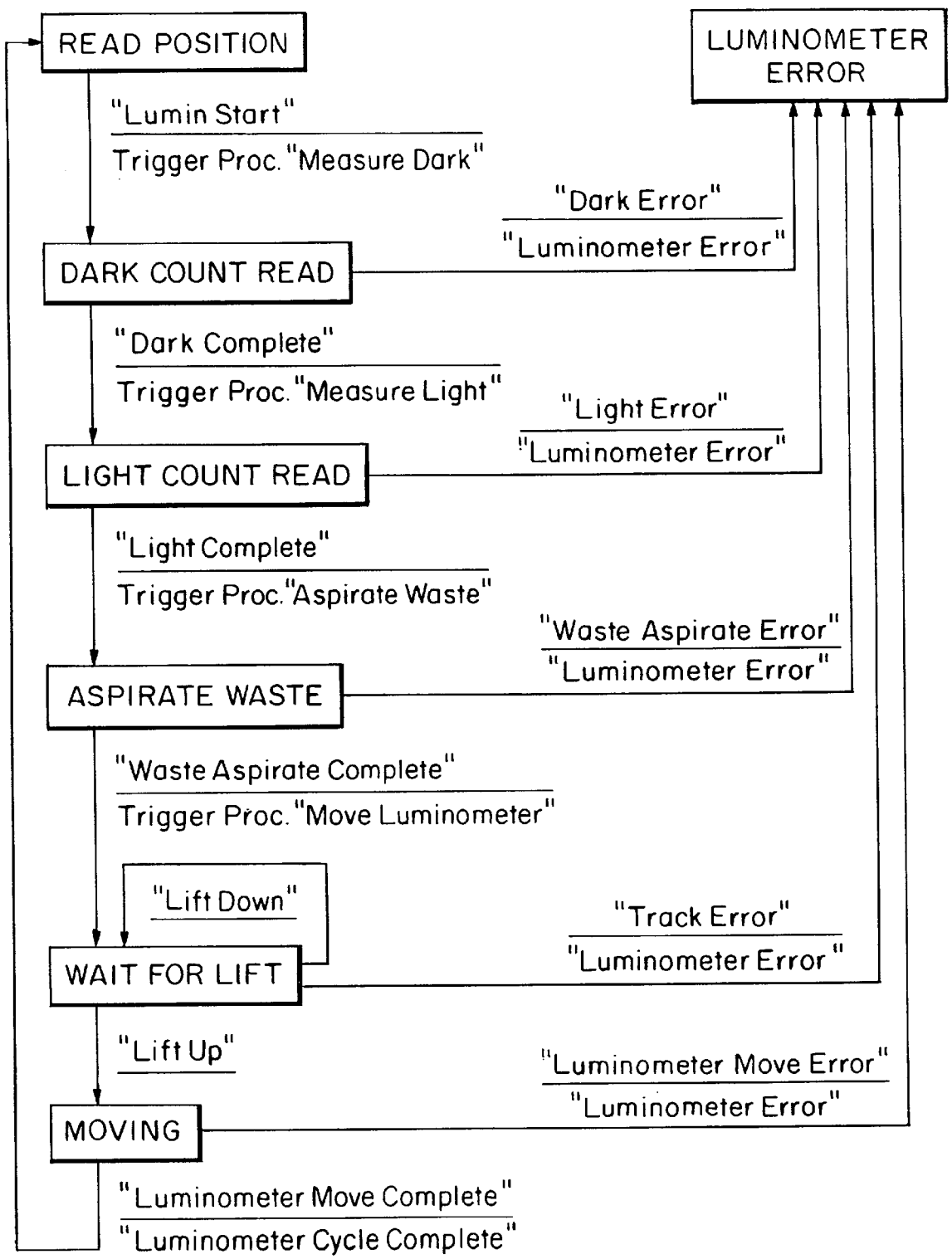

FIG. 102 is a time line diagram which depicts the movements of the luminometer carousel and elevator in coordination with the functions of the luminometer.

Each subunit of the analyzer has its own routine which is determined by software and microprocessor hardware. Each subunit routine is integrated by the CPU with interfacing hardware and software programs. The coordinated movements and functions of all the analyzer subunits are determined by software programming which functions through the electronic hardware, reversible stepper motors, valves, pumps and sensors.

UTILITY OF THE INVENTION

A clinical laboratory instrument which is used to automate heterogeneous immunoassay big. The microprocessor-based instrument fully automates each step of the assay.

It is obvious that minor, changes may be made in the form and construction of the invention without departing from the material spirit thereof. It is not, however, desired to confine the invention to the exact form herein shown and described, but it is desired to include all such as properly come within he scope claimed.

EXAMPLES

The invention is further represented by the following examples which demonstrate the operation of the analyzer. The examples are intended to illustrate the application of the analyzer for performing assays and not to limit the invention. It is to be understood that additional assays, including diagnostic and analytical, of various formats may be implemented for use on the automated analyzer.

Example 1
Free Throxine (FT4)

A free thyroxine (FT4) assay has been developed for the above described automated analyzer. The FT4 assay is a competitive binding assay in which FT4 in a test sample competes with labeled T4 (tracer reagent) for a limited amount of T4 antiserum covalently coupled to the solid phase. In the preferred format of this assay acridinium ester is the label and paramagnetic particles serve as the solid phase. A test sample (25 uL.) acridinium ester labeled T4 (100 uL.) and anti-T4 paramagnetic particles (450 uL.) are dispensed by the analyzer into a cuvette and incubated for 7.5 minutes at 37° C. After incubation, magnetic separation and washes are performed as described prior to detection of the chemiluminescent signal. The amount of FT4 present in the test sample is determined by the level of the signed detected and is converted to a dose by a two-point data reduction algorithm.

The test assay has a sensitivity of 0.107 ng/dL. (minimum detectable dose defined as the 95% confidence limit at 0 ng/dL.) with a range of 0–13 ng/dL. The precision of the assay based on nine test runs over three days is provided in Table 1. The correlation of the automated test assay with a manual test assay (Magic® Lite Free T4, Ciba Corning Diagnostics, Corp.) provided a slope of 1.109, an intercept of 0.308 and correlation coefficient of 0.989 (N=131).

The specificity of the assay, i.e. % cross-reactivity, for various compounds is shown in Table 2.

TABLE 1

PRECISION
Based on 9 runs, 3 days

| Mean FT4 concentration, ng/dL | Within run % CV | Total % CV |
| --- | --- | --- |
| 0.62 | 4.5 | 5.1 |
| 0.79 | 3.5 | 3.6 |
| 1.05 | 3.5 | 7.9 |
| 1.15 | 4.4 | 5.7 |
| 1.39 | 3.5 | 4.4 |
| 1.71 | 2.5 | 5.8 |
| 6.42 | 4.7 | 5.9 |
| 8.98 | 8.0 | 9.1 |

TABLE 2

SPECIFICITY

| Compound | % Cross Reactivity |
| --- | --- |
| L-triiodothyronine | 3.9% |
| D-thyroxine | >64% |
| D-triiodothyronine | 3.6% |
| Diiodotyrosine | <0.002% |
| Monoiodotyrosine | <0.002% |
| 3,5-diiodo-L-thyronine | <0.002% |
| Reverse triiodothyronine | 3.1% |

Example 2
Human Chorionic Gonadotropin (hCG)

A human chorionic gonadotropin (hCG) assay has been developed for the above described automated analyzer. The hCG assay is a sandwich assay which utilizes an antibody-coated capture solid phase and a labeled antibody as a tracer reagent. In the preferred format of this assay acridinium ester is the label on a monoclonal antibody and polyclonal antibody coated paramagnetic particles serve as the capture solid phase. A test sample (50 uL.) and tracer reagent (100 uL.) are dispensed into a cuvette by the analyzer and incubated for 5.0 minutes at 37° C. The capture solid phase reagent (450 uL.) is then added to the cuvette followed by an additional incubation of 2.5 minutes. After the second incubation, magnetic separation and washes are performed as described above prior to detection of the chemiluminescent signal.

All data presented was generated based on a two-point calibration off a full standard master curve, consisting of ten standards. The standards, ranging from zero to 1000 mIU/mL., are calibrated agape the WHO 1st 751537 reference material.

The test assay has a sensitivity of less than 1 mIU/mL. (minimum dectable dose defined as the 95% confidence limit at 0 mIU/mL.) with a range of 0–1,000 mIU/mL. No hook effect seen at 400,000 mIU/mL. The precision of the assay based on five test runs over five weeks is provided in Table 3. The specificity of the assay without cross reactant and with cross reactant is provided in Table 4. Interfering substances added to test samples according to NCCLS protocols were assayed with results provided in Table 5. The correlation of the automated test assay with a manual test assay with a manual test assay (Magic® Lite hCG, Ciba Corning Diagnostics, Corp.) provided a slope of 1.08, an intercept of 1.03 and a correlation coefficient of 0.98 (N=172).

TABLE 3

PRECISION
Based on 5 weeks stored 2-point calibration, 5 runs

| | hCG | % CV of Dose | | |
|---|---|---|---|---|
| Study | Control, mIU/mL | Within Run | Between Run | Total |
| 1 | 13.9 | 3.7 | 3.0 | 4.8 |
| | 124.8 | 3.4 | 3.2 | 4.7 |
| | 329.1 | 2.7 | 6.9 | 7.4 |
| 2 | 13.9 | 4.9 | 9.9 | 11.0 |
| | 129.1 | 3.2 | 6.3 | 7.1 |
| | 331.7 | 4.2 | 7.5 | 8.6 |

TABLE 4

SPECIFICITY

| Cross reactant (level tested) | hCG result no cross reactant, mIU/mL | hCG result with cross reactant, mIU/mL | P value (95% C.I) |
|---|---|---|---|
| TSH | 10.9 | 11.1 | 0.84 |
| (2,000 uIU/mL) | 207.0 | 214.9 | 0.26 |
| | 472.0 | 460.9 | 0.50 |
| | 832.8 | 812.0 | 0.68 |
| FSH | 13.1 | 13.4 | 0.35 |
| (200 mIU/mL) | 123.4 | 120.8 | 0.42 |
| | 431.5 | 427.6 | 0.16 |
| | 849.1 | 910.0 | 0.40 |
| LH | 4.5 | 4.5 | 0.85 |
| (200 mIU/mL) | 207.4 | 205.5 | 0.65 |
| | 459.1 | 480.2 | 0.10 |

TABLE 5

INTERFERING SUBSTANCES
Patient samples were spiked with NCCLS recommended levels of various interfering substances. If P value > 0.05, the difference in hCG dose is not statistically significant.

| Substance (mg/dL) | hCG Control, mIU/mL | hCG Spiked, mIU/mL | Spiked vs. Control | P-Value (95% C.I.) |
|---|---|---|---|---|
| Conjugated | 11.8 | 12.0 | 101% | 0.54 |
| Bilirubin | 214.3 | 218.2 | 102 | 0.25 |
| (20) | 471.2 | 481.4 | 102 | 0.29 |
| Unconjug. | 2.7 | 2.9 | 106 | 0.34 |
| Bilirubin | 46.7 | 45.9 | 98 | 0.32 |
| (20) | 90.2 | 93.1 | 103 | 0.04 |
| | 179.3 | 185.4 | 103 | 0.03 |
| | 889.8 | 875.5 | 98 | 0.78 |
| Lipid | 2.9 | 3.1 | 107 | 0.54 |
| (1,000) | 22.0 | 23.1 | 105 | 0.12 |

TABLE 5-continued

INTERFERING SUBSTANCES
Patient samples were spiked with NCCLS recommended levels of various interfering substances. If P value > 0.05, the difference in hCG dose is not statistically significant.

| Substance (mg/dL) | hCG Control, mIU/mL | hCG Spiked, mIU/mL | Spiked vs. Control | P-Value (95% C.I.) |
|---|---|---|---|---|
| | 48.3 | 50.5 | 105 | 0.04 |
| | 94.3 | 98.7 | 105 | 0.00 |
| | 191.7 | 189.8 | 99 | 0.57 |
| | 871.1 | 934.4 | 107 | 0.31 |
| Hemolysate | 2.4 | 3.1 | 126 | 0.05 |
| (500) | 48.0 | 48.4 | 100 | 0.72 |
| | 92.3 | 94.2 | 102 | 0.21 |
| | 182.5 | 197.7 | 108 | 0.05 |
| | 1,029.6 | 1,046.3 | 102 | 0.63 |

Example 3

Digoxin

A digoxin assay has been developed for the above described automated analyzer. The digoxin assay architecture is a hapten solid phase with a labeled antibody (tracer reagent). In the preferred format of this assay, the tracer reagent is an acridinium ester labeled monoclonal anti-digoxin antibody; and the solid phase is paramagnetic particles to which digoxin-apoferritin has been immobilized. A test sample (150 uL.) and tracer reagent (50 uL.) are dispensed into a cuvette by the analyzer and incubated for 2.5 minutes at 37° C. The solid phase reagent (250 uL.) is then added to the cuvette followed by an additional incubation of 5.0 minutes. After the second incubation, magnetic separation and washes are performed as described above prior to detection of the chemiluminescent signal.

All data presented was generated based upon a two-point recalibration off an original master curve. The master curve was generated using eight standards with values ranging from zero to 6 ng/mL digoxin.

The test assay has a sensitivity of less than 0.1 ng/mL (minimum detectable dose defined as the 95% confidence limit at 0 ng/mL.) with a range of 0–5 ng/mL. The precision of the assay for patient samples and patient pools is provided in Table 6. The specificity of the assay is provided in Table 7. Interfering substances added to test samples according to NCCLS protocols were assayed with results provided in Table 8. The correlation of the automated test assay with a manual test assay (Magic® Digoxin, Ciba Corning Diagnostics, Corp.) provided a slope of 1.00, an intercept of 0.08 and a correlation coefficient of 0.97 (N=130).

TABLE 6

PRECISION

A. Patient samples run in replicates of two. 13 patient samples were studied in each group.

| Mean digoxin concentration | Within run % CV |
|---|---|
| 0.52 ng/mL | 6.5 |
| 0.81 | 4.7 |
| 1.05 | 4.7 |
| 1.22 | 4.9 |
| 1.37 | 5.6 |

TABLE 6-continued

PRECISION

| | | |
|---|---|---|
| 1.49 | | 5.2 |
| 1.86 | | 4.2 |
| 2.68 | | 2.3 |

B. Patient pools and control run in replicates of 12 over 5 runs.

| | Digoxin concentration | Within run % CV | Total % CV |
|---|---|---|---|
| Controls: | 0.79 ng/mL | 7.0 | 7.9 |
| | 1.73 | 5.8 | 5.8 |
| | 2.81 | 4.8 | 5.0 |
| Patient | 0.62 ng/mL | 6.7 | 8.0 |
| Pools: | 0.97 | 3.7 | 4.7 |
| | 1.15 | 5.1 | 5.5 |
| | 1.64 | 4.1 | 4.3 |
| | 2.05 | 4.3 | 4.6 |
| | 4.18 | 4.3 | 5.1 |

TABLE 7

SPECIFICITY

| Compound | % Cross-Rectivity |
|---|---|
| Digitoxin | 0.6% |
| β-Methyldigoxin | 109.4% |
| Deslanoside | 94.6% |
| Digoxigenin | 16.7% |
| Lanatoside C | 87.1% |
| Ouabain | 7.3% |

| Compound | Level Tested | Effect on Dose |
|---|---|---|
| Cortisone | 20 ug/mL | N.S. |
| Estradiol | 1 ug/mL | N.S. |
| Progesterone | 1 ug/mL | N.S. |
| Testosterone | 1 ug/mL | N.S. |
| Prednisone | 20 ug/mL | N.S. |

TABLE 8

INTERFERING SUBSTANCES
Patient samples were spiked with NCCLS recommended levels of various interfering substances. If P value > 0.05, the difference in digoxin dose is not statistically significant.

| Substance (mg/dL) | Digoxin Control, ng/mL | Digoxin Spiked, ng/mL | Spiked vs. Control | P-Value (95% C.I.) |
|---|---|---|---|---|
| Conjugated | 0.003 | 0.008 | — | 0.36 |
| Bilinibin | 0.54 | 0.57 | 106% | 0.20 |
| (20) | 2.23 | 2.21 | 99% | 0.44 |
| Unconjug. | 0.004 | 0.000 | — | 0.30 |
| Bilirubin | 0.56 | 0.59 | 105% | 0.06 |
| (20) | 2.25 | 2.22 | 99% | 0.66 |
| Lipid | 0.010 | 0.012 | — | 0.89 |
| (1,000) | 0.52 | 0.58 | 112% | 0.03 |
| | 2.06 | 2.04 | 99% | 0.69 |
| Hemolysate | 0.0 | 0.0 | — | 1.00 |
| (500) | 0.52 | 0.53 | 102% | 0.75 |
| | 2.09 | 2.10 | 101% | 0.90 |

Example 4
Prostate Specific Antigen (PSA)

A prostate specific antigen PSA) assay has been developed for the above described automated analyzer. The PSA assay utilizes an anti-PSA antibody solid phase and a labeled anti-PSA antibody as a tracer reagent. In the preferred format of this assay acridinium ester is the label on an affinity purified anti-PSA antibody and the solid phase is paramagnetic particles which is coated with anti-PSA monoclonal antibody. A test sample (100 uL.), tracer reagent (5 uL.) and solid phase reagent (250 uL.) are dispersed into a cuvette by the analyzer and incubated for 7.5 minutes at 37° C. After the incubation, magnetic separation and washes are performed as described above prior to detection of the chemiluminescent signal.

All data presented was generated based on a two-point calibration off a standard curve consisting of eight points.

The test assay has a sensitivity of 0.2 ng/mL. (minimum dectable dose defined as the 95% confidence limit at 0 ng/mL.) with a dynamic range of 0–200 ng/mL. and a high dose hook capacity out to 40,000 ng/mL. The precision of the assay based on five separate runs on three instruments over a five day period for commercial controls and patient pools is provided in Table 9. Interfringing substances, including endogenous compounds and cheno therapeutic agents, added to test samples according to NCCLS protocols were assayed with results provided in Tables 10 and 11. The correlation of the automated test assay with a manual test assay (Tandem R-R PSA, Hybritech) provided a slope of 1.01, an intercept of 3.65 and a correlation coefficient of 0.97 (N=73).

TABLE 9

PRECISION
A. Analysis is based on 5 separate run on 3 instruments over a five day period. Each run contained 12–14 repetitions.
Two point calibration was used throughout

| Commercial Controls (N = 70) | PSA Concentration; ng/mL | % CV Within Run | % CV Total |
|---|---|---|---|
| A | 2.76 | 8.7 | 11.15 |
| B | 7.71 | 6.74 | 7.36 |
| C | 17.37 | 5.94 | 6.91 |

| Patient Pools (N = 60) | PSA Concentration, ng/mL | % CV Within Run | % CV Total |
|---|---|---|---|
| 1 | 15.79 | 4.49 | 6.46 |
| 2 | 25.91 | 5.73 | 7.64 |
| 3 | 48.78 | 5.54 | 8.65 |
| 4 | 93.66 | 5.81 | 8.07 |

TABLE 10

INTERFERING SUBSTANCES
(ENDOGENOUS COMPOUNDS)
Patient samples at various PSA levels were spiked with maximal levels of endogenous interferents according to NCCLS protocols.

| Substance (mg/dL) | PSA Control, ng/mL | PSA Spiked, ng/mL | Spiked vs. Control | Mean +/− SD |
|---|---|---|---|---|
| Hemoglobin | 7.08 | 7.32 | 103% | 99 |
| (500) | 28.06 | 27.86 | 99% | +/− 4% |
| | 51.06 | 48.99 | 96% | |
| Triglycerides | 7.08 | 7.29 | 103% | 102 |
| (3000) | 28.06 | 29.78 | 106% | +/− 5% |
| | 51.06 | 49.18 | 96% | |
| Unconjug. | 7.0 | 7.6 | 109% | 103 |
| Bilirubin | 28.06 | 28.45 | 101% | +/− 6% |
| (20) | 57.54 | 56.08 | 98% | |
| Conjug. | 7.08 | 7.57 | 107% | 101 |
| Bilirubin | 28.06 | 29.44 | 105% | +/− 9% |
| (20) | 51.06 | 46.57 | 91% | |

TABLE 10-continued

INTERFERING SUBSTANCES
(ENDOGENOUS COMPOUNDS)
Patient samples at various PSA levels were spiked with maximal levels of endogenous interferents according to NCCLS protocols.

| Substance (mg/dL) | PSA Control, ng/mL | PSA Spiked, ng/mL | Spiked vs. Control | Mean +/− SD |
|---|---|---|---|---|
| Total Protein | 7.08 | 6.51 | 92% | 90 |
| (12 gm/dL) | 28.06 | 25.38 | 90% | +/− 2% |
|  | 57.54 | 50.98 | 89% |  |

TABLE 11

INTERFERING SUBSTANCES
(CHEMOTHERAPEUTIC AGENTS)
Patient samples at various PSA levels were spiked with drugs commonly used in the treatment of cancer of the prostate (N = 5).

| Substance (ug/mL) | PSA Control, ng/mL | PSA Spiked, ng/mL | Spiked vs. Control | Mean +/− SD |
|---|---|---|---|---|
| Cyclophosphamide | 7.55 | 7.17 | 95% | 98 |
| (330) | 28.06 | 27.52 | 97% | +/− 3% |
|  | 49.34 | 49.8 | 101% |  |
| Doxorubicin | 7.55 | 7.32 | 97% | 100 |
| (10) | 28.06 | 28.22 | 101% | +/− 3% |
|  | 49.34 | 50.11 | 102% |  |
| Megestrol | 7.08 | 7.47 | 106% | 101 |
| Acetate | 28.06 | 28.42 | 101% | +/− 5% |
| (79) | 51.06 | 49.7 | 97% |  |
| Diethyl- | 7.08 | 7.52 | 106% | 101 |
| Stilbesterol | 28.06 | 28.10 | 100% | +/− 5% |
| (2.5) | 57.54 | 55.57 | 97% |  |
| Methotrexate | 7.08 | 7.16 | 101% | 101 |
| (13.2) | 28.06 | 28.98 | 103% | +/− 3% |
|  | 51.06 | 49.79 | 98% |  |

Prostatic acid phosphatase (PAP), > 95% pure, showed less taan 0.01% cross reactivity

We claim:

1. A reagent container for use in an automated assay analysis system comprising:
    a bottom wall;
    a tubular vertical side wall which defines an inner chamber;
    a top opening;
    a tubular outer skirt surrounding and attached to said side wall near a top of said side wall and extending downwardly spaced from said side wall and terminating in a free bottom edge, said skirt defining a tubular area surrounding said side wall and wherein the bottom edge of said skirt extends below said bottom wall; and
    at least one fin which is located in said chamber and extends from said bottom wall and from a substantial portion of said sidewall for agitating fluid within said chamber upon rotation of said container about a vertical axis.

2. A reagent container as recited in claim 1, wherein said side wall has an inner surface and an outer surface and there are two fins which extend toward each other from opposite sides of said inner surface, each fin having a terminal inner edge which is spaced from the inner terminal edge of the other of said fins.

3. A reagent container for use in an automated assay analysis system comprising:
    a bottom wall,
    a vertical side wall which defines an inner chamber;
    a top opening; and
    an outer skirt comprising:
        (a) a first flat side,
        (b) a second flat side which is parallel with said first flat side and is equal in length to said first flat side,
        (c) a third flat side which extends from one end of said first flat side to one end of said second flat side which is at a right angle to each of said first and second flat sides, and
        (d) an outwardly curving side which extends from the opposite end of said first flat side to the opposite end of said second flat side, said skirt being attached to said side wall near a top of said side wall and extending downwardly substantially spaced from said side wall and terminating in a free bottom edge, said skirt defining an area surrounding said vertical side wall.

4. A reagent container as recited in claim 3, wherein the bottom edge of said skirt extends below said bottom wall.

* * * * *

Disclaimer 6,063,340—Scott C. Lewis, Amherst; Mary Beth Whitesel, Grafton, both of Ohio. REAGENT CONTAINER FOR AUTOMATED ANALYZER. Patent dated May 16, 2000. Disclaimer filed December 18, 2000, by the assignee, Bayer Corporation.

Hereby enters this disclaimer to all claims of said patent.

*(Official Gazette, June 5, 2001)*